United States Patent
Aye et al.

(10) Patent No.: US 11,506,670 B2
(45) Date of Patent: Nov. 22, 2022

(54) METHOD OF GENOME-WIDE DIRECT IDENTIFICATION OF ELECTROPHILE-SENSING TARGETS

(71) Applicant: Cornell University, Ithaca, NY (US)

(72) Inventors: Yimon Aye, Ithaca, NY (US); Marcus J. C. Long, Ithaca, NY (US); Yi Zhao, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 991 days.

(21) Appl. No.: 15/903,506

(22) Filed: Feb. 23, 2018

(65) Prior Publication Data
US 2019/0265250 A1   Aug. 29, 2019

(51) Int. Cl.
*G01N 33/566* (2006.01)
*G01N 33/68* (2006.01)
*C12Q 1/68* (2018.01)
*G01N 33/58* (2006.01)

(52) U.S. Cl.
CPC ........... *G01N 33/6842* (2013.01); *C12Q 1/68* (2013.01); *G01N 33/566* (2013.01); *G01N 33/58* (2013.01); *G01N 2458/00* (2013.01); *G01N 2500/04* (2013.01); *G01N 2500/10* (2013.01); *G01N 2570/00* (2013.01)

(58) Field of Classification Search
None
See application file for complete search history.

(56) References Cited

PUBLICATIONS

Long et al (Nature Chemical Biology 13:333-8) (Year: 2017).*
Long et al. (Nature Chemical Biology 13:333-8 supplementary information) (Year: 2017).*
Parvez et al. (2016 Nature Protocols 11:2328-56) (Year: 2016).*
Parvez et al (Nature Protocols 11:2328-56 supplementary information) (Year: 2016).*

* cited by examiner

*Primary Examiner* — Christopher M Gross
(74) *Attorney, Agent, or Firm* — Troutman Pepper Hamilton Sanders LLP (Rochester)

(57) ABSTRACT

The present invention relates to a method for identifying endogenous first responder protein-cysteines. Methods for screening candidate compounds suitable for regulating NF-kB signaling and the DNA damage response pathway are also disclosed.

25 Claims, 66 Drawing Sheets
Specification includes a Sequence Listing.

A

B

A Human Ube2V1 and Ube2V2

```
Ube2v1    MPGEVQASYLKSQSKLSDEGRLEPRKFHEKGSKSPSQFRLLEELEEGQKGVGDGTVSWGL    60
Ube2v2    ------------------------MAVSTGVKVPRNFRLLEELEEGQKGVGDGTVSWGL    35
                                   .***  :**************************
                          C69 (Ube2V2) / C94 (Ube2V1)
Ube2v1    EDDEDMTLTRWTGMIIGPPRTIYENRIYSLKIEQGPKYPEAPPFVRFVTKINMNGVNSSN   120
Ube2v2    EDDEDMTLTRWTGMIIGPPRTNYENRIYSLKVEQGPKYPEAPPSVRFVTKINMNGINSSN    95
          ********************* ********:*:********* ************:***

Ube2v1    GVVDPRAISVLAKWQNSYSIKVVLQELRRLMMSKENMKLPQFPEGQTYSN   170  (SEQ ID NO:5)
Ube2v2    GMVDARSIPVLAKWQNSYSIKVVLQELRRLMMSKENMKLPQFPEGQTYNN   145  (SEQ ID NO:6)
          *:**  :* :***************************************:*
```

B Ube2V1

```
Danio_rerio      ----------MRRLFTVGASPLL---SNKMAAAGSGVKVPRNFRLLEELEEGQKGVGDGTVSWGL   53
Homo_sapiens     MPGEVQASYLKSQSKLSDEGRLEPRKFHEKGSKSPSQFRLLEELEEGQKGVGDGTVSWGL          60
Pan_troglodytes  MPGEVQASYLKSQSKLSDEGRLEPRKFHEKGVKVPRNFRLLEELEEGQKGVGDGTVSWGL         60
Mus_musculus     -------------------------M-AATTGSGVKVPRNFRLLEELEEGQKGVGDGTVSWGL     37
Xenopus_laevis   ------------------------QRYG-AATTVSGVKVPRNFRLLEELEEGQKGVGDGTVSWGL   40
                                           .* * :: **************************
                                     C94 (Ube2V1 from human)
Danio_rerio      EDDEDMTLTRWNGMIIGPPRTIYENRIYSLRVEQGRYPETPPFVRFVTKINLNGVHSSN         113
Homo_sapiens     EDDEDMTLTRWTGMIIGPPRTIYENRIYSLKIEQGPKYPEAPPFVRFVTKINMNGVNSSN        120
Pan_troglodytes  EDDEDMTLTRWTGMIIGPPRTIYENRIYSLKIEQGPKYPEAPPFVRFVTKINMNGVNSSN        120
Mus_musculus     EDDEDMTLTRWTGMIIGPPRTIYENRIYSLKIEQGPKYPEAPPSVRFVTKVNMNGVSSSN         97
Xenopus_laevis   EDDEDMTLTRWTGMIIGPPRTQYENRIYSLRVEQGPKYPESPPYVRFTKVNMNGVNNSN        100
                 *********** ********  ******** :**** :*** ** *** *:: *** **

Danio_rerio      GVVDPRAVSVLAKWQNSYSIKVVLQELRRLMMSKENMRLPQFPEGQTYSN   163  (SEQ ID NO:7)
Homo_sapiens     GVVDPRAISVLAKWQNSYSIKVVLQELRRLMMSKENMKLPQFPEGQTYSN   170  (SEQ ID NO:5)
Pan_troglodytes  GVVDPRAISVLAKWQNSYSIKVVLQELRRLMMSKENMKLPQFPEGQTYSN   170  (SEQ ID NO:8)
Mus_musculus     GVVDPRATAVLAKWQNSHSIKVILQELRRLMMSKENMKLPQFPEGQTYSN   147  (SEQ ID NO:9)
Xenopus_laevis   GVVDPRAVSVLKKWQNSYSIKVVLQEMRRLMMSKENMKLPQFPEGQTYSN   150  (SEQ ID NO:10)
                 ******* :*: .*********:****:*********:***********
```

FIGs. 5A-5B

C  Ube2V2

| | | |
|---|---|---|
| Xenopus_laevis_(African | MAYRALTKVPRNFRLLEELEEGQKGVGDGTVSWGLEDDEDMTLTRWTGMIIGPPRTNYEN | 60 |
| Danio_rerio_(Zebrafish) | MAASSGVKVPRNFRLLEELEEGQKGVGDGTVSWGLEDDEDMTLTRWTGMIIGPMRTNYEN | 60 |
| Homo_sapiens | MAYSTGVKVPRNFRLLEELEEGQKGVGDGTVSWGLEDDEDMTLTRWTGMIIGPPRTNYEN | 60 |
| Pan_troglodytes_(Chimpanzee) | MAYSTGVKVPRNFRLLEELEEGQKGVGDGTVSWGLEDDEDMTLTRWTGMIIGPPRTNYEN | 60 |
| Mus_musculus_(Mouse) | MAYSTGVKVPRNFRLLEELEEGQKGVGDGTVSWGLEDDEDMTLTRWTGMIIGPPRTNYEN | 60 |

C89 (Ube2V1 from human)

| | | |
|---|---|---|
| Xenopus_laevis_(African | RIYSLRLEGGPKYPEAPPTVRFVTKINMSNGINSNGTVDVRSIPVLAKWQNSPSIKVLLQ | 120 |
| Danio_rerio_(Zebrafish) | RIYSLKVEGPKYPEVPPTVRFVTKISMNGINKSNURDAKSIPILAKWQGSYSIKVVLQ | 120 |
| Homo_sapiens | RIYSLKVEGPKYPEAPPSVRFVTKINMNGINSSGNUDARSIPVLAKWQNSYSIKVVLQ | 120 |
| Pan_troglodytes_(Chimpanzee) | RIYSLKVEGPKYPEAPPSVRFVTKINMNGINSSGNUDARSIPVLAKWQNSYSIKVVLQ | 120 |
| Mus_musculus_(Mouse) | RIYSLKVEGPKYPEAPPSVRFVTKINMNGINSSGNUDARSIPVLAKWQNSYSIKVVLQ | 120 |

| | | |
|---|---|---|
| Xenopus_laevis_(African | ELRRLMMSKENMKLPQPPEGQTYNN | 145 (SEQ ID NO:11) |
| Danio_rerio_(Zebrafish) | ELRRLMMSKENMKLPQPPEGQTYNN | 145 (SEQ ID NO:12) |
| Homo_sapiens | ELRRLMMSKENMKLPQPPEGQTYNN | 145 (SEQ ID NO:6) |
| Pan_troglodytes_(Chimpanzee) | ELRRLMMSKENMKLPQPPEGQTYNN | 145 (SEQ ID NO:13) |
| Mus_musculus_(Mouse) | ELRRLMMSKENMKLPQPPEGQTYNN | 145 (SEQ ID NO:14) |

D  Ube2V1

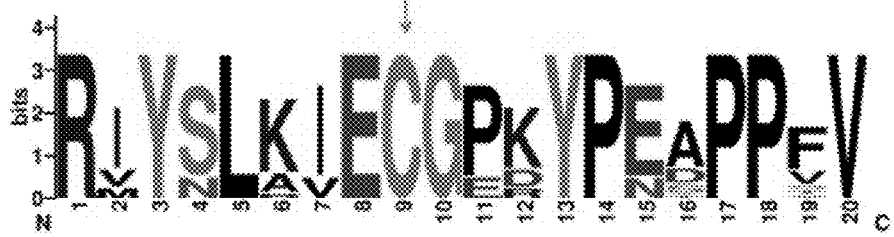

Ube2V2

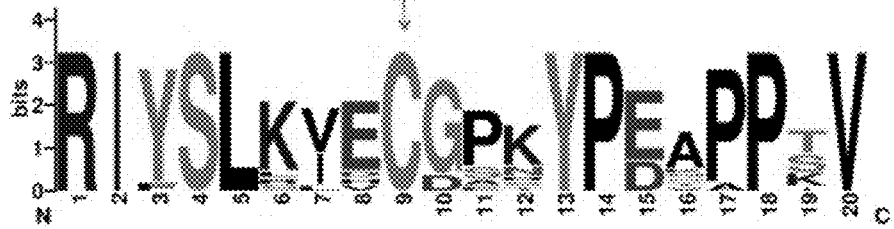

FIGs. 5C-5D

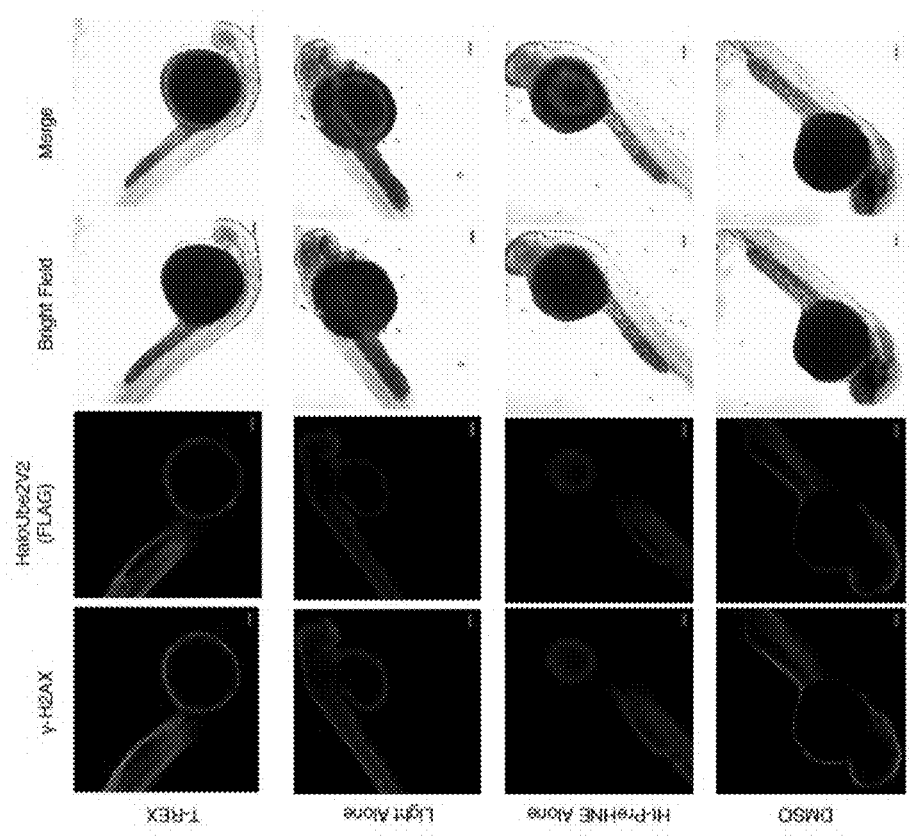
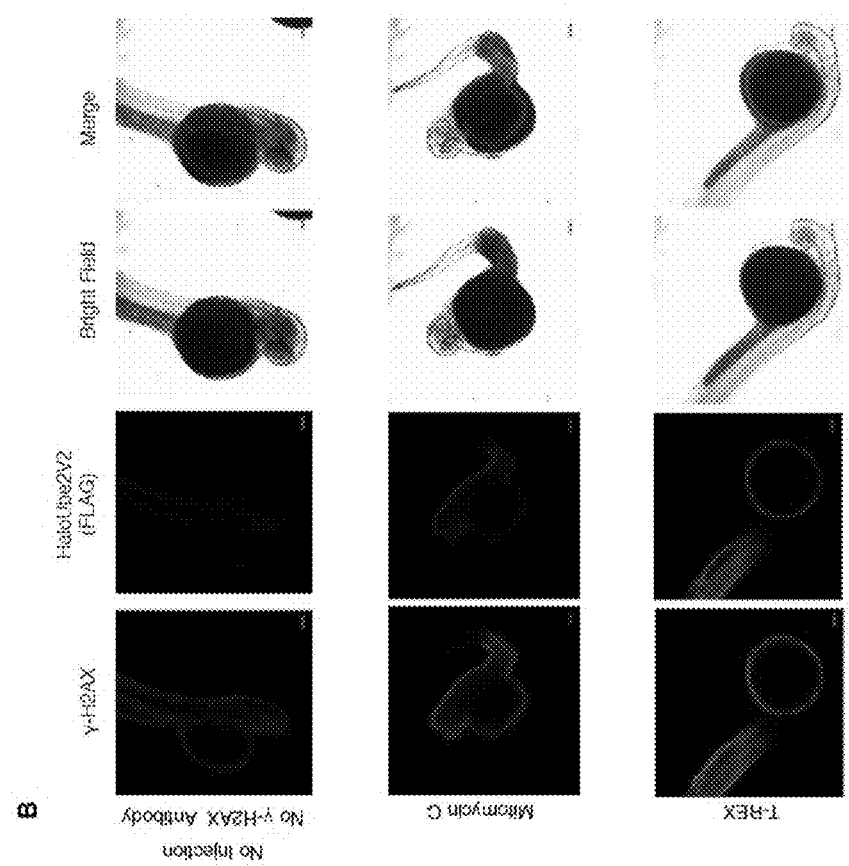
FIG. 14B a) Percentage of POI molecules modified (POI targeting efficiency) and residue modified
   (Step 40 Options A and B)

*(1) Gel-based analysis*[56,57]

T-REX   TEV-protease cleavage ──────▶ Click coupling ──────▶ In-gel fluorescence
   vs.
   Global   Set internal standard ──────▶ Click coupling ──────▶ In-gel fluorescence
            (1:1 HaloTag and photocaged precursor)

*(2) LC-MS/MS-based analysis*[56,57]

Affinity enrichment ──────▶ Trypsin digest ──────▶ LC-MS/MS analysis
                                                      (ion peak integration)

b) Pathway activation analyses
   (Step 40 Options C–F)

Downstream response reporters such as (1) dual luciferase[56,57], (2) GFP reporters (Figure 6),
   (3) immunofluorescence imaging (Figure 8), (4) FRET biosensors (Figure 9), (5) qRT-PCR[20], and
   (6) western blot analysis[20].

*Controls:*

Confirm ablation of response upon overexpressing HaloTag and POI as two separate proteins[56,57]

Confirm similar response in native cells vs. cells overexpressing Halo-POI upon global LDE stimulation[56]

FIGs. 21A-21B

| | |
|---|---|
| Human Keap1 (100%), 70.0 kDa, Mascot Score 769, 47 unique peptides with different modifications, 1 distinct tryptic peptides with added mass of 136 Da for possible modifications of reduced CHE(alkyne)§ Michael adduct. The modified peptide was found present in corresponding unmodified form of the native peptide with Cys being alkylated by carbamidomethylation. 341/624 amino acids (54% coverage). Matched peptide with CHE related modifications shown <u>underlined</u>, other matched peptide shown in *italics*.<br>MQPDPRPSGA GACCRFLPLQ SQCPEGAGDA *VMYASTECKA* EVTPSQHGNR *TFSYTLEDHT KQAFGIMNEL RLSQQLCDVT LQVKYQDAPA AQFMAHKVVL ASSSPVFKAM FTNGLREQGM EVVSIEGIHP* KVMERLIEFA YTASISMGEK CVLHVMNGAV MYQIDSVVR*A CSDFLVQQLD PSNAIGIANF AEQIGCVELH QRAREYIYMH FGEVAKQEEF FNLSHCQLVT LISRDDLNVR CESEVFHACI NWVKYDCEQR RFYVQALLRA* VRCHSLTPNF LQMQLQKCEI *LQSDSRCKDY LVKIFEELTL HKPTQVMPCR APKVGRLIYT AGGYFRQSLS YLEAYNPSDG* TWLRLADLQV PRSGLAGCVV GGLLYAVGGR NNSPDGNTDS SALDCYNPMT NQWSPCAPMS VPRNRIGVGV IDGHIYAVGG SHGCIHHNSV ERYEPERDEW HLVAPMLTRR*IGVGVAVLNR LLYAVGGFDG TNRLNSAECY YPERNEWRMI* TAMNTIRSGA GVCVLHNCIY AAGGYDGQDQ LNSVERY*DVE TETWTFVAPM KHRRSALGIT VHQGRIYVLG GYDGHTFLDS VECYDPDTDT WSEVTRMTSG <u>RSGVGVAVTM EPCR</u>*KQIDQQ NCTC* (SEQ ID NO: 15) | |
| Unique peptide with CHE-alkyne modification (asterisk suggests modification site) | MS spectra |
| <u>C613</u><br>**SGVGVAVTMEPC\*R<br>p-value:0.00016<br>Mascot Ion Score: 38<br>Expectation Values:<br>0.00016<br>(SEQ ID NO: 16)** | 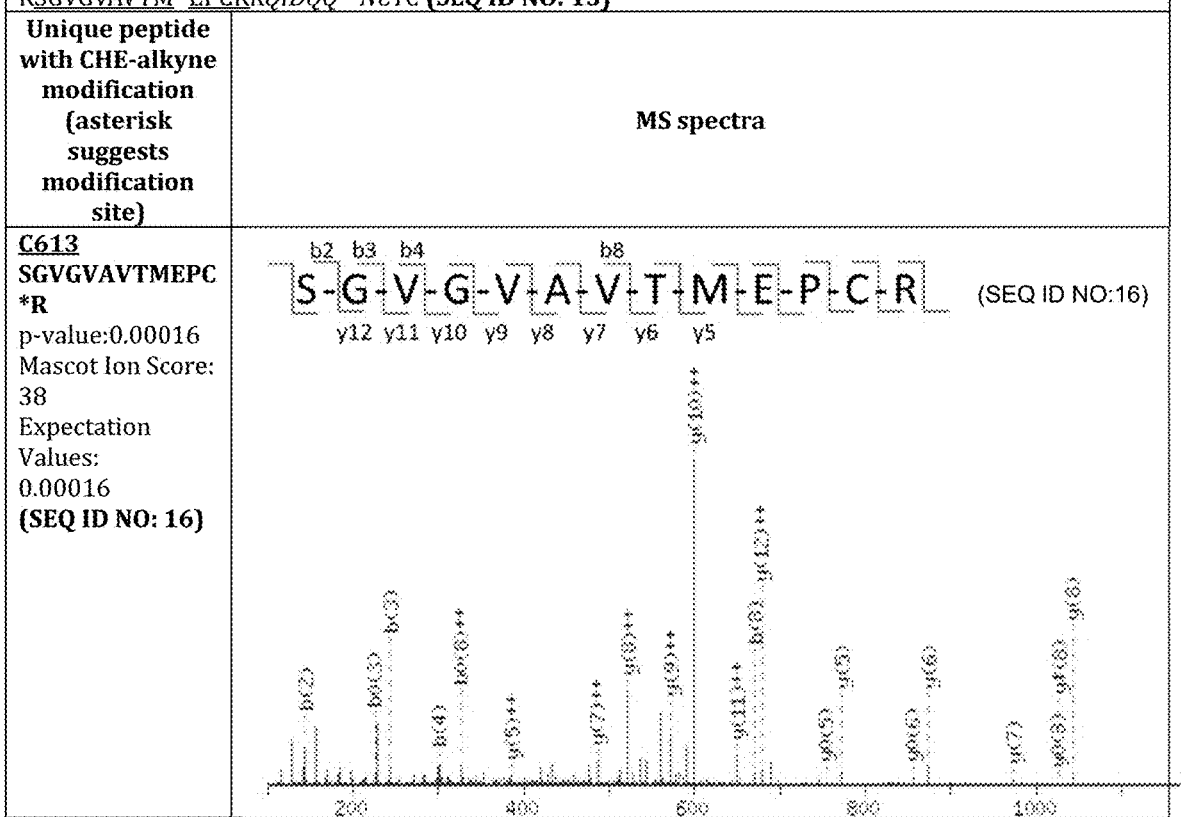 (SEQ ID NO:16) |

§ Chemical synthesis and characterization of Pre-CHE(Alkyne) (also known as Ht-PreCHE) was previously reported (Lin et al., "A Generalizable Platform for Interrogating Target- and Signal-specific Consequences of Electrophilic Modifications in Redox-dependent Cell Signaling," *J. Am. Chem. Soc.* 137:6232-6244 (2015), which is hereby incorporated by reference in its entirety).

FIG. 30

| | |
|---|---|
| Human Keap1 (100%), 70.0 kDa, Mascot Score 1821, 130 unique peptides with different modifications, 1 distinct tryptic peptides with added mass of 136 Da for possible modifications of reduced CHE(alkyne)§ Michael adduct. The modified peptide was found present in corresponding unmodified form of the native peptide with Cys being alkylated by carbamidomethylation. 414/624 amino acids (66% coverage). Matched peptide with CHE related modifications shown in <u>underline</u>, other matched peptide shown in *italics*.<br>MQPDPRPSGA GACCRFLPLQ SQCPEGAGDA VMYASTECKA EVTPSQHGNR *TFSYTLEDHT KQAFGIMNEL RLSQQLCDVT LQVKYQDAPA AQFMAHKVVL ASSSPVFKAM FTNGLREQG M EVVSIEGIH PKVMERLIEFA YTASISMGEK* CVLHVMNGAV MYQIDSVVRA *CSDFLVQQLD PSNAIGIANF AEQIGCVELH QRAREYIYMH FGEVAKQEEF* FNLSHCQLVT *LISRDDLNVR CESEVFHACI NWVKYDCEQRRFYVQALLRA VRCHSLTPNF LQMQLQKCEI LQSDSRCKDY LVKIFEELTLH KPTQVMPCRA PKVGRLIYTAG GYFRQSLSYL EAYNPSDGT WLRLADLQV PRSGLAGCVV GGLLYAVGGR NNSPDGNTDS SALDCYNPMT NQWSPCAPMS VPRNRIGVGV IDGHIYAVGG SHGCIHHNSV ERYEPERDEW HLVAPMLTRR IGVGVAVLNR LLYAVGGFDG TNRLNSAECY YPERNEWRMI TAMNTIRSGA GVCVLHNCIY AAGGYDGQDQ LNSVERYDVE TETWTFVAPM KHRRSALGIT VHQGRIYVLG GYDGHTFLDS VECYDPDTDT* WSEVTRMTSG R<u>SGVGVAVTM EPCRKQIDQQ</u> *NCTC* (SEQ ID NO: 15) | |
| Unique peptide with CHE-alkyne modification (asterisk suggests modification site) | MS spectra |
| <u>C613</u><br>**SGVGVAVTMEPC\*R<br>p-value:0.00079<br>Mascot Ion Score: 31<br>Expectation Values: 0.00079<br>(SEQ ID NO: 16)** | 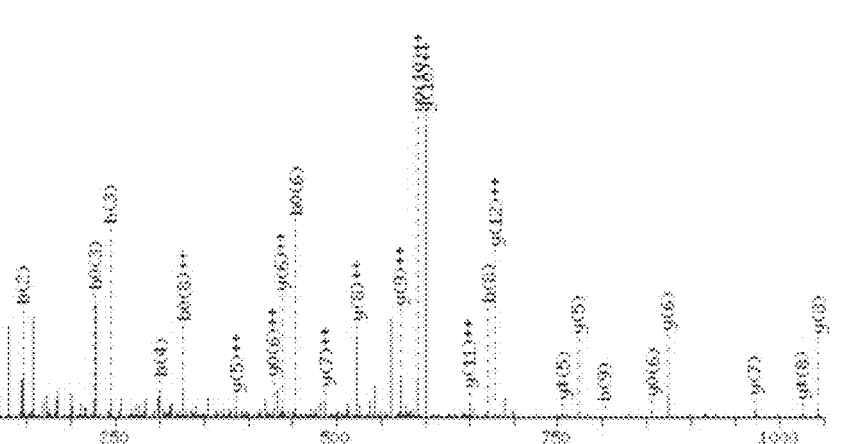<br>(SEQ ID NO:16) |

§ Chemical synthesis and characterization of CHE(Alkyne) was previously reported (Lin et al., "A Generalizable Platform for Interrogating Target- and Signal-specific Consequences of Electrophilic Modifications in Redox-dependent Cell Signaling," *J. Am. Chem. Soc.* 137:6232-6244 (2015), which is hereby incorporated by reference in its entirety).

FIG. 31

| | |
|---|---|
| Human UBE2V2 (100%), 16.3 kDa, Mascot Score 1240.38, 3 unique peptides with different modifications, 1 distinct tryptic peptides with added mass of 154.1 Da for possible modifications of HNE(alkyne) Michael adduct (See Table 1). 92/145 amino acids (63.5% coverage). Matched peptide with HNE related modifications shown in underline, other matched peptide shown in *italics*.<br>*MAVSTGVKVP RNFRLLEELE EGQKGVGDGT VSWGLEDDED MTLTRWTGMI*<br><br>*IGPPRTNYEN R*<u>IYSLKVECG PKYPEAPPSV R</u>*FVTKINMNG INNSSGMVDA*<br><br>*RSIPVLAKWQ NSYSIKVVLQ ELR*<u>R</u>*LMMSKE NMKLPQPPEG QTYNN* (SEQ ID NO:6) | |
| Unique peptide with modification (asterisk suggests modification site) | IYSLKVECG PKYPEAPPSV R    (SEQ ID NO:2) |
| MS1 mass of Cys69 (HNE Alkyne) of human Ube2V2 (M+3H) | <br>IYSLKVEcGPKYPEAPPSVR (SEQ ID NO: 2)<br>M+3H<br><br>Mass of Peptide + HNE-alkyne:<br><br>(2233.6+152.1) / 3 = 795.2 |

FIG. 32

| MS1 mass of Cys69 (HNE Alkyne) of human Ube2V2 (M+4H) | 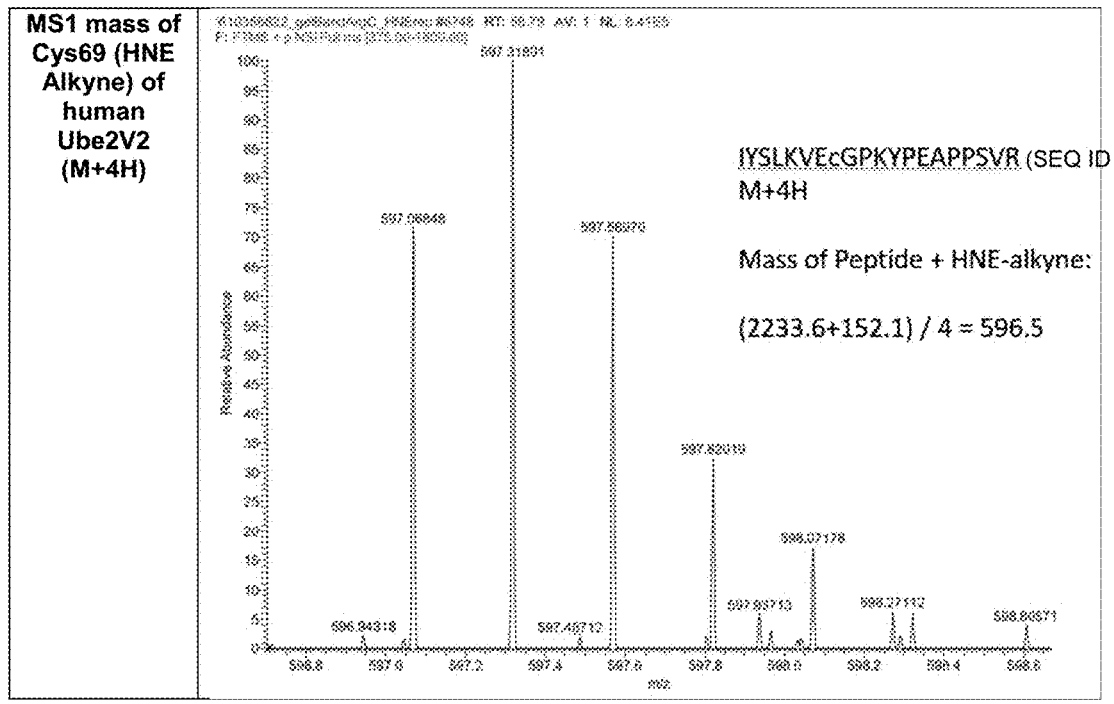 |
|---|---|
IYSLKVEcGPKYPEAPPSVR (SEQ ID NO: 2) M+4H
Mass of Peptide + HNE-alkyne:
(2233.6+152.1) / 4 = 596.5
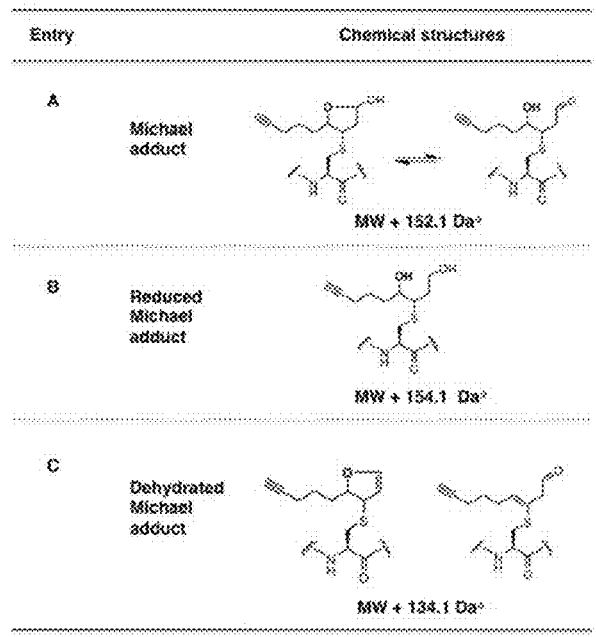
FIG. 32 cont'd Chemical structures of HNE- and HNE-derived-adducts on cysteine residue on peptides.

| | |
|---|---|
| Human UBE2V2 (100%), 16.3 kDa, Mascot Score 1240.38, 3 unique peptides with different modifications, 1 distinct tryptic peptides with added mass of 154.1 Da for possible modifications of HNE(alkyne) Michael adduct (See Table 1). 92/145 amino acids (63.5% coverage). Matched peptide with HNE related modifications shown in underline, other matched peptide shown in *italics*.<br>*MAVSTGVKVP RNFRLLEELE EGQKGVGDGT VSWGLEDDED MTLTRWTGMI*<br><br>*IGPPRTNYEN R*<u>IYSLKVECG PKYPEAPPSV R</u>*FVTKINMNG INNSSGMVDA*<br><br>*RSIPVLAKWQ NSYSIKVVLQ ELR*<i>RLMMSKE NMKLPQPPEG QTYNN</i> (SEQ ID NO:6) | |
| Unique peptide with modification (asterisk suggests modification site) | IYSLKVECG PKYPEAPPSV R (SEQ ID NO:2) |
| MS/MS mass of Cys69 (HNE Alkyne) of human Ube2v2 (M+3H) | 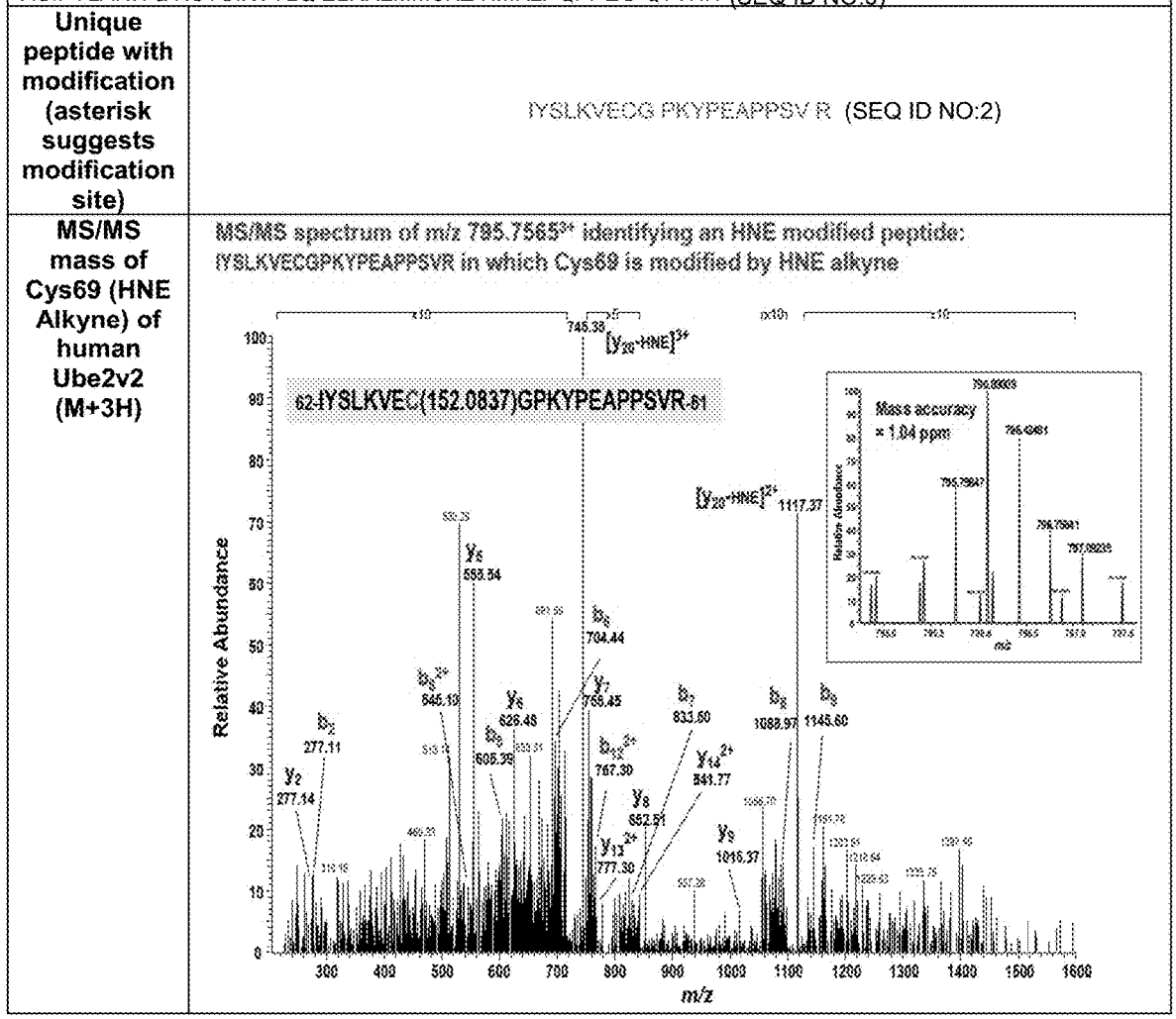 |

FIG. 34 cont'd

METHOD OF GENOME-WIDE DIRECT IDENTIFICATION OF ELECTROPHILE-SENSING TARGETS

This invention was made with government support under 1DP2GM114850-01 awarded by National Institutes of Health. The government has certain rights in the invention.

FIELD OF THE INVENTION

The present invention relates to methods of genome-wide direct identification of electrophile-sensing targets.

BACKGROUND OF THE INVENTION

Through a phenomenal research effort much is now understood about complex post-synthesis regulation in cell signaling. Approximately 10% of the genome is involved in phosphorylation (Pearlman et al., "A Mechanism for the Evolution of Phosphorylation Sites," Cell 147:934-46 (2011)) and ubiquitination (Yau et al., "The Increasing Complexity of the Ubiquitin Code," Nature Cell Biology 18:579-86 (2016); Wilkinson et al., "The Ubiquitin Signal: Assembly, Recognition and Termination," Symposium on Ubiquitin and Signaling EMBO Rep. 6:815-20 (2005)): a complex series of "codes" specific to both healthy and disease states is overseen by this suite of enzymes. Gaining a clearer apprehension of these paradigmatic signaling pathways has impacted several aspects of human health, including prophylaxis, diagnosis, drug design, and personal medicine. Recent years have witnessed success of kinome-targeting pharmaceuticals (Tarrant et al., "The Chemical Biology of Protein Phosphorylation," Annu Rev. Biochem. 78:797-825 (2009)), and an intense pursuit of drug discovery is now also aimed at ubiquitination (Love et al., "Mechanisms, Biology and Inhibitors of Deubiquitinating Enzymes," Nat. Chem. Biol. 3:697-705 (2007); Salami et al., "Waste Disposal—An Attractive Strategy for Cancer Therapy," Science 355:1163-67 (2017)). No approved drugs currently target ubiquitin (Ub) conjugation/deconjugation (Hoeller et al., "Targeting the Ubiquitin System in Cancer Therapy," Nature 458:438-44 (2009)), but the proteasome—a molecular machine intrinsically linked to the ubiquitin pathways—is a bona fide drug target (Salami et al., "Waste Disposal—An Attractive Strategy for Cancer Therapy," Science 355:1163-67 (2017)).

Against the backdrop of these exquisite enzyme-regulated signaling subsystems, the cell has also harnessed reactive small-molecule signaling mediators to fine-tune responses. In this paradigm, reactive oxygen or electrophilic species (ROS/RES) directly modify a specific signal-sensing protein, preempting decision-making (Schopfer et al., "Formation and Signaling Actions of Electrophilic Lipids," Chem. Rev. 111:5997-6021 (2011); Jacobs et al., "Systems Analysis of Protein Modification and Cellular Responses Induced by Electrophile Stress," Acc. Chem. Res. 43:673-83 (2010); Long et al., "The Die Is Cast: Precision Electrophilic Modifications Contribute to Cellular Decision Making," Chem. Res. Toxicol. 30(8):1599-1608 (2016); Brewer et al., "Chemical Approaches to Discovery and Study of Sources and Targets of Hydrogen Peroxide Redox Signaling Through NADPH Oxidase Proteins," Annu. Rev. Biochem. 84:765-90 (2015)). Because ROS and RES exist at low levels during signaling, sensor residues on redox-responsive proteins are likely 'kinetically privileged', i.e., inherently tuned to rapidly react with specific ROS/RES (Long et al., "Subcellular Redox Targeting: Bridging in Vitro and in Vivo Chemical Biology," ACS Chem. Biol. 12(3):586-600 (2017)) with rapid second-order rate constants (high $k_{cat}/K_m$). Unlike phosphorylation, ubiquitination is dominated by reactive thiol chemistry: Ub-conjugation proceeds through multiple enzyme-bound Ub-thioester intermediates. These conjugating enzymes are ROS-sensitive (Lee et al., "Reversible Inactivation of Deubiquitinases by Reactive Oxygen Species In Vitro and in Cells," Nat. Commun. 4:1568 (2013)). Deubiquitinating/deSUMOylating enzymes (DUBs/SENPs) are mostly thiol-active proteases; many DUBs and SENPs are indeed targets of ROS. Many of these ROS adducts involve direct modification of the active-site cysteine residue that is privileged due to its low pKa and low kinetic barrier to reaction with ROS. In most cases, free thiol ushers regain in enzymatic-activity.

The Ub-proteasome pathway is RES-sensitive, although this is more nuanced than ROS-sensing. Many natural electrophiles, including prostaglandins (Mullally et al., "Cyclopentenone Prostaglandins of the J Series Inhibit the Ubiquitin Isopeptidase Activity of the Proteasome Pathway," J. Biol. Chem. 276:30366-373 (2001)), 4-hydroxynonenal (HNE) (Okada et al., "4-Hydroxy-2-Nonenal-Mediated Impairment of Intracellular Proteolysis During Oxidative Stress—Identification of Proteasomes as Target Molecules," J. Biol. Chem. 274:23787-793 (1999)), and dietary isothiocyanates (Keum, Y. S., "Regulation of the Keap1/Nrf2 System by Chemopreventive Sulforaphane: Implications of Posttranslational Modifications," in Nutrition and Physical Activity in Aging, Obesity, and Cancer, Annals of the New York Academy of Sciences, Surh et al., eds., Blackwell Science Publ., Vol. 1229:184-9 (2011)) affect Ub-modification events (semi)-specifically. Several RES target active-site or other important cysteines on Ub-activating (E1), -conjugating (E2), and -ligating (E3, HECT-type) enzymes. Regardless of the site, most RES-modifications are irreversible—an attribute of RES signaling that may improve efficacy/confer different latency/longevity relative to ROS signaling (Long et al., "Subcellular Redox Targeting: Bridging in Vitro and in Vivo Chemical Biology," ACS Chem. Biol. 12(3):586-600 (2017)).

With the resurgence of electrophilic pharmacophores (Singh et al., "The Resurgence of Covalent Drugs," Nat. Rev. Drug Discov. 10:307-17 (2011)) and the search for novel drug-targeting mechanisms (Rask-Andersen et al., "Trends in the Exploitation of Novel Drug Targets," Nat. Rev. Drug Discov. 10:579-90 (2011)), privileged RES-sensing residues and the proteins/pathways they control have come to the fore of disease treatment (Blewett et al., "Chemical Proteomic Map of Dimethyl Fumarate-Sensitive Cysteines in Primary Human T Cells," Sci. Signal 9(445):rs10 (2016)). Recent work indicates that (i) there are specific subsets of orthogonal ROS- and RES-sensing cysteines (Long et al., "Akt3 is a Privileged First Responder in Isozyme-Specific Electrophile Response," Nat. Chem. Biol. 13:333-8 (2017)), meaning specific RES-sensors could be ideal foundations for electrophilic drug discovery (Long et al., "Privileged Electrophile Sensors: A Resource for Covalent Drug Development," Cell Chem. Biol. 24(7):787-800 (2017)); and (ii) privileged electrophile sensors may neither need to be active-site nucleophiles nor present in proteins with any specific chemical function. Hence RES-sensor identification could offer a pipeline to regulate pathway flux and modulate undruggable proteins without the difficulties associated with targeting active-site residues (Crews, C. M., "Targeting the Undruggable Proteome: The Small Molecules of My Dreams," Chem. & Biol. 17:551-5 (2010)).

Identification of bona fide sensor cysteines is difficult (Marino et al., "Analysis and Functional Prediction of Reactive Cysteine Residues," *J. Biol. Chem.* 287:4419-25 (2012)). An extensive series of innovative work has been done to identify electrophile-sensor proteins in cells, and some work has studied model organisms. There are two main strategies. The first is bolus dosing of cells with reactive electrophiles, followed by affinity capture of modified proteins and MS (Yang et al., "The Expanding Landscape of the Thiol Redox Proteome," *Mol. Cell. Proteomics* 15:1-11 (2016)). This strategy excitingly identifies a huge number of targets but is dominated by mass action/hyper-modification and is often prone to artefacts caused by end-point toxicity and perturbation of innate redox balance. A second strategy uses competitive profiling of a specific set of reactive residues (Wang et al., "A Chemoproteomic Platform to Quantitatively Map Targets of Lipid-Derived Electrophiles," *Nat. Methods* 11:79 (2014)). This innovative strategy is very powerful and more sensitive than bolus-dosing.

While much of the current understanding in redox biology has been derived using these pioneering methods, some key limitations remain to be addressed (Long et al., "Privileged Electrophile Sensors: A Resource for Covalent Drug Development," *Cell Chem. Biol.* 24(7):787-800 (2017)). For instance, both of the above methods administer an excess of electrophile from outside the cell/animal thus nuances of low-stoichiometry on-target RES-modifications that drive phenotypically-dominant redox responses at a specific time are often lost. Indeed, RES permeation into the cell, interaction with cellular redox machinery (e.g., glutathione), and build-up of metabolites are complex, time-dependent processes, rendering bulk RES-exposure a far-from-controlled environment. This effect is magnified in whole organisms where phenotypic outputs from bolus-dosing are a function of complex pharmacokinetics as well as amalgamation of on-target and off-target responses elicited by uncontrolled RES-exposure. Furthermore, as the competitive profiling method measures loss of labeling by the proxy (e.g., iodoacetamide), conclusions from the indirect measure of RES-modification may be confounded by off-target and/or secondary modifications/functional coupling: selective labeling of minor isoforms/complexes in low abundance may also be missed.

The present invention is directed to overcoming these and other deficiencies in the art.

SUMMARY OF THE INVENTION

A first aspect of the present invention relates to a method for identifying endogenous first responder protein-cysteines. The method involves culturing, in a culture medium, living cells either transfected or stably integrated with a nucleic acid encoding a protein tag under conditions effective to express the protein tag. The culture medium is treated with a bioinert photocaged precursor to a reactive electrophilic species (RES), which binds to the protein tag under conditions effective to form a bioinert photocaged precursor to an RES-protein tag complex. The culture medium is then subjected to actinic radiation so that the RES is released from the bioinert photocaged precursor to an RES-protein tag complex and binds to endogenous first responder protein-cysteines within the living cells, or subcellular locales where the protein tag is selectively expressed, to thereby form a covalent RES-labeled endogenous first responder protein-cysteine complex. The RES-labeled endogenous first responder protein-cysteine complex is then isolated.

A second aspect of the present invention relates to a method of screening candidate compounds suitable for regulating the DNA damage response. The method involves providing a protein comprising the amino acid sequence of IYSL(K/R)(L/V)ECG(S/P)KYPE(A/V)PP(S/T)VR (SEQ ID NO: 1) and contacting the protein with the candidate compounds under conditions suitable for the candidate compounds to react with cysteine in the protein. Compounds that regulate the DNA damage response are then identified, based on the contacting step.

A third aspect of the present invention is directed to a method of screening candidate compounds suitable for regulating NF-κB signaling. The method involves providing a protein comprising the amino acid sequence of (M/I)YSL(K/R)(V/I)ECGP(K/R)YPE(S/A/T)PP(F/S/Y)VR (SEQ ID NO: 3) and contacting the protein with the candidate compounds under conditions suitable for the candidate compounds to react with cysteine in the protein. Compounds that regulate NF-κB signaling are then identified, based on the contacting step.

A method that is able to recapitulate many of the nuanced aspects of endogenous RES-signaling, and identify proteins that sense low concentrations of lipid derived electrophiles (LDEs) at a specific time in intact living models is described herein, namely, G-REX™ profiling (genome-wide reactive glectrophile and oxidants) privileged-sensor profiling method. G-REX™ profiling enables a controlled release of a limited amount of specific LDE in situ (in a specific compartment of the live cells), at a pre-determined dose, and for a given time. The cell (and fish/worm)-permeable bio-inert photocaged precursor to an RES contains two key modular and transposable motifs: (1) a photo-activatable motif which masks the reactivity of the LDE until light shining initiates its rapid release; and (2) an anchor which can bind to a non-intrusive protein tag that serves to localize the caged LDE to an organelle of interest and limit concentration of LDE (maximally around 6 μM is achievable). Upon light exposure, the "first-responding" privileged sensors within the given microenvironment of the intact cell are given first refusal to the limited amounts of specific LDE chemotype delivered in a specific locale. After cell harvest and lysis, LDE-modified first-responding privileged sensors are enriched using affinity capture using chemoselective modification of alkyne handle on the LDE via biotin Click, followed by streptavidin pulldown. Liquid chromatography-high-resolution mass spectrometry (LC-MS) identifies the proteins. Importantly, once identified, another method, T-REX™ delivery (targetable reactive electrophiles and oxidants), is used to validate the hits. Using this G-REX™ profiling—T-REX™ delivery couple, new LDE sensors important in DNA damage, transcriptional and metabolic control are able to be identified.

BRIEF DESCRIPTION OF THE DRAWINGS

FIG. 3A shows treatment of HEK293T cells ectopically expressing HaloTag results in specific binding of the inert photocaged RES-precursor [e.g., Ht-PreHNE(alkyne)]. (In dotted box is the ribbon model of Halo bound to Ht-PreHNE(alkyne), chemical structure of which is shown in FIG. 4B). Any unbound probe is washed out. Upon low-energy light exposure of cells (see methods section of Example 1), this Halo-Ht-PreHNE(alkyne) complex releases stoichiometric amount of HNE(alkyne) ($t_{1/2}$<1-2 min) (red dot) within the microenvironment of Halo, enabling sub-stoichiometric covalent tagging of native PFRs to HNE. Indicated established pull-down-proteomics analysis permits HT-target-ID genome-wide. FIG. 3B is an illustrative model of N-terminal HaloT-agged Ube2V2 complexed to Ube2N with the photocaged-precursor, Ht-PreHNE, bound at Halo. (See FIG. 4B for general T-REX™ delivery set-up). Ribbon structure is adapted from PDB:1J7D. The newly-discovered HNE-responsive C69 (this work) within Ube2V2, and the catalytic cysteine (C87) within Ube2N, are both highlighted. FIG. 3C shows MS-analysis subsequent to T-REX™ delivery-redox-targeting in cells expressing Halo-(FLAG)Ube2v2 followed by enrichment using anti-FLAG beads, identifies an HNE-modified peptide—IYSLKVECG PKYPEAPPSV R (SEQ ID NO: 2) ion at m/z 795.2—on Ube2v2. Also see Table 1 and FIG. 34. FIG. 3D shows HEK293T cells transfected with the indicated plasmids, treated with Ht-PreHNE, and either exposed to light, or not irradiated. Normalized lysates from these two sets of cells were treated with either TEV-protease or buffer alone, respectively. Lysates were then subject to Click coupling with Cy5-azide, and analyzed by in-gel fluorescence for Cy5 signal. "1, 2, and N" respectively designate Ube2v1, Ube2v2, and Ube2N. Refer to FIG. 19A for Cy5 gel and blots in full-view. FIG. 3E is similar to FIG. 3D but cells were co-transfected with either empty vector (−) or a plasmid of the same vector expressing HA-Ube2N (+). Region of interest on Cy5 gel is marked by a red rectangle. Refer to FIG. 19B for Cy5 gel and blots in full-view. FIG. 3F is similar to FIG. 3E. Refer to FIG. 6C for Cy5 gel and blots in full-view. M designates molecular weight marker lane in all gels/blots in this and all figures elsewhere.

FIG. 4A shows the workflow for executing T-REX™ delivery on-demand RES-targeting in cells/in vivo to a specific privileged first responder (PFR), one of the hits from G-REX™ profiling screen in this study (see FIG. 3A for G-REX™ profiling set-up). PFR fused to HaloTag is ectopically expressed in live cells or fish. The bioinert photocaged precursor targetable to Halo [Ht-PreHNE (alkyne)] (see FIG. 4B) binds to Halo domain. After excess probe has been rinsed out, low-energy light exposure liberates of HNE(alkyne) ($t_{1/2}$<1-2 min) in substoichiometric amounts and 'Class II proximity enhancement' (Long et al., "On-Demand Targeting: Investigating Biology with Proximity-Directed Chemistry," J. Am. Chem. Soc. 138(11): 3610-22 (2016), which is hereby incorporated by reference in its entirety)) enables (1) targeted HNEylation of PFR in cells/fish and (2) direct readout of functional redox responses downstream in an otherwise unperturbed proteome. [Light source: 365 nm, 0.3 mW/cm2 hand-held UV-lamp placed 1 inch above samples [3-20 min in cells (G-REX™ profiling/T-REX™ delivery) or fish embryos (T-REX™ delivery)]. FIG. 4B is a schematic illustration of T-REX™ delivery/G-REX™ profiling experimental setup and chemical structures of Ht-PreHNE(alkyne) and Ht-PreHNE(no alkyne). M designates molecular weight marker lane in all gels/blots in this and all figures elsewhere.

FIG. 4C shows a control experiment for G-REX™ profiling proof-of-concept. Samples from G-REX™ profiling-treated cells analyzed by Coomassie. See FIG. 4B for workflow except that proteins eluted from streptavidin beads were analyzed by SDS-PAGE in place of proteomics analysis. 'Alkyne' vs. 'no-alkyne' respectively describes whether the small-molecule photocaged precursor, upon photouncaging, liberates alkyne functionalized-HNE (capable of biotinylation via Click coupling with biotin-azide) or native HNE (incapable of biotinylation). As expected, the 'Elute' fraction in the case of 'no-alkyne' probe showed no detectable proteins, validating specificity of Click biotinylation and streptavidin pulldown. [Unless otherwise stated, "Ht-PreHNE" designates the version with alkyne functionalization. See FIG. 4B for chemical structure of Ht-PreHNE (alkyne vs. no-alkyne)]. Note: the Cy5 signal in the "+alkyne sample" at ~39 kDa corresponds to the TEV-cleaved Halo domain carrying the remaining non-photouncaged Ht-PreHNE that is also recognized by Click. FIG. 4D shows a control experiment for G-REX™ profiling proof-of-concept. Samples analyzed by Coomassie (top) and streptavidin-HRP blot (bottom). Workflow is identical to FIG. 4B except in place of proteomics analysis, the eluted samples from streptavidin beads were analyzed as indicated. 'No-alkyne' version of Ht-PreHNE (designated as "−" for corresponding gel lanes) gave no detectable biotinylated proteins in 'Elute' fraction, confirming specific binding. FIG. 4E shows a similar experiment to workflow in FIG. 3A and FIG. 4B. Sample eluted from streptavidin beads was resolved by SDS PAGE. A band between 15-25 kDa (shown by a black box) was excised and analyzed by digest LC-MS/MS. FIG. 4F shows top hits from LC-MS/MS analysis of excised band within the gel from FIG. 4E. The Ubiquitin-conjugating enzyme E2 variant 2 and Ubiquitin-conjugating enzyme E2 variant 1 are novel HNE sensors discovered by G-REX™ profiling in this study; the peptidyl-prolyl cis-trans isomerase, ADP ribosylation factor 3, Cofilin 1 (Non-muscle), Nucleoside diphosphate kinase, ADP ribosylation factor 4, and ADP ribosylation factor 5 (Fragment) are known HNE-sensors. (A slightly higher MW observed for the Halo band in FIG. 4C compared to FIG. 4E, was due to the extra genetically-encoded tag present in the construct used for FIG. 4C).

FIGS. 5A-5D show inter-isoform and inter-species conservation of Ube2V1 and Ube2V2. FIG. 5A shows a Clustal-Ω alignment of human Ube2V1 (SEQ ID NO: 5) (isoform 2, the longest isoform) and Ube2V2 (SEQ ID NO: 6). Cysteines are highlighted in yellow. C94 and C69 are conserved between the two proteins. C69 of Ube2V2 was identified as an HNE-sensitive residue (see ribbon structure in FIG. 3C). FIGS. 5B-5C show Clustal-Q alignment of zebrafish (SEQ ID NO: 7, SEQ ID NO: 12), human (SEQ ID NO: 5, SEQ ID NO: 6), chimpanzee (SEQ ID NO: 8, SEQ ID NO: 13), mouse (SEQ ID NO: 9, SEQ ID NO: 14), and African-clawed frog Ube2V1 (SEQ ID NO: 10, SEQ ID NO: 11) (FIG. 5B) and Ube2V2 (FIG. 5C). FIG. 5D shows a sequence logo highlighting amino-acid conservation within the linker region of either Ube2V1 (top) and Ube2V2 (bottom), across 16 and 12 species, respectively (vide infra). Relative sizes of residues reflect their frequency and the Y-axis indicates the information content of the position in bits. The arrows indicate the respective conserved cysteines. The sequence logo was generated using WebLogo (invented by Steven E. Brenner et al., Computational Genomics Research Group, University of California, Berkeley). For Ube2V1, the human protein sequence has been aligned with: *Bos taurus* (100%), *Canis lupus familiaris* (100%), *Sus scrofa* (100%), *Heterocephalus glaber* (99%), *Taeniopygia guttata* (99%), *Castor Canadensis* (99%), *Gallus gallus* (98%), *Xenopus laevis* (93%), *Danio rerio* (88%), *Salmo*

*salar* (87%), *Xenopus tropicalis* (90%), *Trichinella britovi* (64%), *Trichinella* T8 (64%), *Mus musculus* (91%), *Trichinella* native (51%). For Ube2V2: *Sus scrofa* (99%), *Orcinus orca* (99%), *Mus musculus* (98%), *Gallus gallus* (97%), *Danio Rerio* (94%), *Xenopus laevis* (1000/%), *Schizosaccharomyces pombe* (94%), *Saccharomyces cerevisiae* (93%), *Kluyveromyces marxianus* (91%), *Scheffersomyces stipites* (93%). The number in parenthesis indicates the extent of sequence identity (in percentage) when aligned with the full-length sequences (see FIG. 5A) of *Homo Sapiens* Ube2V1 and Ube2V2, respectively.

Figure 3A:
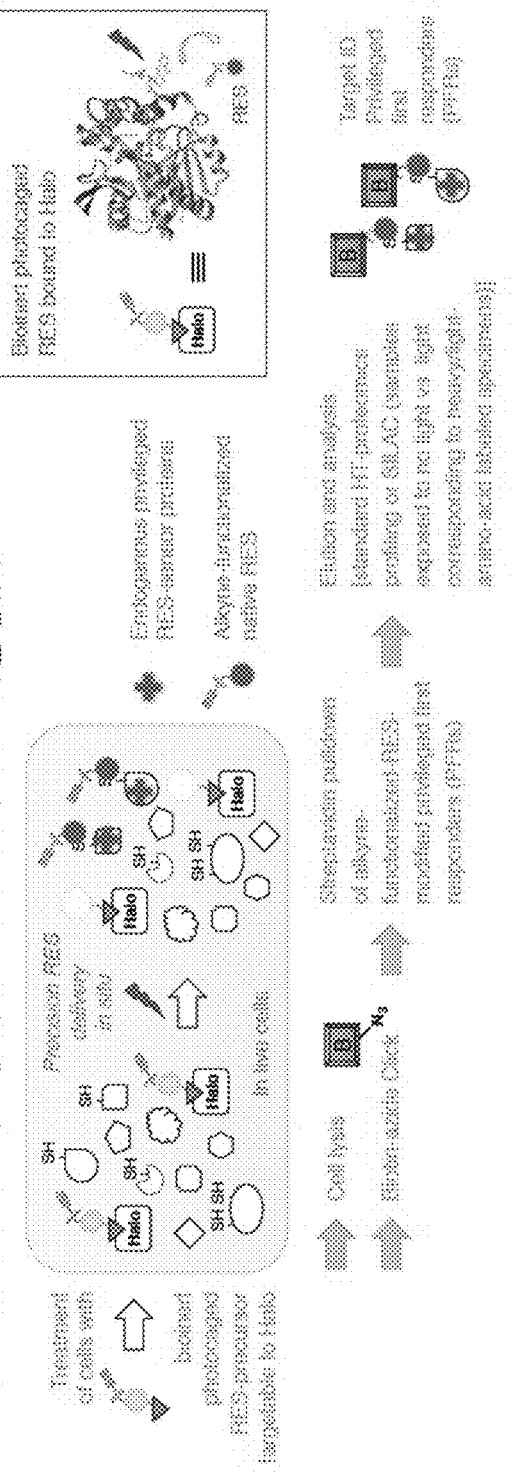
FIGS. 3A-3F demonstrate that G-REX™ profiling identifies endogenous privileged first responder (PFR)-cysteines, including two novel sensors, Ube2v1 and Ube2v2 through its capability to genome-wide target-ID endogenous PFRs under electrophile-limited conditions.
Figure 3B:
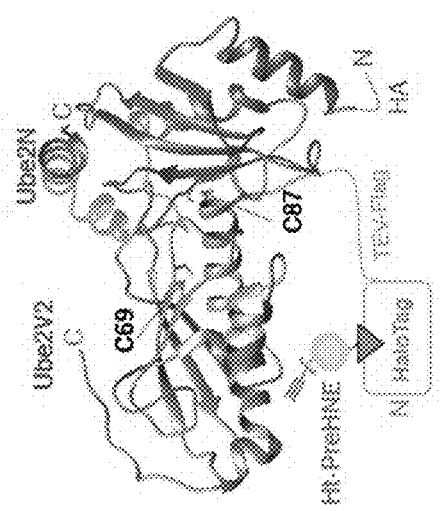
Figures 6A, 6B:
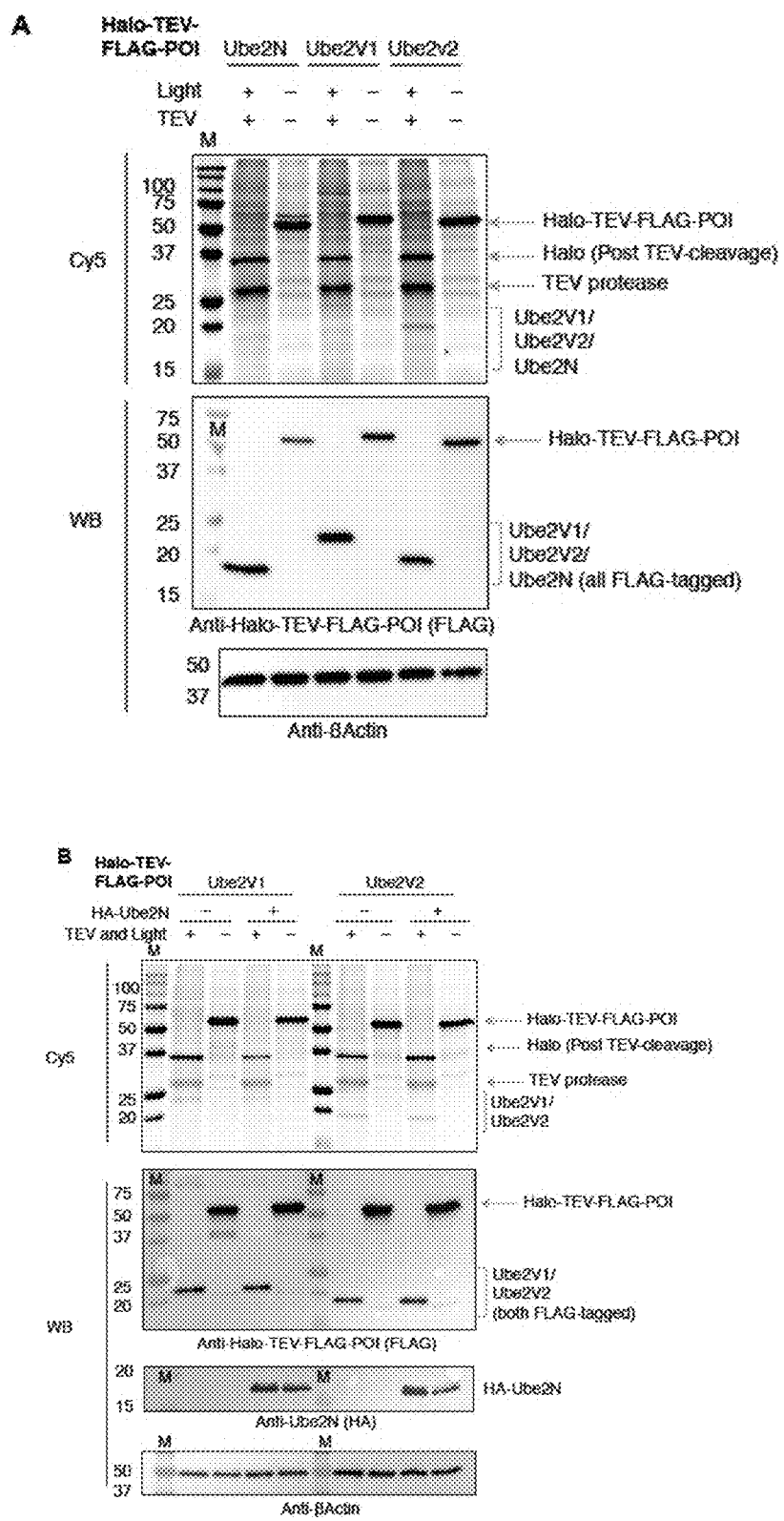
Figures 6C, 6D:
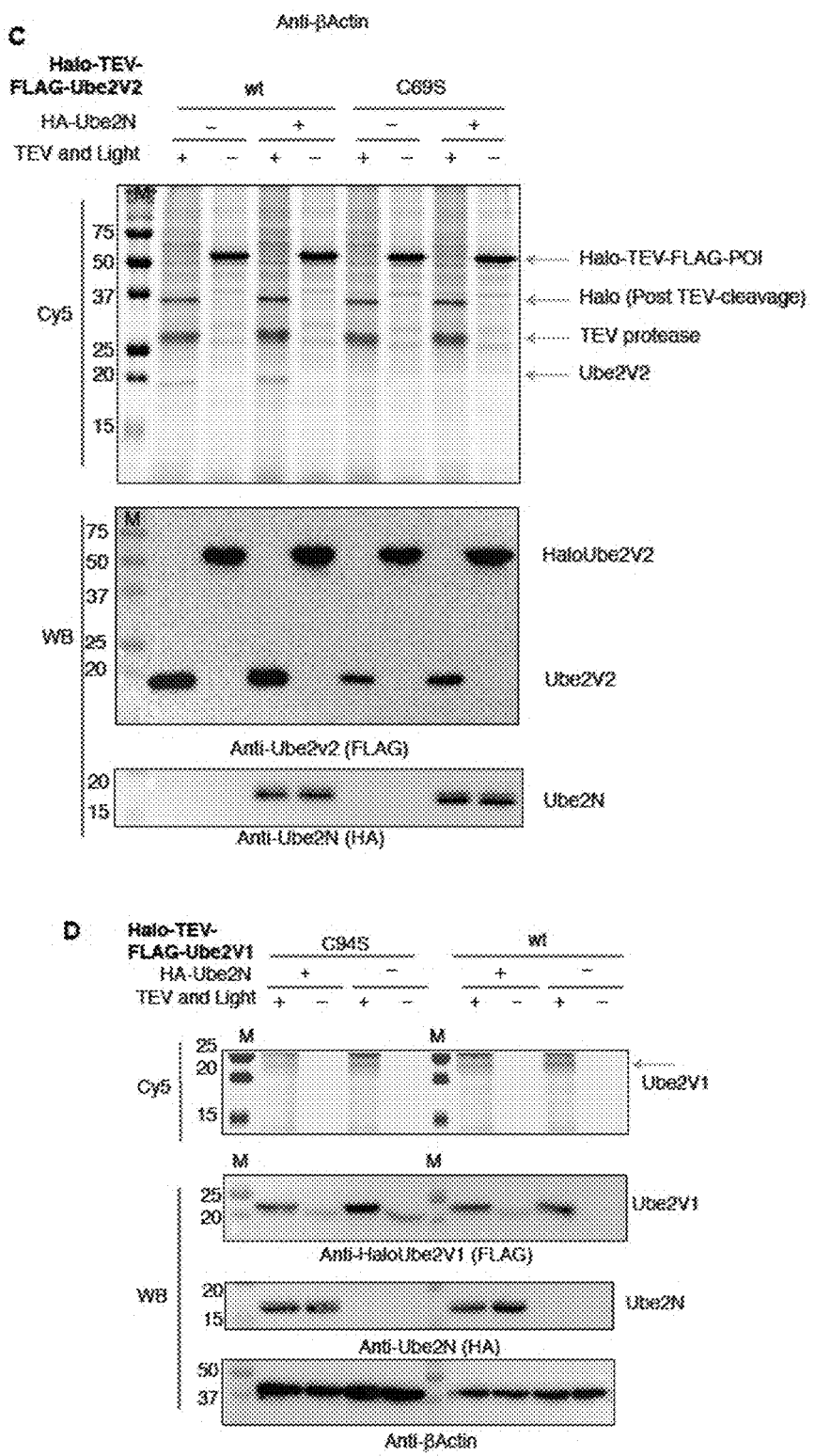
Figure 6E:
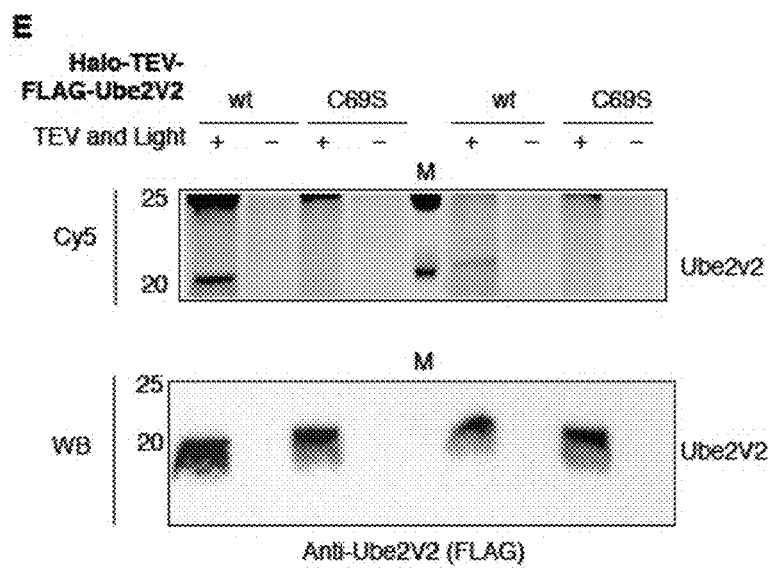
Figure 6F:
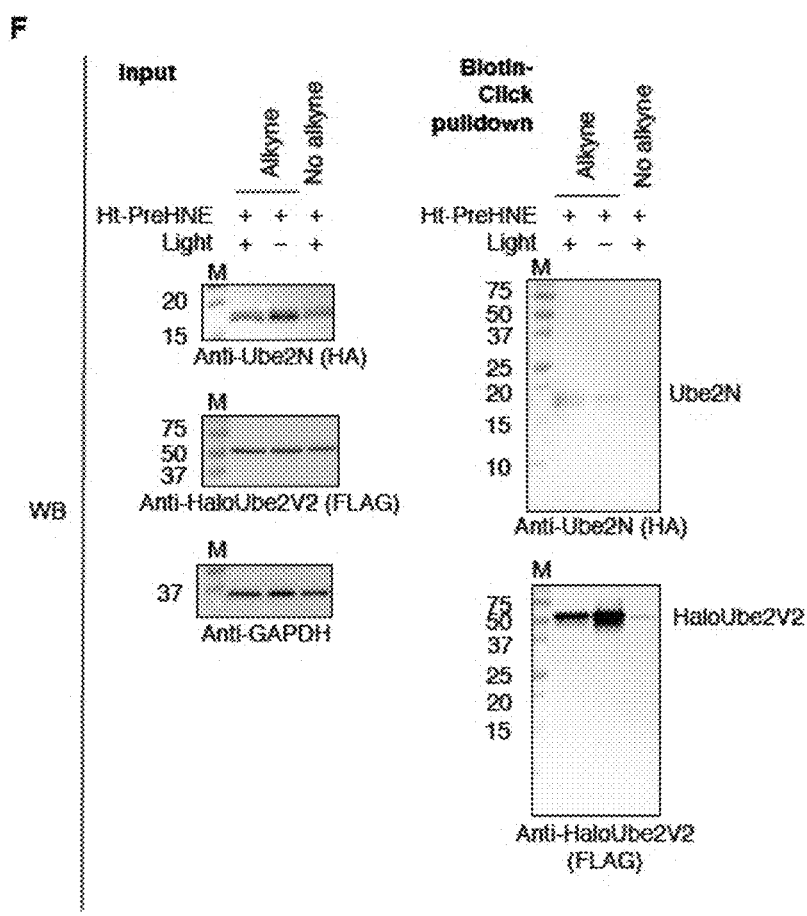

FIGS. 6A-6F show Ube2V2 is the most efficient electrophile-sensor among Ube2V1, Ube2V2, and Ube2N, and its sensing function is specific to C69. FIG. 6A shows a whole Cy5 gel and corresponding western blots for FIG. 3D. FIG. 6B shows whole Cy5 gel and corresponding western blots for FIG. 3E. FIG. 6C shows whole Cy5 gel and corresponding western blots for FIG. 3F. FIG. 6D is an identical experiment to FIG. 6C except Halo-(FLAG)-Ube2V1-expression plasmid replaces that for Ube2V2. FIG. 6E is an identical experiment to FIG. 6A except no co-transfection with Ube2N or empty vector. FIG. 6F shows cells transfected with Halo-(FLAG)-Ube2V2 and HA-Ube2N. Cells were then treated either with Ht-PreHNE, or its no-alkyne variant (incapable of Click coupling) (see chemical structures in FIG. 4B). These samples were either exposed to light or not as indicated. Cells were lysed, biotin was attached to HNE(alkyne)-modified proteins via Click coupling with biotin-azide, and samples were enriched by streptavidin pulldown. Inputs (left panel) were analyzed by western blot using indicated antibodies for loading control and for validation of similar protein expression across different conditions. Eluate (right panel) was analysed by anti-HA(Ube2N) blot to examine the extent of Ube2N-HNEylation under these various conditions (see workflow in FIG. 4A: 'biotin azide Click' panel on the lower right of the flow chart; however, note: there is no TEV treatment in this experiment; thus the band intensity on the Halo-POI in "no-light" lane is greater than "post T-REX™ delivery (light exposed sample)".

Figure 7A:
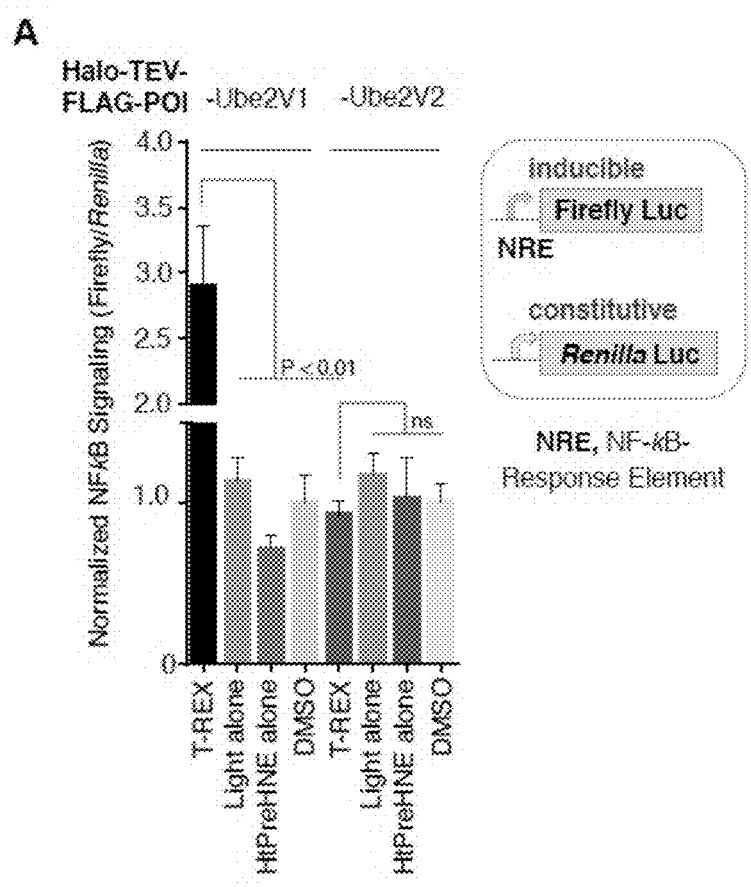
Figure 7B:
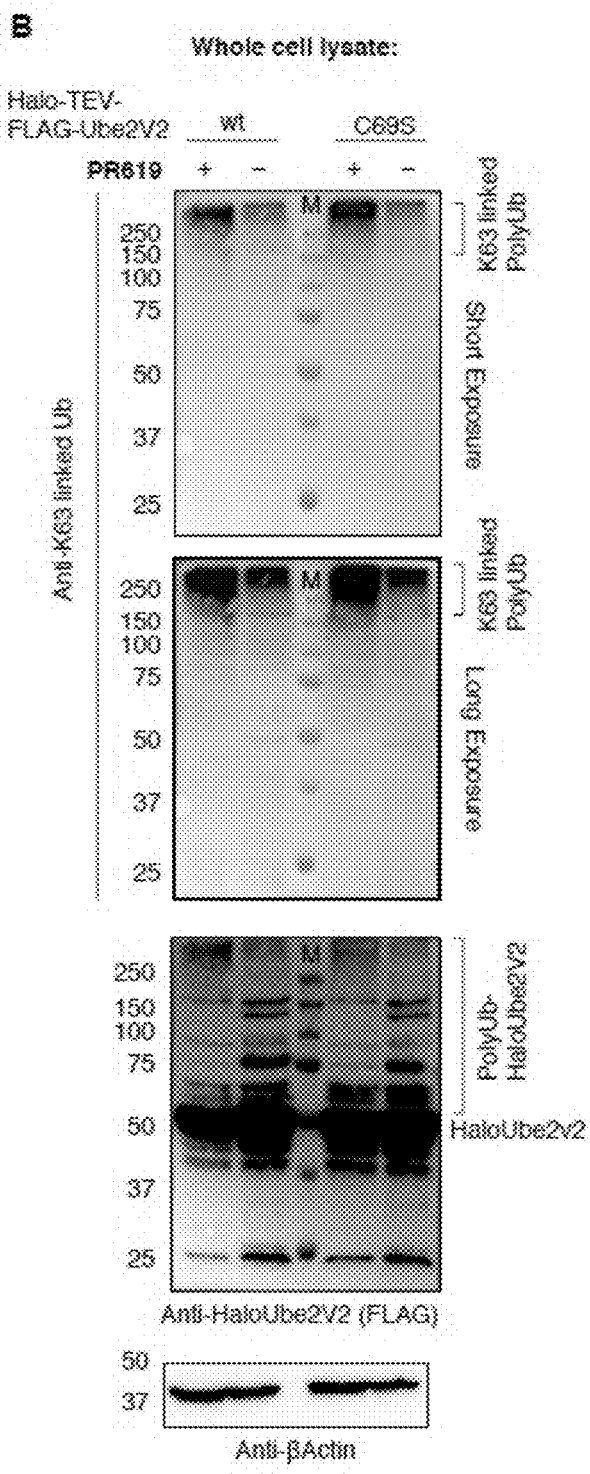
Figure 7C:
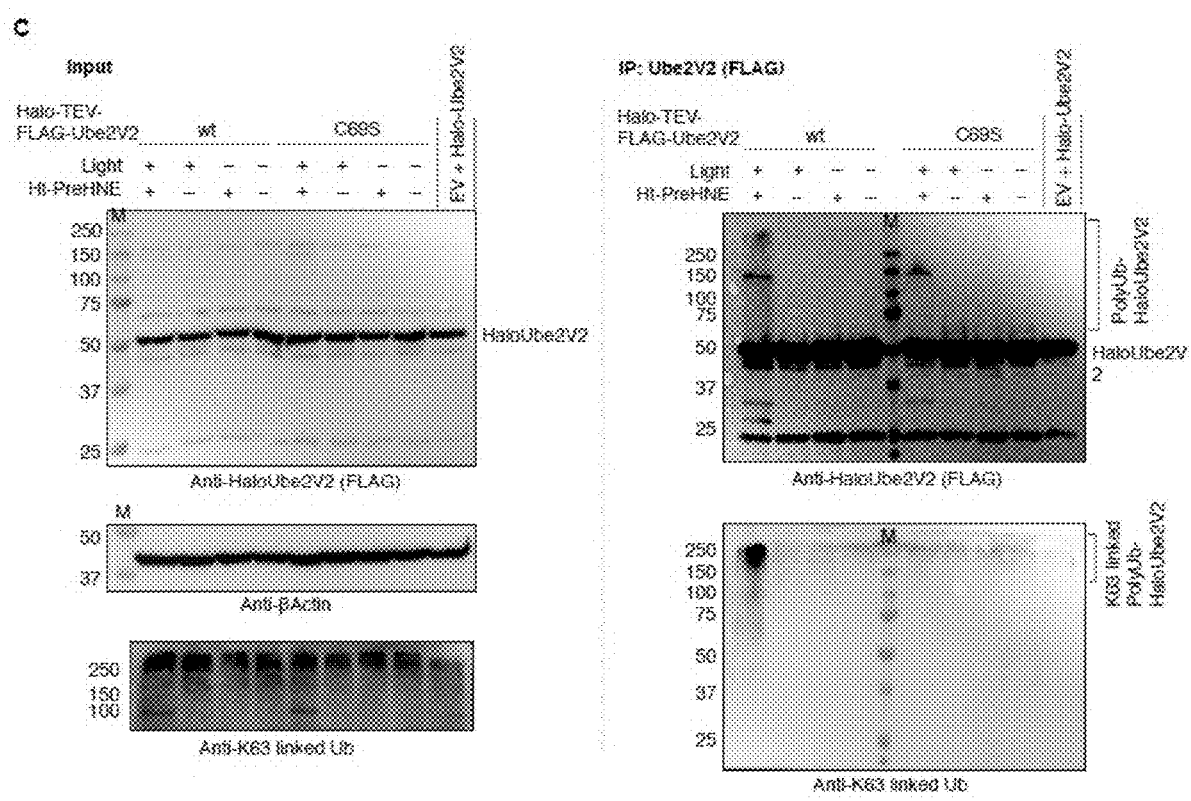
Figures 7D, 7E:
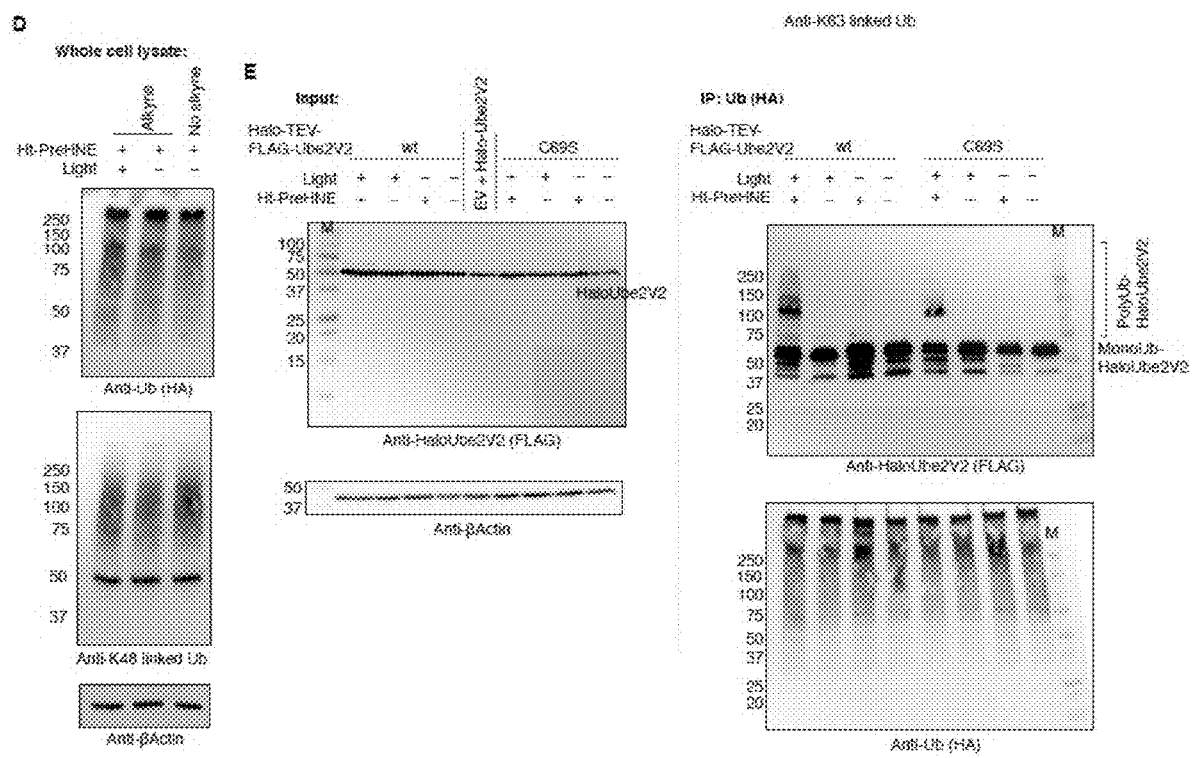

FIGS. 7A-7E show T-REX™ delivery-assisted Ube2V2 (C69)-specific HNEylation elicits K63-linked-polyubiquitination that is lost in the C69S mutant. FIG. 7A shows HNEylation of Ube2V1 (but not Ube2V2) selectively elicits upregulation in NF-κB-signaling. (mean+/−s.d., n=3 independent sets of biological replicates at different passages; each set of replicates consists of independent triplicates.) FIG. 7B shows HEK293T cells expressing wt-Halo-(FLAG)-Ube2V2 or the C69S-mutant treated with the DUB-inhibitor PR619 and high-molecular-weight (HMW) poly-ubiquitylated-Ube2V2 and assessed by western blot. FIG. 7C shows HEK293T cells expressing wt-Halo-(FLAG)-Ube2V2 (or the C69S-mutant) and HA-Ubiquitin exposed to the indicated conditions. Halo-(FLAG)-Ube2V2 from these cells was enriched by FLAG-immunoprecipitation (IP), and resulting samples were analyzed using the indicated antibodies. Left panel='Input lanes'; Right panel='IP-samples'. FIG. 7D shows a similar experiment to FIG. 7C, except non-enriched whole cell lysates were analyzed using the indicated antibodies, and an additional sample from the use of no-alkyne-variant of Ht-PreHNE but otherwise treated under identical conditions was also analyzed. FIG. 7E shows a similar experiment to FIG. 7C except global Ub pools were precipitated using HA IP (right panel) (there is no change in Ub since Ub is being IP-ed).

Figures 8A, 8B:
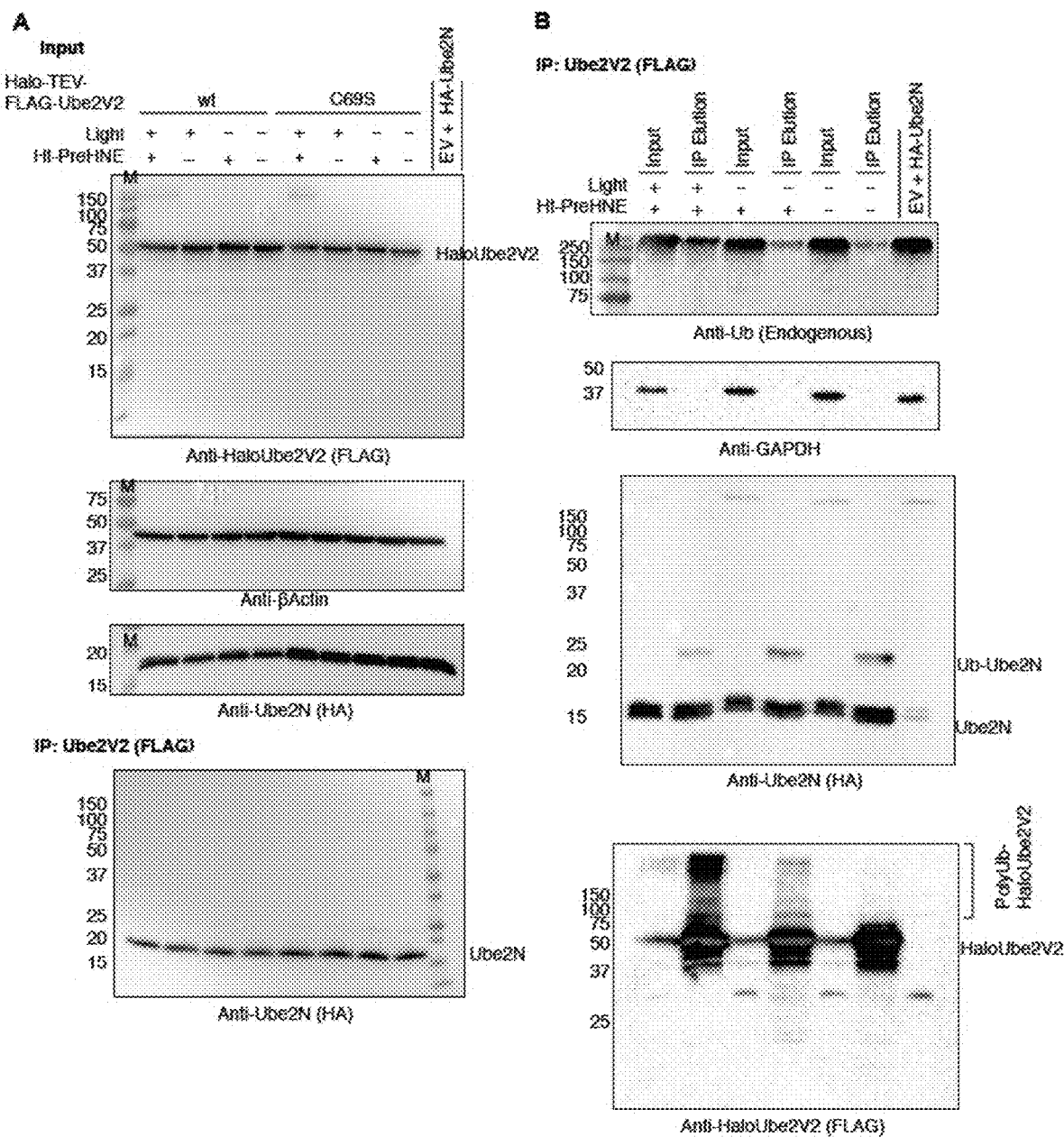
Figures 8C, 8D:
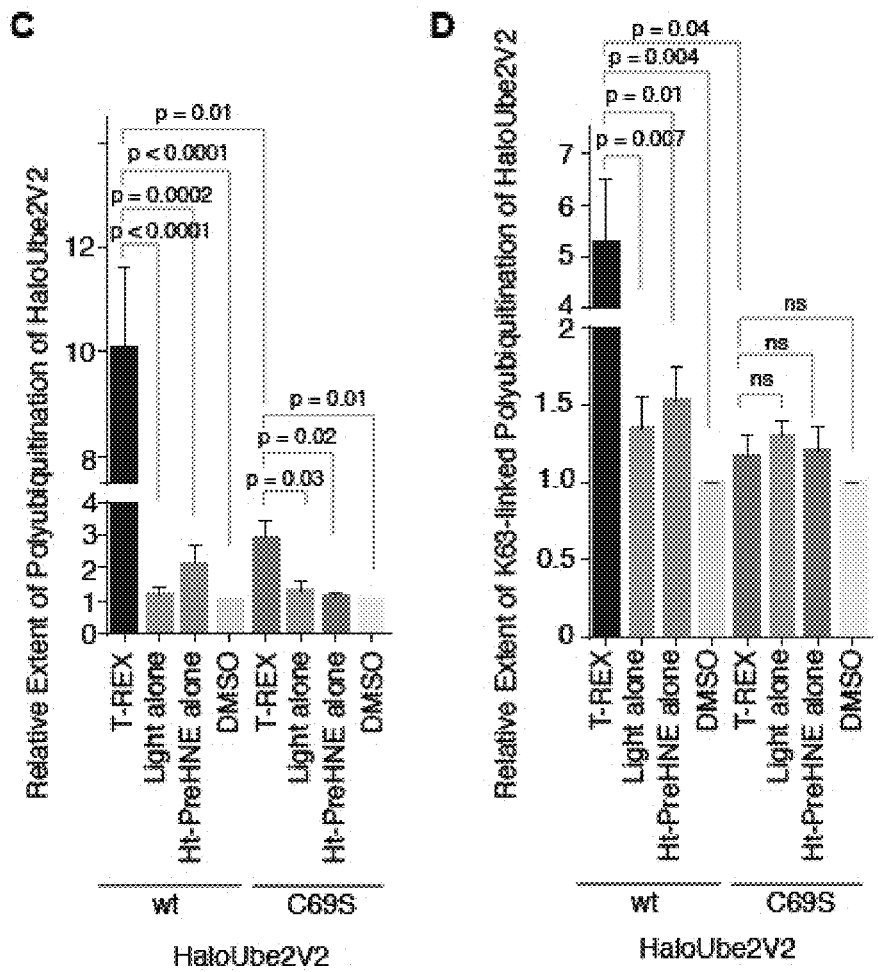
Figure 8E:
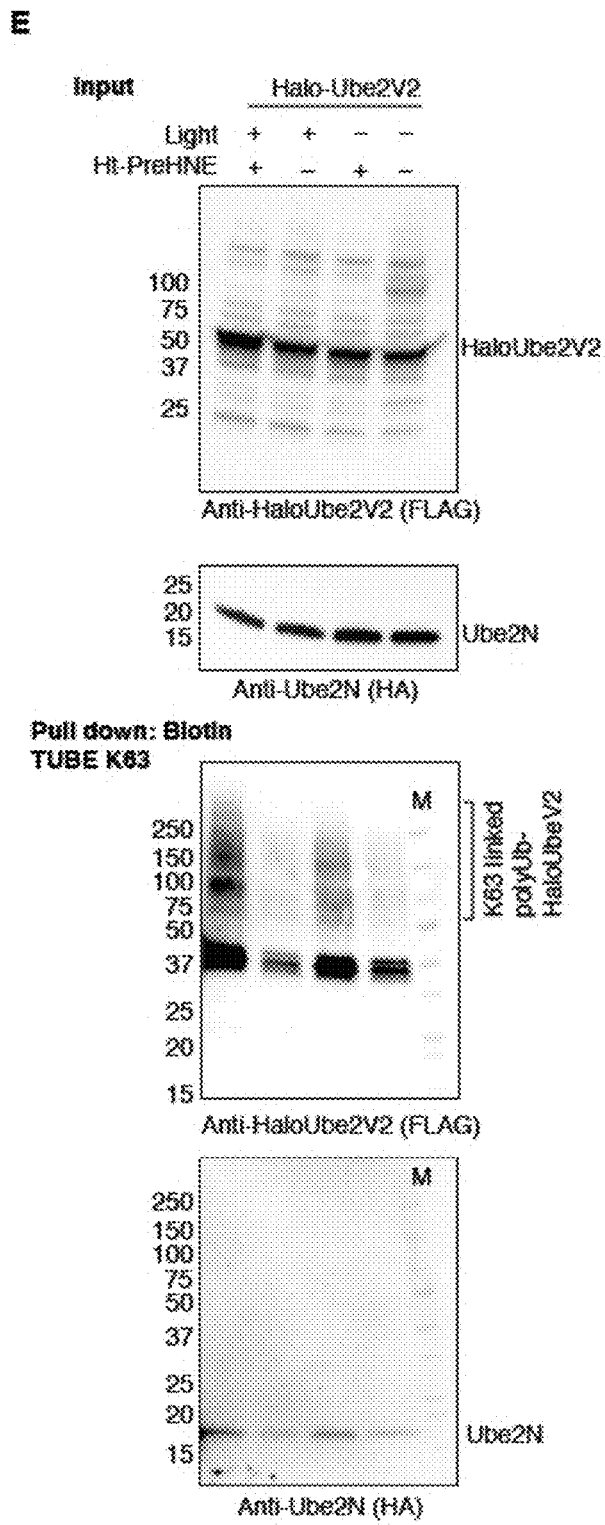
Figures 8F, 8G:
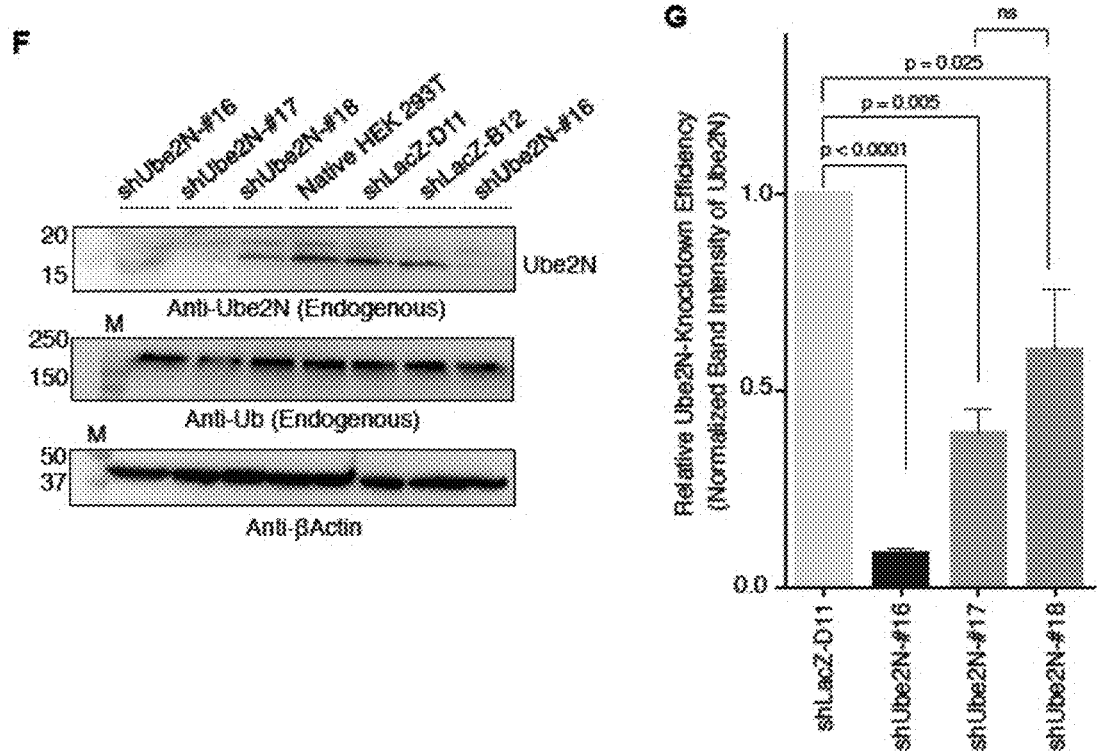

FIGS. 8A-8G show Ube2V2(C69)-specific HNEylation enhances its (K63-linked)-poly-ubiquitylation. FIG. 8A shows HEK293T cells ectopically expressing either [Halo-(FLAG)-Ube2V2 (either wt or C69S-mutant) and 'HA-Ube2N] or [empty plasmid (EV) and HA-Ube2N] treated with either Ht-PreHNE or DMSO, and subsequently exposed to light or not, as indicated. Cells were lysed, and expressed protein was immunoprecipitated using FLAG resin (IP: lower panel; Input: top panel). Eluates and inputs were analyzed by western blot using indicated antibodies. FIG. 8B shows a similar experiment to FIG. 8A, except Input and IP (FLAG) samples were loaded on the same gel. FIG. 8C shows quantitation of the relative amount of poly-ubiquitinated Halo-Ube2V2 (wt or C69S) enriched from cells subjected to T-REX™ delivery against controls. See FIG. 7C, 7E, and FIG. 8B for representative blots. (mean+/−s.e.m., at least four independent sets of biological replicates at different passages were performed, n=9 for wt-Halo-(FLAG)Ube2V2, including T-REX™ delivery and controls; n=4 for C69S-mutant, including T-REX™ delivery and controls). FIG. 8D shows quantitation of the relative amount of K63-linked poly-ubiquitinated Halo-Ube2V2 (wt or C69S) enriched from cells subjected to T-REX™ delivery against controls. See FIG. 7C for a representative blot. [mean+/−s.e.m., at least three independent sets of biological replicates at different passages were performed, for wt-Halo-(FLAG)Ube2V2, n=5 (T-REX™ delivery), n=6 (light alone), n=6 (Ht-PreHNE alone), n=6 (DMSO); for C69S-mutant, n=3 (T-REX™ delivery), n=3 (light alone), n=3 (Ht-PreHNE alone), n=2 (DMSO)]. FIG. 8E shows HEK293T cells transfected with wt-Halo-(FLAG)Ube2V2 and HA-Ube2N and subject to T-REX™ delivery conditions against controls. Cells were lysed, and expressed protein was pulled down using biotin K63 tandem ubiquitin binding entity (TUBE) (procedures described in Example 1) (pull-down: lower panel; Input: top panel) Changes in K63-linked Ube2V2-polyubiquitination were assessed by western blot. FIG. 8F shows knockdown lines expressing different shRNAs targeting Ube2N (line #'s: 16; 17; and 18) were generated using lentiviral transduction. Levels of Ube2N in these lines were assessed relative to wt and lines expressing two different control shRNAs (namely, shLacZ-D11 and shLacZ-B12). Also see quantitation in FIG. 8G. FIG. 8G shows quantitation of Ube2N knockdown efficiencies. (mean+/−s.d., Two independent replicates were performed. In total, n=3 for shUbe2N-#16, n=2 for shUbe2N-#17, n=4 for shUbe2N-#18, n=2 for sh-LacZ-D11 control).

Figures 9A, 9B:
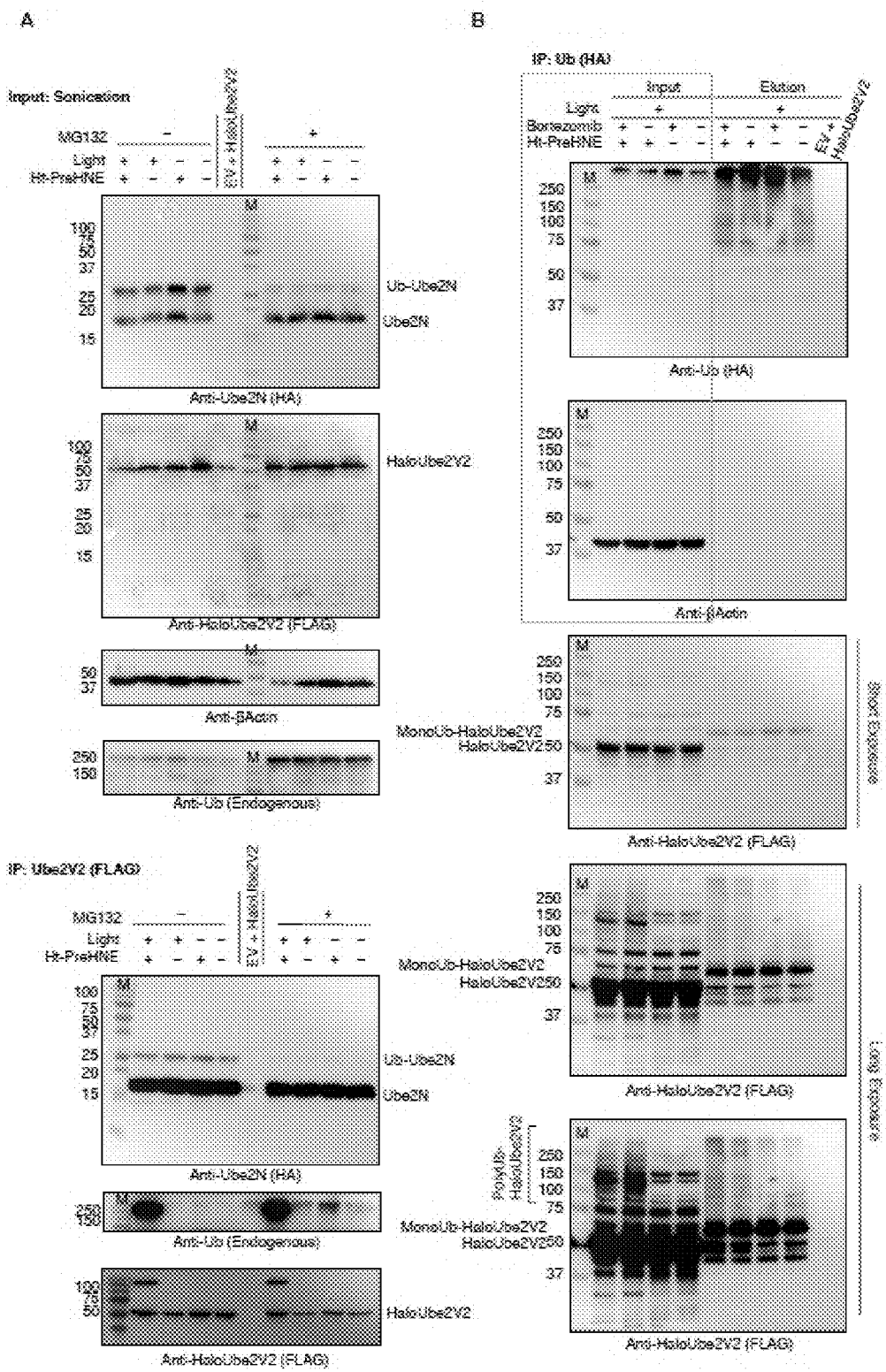
Figures 9C, 9D:
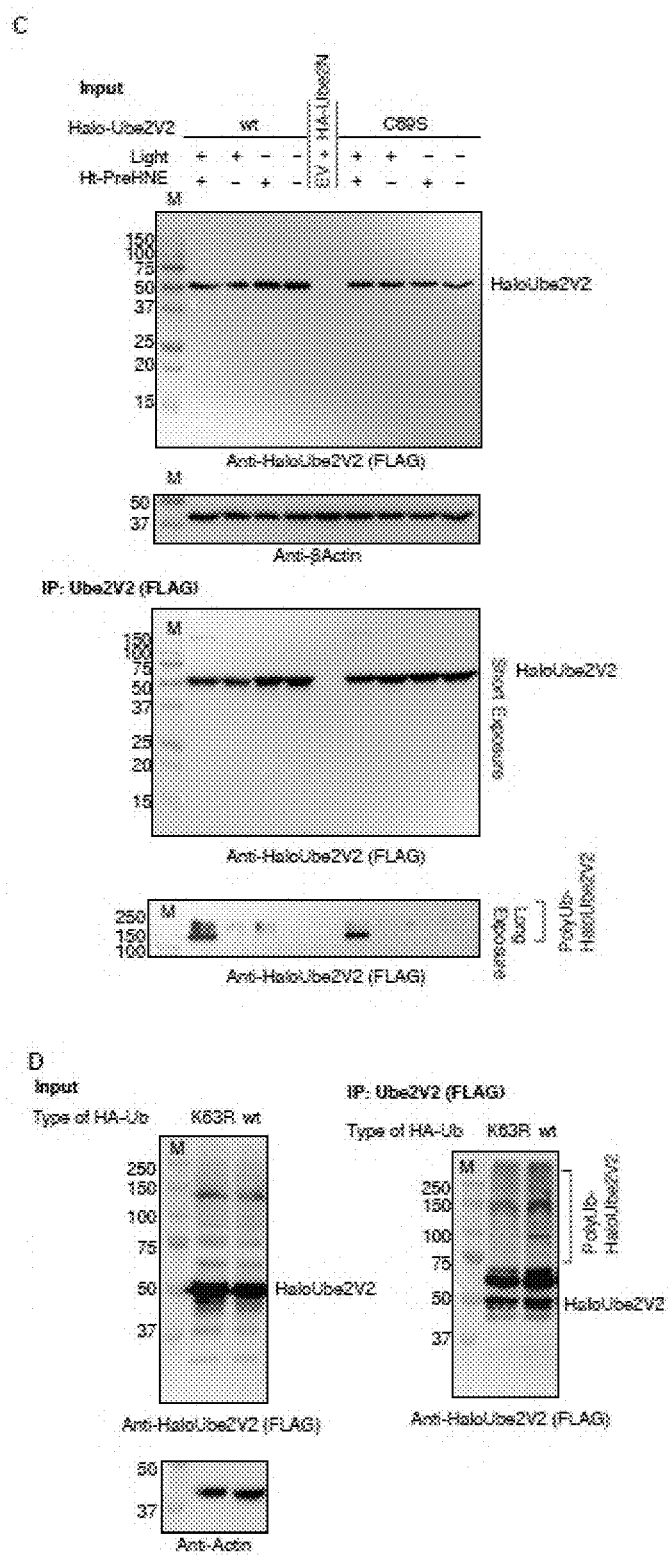

FIGS. 9A-9D show Ube2V2(C69)-specific HNEylation does not elicit K48-linked poly-ubiquitylation FIG. 9A shows HEK293T cells co-expressing Halo-(FLAG)-Ube2V2 and HA-Ube2N subjected to T-REX™ delivery [against various T-REX™ delivery-controls (from right to left): untreated, Ht-PreHNE probe alone, and light alone]. At 1.5 h prior to T-REX™ delivery execution, half of the set was treated with MG132 (5 µM, 1.5 h), and this concentration of MG132 was maintained for an additional 3 h post light shining until cell harvest. Cells were lysed by sonicating cell pellets, and Halo-(FLAG)-Ube2V2 was immunoprecipitated using FLAG resin. Changes in the extent of mono-Ubiquitination on Ube2N and the extent of endogenous ubiquitination as a consequence of T-REX™ delivery with or without MG132 treatment, were analyzed by western blot using indicated antibodies (IP, lower panels; Input, top panels). FIG. 9B shows HEK293T cells transfected with the same plasmids as in A subjected to T-REX™ delivery conditions against 'no-Ht-PreHNE'-controls. Cells were treated with or without bortezomib (200 nM, 2 h prior to T-REX™ delivery, maintained over 3 h post light-shining period, until cell harvest). Post lysis, Ube2V2 was enriched using HA IP (for ubiquitinated proteins), then both input and IP were analyzed on the same blot. FIG. 9C shows HEK293T cells co-expressing HA-Ube2N and either Halo-(FLAG)-Ube2V2 (either wt or C69S mutant) or empty vector (EV) subjected to T-REX™ delivery against indicated controls. The extent of poly-ubiquitination on the wt and mutant protein was analyzed subsequent to FLAG-immunoprecipitation. FIG. 9D shows HEK293T cells co-expressing HA-Ubiquitin (either wt or K63R mutant) and Halo-(FLAG)-Ube2V2 subjected to T-REX™ delivery. Following FLAG-immunoprecipitation (Input: left panel; IP: right panel), the role of K63R-mutation on Ub, in regulating the Halo-(FLAG)-Ube2V2 poly-ubiquitination was analyzed by western blot.

Figure 10A:
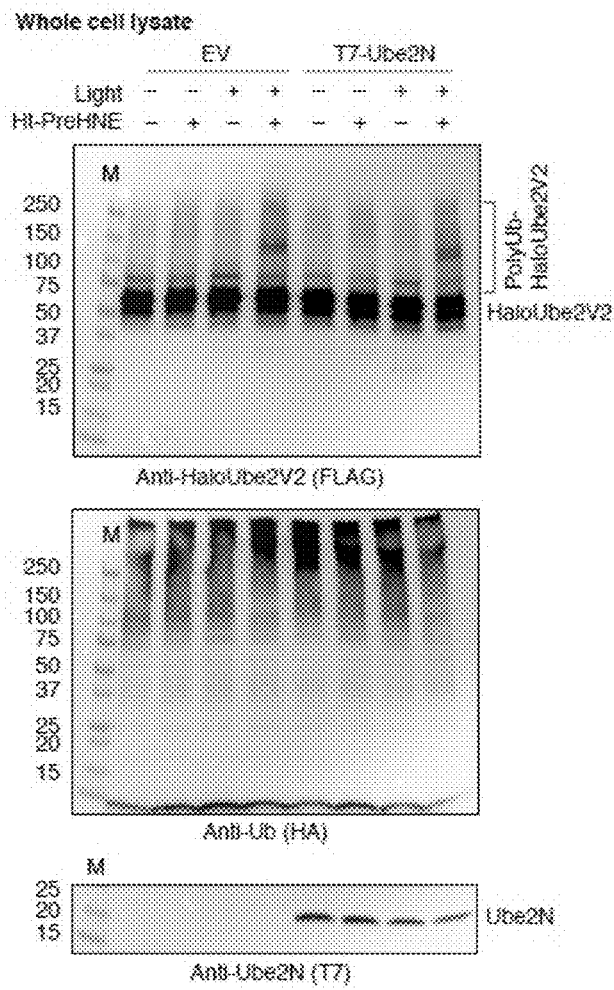
Figure 10B:
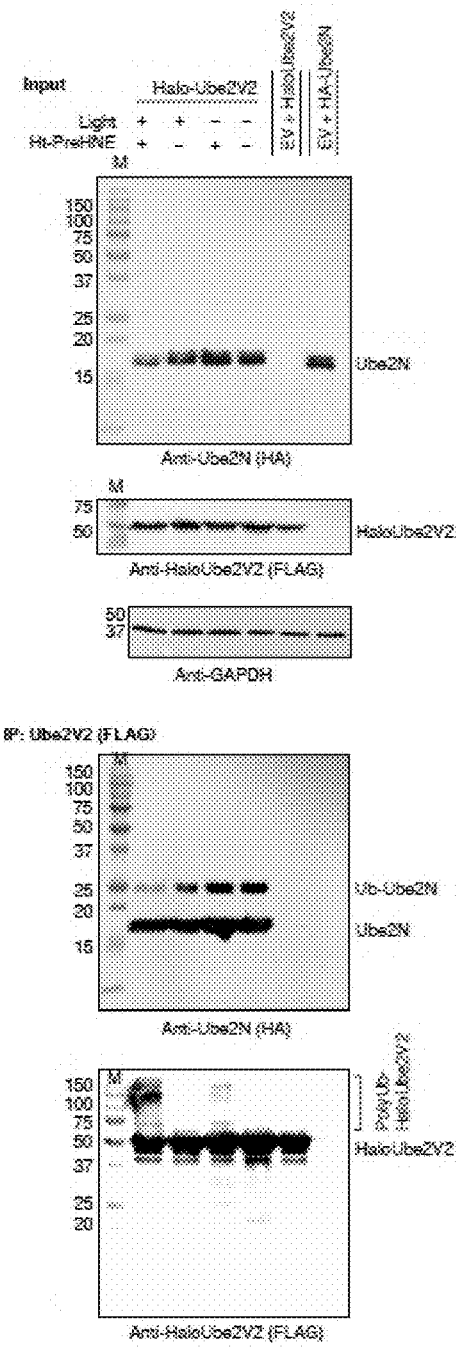
Figure 10C:
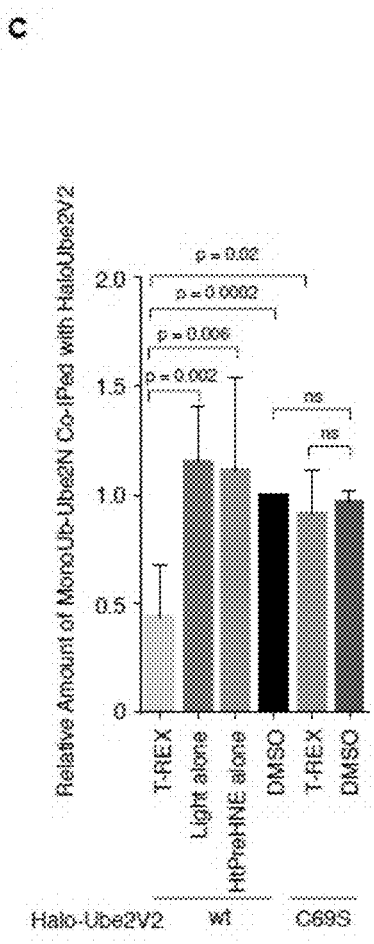
Figure 10D:
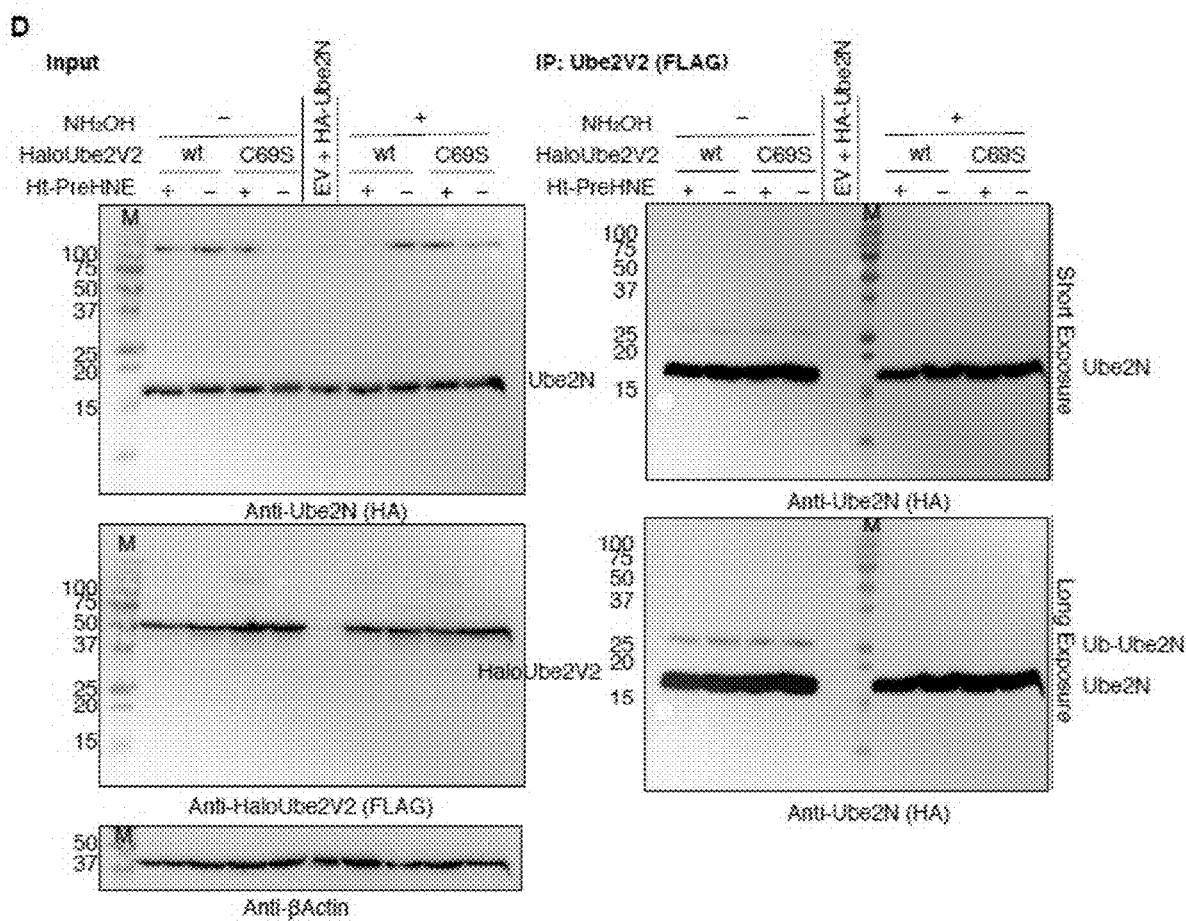

FIGS. 10A-10D show Ube2V2(C69)-specific HNEylation functionally impacts the mono-ubiquitinated state of Ube2N. FIG. 10A shows HEK293T cells ectopically expressing wt-Halo-(FLAG)-Ube2V2 and HA-Ubiquitin co-transfected with either empty vector (EV) or a plasmid of the same backbone expressing HA-Ube2N and analyzed for HMW band of HaloUbe2v2 (i.e., Ube2v2-polyUbiquitin) by indicated antibodies. FIG. 10B shows HEK293T cells transfected with the indicated plasmids subjected to T-REX™ delivery conditions against controls followed by immunoprecipitation using FLAG resin (Input: top panel; IP: lower panel). Eluates and inputs were analyzed by western blot using indicated antibodies. Levels of Ube2N/Ube2N-monoUb bound to Ube2V2 were analyzed by western blot. See FIG. 10C for quantitation. FIG. 10C shows quantitation of the relative amount of mono-Ub-Ube2N bound to Halo-Ube2V2 enriched from cells subjected to T-REX™ delivery against controls. See representative blots, for instance, in FIG. 10B and FIG. 9A (mean+/−s.d., n=3 independent sets of biological replicates at different passages). FIG. 10D shows HEK293T cells transfected with the indicated plasmids and subjected to T-REX™ delivery conditions against indicated controls. Levels of Ube2N/Ube2N-monoUb bound to Halo-(FLAG)-Ube2V2 were analyzed by western blot subsequent to enrichment using anti-FLAG-beads (IP: right panel). Half of precipitated fractions were treated with $NH_2OH$ (conditions known to hydrolyse thioester bonds; detailed in Example 1 methods) and analyzed separately. All samples were exposed to light in this experiment.

Figures 11A, 11B:
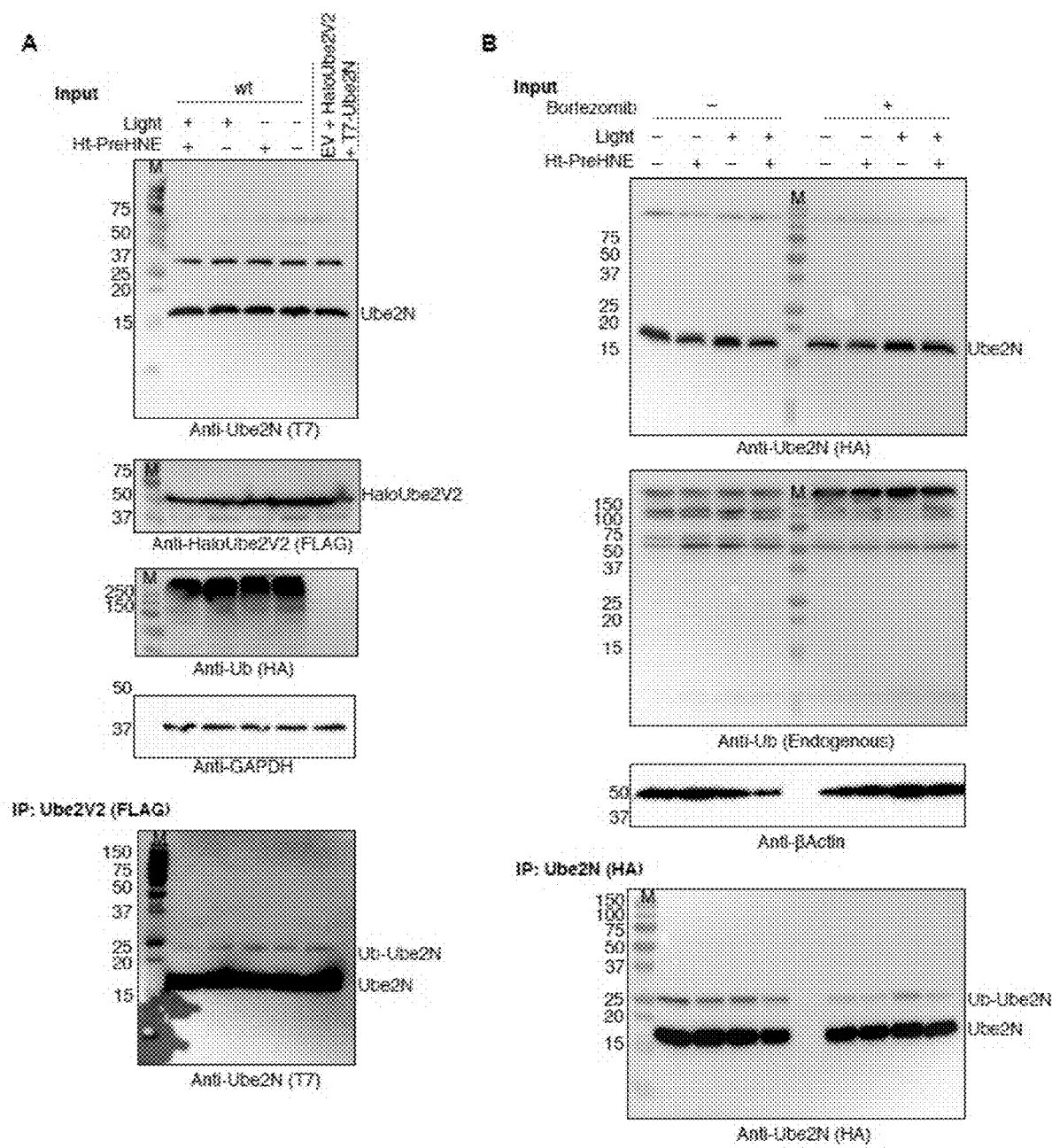
Figure 11C:
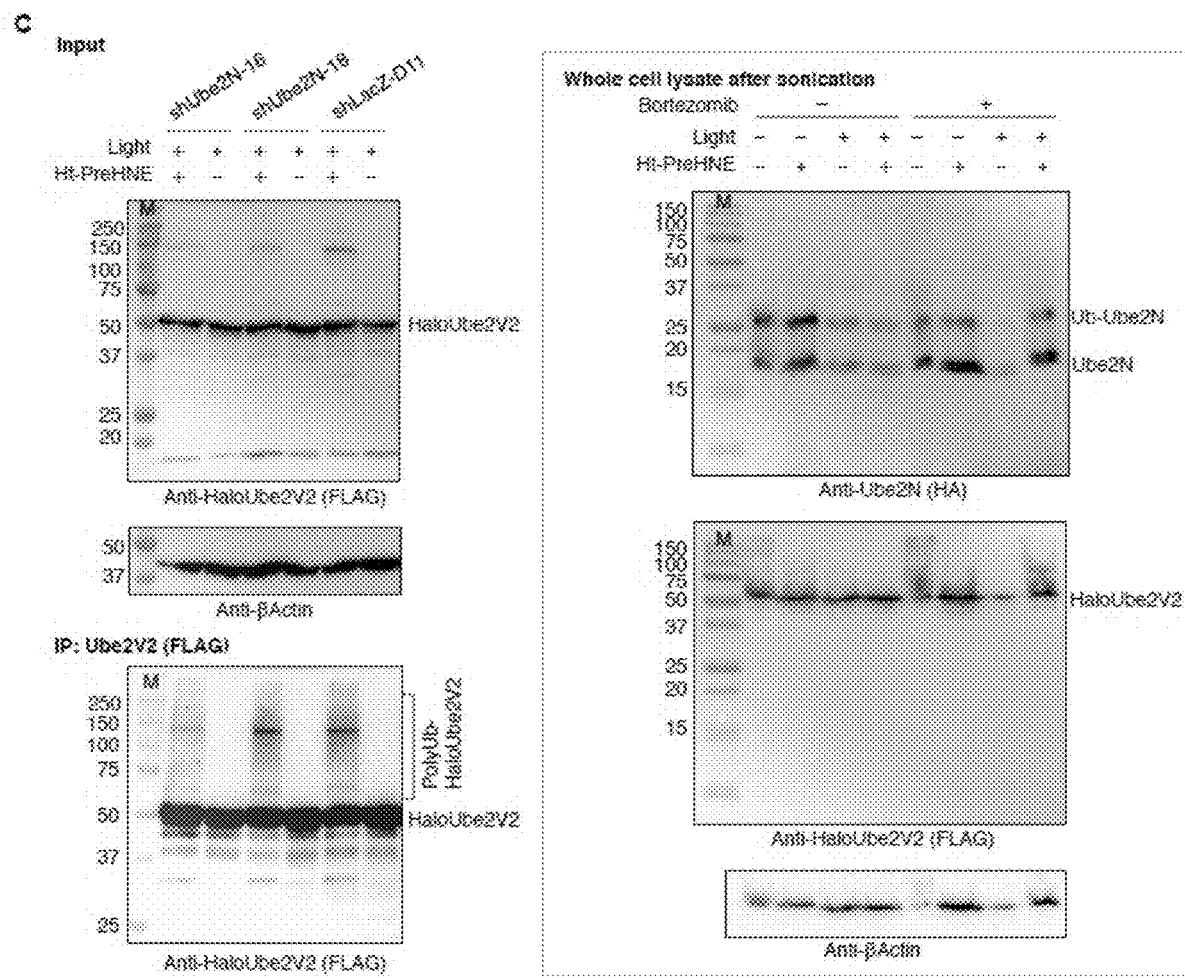
Figure 11D:
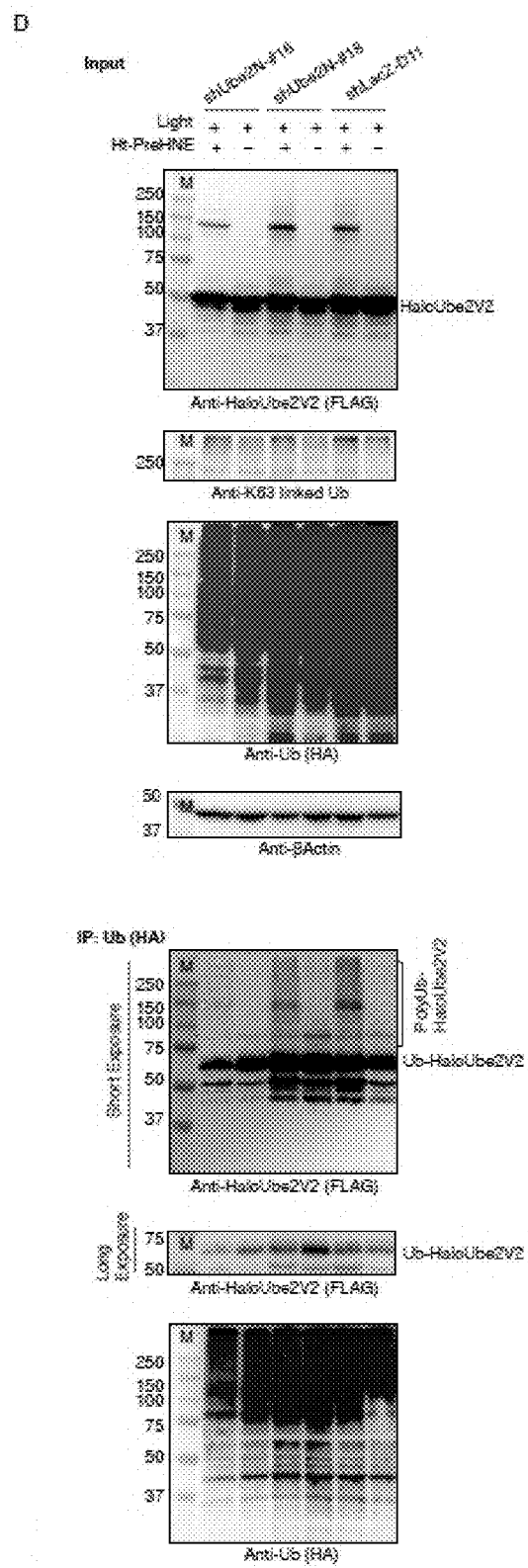

FIGS. 11A-11D show Ube2V2(C69)-specific HNEylation and K63-linked-poly-ubiquitination is accompanied by reduced mono-ubiquitinated Ube2N: this redox-Ub signaling exchange process requires Ube2N. FIG. 11A shows HEK293T cells co-expressing Halo-(FLAG)-Ube2V2, T7-Ube2N, and either empty (EV) or HA-Ubiquitin and subjected to T-REX™ delivery against all controls. 3-h Post light shining, cells were lysed, immunoprecipitated with FLAG resin (Input: top panels; IP: lower panels), and analyzed for the extent of reduced mono-ubiquitination on Ube2N by western blot using anti-HA(Ub) as well as anti-T7(Ube2N). FIG. 11B shows HEK293T cells co-expressing Halo-(FLAG)-Ube2V2 and HA-Ube2N and subjected to T-REX™ delivery and treated with DMSO or the proteasome inhibitor bortezomib (Bz, 200 nM) for a further 3 h before harvest. HA-immunoprecipitated samples (IP: lower panels; Input: top panels) were analyzed by western blot using indicated antibodies in order to evaluate the extent to which the proteasome degradation pathway is influenced by the newly-discovered HNE-initiated signalling response. 1. There is no further Ubiquitination of Ube2N upon Bz treatment (conditions that stop proteasome degradation; validated by increase in endogenous HMW-Ubiquitinated proteins in an anti-Ub blot). 2. Sonication of pellet (insoluble fraction) shows there is no formation of insoluble HMW-Ubiquitinated-Ube2N complex, further consistent with mono-ubiquitination of Ube2N. FIG. 11C shows HEK293T cells expressing either shRNA targeting Ube2N (lines #16 and #18 that express different shRNA's) or a control shRNA, that were transfected with Halo-(FLAG)-Ube2V2, and subjected to T-REX™ delivery against 'light-alone'-T-REX™ delivery-control. Halo-(FLAG)-Ube2V2 was immunoprecipitated (IP: lower panels) and input and eluates were analyzed by western blot using anti-FLAG antibody. See FIG. 8F-8G for knockdown efficiencies. FIG. 11D shows the same as the set-up in FIG. 11C except that the cells were co-transfected with HA-Ubiquitin, and HA-immunoprecipitation (instead of FLAG) was performed (IP: lower panels) and input and eluted samples were analyzed by western blot using indicated antibodies to evaluate the Ube2N-dose-dependent changes in the extent of polyUb of HaloUbe2V2.

Figure 12A:
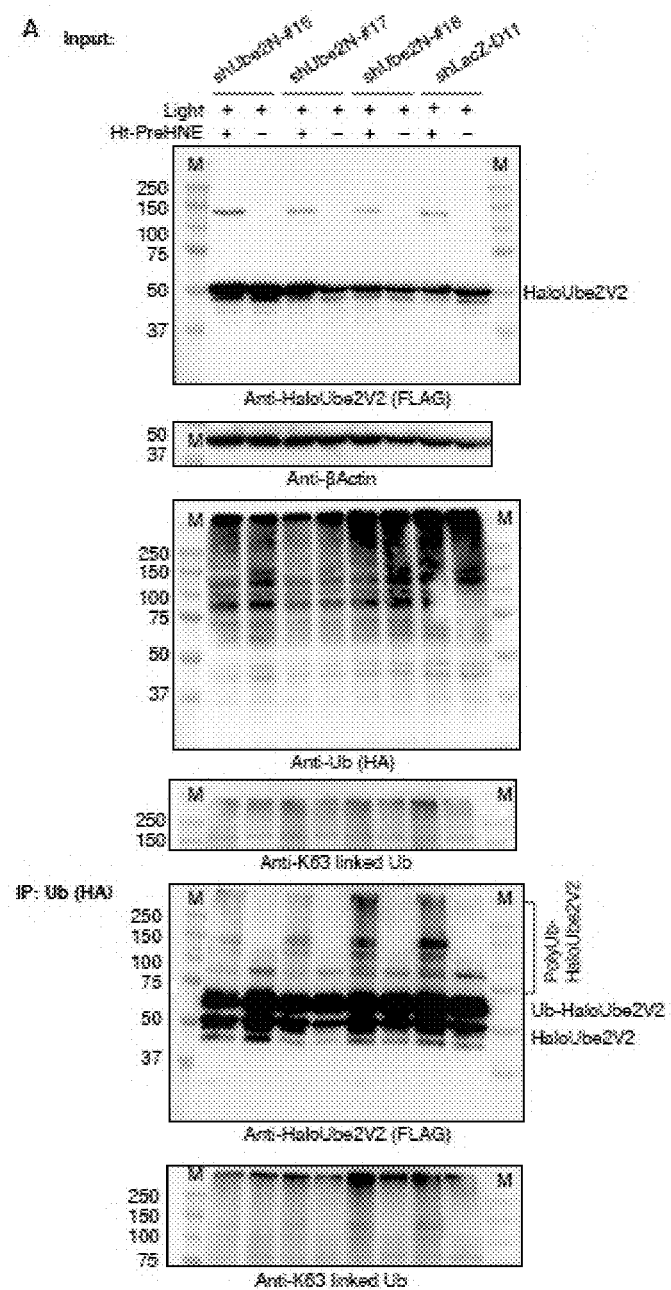
Figures 12B, 12C:
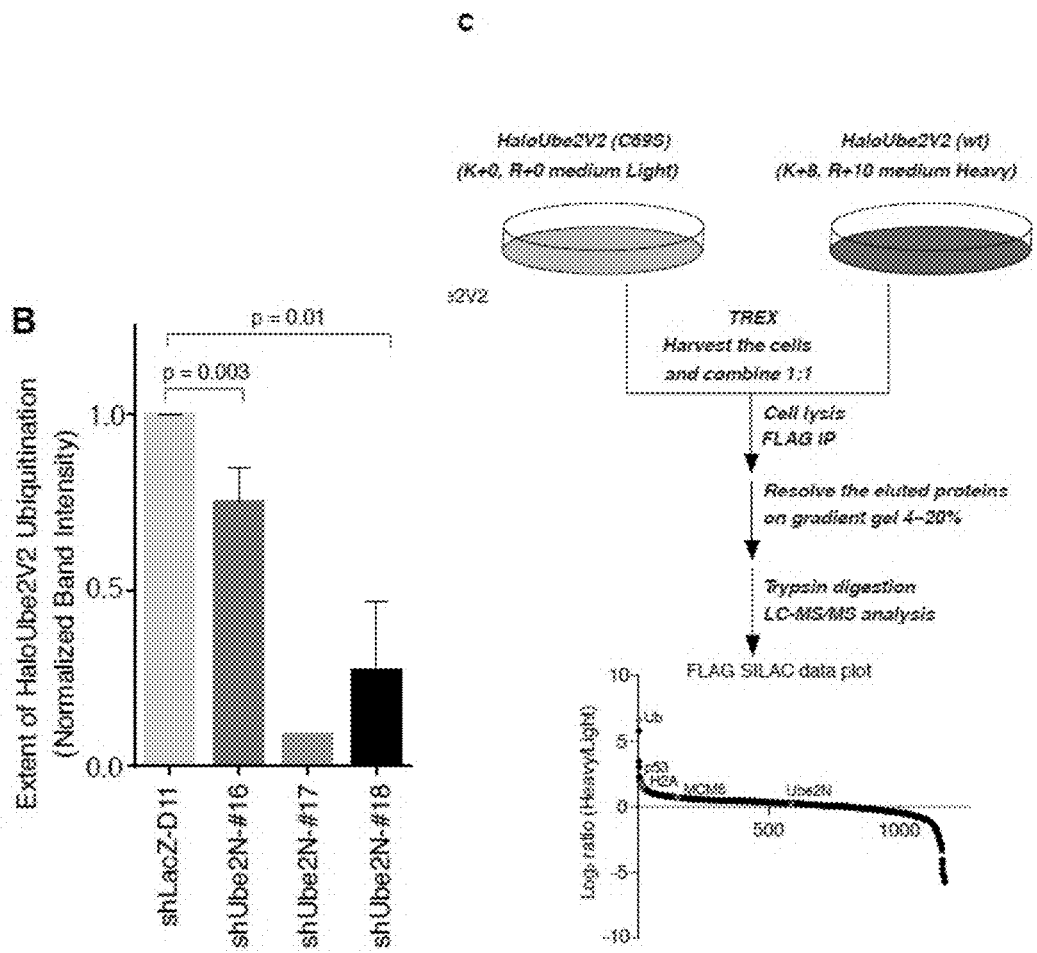
Figures 12D, 12E:
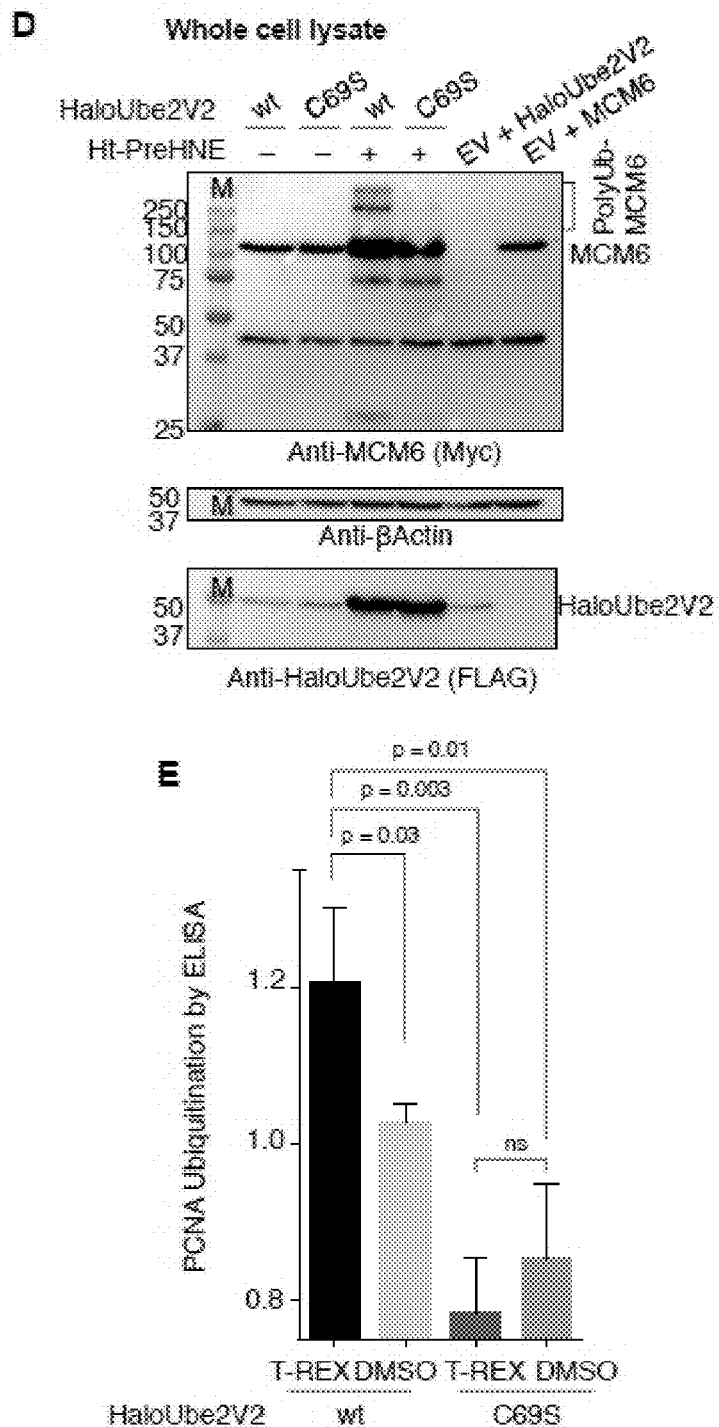
Figures 12F, 12G:
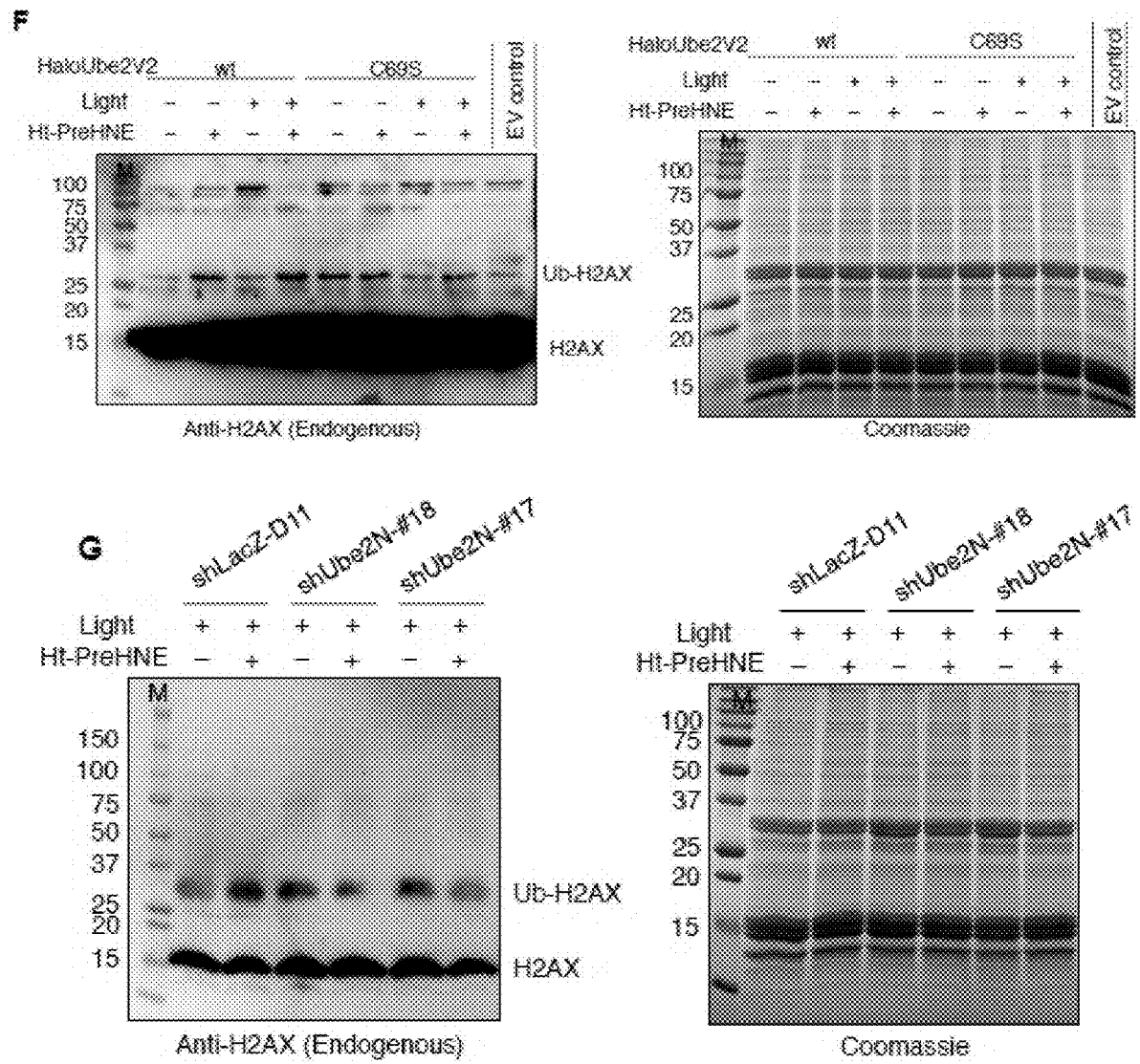
Figure 12H:
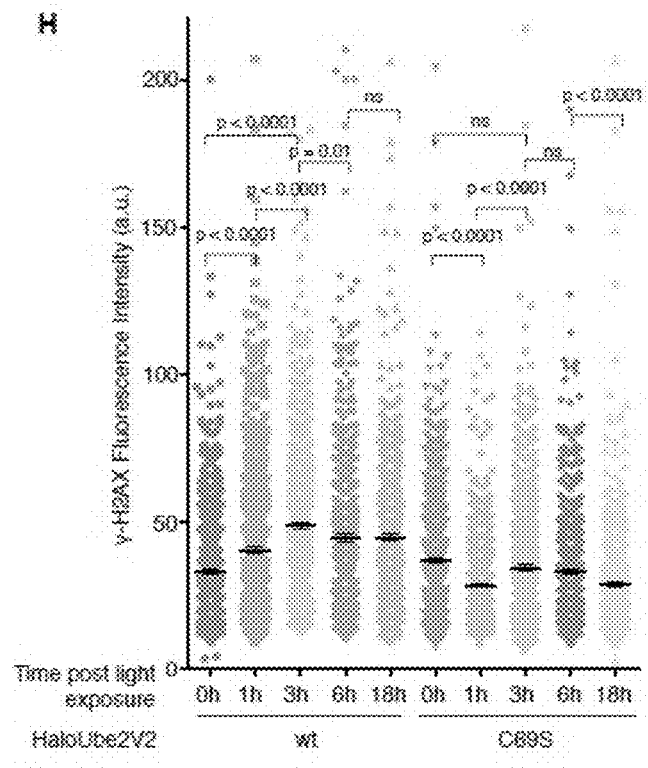
Figure 12I:
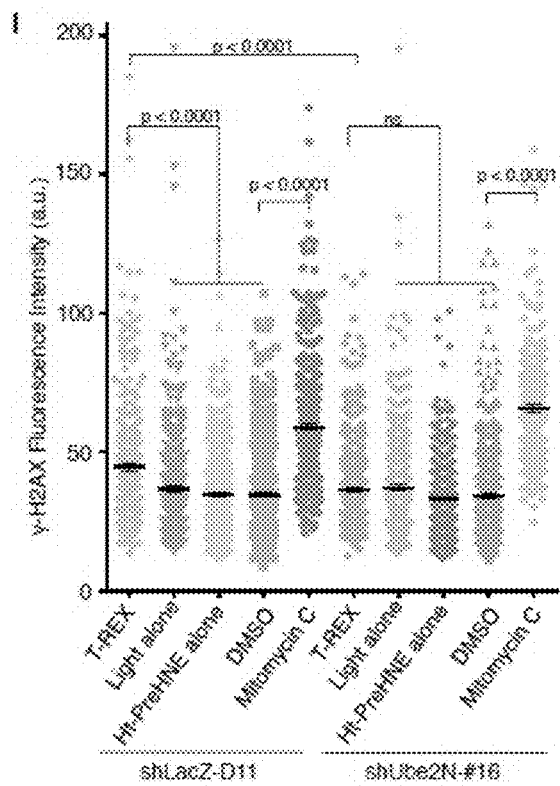
Figure 12J:
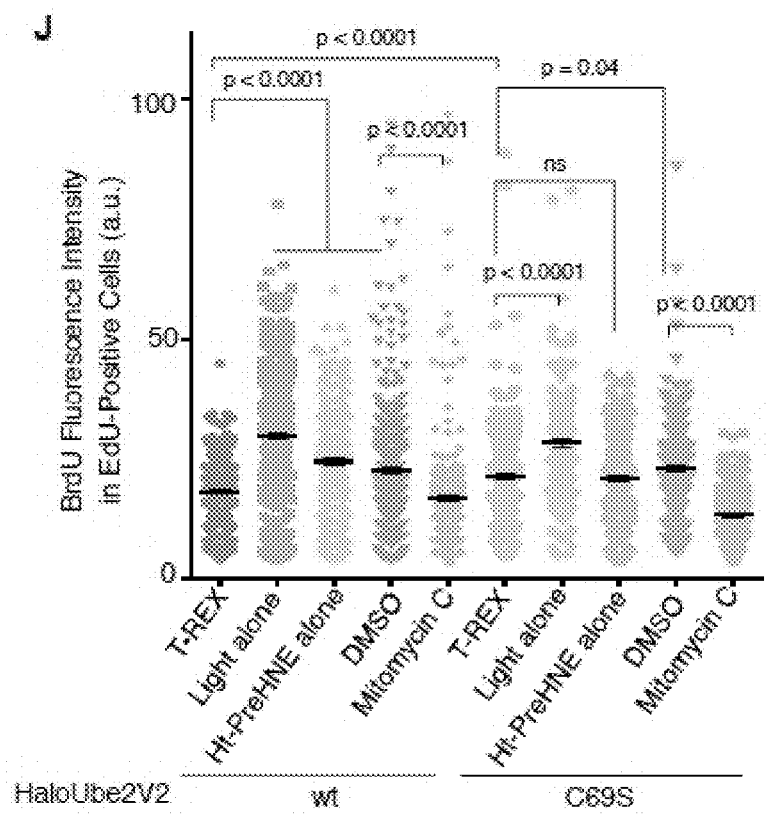

FIGS. 12A-12J shows HNEylation of Ube2V2 upregulates γ-H2AX and decreases DNA synthesis: these phenotypes depend on both C69 and Ube2N. FIG. 12A shows Ube2N knockdown lines #16, 17, 18, and control-knockdown line were transfected with Halo-(FLAG)-Ube2V2 and HA-Ubiquitin; then subjected to T-REX™ delivery against no-'Ht-PreHNE'-controls. HA-Ubiquitin was immunoprecipitated, and inputs (top panels) and elutions (lower panels) were analyzed by western blot using indicated antibodies. See FIG. 12B for quantitation. [n=3 independent biological replicates at different passages except shUbe2N-#17 (n=1)]. FIG. 12B shows quantitation of data from FIG. 12A. FIG. 12C shows the workflow used to identify proteins that bind preferentially to HNEylated-Ube2V2/Ube2N complex (top) and graphical depiction of hits (bottom). FIG. 12D shows HEK293T cells co-expressing Myc-MCM6 and either wt-Halo-(FLAG)-Ube2V2 or C69S-Halo-(FLAG)-Ube2V2 and subjected to T-REX™ delivery conditions against 'no Ht-PreHNE'-controls. 3-h-Post light exposure, cells were lysed and analysed by western blot using the indicated antibodies. FIG. 12E shows a similar experiment to FIG. 12C, except cells were transfected with Halo-(Flag)-Ube2V2 (wt- or C69S-mutant) and HA-Ubiquitin, and lysates were analyzed for endogenous PCNA-ubquitination using sandwich ELISA [binding: anti-HA(Ub); detection: anti-PCNA (endogenous) antibody] as detailed in Example 1 methods. [mean+/−s.d., two independent replicates were performed. N=3 for each set of cells transfected with either wt- or C69S-Halo-(FLAG)-Ube2V2, under individual experimental conditions as indicated. FIG. 12F shows HEK293T cells transfected with Halo-(FLAG)-Ube2V2 (or the C69S-mutant), then exposed to T-REX™ delivery conditions. Histones were acid extracted (details in Example 1 methods), and analyzed by western blot (left panel) using indicated antibodies or stained by Coomassie (right panel). FIG. 12G is similar to FIG. 12F but using Ube2N knock down lines #17, #18, and control-knockdown lines; then cells were subjected to T-REX™ delivery against 'no Ht-PreHNE'-controls. FIG. 12H shows HEK293T cells transfected with Halo-(FLAG)-Ube2V2 (or the C69S-mutant), then exposed to T-REX™ delivery conditions. Levels of γ-H2AX were assessed by immunofluorescence (detailed in Example 1 methods) as a function of time post light exposure. [mean+/−s.e.m., for wt-Halo-(FLAG)-Ube2V2, n=648 (0 h), n=624 (1 h), n=634 (3 h), n=571 (6 h), n=542 (18 h); for C69S-Halo-(FLAG)-Ube2V2, n=585 (0 h), n=615 (1 h), n=644 (3 h), n=649 (6 h), n=646 (18 h)]. FIG. 12I shows Ube2N knockdown lines #16 (shUbe2N-16) and control-knockdown line (shLacZ-D11) transfected with wt-Halo- (FLAG)-Ube2V2, then exposed to T-REX™ delivery conditions. Levels of γ-H2AX were assessed by immunofluorescence at the similar peak hour (3 h) as in FIG. 12F. [mean+/−s.e.m., for shUbe2N-#16, n=379 (T-REX™ delivery), n=297 (Light alone), n=342 (Ht-PreHNE alone), n=402 (DMSO), n=241 (Mitomycin C); for shLacZ-D11, n=434 (T-REX™ delivery), n=390 (Light alone), n=483 (Ht-PreHNE alone), n=434 (DMSO), n=445 (Mitomycin C)]. FIG. 12J shows HEK293T cells transfected with Halo-(FLAG)-Ube2V2 (or the C69S-mutant), then exposed to T-REX™ delivery conditions. The EdU/BrdU-dual-pulse DNA-labeling (detailed in Example 1 methods) was measured and levels of second pulse (BrdU) from EdU-positive-only cells were quantified and displayed. [mean+/−s.e.m., for wt-Halo-(FLAG)-Ube2V2, n=339 (T-REX™ delivery), n=375 (Light alone), n=300 (Ht-PreHNE alone), n=465 (DMSO), n=280 (Mitomycin C), for C69S-Halo-(FLAG)-Ube2V2, n=266 (T-REX™ delivery), n=212 (Light alone), n=283 (Ht-PreHNE alone), n=312 (DMSO), n=305 (Mitomycin C)]. See FIG. 13E for representative images for data in FIG. 12J.

Figure 13A:
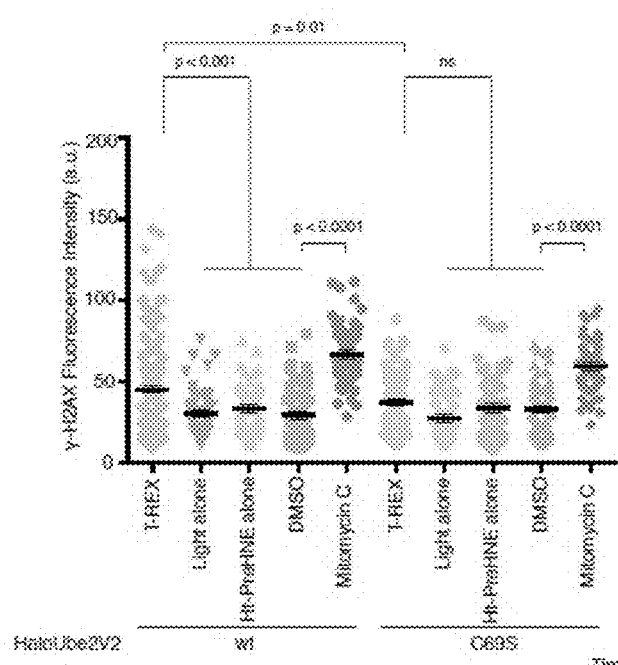
Figure 13B:
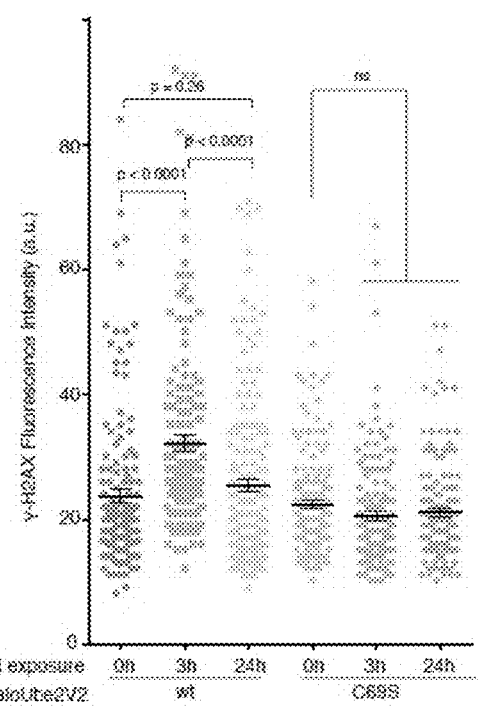
Figure 13C:
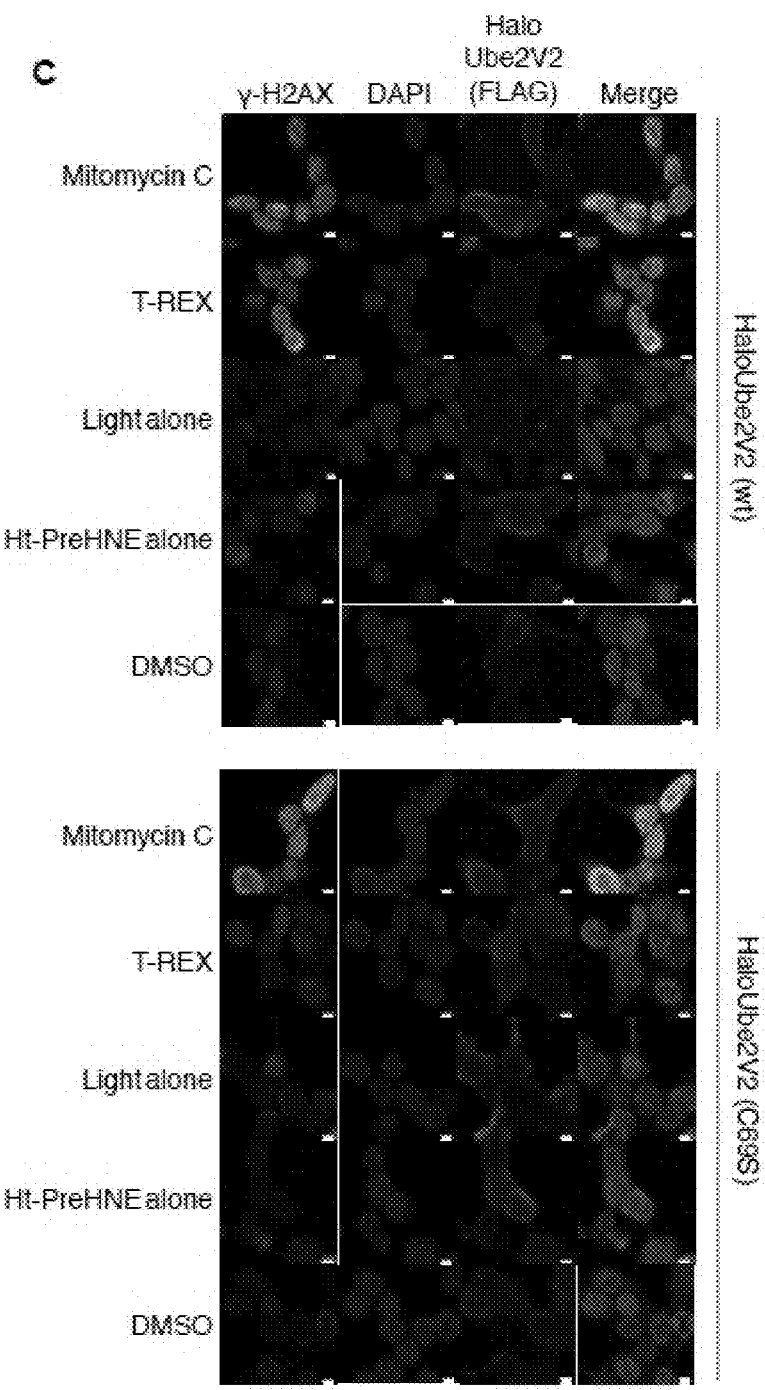
Figure 13D:
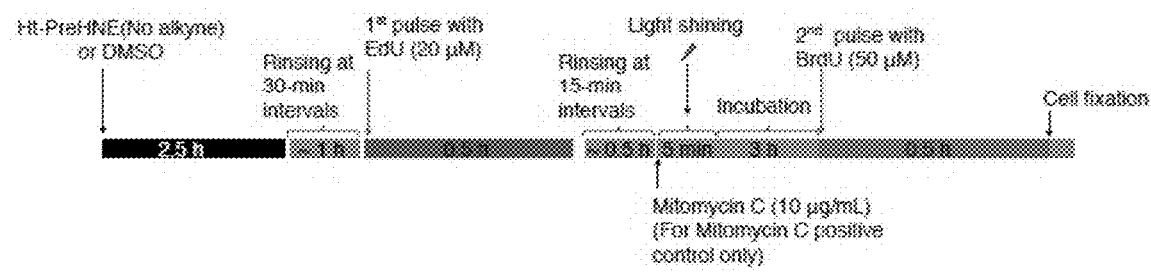
Figure 13E:
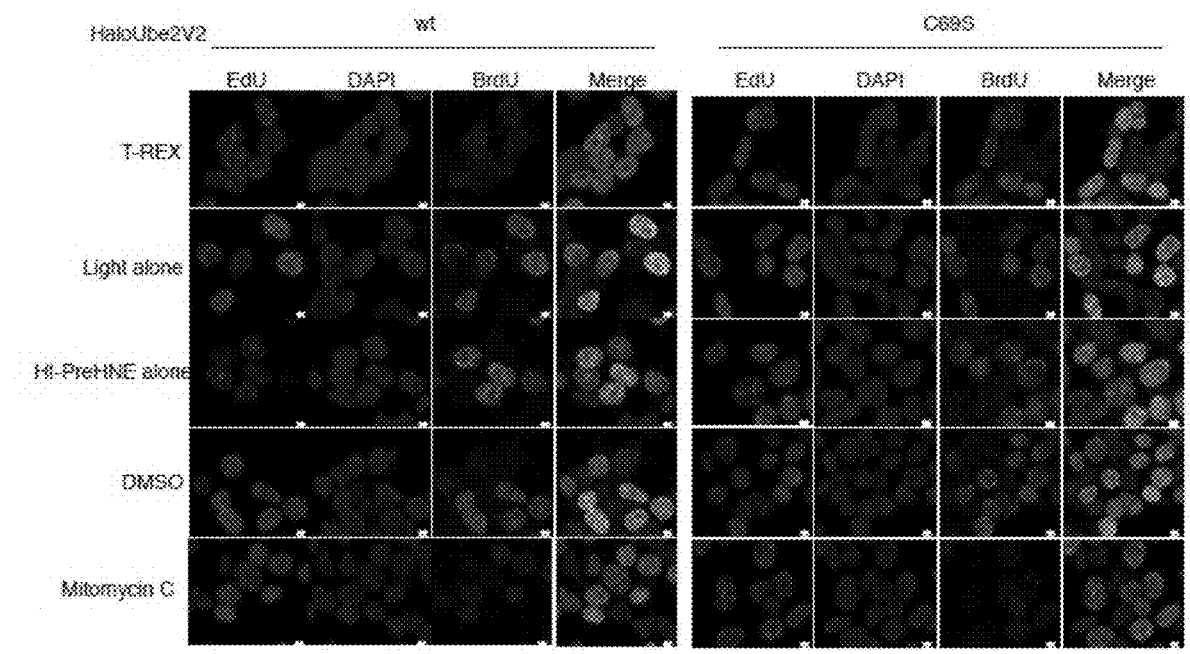
Figure 13F:
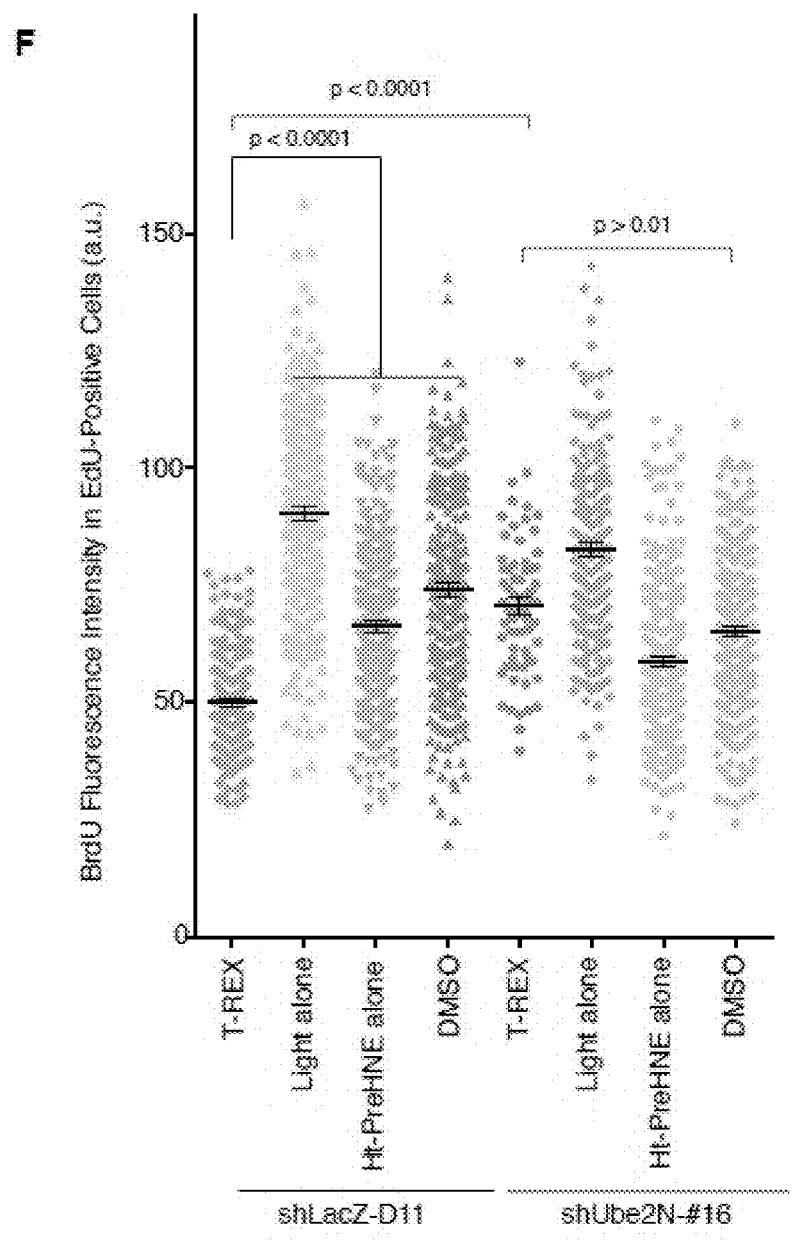

FIGS. 13A-13F show that both Ube2V2(C69S) and Ube2N-knockdown cells are hypomorphic for γ-H2AX upregulation and DNA-synthesis suppression. FIG. 13A shows HEK293T cells transfected with Halo-(FLAG)-Ube2V2 (wt or C69S mutant) and exposed to T-REX™ delivery conditions against various T-REX™ delivery-controls, or treated with mitomycin C (10 μg/mL, 3 h). 3-h post light exposure (or equivalent time in respective controls), cells were fixed, immunostained for γ-H2AX and analyzed by immunofluorescence (detailed in Example 1 methods). [mean+/−s.e.m., for wt-Halo-(FLAG)-Ube2V2, n=50 (T-REX™ delivery), n=50 (Light alone), n=50 (PreHNE alone), n=50 (DMSO), n=180 (Mitomycin C); for C69S-Halo-(FLAG)-Ube2V2, n=95 (T-REX™ delivery), n=59 (Light alone), n=55 (Ht-PreHNE alone), n=55 (DMSO), n=55 (Mitomycin C)]. FIG. 13B shows HEK293T cells transfected with Halo-(FLAG)-Ube2V2 (wt or C69S mutant). Cells were exposed to T-REX™ delivery conditions, then γ-H2AX levels were assessed as a function of time post light exposure by immunofluorescence microscopy. [mean+/−s.e.m., for wt-Halo-(FLAG)-Ube2V2, n=143 (0 h), n=137 (3 h), n=172 (24 h); for C69S-Halo-(FLAG)-Ube2V2, n=164 (0 h), n=138 (3 h), n=156 (24 h)]. FIG. 13C shows representative images for FIG. 13A. HEK293T cells that had been transfected with Halo-(FLAG)-Ube2V2 (wt or C69S mutant) were subsequently exposed to the indicated conditions and analyzed by immunofluorescence microscopy (detailed in Example 1 methods). Scale bars, 5 μm. FIG. 13D is a schematic illustration for dual-pulse experiment. FIG. 13E shows representative images for FIG. 12J. HEK293T cells that had been transfected with Halo-(FLAG)-Ube2V2 (wt or C69S mutant), and subsequently exposed to the indicated conditions; followed by immunofluorescence analyses (detailed in Example 1 methods). Scale bars, 5 μm. FIG. 13F shows HEK293T cells expressing control shRNA (shLacZ-D11) or shRNA targeting Ube2N were transfected with Halo-(FLAG)-Ube2V2 (wt); and subjected to T-REX™ delivery conditions against various T-REX™ delivery-controls. 3-h post light exposure (or equivalent time in respective controls), cells were sequentially treated with EdU then BrdU. Cells where then fixed, immunostained and analyzed (detailed in Example 1 methods). [mean+/−s.e.m., for shUbe2N-#16, n=66 (T-REX™ delivery), n=186 (Light alone), n=270 (Ht-PreHNE alone), n=240 (DMSO); for shLacZ-D11, n=185 (T-REX™ delivery), n=247 (Light alone), n=233 (Ht-PreHNE alone), n=234 (DMSO)].

Figure 14A:
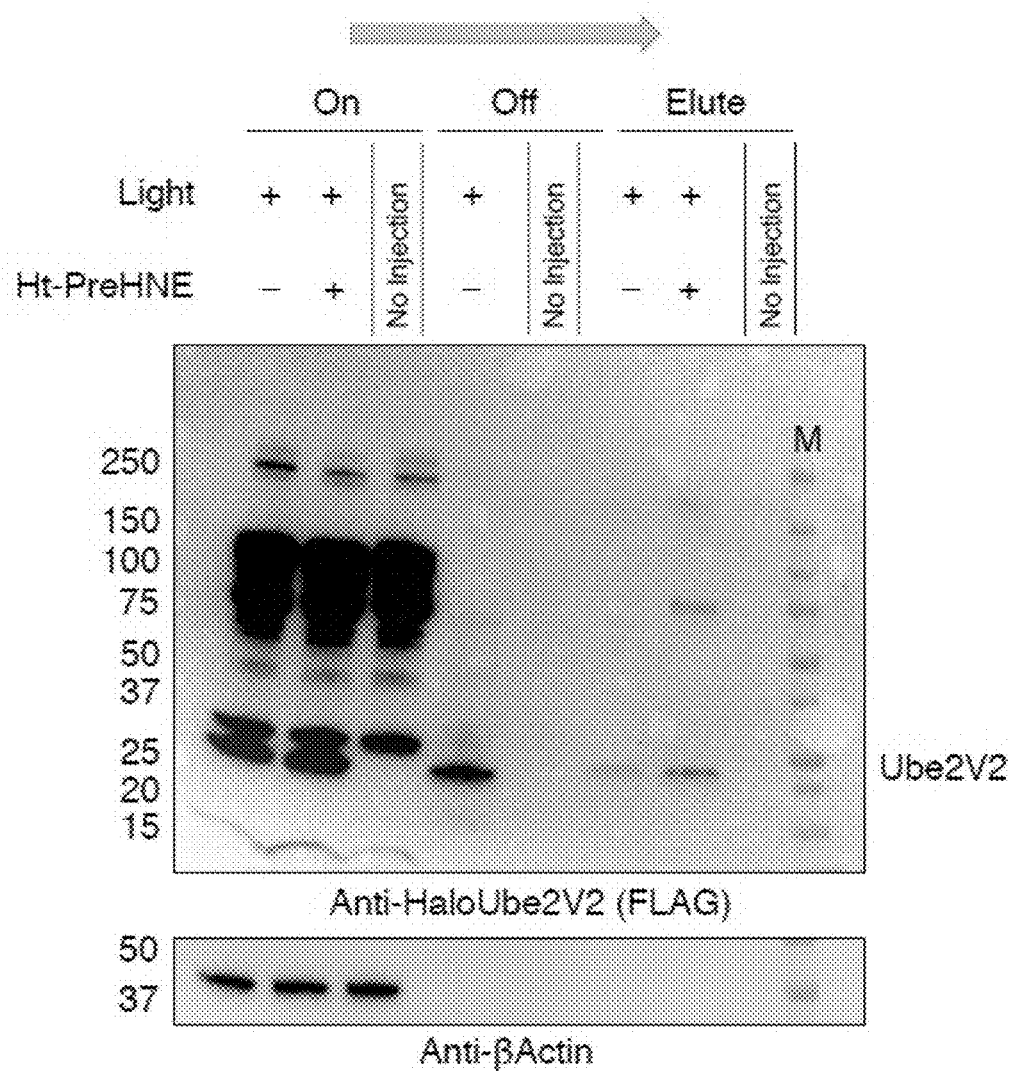
Figure 14C:
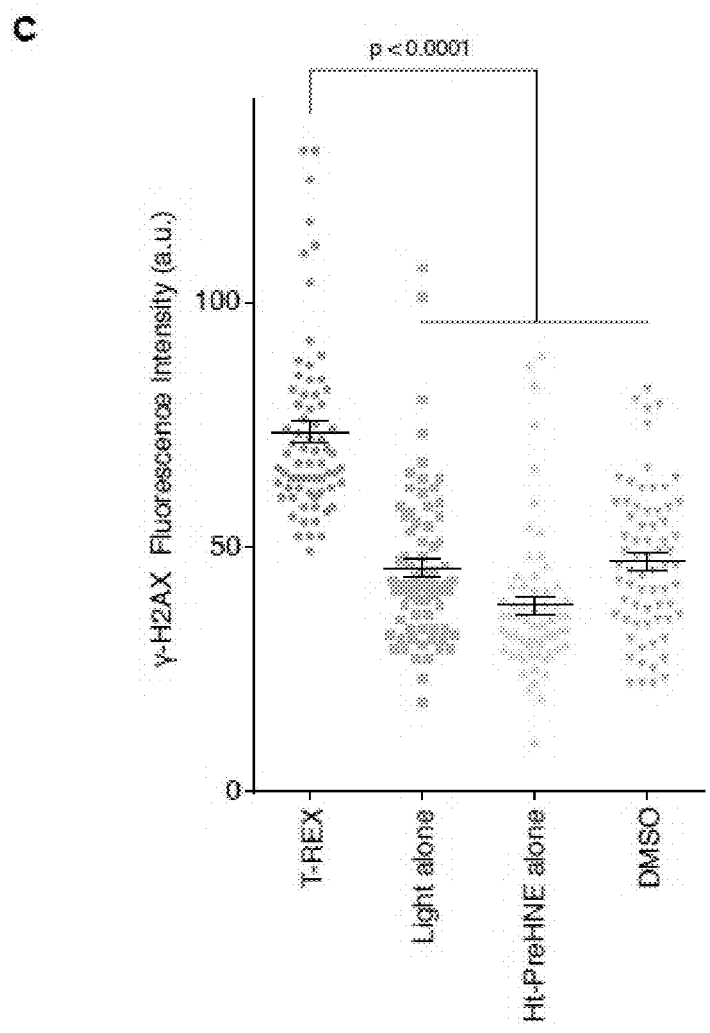

FIGS. 14A-14C show Ube2V2-Specific HNEylation regulates γ-H2AX levels in zebrafish. FIG. 14A shows casper zebrafish embryos that were injected with mRNA-encoding Halo-(FLAG)-Ube2V2 at the 1-4 cell stage. Once injection was complete, eggs were either exposed to Ht-PreHNE or DMSO. After 24-h-incubation, fish were washed and exposed to light. After dechorionation and de-yolking at 4° C., embryos were lysed, biotin was attached using Click chemistry by biotin-azide, and lysates were ethanol precipitated. After re-solubilization, biotinylated [i.e., HNE (alkyne)-modified]proteins were pulled down using streptavidin and analyzed by western blot. (See FIG. 4A for workflow; Clicking with biotin-azide). FIG. 14B shows a similar experiment to FIG. 14A, but at 3-h post-light-exposure, fish were fixed, permeabilized, and analysed by whole-mount immunofluorescence using indicated antibodies. Scale bars, 100 μm. FIG. 14C shows quantitation of images in FIG. 14B. [mean+/−s.e.m., n=69 (T-REX™ delivery), n=74 (Light alone), n=64 (Ht-PreHNE alone), n=69 (DMSO)].

Figure 15A:
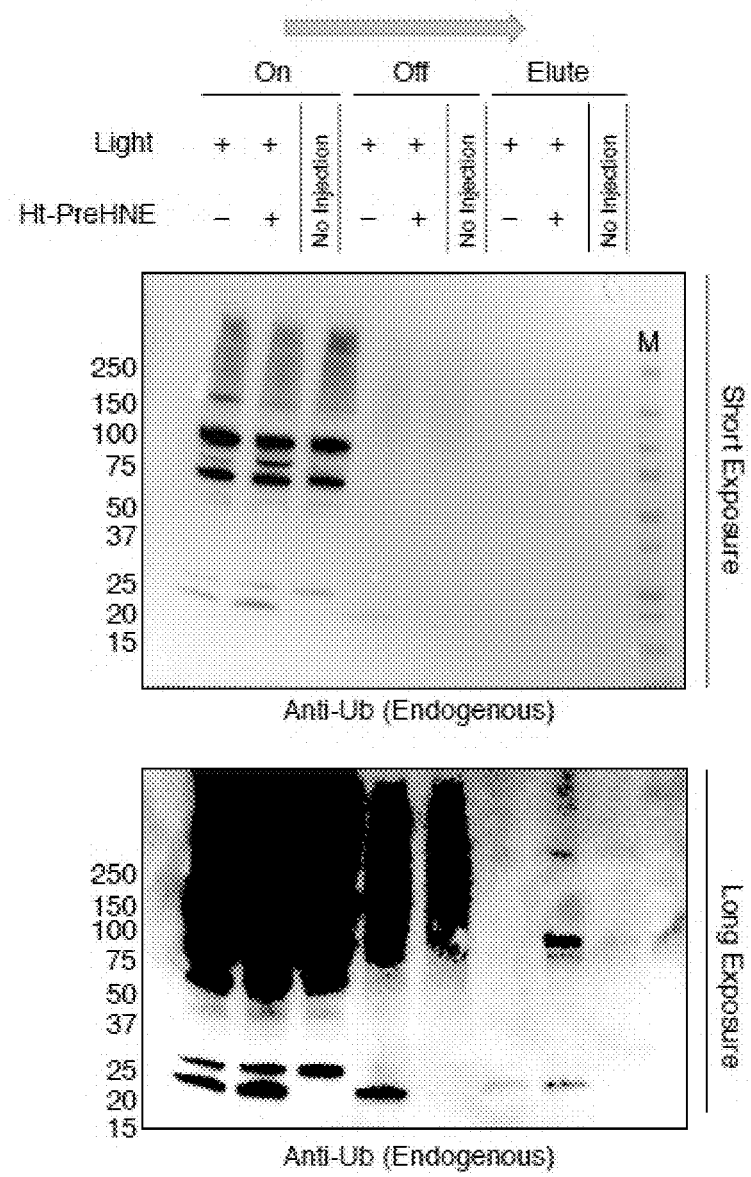
Figure 15B:
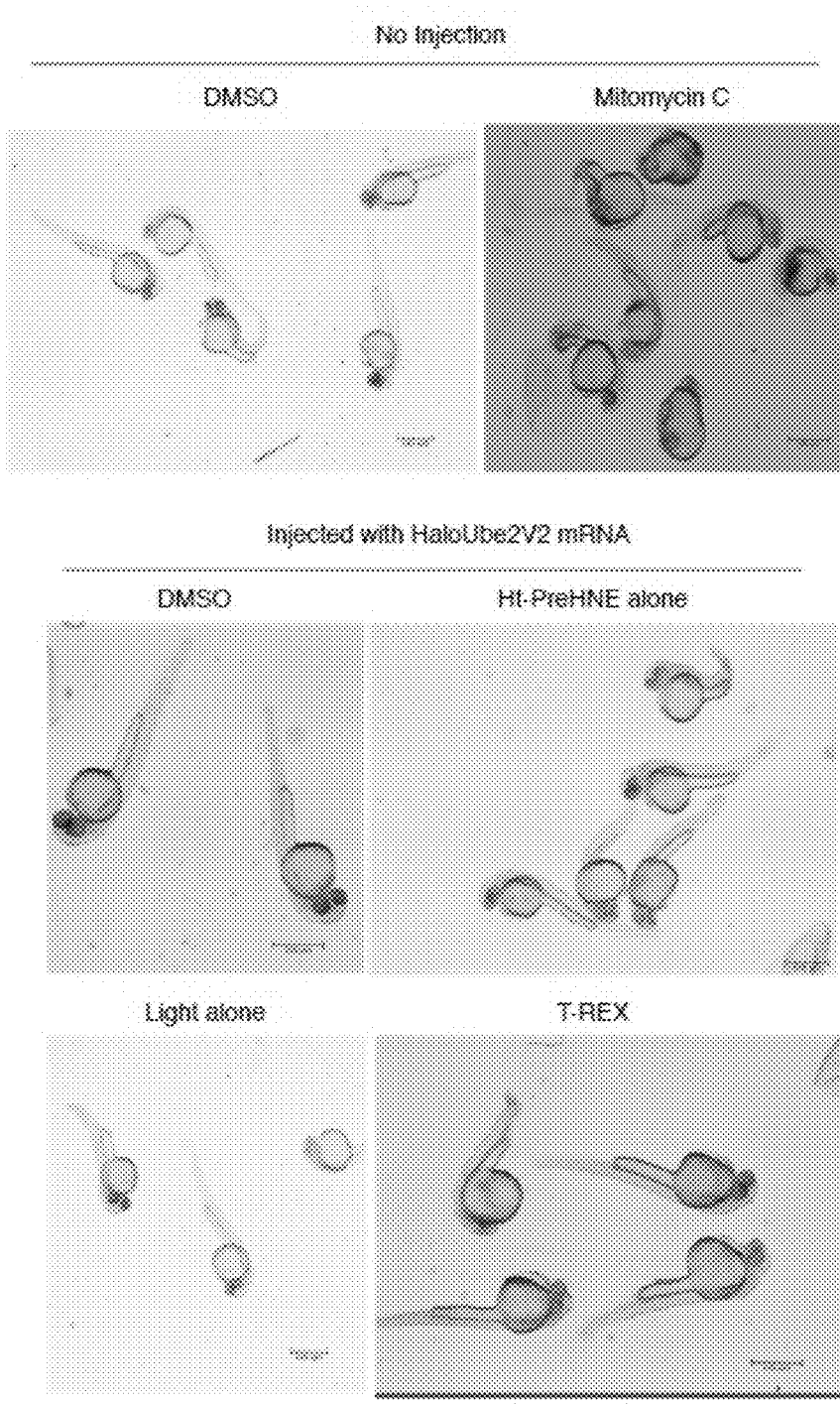

FIGS. 15A-15B shows HNEylation of Ube2V2 in zebrafish upregulates γ-H2AX. FIG. 15A shows casper zebrafish that were either not injected or injected with mRNA encoding Halo-(FLAG)-Ube2V2 and subjected to T-REX™ delivery against 'light-alone' control. Fish were then dechorionated, deyolked, lysed and HNEylated proteins were captured by Click coupling with biotin-azide and subsequent streptavidin pulldown (see workflow in FIG. 4A, Clicking with biotin-azide). HNEylation of Ube2V2 in fish also led to polyubiquitination of Ube2V2, indicating mechanistic conservation between fish and humans, and functional relevance of this electrophile regulatory pathway in vivo. Also see FIG. 14C. FIG. 15B shows casper embryos that were either non-injected or injected with mRNA coding for Halo-Ube2V2 and treated with the stated conditions. After 36-h fish were dechorionated and imaged using a stereomicroscope. Scale bars, 545 μm.

Figure 16:
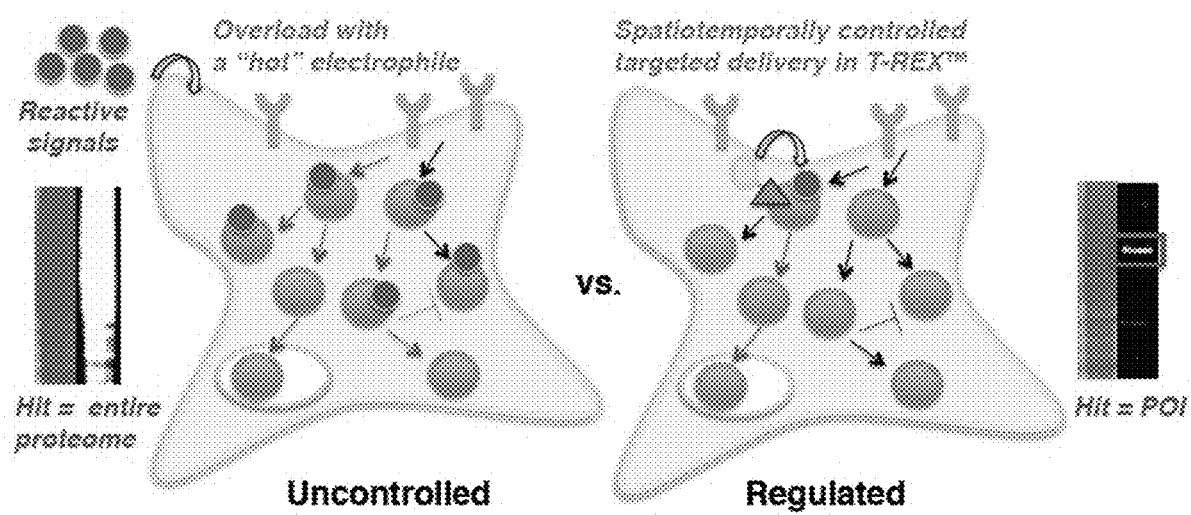

FIG. 16 shows strategies for studying cellular redox responses. A general small-molecule-based strategy with which to study cellular redox responses typically constitutes bolus dosing of a cell with reactive signals (left panel). T-REX™ delivery offers a complementary and previously not recognized "on-demand redox targeting" approach to study gain-of-function or dominant loss-of-function consequences of specific redox modifications with precise timing and target specificity (this protocol, right panel). Blue circles designate cellular proteins. The accompanying gel-based data represent the specificity in terms of targeted modification achieved in T-REX™ delivery, which also offers temporal control through light-driven signal delivery. See FIG. 17 and FIG. 21 for approaches to probe downstream response.

Figure 17:
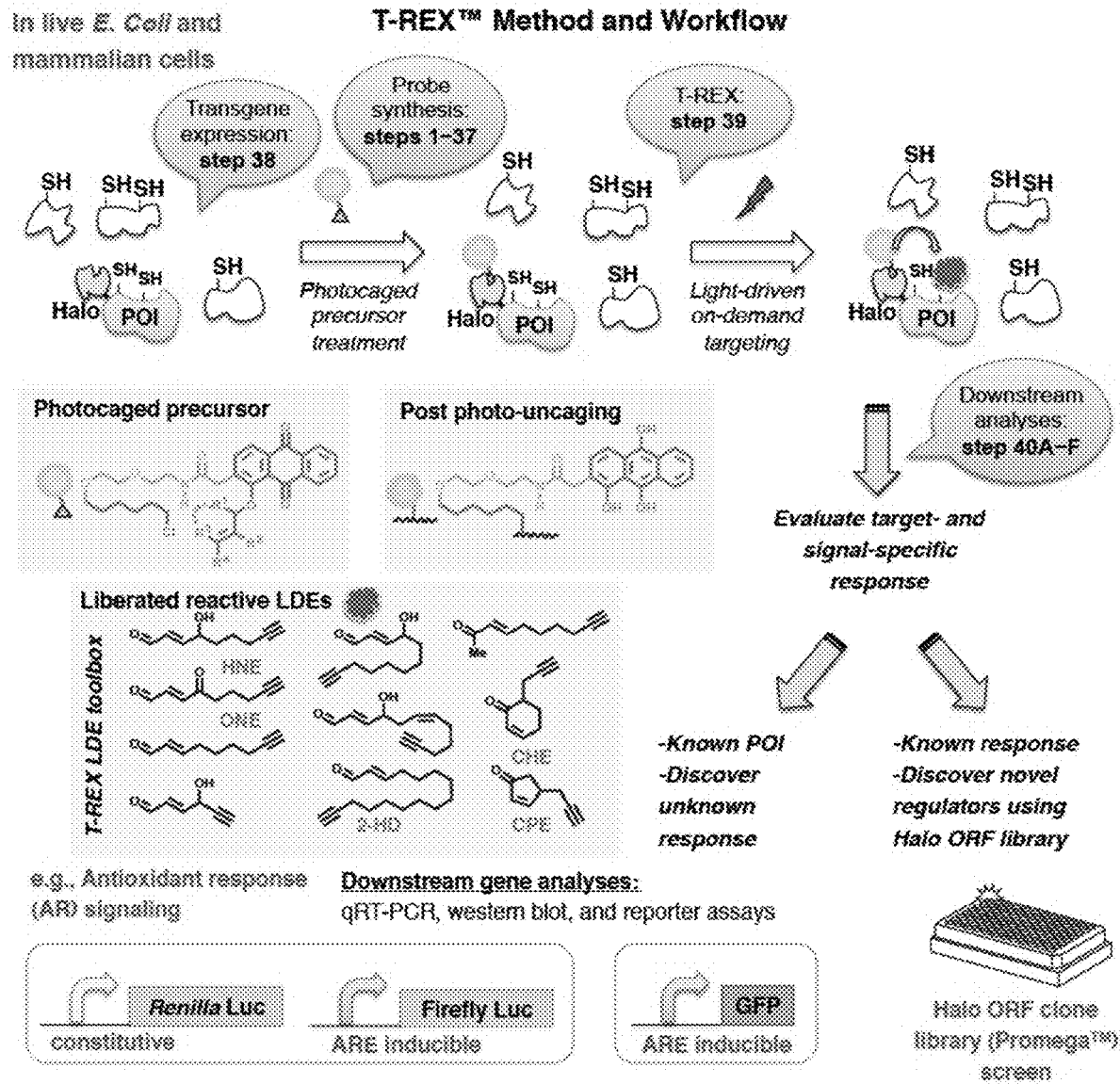

FIG. 17 shows on-target, on-demand redox signaling enabled by T-REX™ delivery (targetable reactive glectrophiles and oxidants). Bubbles indicate experimental steps described in the Protocol. Either E. coli or mammalian cells expressing HaloTag-fused proteins of interest (POI) are treated with designated photocaged precursors (5-25 μM, 2 h) to achieve a 1:1 covalent binding between the HaloTag and the photocaged probe. After rinsing cycles, low-energy light (0.3 mW/cm$^2$, 365 nm) exposure of the cells (3-20 min) at room temperature elicits rapid liberation of a reactive signal [lipid derived electrophiles (LDEs), inset] from the photocaged probe bound to HaloTag. Proximity-enhancement (Long et al., "On-Demand Targeting: Investigating Biology with Proximity-Directed Chemistry," *J. Am. Chem. Soc.* 138:3610-22 (2016), which is hereby incorporated by reference in its entirety) facilitates on-target, on-demand covalent modification of amino acid residue(s) on POI, typically cysteines. HNE is also known to be capable of modifying lysine and histidine (see Example 2). Regardless of residue specificity, T-REX™ delivery is able to ping one potential responsive protein with a precision dose of reactive lipid. Irrespective of residue identity, in-gel fluorescence analysis reports on the presence of HNE-modification on POI. Residue specificity in POI modification is determined by LC-MS/MS analysis post cell lysis and resin-assisted enrichment (see FIG. 24C). Once a specific sensor protein has been earmarked by T-REX™ delivery, target- and residue(s)-specific posttranslational modification can be directly linked to the signaling function of interest in an otherwise unperturbed cellular background. T-REX™ delivery can (1) interrogate specific redox-linked signaling responses, and (2) discover novel regulators that upon selective lipidation are sufficient to elicit a biologically relevant response. Generality and scope in terms of both target and signal specificity are exemplified with distinct vertebrate sensor proteins (e.g., Keap1, RRM1, HSPB7) and structurally distinct LDEs (inset). Pathway activation is analyzed using dual-luciferase reporter assays or GFP reporter assays by flow cytometry. Endogenous downstream gene activation can be analyzed by qRT-PCR and western blot.

Figure 18A:
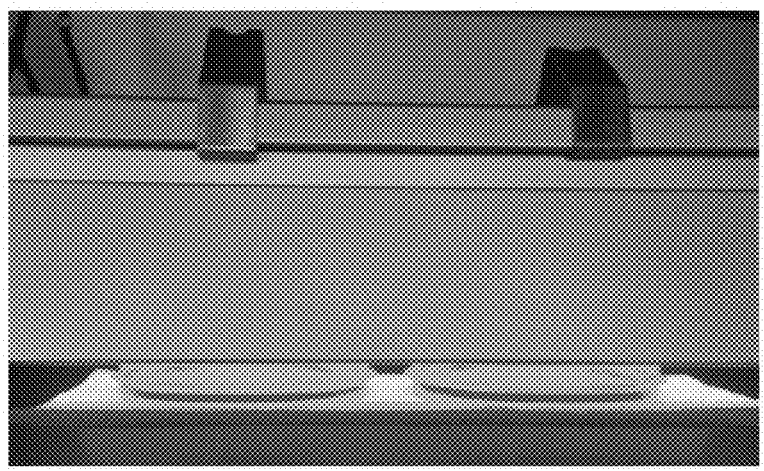
Figure 18B:
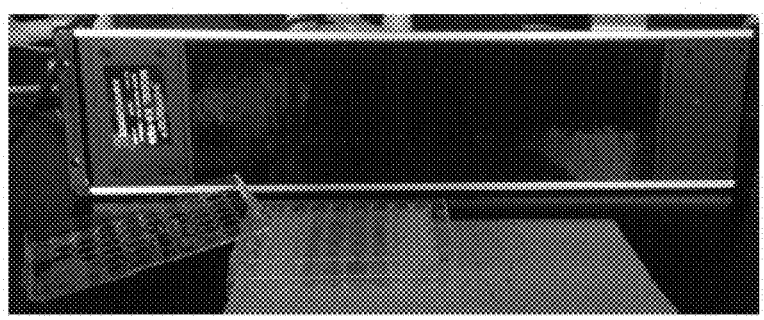
Figure 18C:
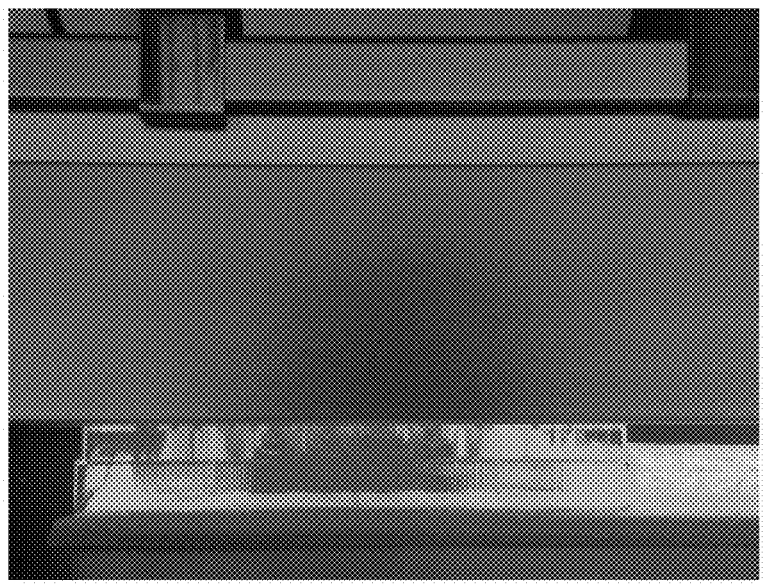

FIGS. 18A-18C demonstrates execution of T-REX™ delivery in live mammalian cells. HEK-293 cells cultured (FIG. 18A) in 2×55 cm$^2$ adherent cell culture plates, and (FIGS. 18B and 18C) in a 48-well multi-well adherent cell culture plate. No cover was placed on the plates during photo-uncaging. See Example 2 for detailed experimental conditions and equipment specifications.

Figures 19A, 19B:
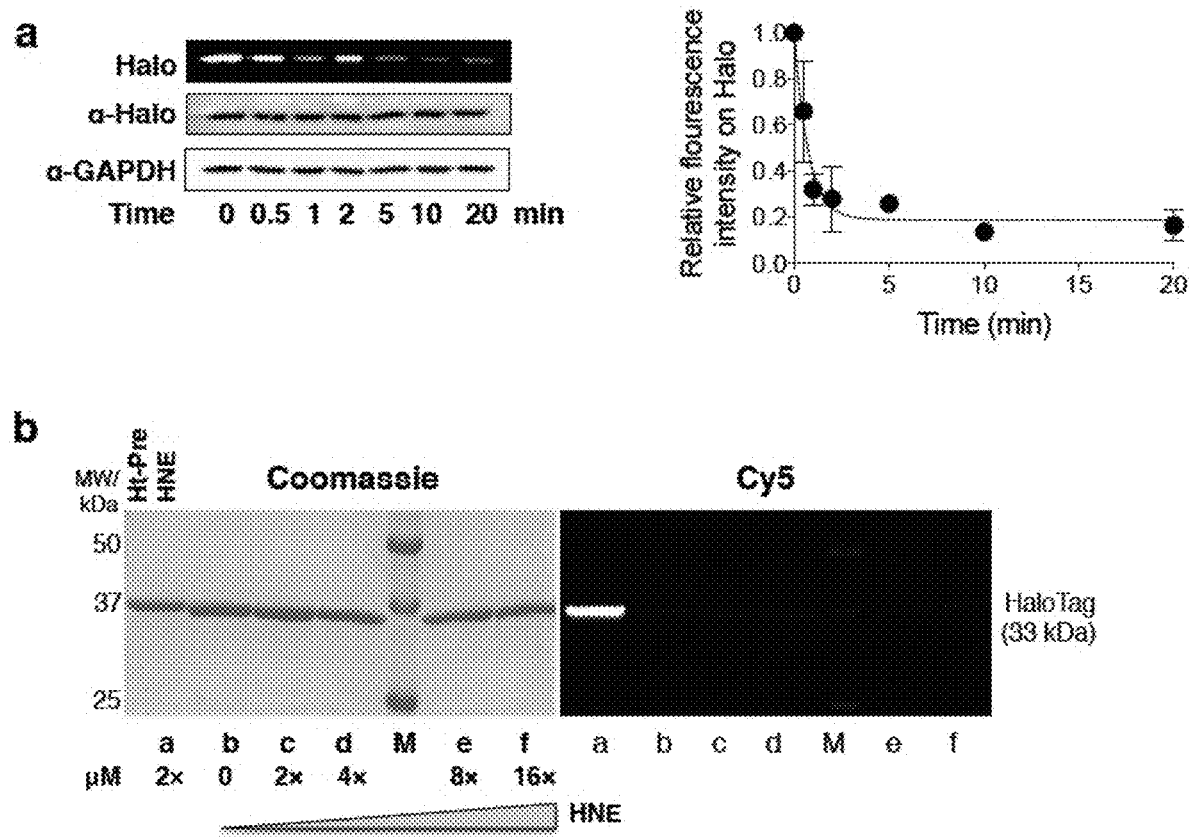

FIGS. 19A-19B show evaluation of time-dependent redox signal release in cells in T-REX™ delivery method and validation that HaloTag does not react with HNE. FIG. 19A shows measurements of HNE release efficiency in cells. HEK293T cells expressing HaloTag alone treated under standard T-REX™ delivery conditions with Ht-PreHNE were exposed to UV light (0.3 mW/cm$^2$, 365 nm) for the indicated time periods at which point the cells were harvested, lysed, and subjected to Click coupling and in-gel fluorescence analysis followed by western blot. Error bars designate SD (N=3). FIG. 19B are controls to show that HaloTag does not react with HNE. Purified recombinant HaloTag was treated with either the photocaged precursor Ht-PreHNE (FIG. 17, inset, and FIG. 29) (2 equiv., lane a, positive control), or directly with reactive electrophile HNE (FIG. 29) (0, 2, 4, 8, 16 equiv., lane b, c, d, e, f, respectively). After 20-min incubation, the samples were analyzed by in-gel fluorescence. M, molecular weight ladder.

Figures 20A, 20B:
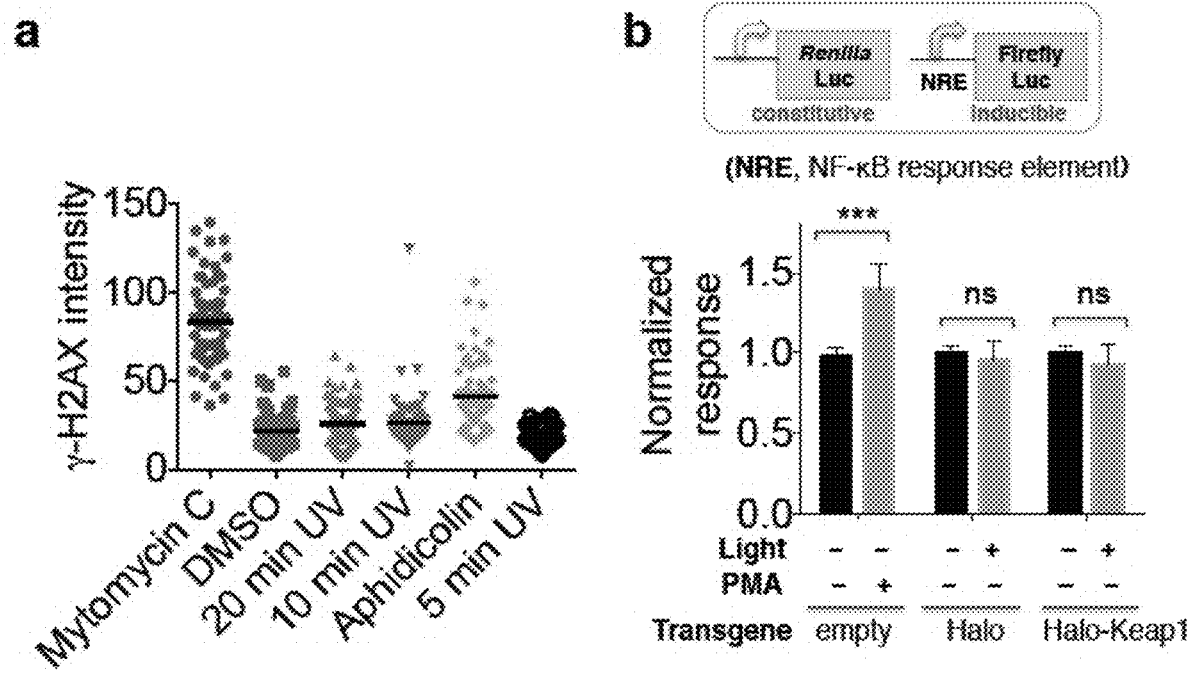

FIGS. 20A-20B shows UV light exposure employed in T-REX™ delivery is non-invasive. Representative data for γ-H2AX (Rogakou et al., "DNA Double-stranded Breaks Induce Histone H2AX Phosphorylation on Serine 139," *J. Biol. Chem.* 273:5858-5868 (1998), which is hereby incorporated by reference in its entirety) and NF-κB (Morgan et al., "Crosstalk of Reactive Oxygen Species and NF-kappaB Signaling," *Cell Res.* 21:103-115 (2011), which is hereby incorporated by reference in its entirety), markers for DNA damage and inflammatory signaling, respectively, is shown. In FIG. 20A, HEK293T cells were exposed to UV light (0.3 mW/cm$^2$, 340 nm) for the indicated time periods. Mitomycin C (10 µg/ml for 24 h) (Tomasz, "Mitomycin C: Small, Fast and Deadly (But Very Selective)," *Chem. Biol.* 2:575-579 (1995), which is hereby incorporated by reference in its entirety) and aphidicolin (10 µg/ml for 36 h) (Kurose et al., "Effects of Hydroxyurea and Aphidicolin on Phosphorylation of Ataxia Telangiectasia Mutated on Ser 1981 and Histone H2AX on Ser 139 in Relation to Cell Cycle Phase and Induction of Apoptosis," *Cytometry A* 69:212-221 (2006), which is hereby incorporated by reference in its entirety) serve as positive controls. After 12 hours post the end of UV illumination, cells were fixed and analyzed by standard immunofluorescence imaging method using γ-H2AX antibody (Millipore 05-636 at 1:1000 dilution). Data show mean+/−S.D. N>50 cells. In FIG. 20B, HEK293T cells stably expressing NRE-inducible firefly luciferase (Bellis et al., "Cellular Arrays for Large-scale Analysis of Transcription Factor Activity," *Biotechnol. Bioeng.* 108:395-403 (2011), which is hereby incorporated by reference in its entirety) were transfected with the respective plasmids encoding indicated transgene (empty vector, HaloTag alone, or Halo-Keap1 and Renilla luciferase) under constitutive CMV promoters. 24 hours post transfection, half of the plates were exposed to UV light (0.3 mW/cm$^2$, 365 nm) over 20 min. Phorbol 12-myristate 13-acetate (PMA) (10 ng/mL, 18 h) was used as a positive control for NRE activation (Bellis et al., "Cellular Arrays for Large-scale Analysis of Transcription Factor Activity," *Biotechnol. Bioeng.* 108:395-403 (2011), which is hereby incorporated by reference in its entirety). NRE activation was measured after 18 hrs. Error bars designate S.D. (N=8 biological replicates).

FIGS. 21A-21B demonstrate that the T-REX™ delivery approach allows flexibility, while enabling quantification of modification and response at numerous points. FIG. 21A shows validation of protein as redox sensitive. Biochemical information expected: (1) identification of percentage of LDE modification and (2) residue specificity. FIG. 21B shows evaluation of pathway activation alongside recommended controls. Functional information expected: (1) global transcriptional response; (2) cell-to-cell transcriptional response; (3) changes in endogenous biological species; (4) perturbation of signaling activities; and (5) alterations in mRNA abundance and (6) protein levels of downstream genes.

Figures 22A, 22B:
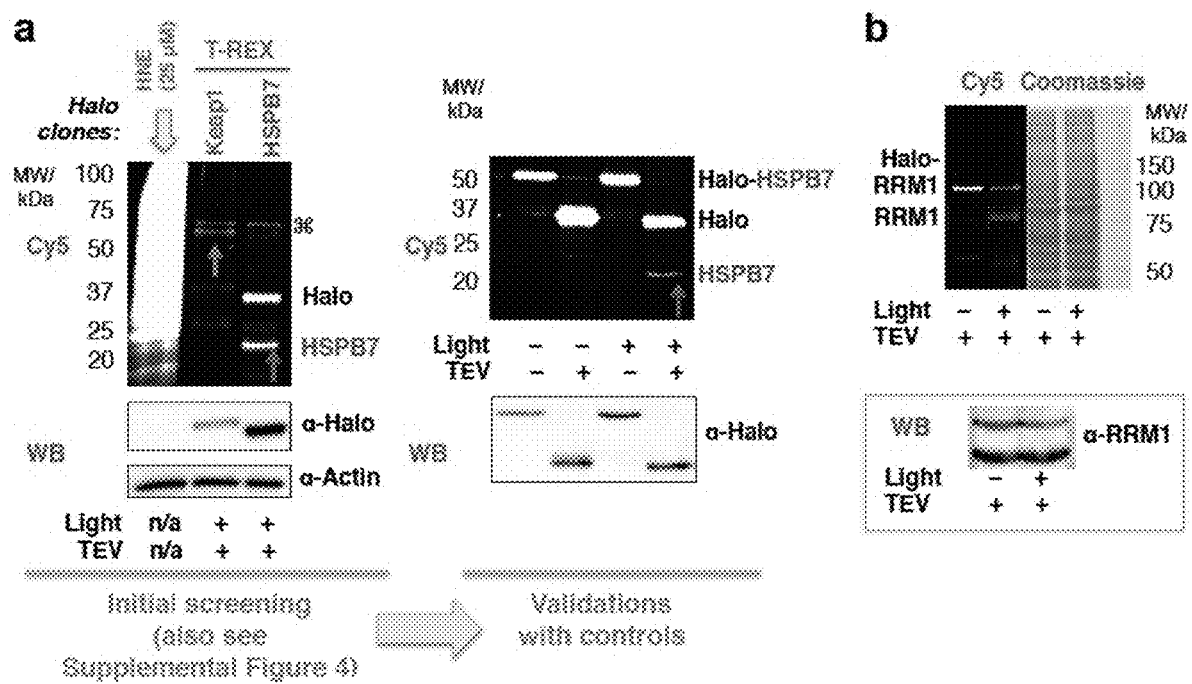
Figures 23A, 23B:
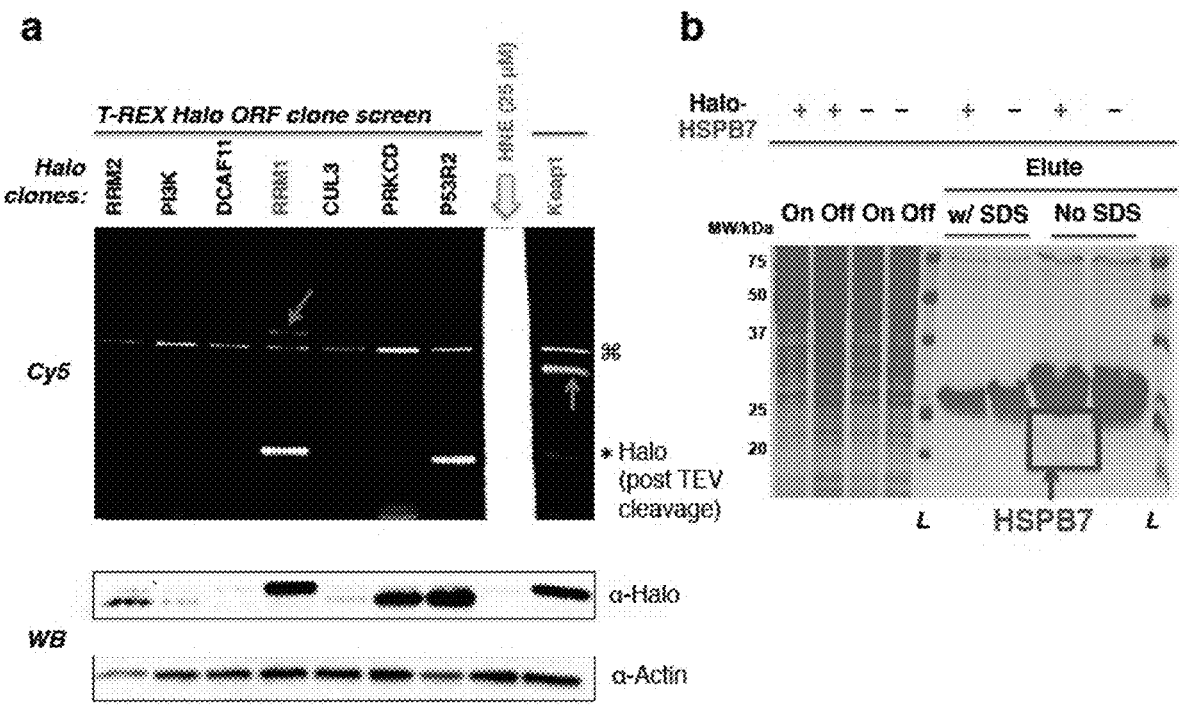

FIGS. 22A-22B shows commercial HaloTag library allows discovery and validation of "first responders to a specific LDE using T-REX™ delivery. The screen first identified first responders to basal amounts of HNE (FIG. 22A). This was coupled with T-REX™ delivery secondary validations using appropriate controls for effects of light alone with or without separation of Halo and POI domains during processing. As an example, T-REX™ delivery targeted HNEylation using a panel often distinct Halo ORF clones identified (a) zebrafish HSPB7 (theoretical MW~18 kDa), and (b) human RRM1 (theoretical MW~90 kDa) as novel HNE-sensitive targets. In FIG. 22A, the established Keap1 (theoretical MW~70 kDa) targeting was used as a diagnostic positive control (Also see FIG. 23A). Global HNE shows comparison to established protocols [left panel in (a)]. ⌘, shown in FIG. 22A, is a non-specific band in the data set from a representative rapid initial screen of multiple HaloTag clones (see FIG. 23A). Secondary validation of HSPB7 HNEylation was performed with a full set of controls [right panel in (a)]. HSPB7 protein identity was confirmed by pulldown (FIG. 23B). Actin was used as loading control. Halo antibody was used to evaluate the expression level of Halo fusion proteins. FIG. 22B shows secondary validation of RRM1 HNEylation (Also see FIG. 23A for an initial screen). RRM1 protein identity was confirmed by western blot (Top band, Halo-RRM1. Bottom, RRM1 post TEV-protease-assisted separation of Halo and RRM1. (Note: the expression plasmid vector for Halo-Keap1, -HSPB7, and -RRM1, encodes bicistronic expression of an internal fluorescent protein control DsRed alongside the Halo-tagged protein of interest, explaining the fluorescent band at 27 kDa in these gels.)

FIGS. 23A-23B shows a T-REX™ delivery screen of Halo ORF clones for the discovery of novel electrophile-sensitive targets and pulldown validation of expressed proteins exemplified by zebrafish HSPB7. FIG. 23A shows a T-REX™ delivery-enabled gel-based screen for bona fide HNE-sensitive targets using Halo-ORFeome library (Promega). Individual wells in a 48-well plate contained live HEK-293 cells ectopically expressing a unique HaloTagged gene of interest. The cells were subjected to T-REX™ delivery-HNE(alkyne) targeting on demand. Post cell lysis, all samples were treated with TEV protease and subsequently subjected to Click coupling reaction with Cy5 azide. Probing with Halo antibody allowed evaluation of expression level (and/or solubility under the lysis conditions used). The "hit" bands on Cy5-fluorescent gel were judged against Halo protein level revealed by western blot. For example, RRM1, PRKCD, p53R2, and Keap1 (positive control) had roughly similar expression levels. Only RRM1 and Keap1 were HNE-sensitive although all four targets have been previously identified to be potentially redox/HNE-sensitive (Holmstrom et al., "Cellular Mechanisms and Physiological Consequences of Redox-Dependent Signalling," *Nat. Rev. Mol. Cell. Biol.* 15:411-21 (2014); Jacobs et al., "Systems Analysis of Protein Modification and Cellular Responses Induced by Electrophile Stress," *Acc. Chem. Res.* 43:673-83 (2010); Delmastro-Greenwood et al., "Redox-Dependent Anti-Inflammatory Signaling Actions of Unsaturated Fatty Acids," *Annu. Rev. Physiol.* 76:79-105 (2014); Crunkhorn S., "Deal Watch: Abbott Boosts Investment in NRF2 Activators for Reducing Oxidative Stress," *Nat. Rev. Drug Discov.* 11:96 (2012); Dinkova-Kostova et al., "Glucosinolates and Isothiocyanates in Health and Disease," *Trends Mol. Med.* 18:337-47 (2012), which are hereby incorporated by reference in their entirety. See Example 2 for discussion. ⌘, shown in FIG. 23A, a non-specific band. Also see FIG. 22 and procedural details in Example 2. FIG. 23B shows Zebrafish HSPB7 expression and protein ID of the band shown in FIG. 22A was validated by enrichment from HEK-293 cells ectopically expressing Halo-HSPB7 with the use of HaloTag PEG-Biotin ligand (Promega G8592) and streptavidin sepharose beads (GE Healthcare, cat. no. 17-5113-01), and subsequent on-bead TEV-protease cleavage followed by gel electrophoresis analysis. Theoretical MW of HSPB7~18 kDa. L, MW ladder.

Figures 24A, 24B, 24C:
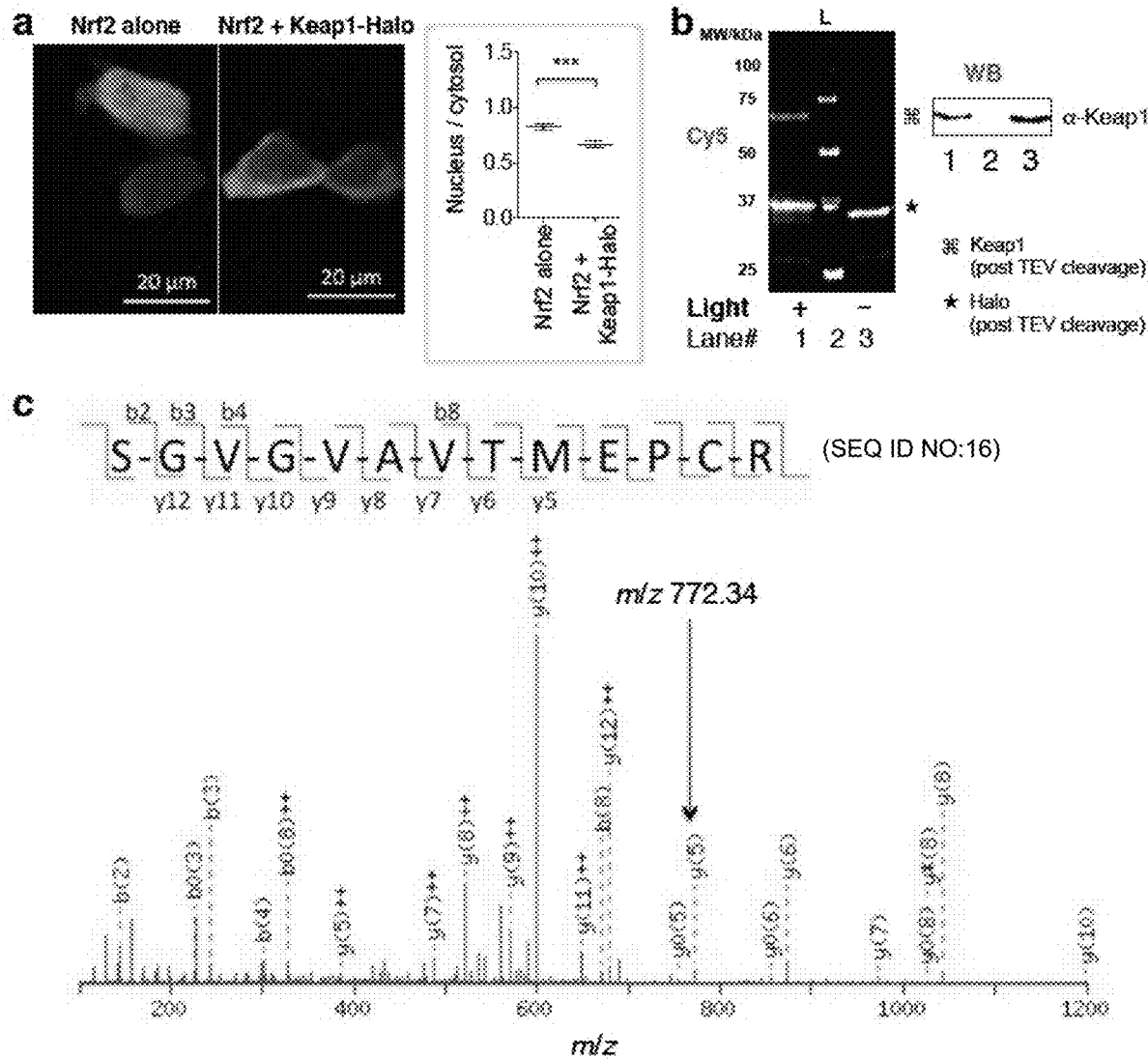

FIGS. 24A-24C shows assessment of N- vs. C-terminal HaloTagging on T-REX™ delivery functionality, exemplified by Keap1 LDE targeting. Results with Halo-Keap1 were previously reported (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety). FIG. 24A is live imaging analysis showing Keap1-Halo promotes Nrf2 nuclear exclusion as with Halo-Keap157. Inset shows quantitation performed using ImageJ (NIH). FIG. 24B is in-gel fluorescence analysis showing targeted HNEylation of Keap1 in HEK-293 cells using Keap1-Halo construct is equally as efficient as using Halo-Keap1 (Lin et al., "A Generalizable Platform for Interrogating Target- and Signal-Specific Consequences of Electrophilic Modifications in Redox-Dependent Cell Signaling," *J. Am. Chem. Soc.* 137: 6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety). L, MW ladder. FIG. 24C shows the ionization spectrum of Keap1 peptide (SEQ ID NO: 16) modified by a representative cyclohexenone-derived LDE (CHE, FIG. 17 inset) as a result of T-REX™ delivery on HEK-293 cells expressing C-terminal HaloTagged Keap1, subsequent enrichment of modified Keap1-Halo from T-REX™ delivery-treated cells and LC-MS/MS analysis. The same Cys residue (C613) was modified in the corresponding experiment in which N-terminally HaloTagged-Keap1 was used (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). Also see Tables 3 and 4. Arrow points to the diagnostic m/z peak for C613 modification.

Figures 25A, 25B:
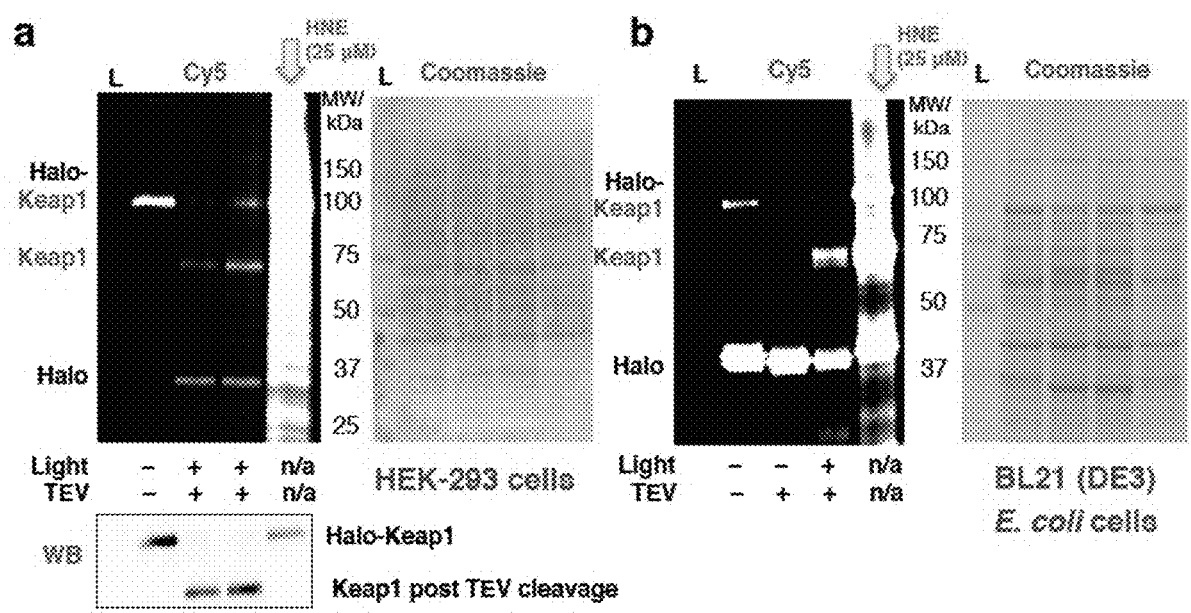

FIGS. 25A-25B show T-REX™ delivery targeting is equally efficient in both human cells (HEK-293) and *E. coli*. Halo-Keap1 human protein (Fang et al., "Temporally Controlled Targeting of 4-hydroxynonenal to Specific Proteins in Living Cells," *J. Am. Chem. Soc.* 135; 14496-99 (2013); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety) is used as a model protein. Coomassie-stained membrane is used to evaluate uniform loading of total lysate proteins in each lane. Independent duplicates of Keap1 targeting results are presented in FIG. 25A. Partial cleavage of the fusion protein (into Halo and Keap1 separate proteins) was often observed during standard *E. coli* growth conditions, accounting for the observed Cy5 signal on the Halo band [see no-light, no-TEV sample lane in FIG. 25B]. Theoretical MW's: Halo, ~33 kDa; and Keap1, ~70 kDa. TEV, TEV protease. L, MW Ladder.

Figures 26A, 26B, 26C, 26D, 26E:
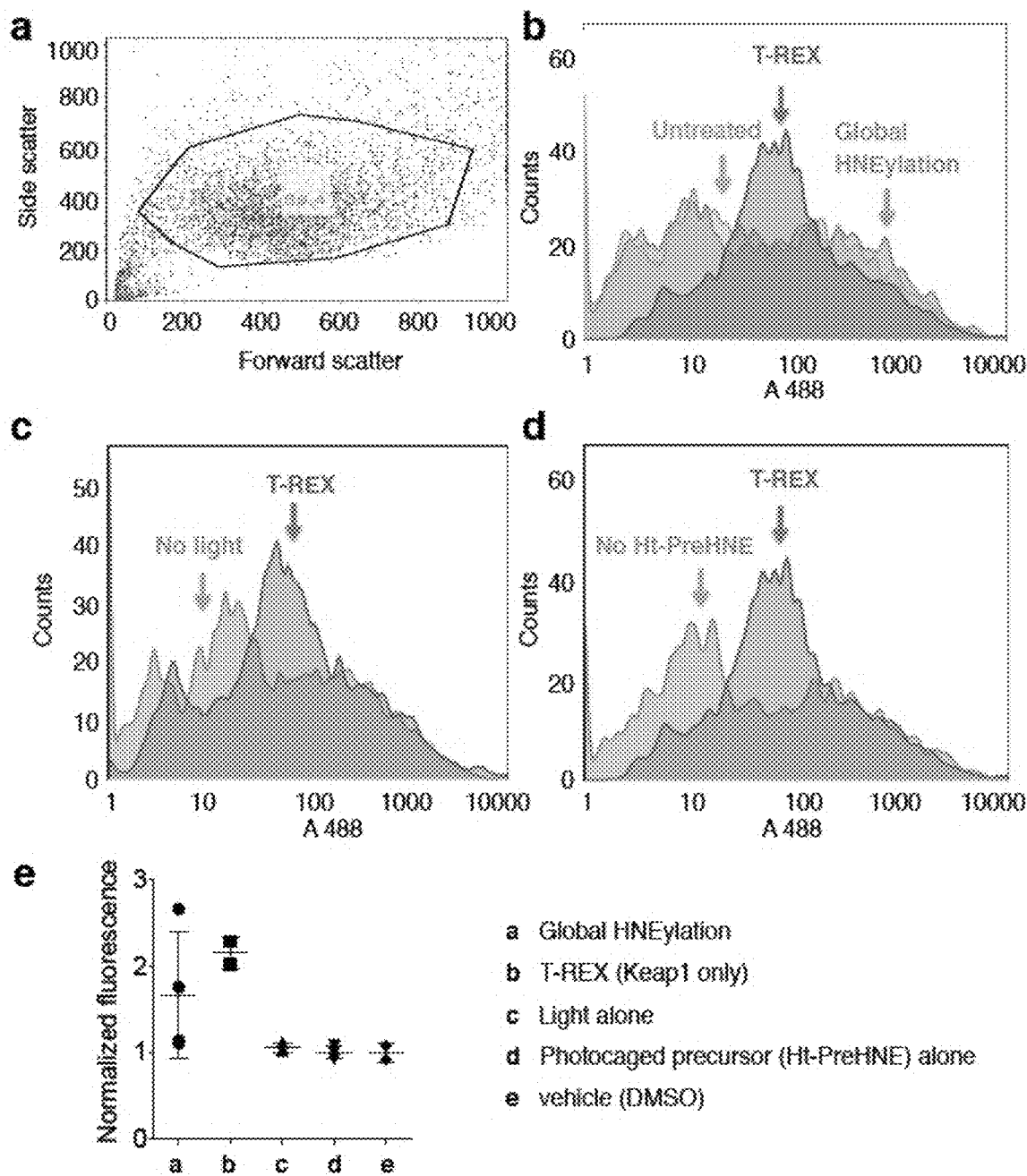

FIGS. 26A-26E show flow cytometry-based ARE-GFP reporter assay quantitating T-REX™ delivery-mediated activation of antioxidant response in subpopulation of live HEK-293 cells. FIG. 26A shows representative GFP expression level in cells transiently transfected with plasmids encoding Halo-Keap1, Nrf2, and ARE-GFP. FIGS. 26B-26D show representative single-parameter (GFP signal) histograms obtained from cells transiently transfected with plasmids encoding Halo-Keap1, Nrf2, and ARE-GFP that have been treated as indicated: (FIG. 26B) comparisons of the results between whole-cell HNE stimulation, T-REX™ delivery-assisted Keap1-specific activation, and untreated (no photocaged precursor and no light); (FIG. 26C) comparison between T-REX™ delivery and "no light exposure" control; (FIG. 26D) comparison between T-REX™ delivery (red) and "no photocaged precursor" control (FIG. 26E) Representative data from total fluorescence analysis of GFP signal. Error bars designate S.D. (n=3).

Figure 27:
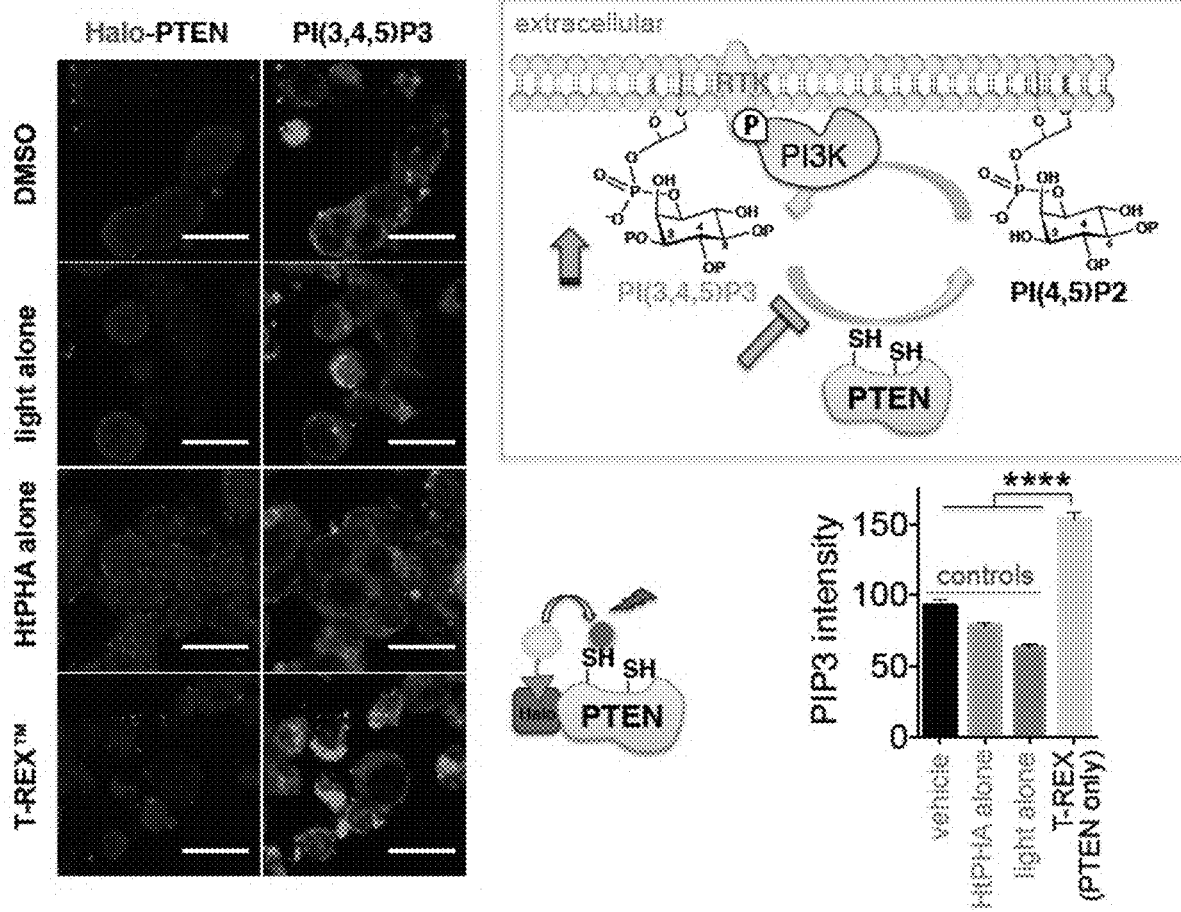

FIG. 27 shows immunofluorescence analysis of endogenous PIP3 phosphoinositide in fixed cells subsequent to PTEN-targeted redox modification enabled by T-REX™ delivery in live cells. Live HEK-293 cells expressing Halo-PTEN was subjected to T-REX™ delivery targeted HNEylation of PTEN. Dominant loss-of-function inactivation of PTEN results in upregulation of PIP3. The cells were fixed and immunostained by anti-PIP3 and anti-Halo. Error bars are S.E.M (N=86). Scale bar: 20 µm. Inset: Schematic of the PI3K/PTEN signaling. Partial inactivation of PTEN raises the levels of PIP3.

Figure 28:
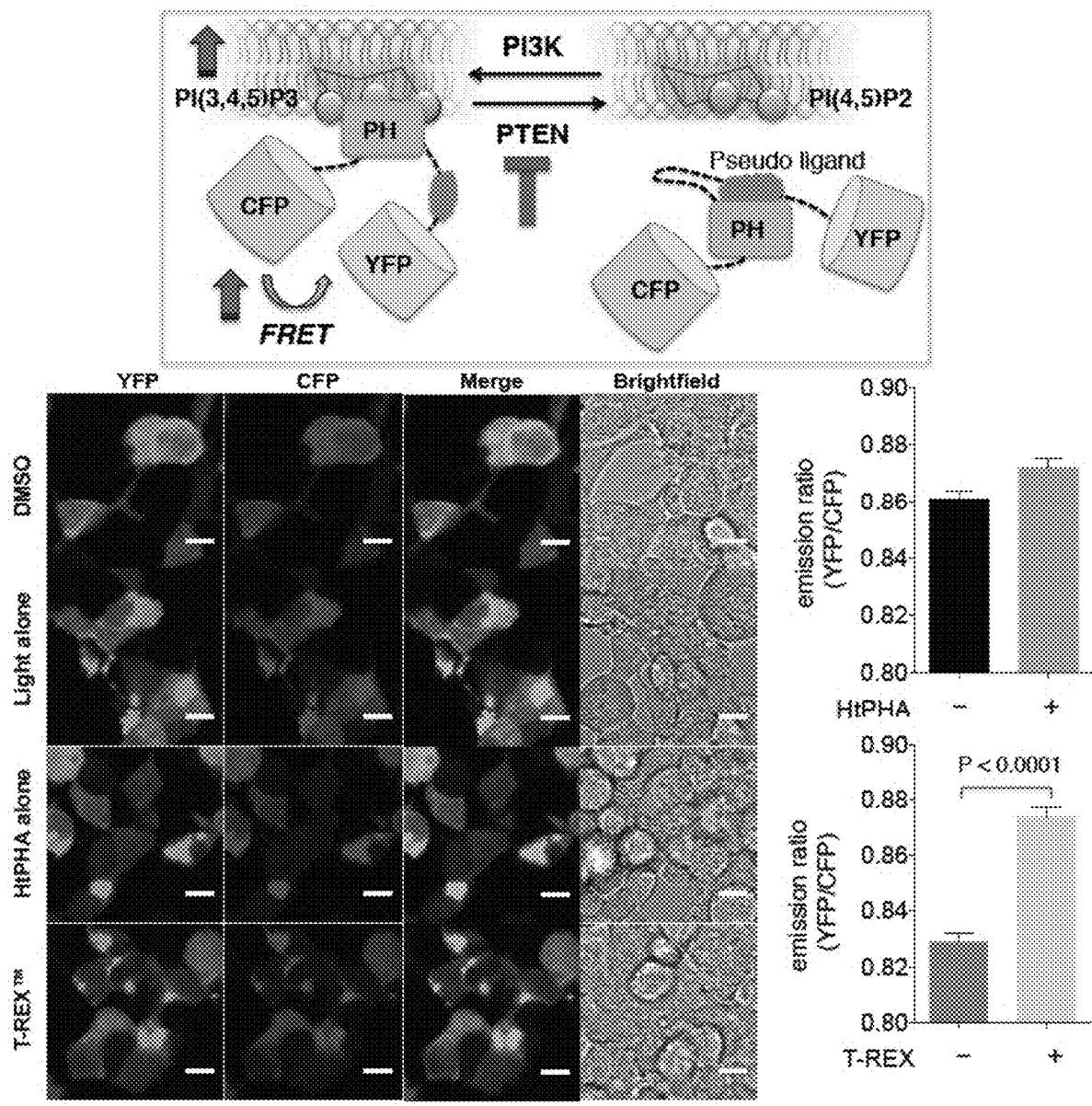

FIG. 28 shows FRET-based biosensor assay in live cells reporting the levels of endogenous PIP3 subsequent to PTEN-targeted redox modification enabled by T-REX™ delivery. Inset: Live HEK-293 cells expressing "lnPAkt" FRET biosensor (Covey et al., "Akt Activation by Arachidonic Acid Metabolism Occurs via Oxidation and Inactivation of PTEN Tumor Suppressor," *Oncogene* 26:5784-92 (2007), which is hereby incorporated by reference in its entirety) and HaloPTEN were subjected to T-REX™ delivery conditions that enabled substoichiometric HNEylation of PTEN (Fang et al., "Temporally Controlled Targeting of 4-hydroxynonenal to Specific Proteins in Living Cells," *J. Am. Chem. Soc.* 135; 14496-99 (2013), which is hereby incorporated by reference in its entirety). Dominant loss-of-function inactivation of PTEN upregulates the membrane-bound PIP3 phosphoinositide. Increase in cellular PIP3 competitively binds the pleckstrin homology (PH) domain of Akt, displacing the "pseudo ligand" (Covey et al., "Akt Activation by Arachidonic Acid Metabolism Occurs via Oxidation and Inactivation of PTEN Tumor Suppressor," *Oncogene* 26:5784-92 (2007), which is hereby incorporated reference in its entirety). Conformational change associated with the membrane recruitment results in increase in FRET signal (Covey et al., "Akt Activation by Arachidonic Acid Metabolism Occurs via Oxidation and Inactivation of PTEN Tumor Suppressor," *Oncogene* 26:5784-92 (2007), which is hereby incorporated reference in its entirety). Representative live cell images and quantitation of YFP:CFP emission ratio. Scale bar: 20 µm. Top: Control: HtPHA treatment alone did not perturb the emission ratio significantly. Bottom: T-REX™ delivery redox targeting of PTEN selectively enhances FRET signal (right bar) compared to samples exposed to light alone (left bar). Error bars designate S.E.M (N=170 cells).

Figure 29:
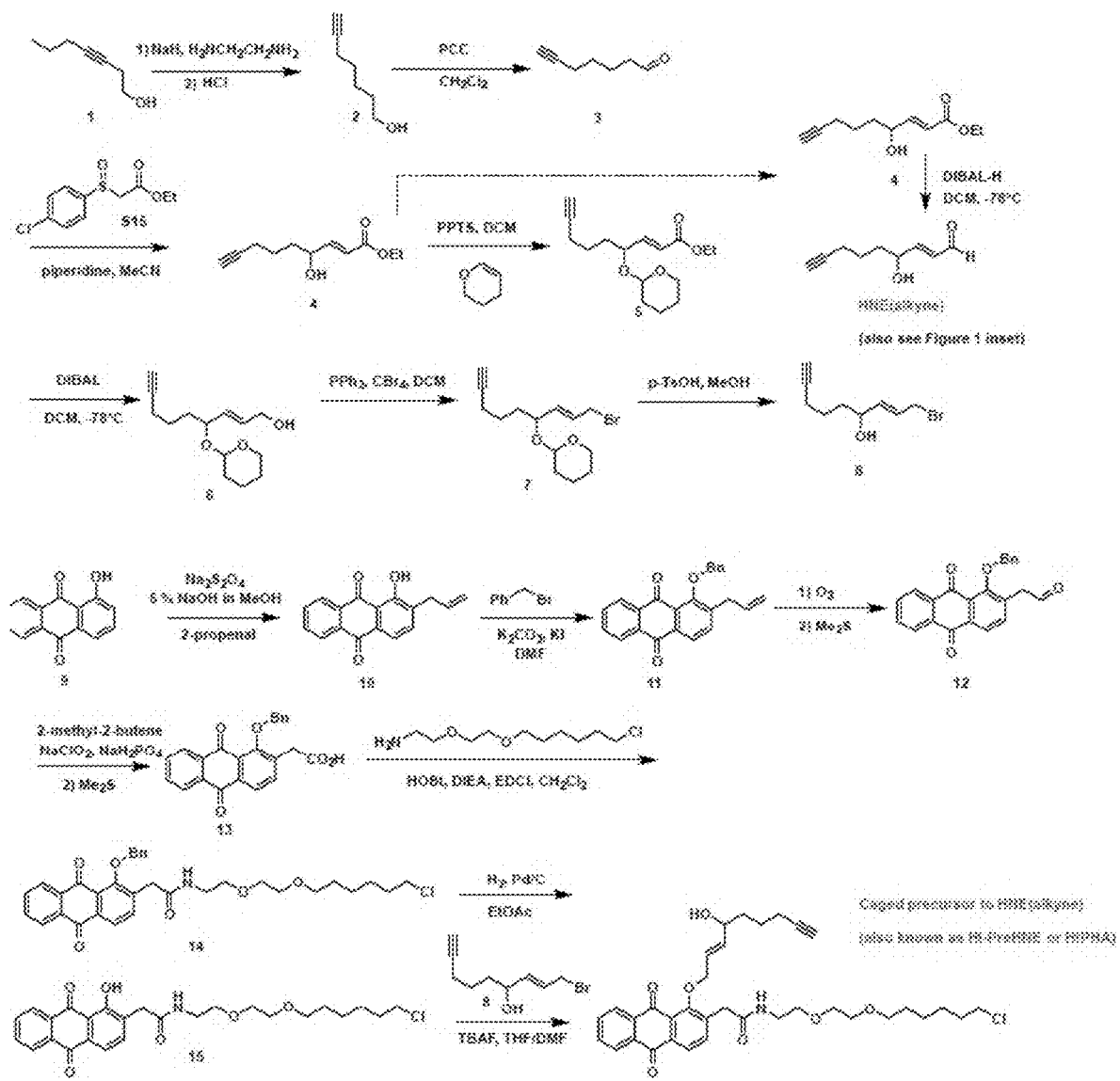

FIG. 29 shows chemical syntheses of HNE(alkyne) (Fang et al., "Temporally Controlled Targeting of 4-hydroxynonenal to Specific Proteins in Living Cells," *J. Am. Chem. Soc.* 135; 14496-99 (2013), which is hereby incorporated by reference in its entirety) (also see FIG. 29), and HaloTag-targetable caged precursor to HNE(alkyne) (Fang et al., "Temporally Controlled Targeting of 4-hydroxynonenal to Specific Proteins in Living Cells," *J. Am. Chem. Soc.* 135; 14496-99 (2013); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety), also known as Ht-PreHNE56 or HtPHA (Fang et al., "Temporally Controlled Targeting of 4-hydroxynonenal to Specific Proteins in Living Cells," *J. Am. Chem. Soc.* 135; 14496-99 (2013), which is hereby incorporated by reference in its entirety).

FIG. 30 shows LC-MS/MS identification of site of electrophilic modification on C-terminal HaloTagged Keap1 (SEQ ID NO: 16) ectopically expressed in HEK-293 cells subsequent to T-REX™ delivery redox targeting. The amino acid sequence of human KEAP1 (SEQ ID NO: 15) is also shown.

FIG. 31 shows LC-MS/MS identification of site of electrophilic modification on C-terminal HaloTagged Keap1 (SEQ ID NO: 16) ectopically expressed in HEK-293 cells subsequent to whole-cell CHE treatment. The amino acid sequence of human KEAP1 (SEQ ID NO: 15) is also shown.

FIG. 32 shows LC-MS/MS-based identification of the site of modification on Ube2V2 (SEQ ID NO: 2) post T-REX™ delivery-targeted HNEylation in HEK 293T cells and chemical structures of HNE- and HNE-derived-adducts on cysteine residue on peptides.

Figure 33:
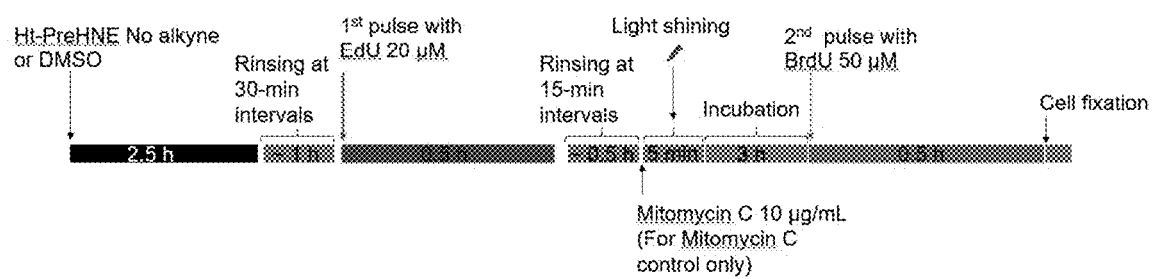

FIG. 33 shows measurement of DNA-replication efficiency by BrdU/EdU staining (in fixed cells).

Figure 34:
Figure 34:
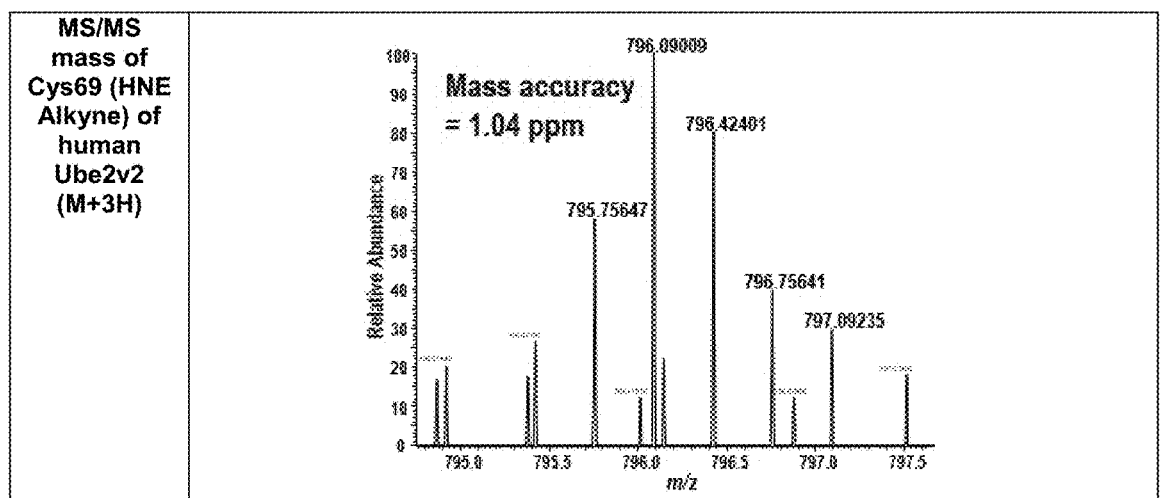

FIG. 34 chemical structures of HNE- and HNE-derived-adducts on cysteine residue peptides as well as LC-MS/MS-based identification of the site of modification on Ube2v2 (SEQ ID NO: 2) post T-REX™ delivery-targeted HNEylation in HEK 293T cells.

DETAILED DESCRIPTION OF THE INVENTION

A first aspect of the present invention relates to a method for identifying endogenous first responder protein-cysteines. The method involves culturing, in a culture medium, living cells either transfected or stably integrated with a nucleic acid encoding a protein tag under conditions effective to express the protein tag. The culture medium is treated with a bioinert photocaged precursor to a reactive electrophilic species (RES), which binds to the protein tag under conditions effective to form a bioinert photocaged precursor to an RES-protein tag complex. The culture medium is then subjected to actinic radiation so that the RES is released from the bioinert photocaged precursor to an RES-protein tag complex and binds to endogenous first responder protein-cysteines within the living cells, or subcellular locales where the protein tag is selectively expressed, to thereby form a covalent RES-labeled endogenous first responder protein-cysteine complex. The RES-labeled endogenous first responder protein-cysteine complex is then isolated.

Cysteine containing proteins encompass a large repertoire of proteins that participate in numerous cellular functions such as mitogenesis, proliferation, apoptosis, gene regulation, and proteolysis. These proteins include enzymes, transporters, receptors, channel proteins, adaptor proteins, chaperones, signaling proteins, plasma proteins, transcription related proteins, translation related proteins, mitochondrial proteins, or cytoskeletal related proteins. Dysregulated expression of a cysteine containing protein, in many cases, is associated with or modulates a disease, such as an inflammatory related disease, a neurodegenerative disease, or cancer.

Cysteine is unique owing to its intrinsically high nucleophilicity, which renders its sensitivity to modification by endogenous electrophiles and oxidants, as well as electrophile xenobiotics and candidate therapeutics. Previous studies have, for the most part, confirmed the preferential reactivity that Michael acceptor electrophiles like 4-Hydroxynonenal (HNE) show for cysteine over other potentially nucleophilic amino acids (e.g., lysine, histidine) in proteomes.

As used herein, the term "endogenous" is defined as a substance (i.e., a protein) occurring naturally in a living organism.

As used herein, "first responder protein-cysteines" are cysteine's present in endogenous proteins which are inherently tuned to rapidly react with specific reactive oxygen species or reactive electrophilic species (ROS/RES).

Figure 1:
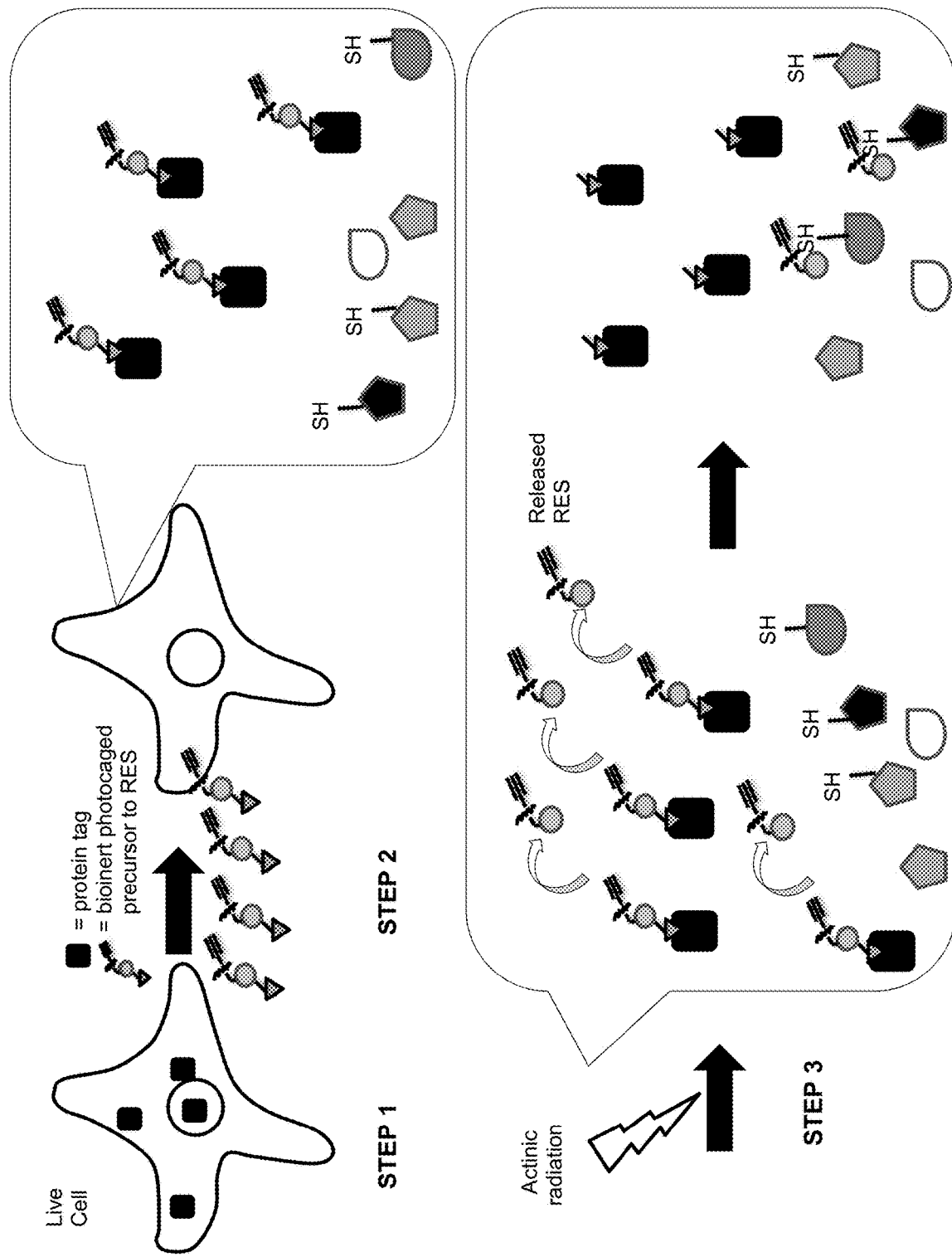
FIG. 1 is an illustration of the general method of G-REX™ profiling.
Figure 1:
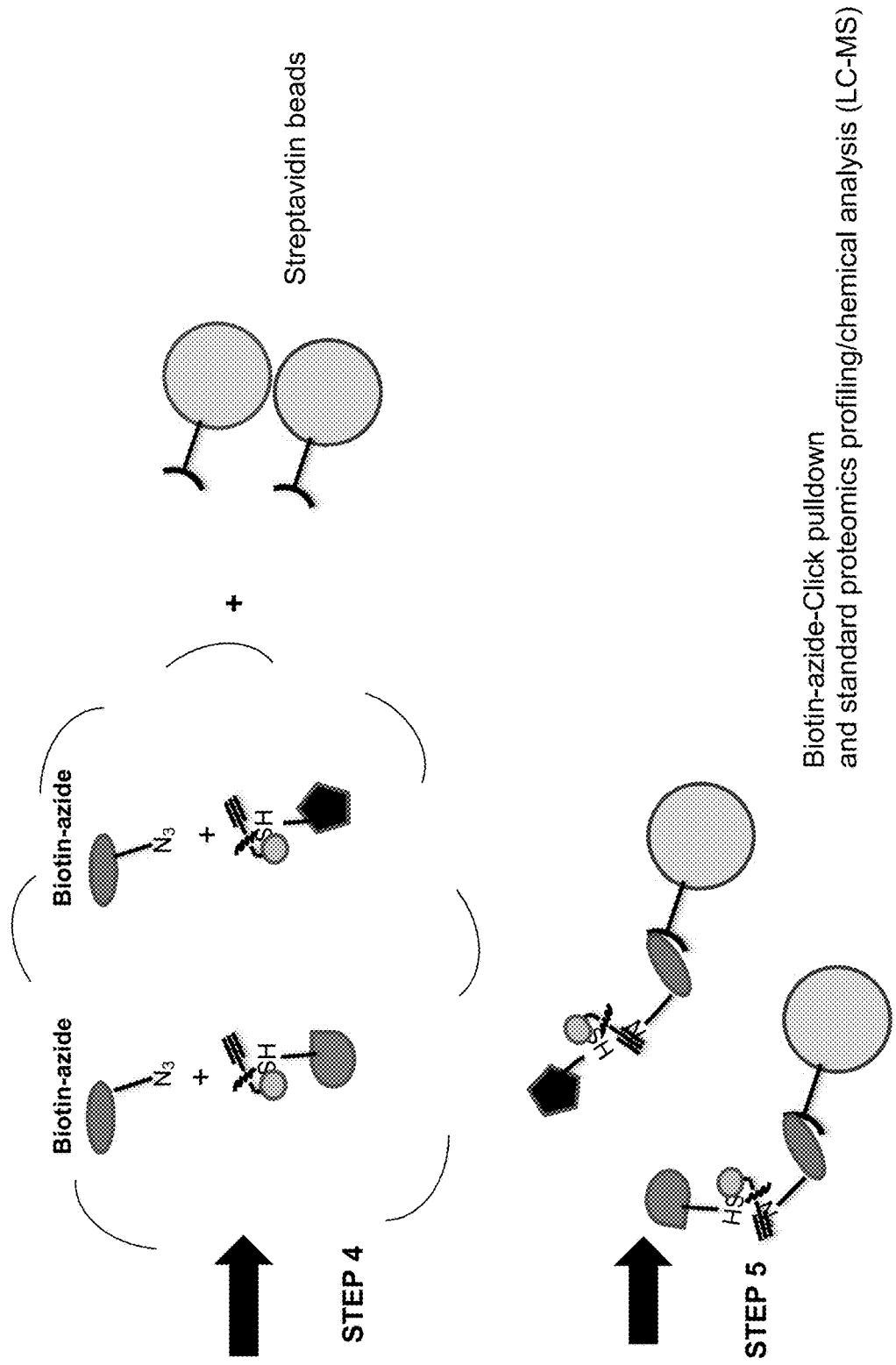

The methods described herein, termed G-REX™ profiling, identifies endogenous reactive cysteines in a native cellular environment. G-REX™ profiling enables a controlled release of a limited amount of an RES in situ, at a pre-determined dose, and for a given time. Generally, the method uses a live cell-permeable bioinert chemical probe that contains two key modular and transposable motifs: (1) a photo-activatable motif which masks the reactivity of the RES until light shining initiates its rapid release; and (2) an anchor which can bind to a non-intrusive protein tag that serves to localize the caged RES to a specific region of the live cell and limit the concentration of RES. The general G-REX™ profiling method is illustrated in FIG. 1. As shown in STEP 1 of FIG. 1, a live cell is cultured, in a culture medium, and the live cell is either transfected or stably integrated with a nucleic acid encoding a protein tag (shown as black square) under conditions effective to express the protein tag. Methods of transfecting cells are well known in the art and are described infra. The live cell is thus cultured and ectopically expresses the protein tag. STEP 2 of FIG. 1 further illustrates treatment of the culture medium with a bioinert photocaged precursor (i.e., a photo-activatable motif which masks the reactivity of the RES) to a reactive electrophilic species (RES), which binds to the protein tag. This forms a bioinert photocaged precursor to an RES-protein tag complex. As shown in FIG. 1, only the expressed protein tags are capable of binding to the bioinert photocaged precursor to an RES. As illustrated in STEP 3 of FIG. 1, upon light exposure, the RES is released from the bioinert photocaged precursor to an RES-protein tag complex. This results in the RES binding to endogenous first responder protein-cysteines (labeled with —SH) within the live cell, or subcellular locales where the protein tag is selectively expressed. The first responder protein cysteines within the given microenvironment of the live cell are given the first refusal to the limited amounts of released RES. A covalent RES-labeled endogenous first responder protein-cysteine complex can then be formed. As shown in STEP 4 of FIG. 1, the live cell is then lysed and the RES-labeled endogenous first responder protein-cysteine complexes are enriched using affinity capture via biotin-azide Click such that the azide chemically reacts with a functional group on the RES. This newly formed biotin-azide-RES-labeled first responder protein complex is incubated with streptavidin coated beads. STEP 5 of FIG. 1 illustrates the binding of the streptavidin and the biotin from the biotin-azide-RES-labeled first responder protein complex, thereby allowing Biotin-azide-Click pulldown and standard proteomics profiling/chemical analysis, such as liquid chromatography-high-resolution mass spectrometry (LC-MS) described infra, which identifies the first responder protein.

As described above, a live cell is either transfected or stably integrated with a nucleic acid encoding a protein tag. Methods of transfecting or stably integrating a nucleic acid encoding a protein tag under conditions effective to express the protein tag are well known in the art. For example, the nucleic acid can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences. A recombinant gene or DNA construct can be prepared prior to its insertion into an expression vector. For example, using conventional recombinant DNA techniques, a promoter-effective DNA molecule can be operably coupled 5' of a DNA molecule encoding the polypeptide and a transcription termination (i.e., polyadenylation sequence) can be operably coupled 3' thereof.

In accordance with this aspect of the invention, the nucleic acids encoding a protein tag of the present invention are inserted into an expression system or vector to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by SAMBROOK & RUSSELL, MOLECULAR CLONING: A LABORATORY MANUAL (Cold Springs Laboratory Press, 2001), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18 or pBR322 may be used. When using insect host cells, appropriate transfer vectors compatible with insect host cells include, pVL1392, pVL1393, pAcGP67 and pAcSecG2T, which incorporate a secretory signal fused to the desired protein, and pAcGHLT and pAcHLT, which contain GST and 6×His tags (BD Biosciences, Franklin Lakes, N.J.). Viral vectors suitable for use in carrying out this aspect of the invention include, adenoviral vectors, adeno-associated viral vectors, vaccinia viral vectors, nodaviral vectors, and retroviral vectors. Other suitable expression vectors are described in SAMBROOK AND RUSSELL, MOLECULAR CLONING: A LABORATORY MANUAL (Cold Springs Laboratory Press, 2001), which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in CURRENT PROTOCOLS IN MOLECULAR BIOLOGY (Fred M. Ausubel et al. eds., 2003), which is hereby incorporated by reference in its entirety.

Different genetic signals and processing events control many levels of gene expression (e.g., DNA transcription and messenger RNA ("mRNA") translation) expressed by the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression. Depending upon the host system utilized, any one of a number of suitable promoters may be used. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. When using insect cells, suitable baculovirus promoters include late promoters, such as 39K protein promoter or basic protein promoter, and very late promoters, such as the p10 and polyhedron promoters. In some cases it may be desirable to use transfer vectors containing multiple baculoviral promoters. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. The promoters can be constitutive or, alternatively, tissue-specific or inducible. In addition, in some circumstances inducible (TetOn) promoters can be used.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and promote binding of mRNA to ribosomes by duplexing with the rRNA to allow correct positioning of the ribosome. For a review on maximizing gene expression, see Roberts and Lauer, "Maximizing Gene Expression on a Plasmid Using Recombination In Vitro," *Methods in Enzymology*, 68:473-82 (1979), which is hereby incorporated by reference in its entirety.

The present invention may also include a host cell transformed with the DNA construct of the present invention. The host cell can be a prokaryote or a eukaryote. Host cells suitable for expressing the protein tags of the present invention include any one of the more commonly available gram negative bacteria. Suitable microorganisms include *Pseudomonas aeruginosa, Escherichia coli, Salmonella gastroenteritis (typhimirium), S. typhi, S. enteriditis, Shigellaflexneri, S. sonnie, S. dysenteriae, Neisseria gonorrhoeae, N. meningitides, Haemophilus influenzae, H. pleuropneumoniae, Pasteurella haemolytica, P. multilocida, Legionella pneumophila, Treponemapallidum, T. denticola, T. orales, Borrelia burgdorferi, Borrelia* spp., *Leptospira interrogans, Klebsiella pneumoniae, Proteus vulgaris, P. morganii, P. mirabilis, Rickettsia prowazeki, R. typhi, R. richettsii, Porphyromonas (Bacteroides) gingivalis, Chlamydia psittaci, C. pneumoniae, C. trachomatis, Campylobacterjejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A. salmonicida,* and *Yersinia pestis*.

In addition to bacteria cells, animal cells, in particular mammalian and insect cells, yeast cells, fungal cells, plant cells, or algal cells are also suitable host cells for transfection/transformation of the recombinant expression vector carrying an isolated polynucleotide molecule of the present invention. Mammalian cell lines commonly used in the art include Chinese hamster ovary cells, HeLa cells, baby hamster kidney cells, COS cells, and many others. Suitable insect cell lines include those susceptible to baculoviral infection, including SJ9 and Sf21 cells.

Methods for transforming/transfecting host cells with expression vectors are well-known in the art and depend on the host system selected, as described in SAMBROOK & RUSSELL, MOLECULAR CLONING: A LABORATORY MANUAL (Cold Springs Laboratory Press, 2001), which is hereby incorporated by reference in its entirety. For bacterial cells, suitable techniques include calcium chloride transformation, electroporation, and transfection using bacteriophage. For eukaryotic cells, suitable techniques include calcium phosphate transfection, DEAE-Dextran, electroporation, liposome-mediated transfection, and transduction using retrovirus or any other viral vector. For insect cells, the transfer vector containing the polynucleotide construct of the present invention is co-transfected with baculovirus DNA, such as AcNPV, to facilitate the production of a recombinant virus. Subsequent recombinant viral infection of Sf cells results in a high rate of recombinant protein production. Regardless of the expression system and host cell used to facilitate protein production, the expressed protein tag of the present invention can be readily purified using standard purification methods known in the art and described in PHILIP L. R. BONNER, PROTEIN PURIFICATION (Routledge 2007), which is hereby incorporated by reference in its entirety.

In one embodiment, the living cells are mammalian cells or bacterial cells.

Suitable mammalian cells and bacterial cells for use in the present invention are described above.

As described supra, the live cells are treated in culture medium with a bioinert photocaged precursor to a reactive electrophilic species (RES). This bioinert photocaged precursor to an RES then binds to the protein tag and forms a bioinert photocaged precursor to an RES-protein tag complex.

As described above, an RES is capable of reacting with cysteines of first-responder proteins. In one embodiment, the RES is a native lipid-derived electrophile. Lipid-derived electrophiles (LDEs) are a group of endogenous reactive metabolites generated as products of lipid peroxidation when cells are under oxidative stress. LDEs are able to covalently modify nucleophilic residues in proteins to alter their structures and activities, either resulting in irreversible functional damage or triggering aberrant signaling pathways. LDEs are well known in the art. By way of example, 4-Hydroxynonenal (HNE) is a major product generated when free radicals initiate the non-enzymatic fragmentation of lipids in biological membranes (Jacobs et al., "Systems Analysis of Protein Modification and Cellular Responses Induced by Electrophile Stress," *Acc Chem Res.* 43:673-683 (2010); Fritz et al., "Exploring the Biology of Lipid Peroxidation-derived Protein Carbonylation," *Chem Res Toxicol.* 24:1411-1419 (2011), which are hereby incorporated by reference in their entirety). The levels of HNE and HNE-protein adducts are elevated in cells and tissues exposed to oxidative stress, and HNE can regulate redox-responsive signaling pathways by still poorly understood mechanisms (Jacobs et al., "Systems Analysis of Protein Modification and Cellular Responses Induced by Electrophile Stress," *Acc Chem Res.* 43:673-683 (2010); Leonarduzzi et al., "Signaling Kinases Modulated by 4-hydroxynonenal," *Free Radic Biol Med.* 37:1694-1702 (2004); Jacobs et al., "Heat Shock Factor 1 Attenuates 4-Hydroxynonenal-mediated Apoptosis: Critical Role for Heat Shock Protein 70 Induction and Stabilization of Bcl-XL," *J Biol Chem.* 282:33412-33420 (2007), which are hereby incorporated by reference in their entirety). 15-deoxy-$\Delta$12,14-prostaglandin J2 (15d-PGJ2) is another LDE produced by a set of enzymes that metabolize arachidonic acid (Surh et al., "15-Deoxy-Delta(1)(2),(1)(4)-

Prostaglandin J(2), an Electrophilic Lipid Mediator of Anti-inflammatory and Pro-resolving Signaling," *Biochem Pharmacol.* 82:1335-1351 (2011), which is hereby incorporated by reference in its entirety). 15d-PGJ2 exhibits anti-inflammatory and cytoprotective properties and has therefore been designated as a pro-resolving signal (Surh et al., "15-Deoxy-Delta(1)(2),(1)(4)-Prostaglandin J(2), an Electrophilic Lipid Mediator of Anti-inflammatory and Pro-resolving Signaling," *Biochem Pharmacol.* 82:1335-1351 (2011), which is hereby incorporated by reference in its entirety). A third example is the LDE 2-trans-hexadecenal (2-HD), which is a product of sphingolipid metabolism and has recently been shown to function as a protein-modifying cofactor that promotes mitochondrial pathways for apoptosis (Chipuk et al., "Sphingolipid Metabolism Cooperates with BAK and BAX to Promote the Mitochondrial Pathway of Apoptosis," *Cell* 148:988-1000 (2012), which is hereby incorporated by reference in its entirety).

In some embodiments, the RES is a Michael-acceptor electrophile. A Michael acceptor is a conjugated system attached to an electron withdrawing group such as keto, cyano or ester (mostly an electrophile). A Michael acceptor may refer to an activated alkene, for example, such as an alkenyl group proximate to an electron-withdrawing group such as a ketone, nitro, halo, nitrile, carbonyl, or nitro group.

In one embodiment, the released RES is alkyne functionalized. By way of example, alkenal-based linear Michael acceptors have been implicated to regulate various cellular functions and cytoprotective responses. The alkyne functionalization at the chain terminus enables tracking of proteins covalently bound (e.g., via HaloTag, FIG. 3A) to the photocaged precursors, or quantitative assessment of the extent to which specific proteins are modified by the liberated electrophile (e.g., via Cy5-azide).

Exemplary alkyne functionalized RES include, without limitation, HNE(alkyne), ONE(alkyne), dHNE(alkyne), HHE(alkyne), HDE(alkyne), HDDE(alkyne), 2-HD (alkyne), DE(alkyne), CHE(alkyne), and CPE(alkyne).

In certain embodiments, the alkyne functionalized RES is 4-hydroxynonenal alkyne (HNE(alkyne)).

As described above and illustrated in FIG. 1 a protein tag is expressed in live cells that is capable of reacting with an RES. In certain embodiments, the protein tag is selected from the group consisting of a haloalkane dehalogenase, an O2-benzylcytosine derivative, an O6-alkylguanine-DNA-allkytransferase, and *E. coli* dihydrofolate reductase.

As described above and illustrated in FIG. 1, the culture medium is then treated with a bioinert photocaged precursor to an RES, which binds to the protein tag under conditions effective to form a bioinert photocaged precursor to an RES-protein tag complex.

As used herein, "a bioinert photocaged precursor to a reactive electrophilic species (RES)" refers to a photoactivatable reagent, which is a photocaged complex having an active agent (i.e., RES) contained within a photocage. The photocage molecule liberates the active agent into the medium when the photocage complex is photoactivated.

It should be understood that the method described herein is not limited to reliance on engineered mediator protein platforms (i.e., HaloTag), but can be used in conjunction with a known ligand specific to an endogenous protein when this ligand can be modified to include a photocaged RES without perturbing the binding efficiency of the ligand.

As described above and in FIG. 1, the culture medium is then subjected to actinic radiation so that the RES is released from the bioinert photocaged precursor to an RES-protein tag complex and binds to endogenous first responder protein-cysteines within the living cells, or subcellular locales where the protein tag is selectively expressed, to thereby form a covalent RES-labeled endogenous first responder protein-cysteine complex.

As used herein, "actinic radiation" refers to electromagnetic radiation that is capable of initiating a chemical reaction. In one embodiment, the subjecting is carried out with ultraviolet light at an energy level of 0.5-5.0 mW/cm$^2$.

In one embodiment, the bioinert photocaged RES precursor species is selected from the group consisting of

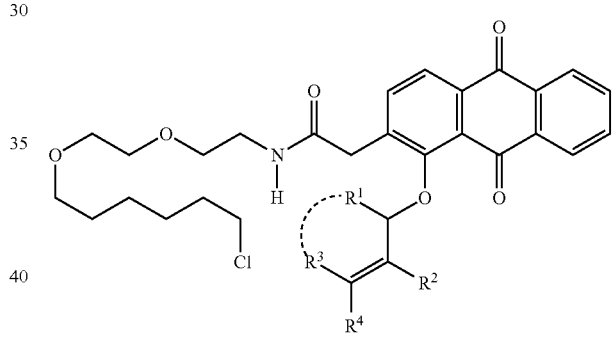

wherein R$^1$=H, Me; R$^2$=H; R$^3$=H; R$^4$=(C3 to C8)-alkynyl, 1-hydroxy(C3 to C8)-alkynyl, 1-oxo(C3 to C8)-alkynyl; R$^1$/R$^3$=—CH(CH$_2$C$_2$H)CH$_2$CH$_2$—, —CH$_2$CH(CH$_2$C$_2$H)—.

In another embodiment, the bioinert photocaged RES precursor is

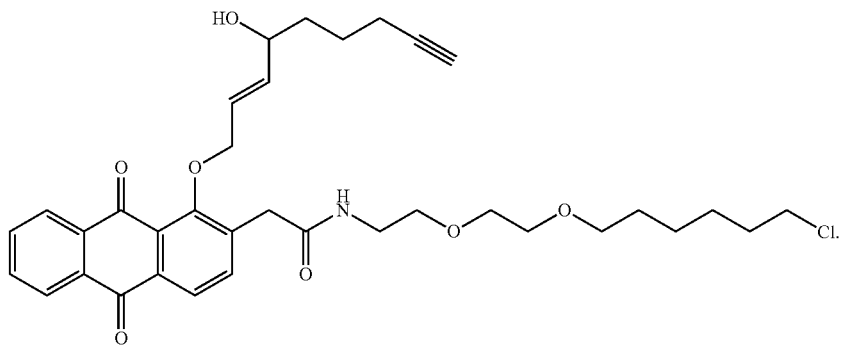 [SMILES: C#CCCCC(O)/C=C/COc1c(CC(=O)NCCOCCOCCCCCCCl)ccc2c1C(=O)c1ccccc1C2=O]

As shown in FIG. 1 and described in the Examples herein, isolation of the RES-labeled endogenous first responder protein-cysteine complex comprises biotinylating the RES-labeled endogenous first responder protein-cysteine complex and capturing the biotinylated RES-labeled endogenous first responder protein-cysteine complex with streptavidin. Methods of using biotin and streptavidin for isolation of proteins are well known in the art.

In one embodiment, and as shown in FIG. 1, following actinic radiation, the living cells may be lysed using methods known in the art specific for the cell type being used. Click chemistry can then be performed. The term "click chemistry" refers to a chemical philosophy introduced by K. Barry Sharpless of The Scripps Research Institute, describing chemistry tailored to generate covalent bonds quickly and reliably by joining small units comprising reactive groups together. Click chemistry does not refer to a specific reaction, but to a concept including reactions that mimic reactions found in nature. Click chemistry involves a reactant, or a reactive group, that can partake in a click chemistry reaction. For example, as described herein, an alkyne can partake in a reaction. By way of example, and as described herein, an azide is a partner in click chemistry to an alkyne. The biotin-azide labeled alkyne-functionalized-RES-modified first responder protein may then be incubated with streptavidin (e.g., Streptavidin Sepharose beads). Bound protein can then be eluted and subjected to western blot analysis. In another embodiment, Cy5-azide may be used and lysates may be analyzed by in-gel fluorescence of Cy5 signal.

In a further embodiment, and as shown in FIG. 1, the RES-labeled endogenous first responder protein-cysteine complex is subjected to chemical analysis effective to identify the first responder protein.

By way of example, in some instances, RES-labeled endogenous first responder protein-cysteine complex is further fragmentized to generate protein fragments. In some instances, fragmentation is generated through mechanical stress, pressure, or chemical means. In some instances, the protein from the RES-labeled endogenous first responder protein-cysteine complex is fragmented by a chemical means. In some embodiments, the chemical means is a protease. Exemplary proteases include, but are not limited to, serine proteases such as chymotrypsin A, penicillin G acylase precursor, dipeptidase E, DmpA aminopeptidase, subtilisin, prolyl oligopeptidase, D-Ala-D-Ala peptidase C, signal peptidase I, cytomegalovirus assemblin, Lon-A peptidase, peptidase Clp, *Escherichia coli* phage KIF endosialidase CIMCD self-cleaving protein, nucleoporin 145, lactoferrin, murein tetrapeptidase LD-carboxypeptidase, or rhomboid-1; threonine proteases such as ornithine acetyltransferase; cysteine proteases such as TEV protease, amidophosphoribosyltransferase precursor, gamma-glutamyl hydrolase (*Rattus norvegicus*), hedgehog protein, DmpA aminopeptidase, papain, bromelain, cathepsin K, calpain, caspase-1, separase, adenain, pyroglutamyl-peptidase I, sortase A, hepatitis C virus peptidase 2, sindbis virus-type nsP2 peptidase, dipeptidyl-peptidase VI, or DeSI-1 peptidase; aspartate proteases such as beta-secretase 1 (BACE1), beta-secretase 2 (BACE2), cathepsin D, cathepsin E, chymosin, napsin-A, nepenthesin, pepsin, plasmepsin, presenilin, or renin; glutamic acid proteases such as AfuGprA; and metalloproteases such as peptidase_M48.

In some instances, the fragmentation is a random fragmentation. In some instances, the fragmentation generates specific lengths of protein fragments, or the shearing occurs at particular sequence of amino acid regions.

In some embodiments, and as indicated in FIG. 1, the chemical analysis effective to identify the first responder protein involve a proteomic method such as liquid chromatography (LC) (e.g. high performance liquid chromatography), liquid chromatography-mass spectrometry (LC-MS), matrix-assisted laser desorption/ionization (MALDI-TOF), gas chromatography-mass spectrometry (GC-MS), capillary electrophoresis-mass spectrometry (CE-MS), or nuclear magnetic resonance imaging (NMR).

In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC).

In some embodiments, and as indicated in FIG. 1, the LC is coupled to a mass spectroscopy as a LC-MS method. In some embodiments, the LC-MS method includes ultra-performance liquid chromatography-electrospray ionization quadruple time-of-flight mass spectrometry (UPLC-ESI-QTOF-MS), ultra-performance liquid chromatography-electrospray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ERLIC-MS), liquid chromatography time-of-flight mass spectrometry (LC-QTOF-MS), liquid chromatography-tandem mass spectrometry (LC-MS/MS), multidimensional liquid chromatography coupled with tandem mass spectrometry (LC/LC-MS/MS). In some instances, the LC-MS method is LC/LC-MS/MS. In some embodiments, the LC-MS methods of the present disclosure are performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

In some embodiments, the nuclear magnetic resonance (NMR) method is any suitable method well known in the art for the detection of one or more cysteine binding proteins or protein fragments disclosed herein. In some embodiments, the NMR method includes one dimensional (1D) NMR methods, two dimensional (2D) NMR methods, solid state NMR methods and NMR chromatography. Exemplary ID NMR methods include $^{1}$Hydrogen, $^{13}$Carbon, $^{15}$Nitrogen, $^{17}$Oxygen, $^{19}$Fluorine, $^{31}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and ID-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR techniques include diffusion ordered spectroscopy (DOSY), DOSY-TOCSY and DOSY-HSQC.

In some embodiments, the results from the mass spectroscopy method are analyzed by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot.

Figure 2:
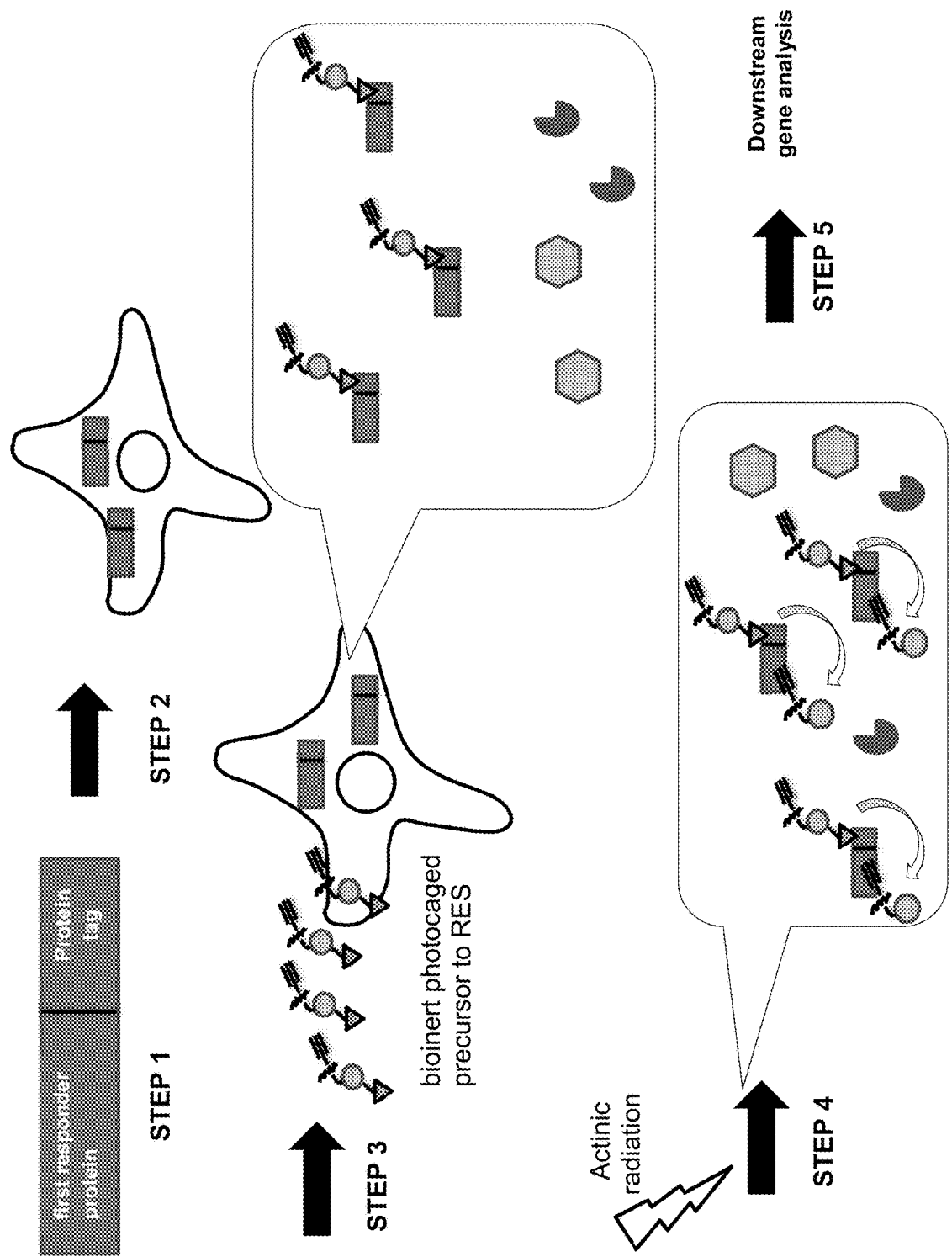
FIG. 2 is an illustration of the general method of T-REX™ delivery.

In accordance with the first aspect of the present invention, the method described herein may further include, using the T-REX™ delivery (targetable reactive glectrophiles and oxidants) methodology following the G-REX™ profiling methodology, to validate the first responder protein identified by the G-REX™ profiling methodology via T-REX™ delivery methodology. Generally, similar to G-REX™ profiling, the T-REX™ delivery method uses a live cell-permeable bioinert chemical probe that contains two key modular and transposable motifs: (1) a photo-activatable motif which masks the reactivity of the RES until light shining initiates its rapid release; and (2) an anchor which can bind to a non-intrusive protein tag that serves to localize the caged RES to a specific region of the live cell and limits the concentration of RES. The general T-REX™ delivery method is illustrated in FIG. 2. As shown in STEP 1 of FIG. 2, this method involves preparing a nucleic acid construct encoding a fusion protein comprising the first responder protein identified using G-REX™ profiling, where the first responder protein is coupled to the protein tag. As shown in STEP 2 of FIG. 2, living cells transfected with the nucleic acid construct are then cultured in a culture medium. Methods of transfecting cells are well known in the art and are described supra. STEP 3 of FIG. 2 illustrates treatment of the culture medium with a bioinert photocaged precursor to an RES (i.e., a photo-activatable motif which masks the reactivity of the RES) which binds to the protein tag of the fusion protein under conditions effective to form a bioinert photocaged precursor to an RES-protein tag complex. As illustrated in STEP 4 of FIG. 2, upon light exposure, the RES is released from the bioinert photocaged precursor to an RES-protein tag complex and binds to cysteines on the first responder protein component of the fusion protein.

In some embodiments, the method is as described in Example 2. There, either *E. coli* or mammalian cells, in a culture medium, are transfected with a nucleic acid which expresses HaloTag-fused proteins of interest (POI) (i.e., a fusion protein comprising the first responder protein obtained from the isolated RES-labeled endogenous first responder protein-cysteine complex). The culture medium is treated with a bioinert photocaged precursor to an RES to achieve a 1:1 covalent binding between the HaloTag and the photocaged probe. This forms the bioinert photocaged precursor to an RES-protein tag complex. The culture medium is then subjected to low-energy light (i.e., actinic radiation) to elicit rapid liberation of the RES from the photocaged probe bound to HaloTag. Proximity-enhancement (Long et al., "On-Demand Targeting: Investigating Biology with Proximity-Directed Chemistry," *J. Am. Chem. Soc.* 138: 3610-22 (2016), which is hereby incorporated by reference in its entirety) facilitates on-target, on-demand covalent modification of cysteines on the protein of interest (POI). HNE is also known to be capable of modifying lysine and histidine (see Example 2). Regardless of residue specificity, this method is able to ping one potential responsive protein with a precision dose of reactive lipid.

Methods of preparing nucleic acid constructs, cells, RES, protein tags, and bioinert photocaged RES precursors are described above.

In a further embodiment, cellular responses to the RES binding to cysteines on the first responder protein component of the fusion protein are assessed. By way of example, pathway activation may be analyzed using dual-luciferase reporter assays or GFP reporter assays by flow cytometry. Endogenous downstream gene activation can be analyzed by qRT-PCR and western blot. All of these methods are well known in the art.

In general, reporter assays have found wide use in the study of cellular genetic regulation and gene function. In studies of genetic regulation, a regulatory element (e.g. promoter or enhancer) fused to a reporter gene is transfected into cells. The amount of reporter molecule subsequently generated reflects the transcriptional activity of the regulatory element.

Reporter genes can be used to measure, among others, transcriptional activities of synthetic enhancers (e.g. enhancers formed by multimerization of a single nuclear binding site motif), and protein-protein interactions using two-hybrid systems.

In studies of gene function, marker molecules (e.g., GFP) distinguish cells expressing transfected/infected genes from uninfected cells. A gene of interest is co-transfected with a marker gene. Cells expressing the gene of interest are identified by the presence of marker molecule. Alternatively, expression of a reporter gene, such as GFP, can be placed under the control of a particular transcription factor. Upon activation of the transcription factor, for example by an RES binding to cysteines on the first responder protein, GFP will be expressed in the transfected cell and quantified by flow cytometry.

Briefly, in the case of a dual-luciferase reporter assay, one reporter enables measuring the response of an experimental target to the RES binding to cysteines on the first responder protein, while the other reporter acts as an internal control to standardize the data received from the first reporter. Such assays can be used to assess receptor activity, transcription factors, intracellular signaling, mRNA processing and protein folding.

A second aspect of the present invention relates to a method of screening candidate compounds suitable for regulating the DNA damage response. The method involves providing a protein comprising the amino acid sequence of IYSL(K/R)(L/V)ECG(S/P)KYPE(A/V)PP(S/T)VR (SEQ ID NO: 1) and contacting the protein with the candidate compounds under conditions suitable for the candidate compounds to react with cysteine in the protein. Compounds that regulate the DNA damage response are then identified, based on the contacting step.

A variety of genes are involved in the control of cell growth and division. The cell cycle, or cell-division cycle, is the series of events that ensures faithful, error-free duplication of the cellular genome (replication) and subsequent physical division into two daughter cells. Tight regulation of this process ensures that the DNA in a dividing cell is copied correctly, any damage in the DNA is repaired, and that each daughter cell receives a full set of chromosomes. The cell cycle has checkpoints, which ensure that a cell cannot advance from one phase to another if the genome is in need of repair. Genes involved in this process are referred to as being part of the cellular DNA damage response (DDR) machinery.

As described herein, candidate compounds, such as small-molecule electrophiles, can be photocaged and contacted with the protein of SEQ ID NO: 1 in a manner as illustrated in FIG. 2. For example, a nucleic acid encoding a fusion protein comprising SEQ ID NO: 1 and a protein tag can be transfected into live cells as described above. The cells can then be treated with a bioinert photocaged precursor to a candidate small molecule electrophile (i.e., a photo-activatable motif which masks the reactivity of the electrophile) which binds to the protein tag of the fusion protein under conditions effective to form a bioinert photocaged precursor to small molecule electrophile-protein tag complex. Upon light exposure, the small molecule electrophile is released and binds to cysteines on the protein comprising SEQ ID NO: 1.

In one embodiment, the protein comprises the amino acid sequence of IYSLKVECGPKYPEAPPSVR (SEQ ID NO: 2).

Identification of the candidate compounds which regulate the DNA damage response may be achieved, for example, and as described herein, by measuring the ubiquitination levels of proteins during DNA damage as increases in ubiquitination of DDR related proteins promotes DDR-like responses.

As described in Example 1 infra, Biotin® Anti-K63 TUBE is an ideal reagent for efficient isolation and enrichment of K63-polyubiquitinated proteins from cell & tissue extracts or in vitro synthesized mixtures. This method involves a peptide consisting of multiple ubiquitin interaction motifs (UIMs) joined by a rigid, helical linker that spaces the UIMs for selective binding to extended K63-linked polyubiquitin chains. The result is a peptide the exhibits high affinity binding to K63-linked polyubiquitin together with 1000 to 10,000-fold selectivity over K48- and K11-linkages. This method allows for suitable isolation, purification, and characterization of proteins modified by K63-linked polyubiquitin as well as isolation of K63-linked polyubiquitin without the need for overexpression of ubiquitin mutants, tagged ubiquitins or the inclusion of DUB inhibitors any of which could alter cellular physiology. Isolated ubiquitinated proteins can then be characterized by Western blot, mass spectometry or further biochemical analysis.

Alternatively, DNA synthesis stall can be measured, as shown in Example 1 herein, using a dual-pulse assay, which involves sequential, timed pulsing with two orthogonal DNA-labeling agents (EdU, followed by BrdU) that can be detected by fluorescence imaging In certain embodiments, the identified compound is suitable for treating conditions selected from the group consisting of cancer, autoimmune diseases, inflammatory diseases, and neurological diseases.

A third aspect of the present invention is directed to a method of screening candidate compounds suitable for regulating NF-κB signaling. The method involves providing a protein comprising the amino acid sequence of (M/I)YSL(K/R)(V/I)ECGP(K/R)YPE(S/A/T)PP(F/S/Y)VR (SEQ ID NO: 3) and contacting the protein with the candidate compounds under conditions suitable for the candidate compounds to react with cysteine in the protein. Compounds that regulate NF-κB signaling are then identified, based on the contacting step.

The transcription factor NF-κB is involved in regulating the expression of a number of genes involved in mediating inflammatory and immune responses. NF-κB regulates the transcription of genes including TNF-α, IL-I, IL-2, IL-6, adhesion molecules (such as E-selectin) and chemokines (such as Rantes), among others. A kinase critical to the activation of NF-κB is the IKB kinase (IKK). This kinase plays a key role in the phosphorylation of IKB. Once IKB is phosphorylated it undergoes degradation leading to the release of NF-κB which can translocate into the nucleus and activate the transcription of the genes described above.

Candidate compounds, such as small-molecule electrophiles, may be contacted with the protein of SEQ ID NO: 2 in a manner as described above.

Identification of whether candidate compounds regulate NF-kB can be achieved using various methods known in the art. By way of example, a cellular transrepressional assay may be performed. In such assays, a plasmid containing NF-κB DNA binding sites, such as pNF-κB-Luc, (Stratagene, LaJolla Calif.), followed by the gene for luciferase, is transfected into cells. Cells can then be activated with phorbol myristic acid (PMA) plus or minus test molecules for 7 hours. Other stimuli, such as TNF-α or lipopolysaccharide, may also be used. After 7 hours, a luciferase reagent is added to measure luciferase enzymatic activity in the cell. After a 10 minute incubation of luciferase reagent with cells, luminescence is measured using a luminescence counter. NF-kB activity is then calculated as the percentage decrease or increase in the signal induced by stimulus alone. NF-κB assays similar to this are described in Yamamoto K., et al., *J Biol Chem* 270(52):31315-20 (1995), which is hereby incorporated by reference in its entirety, and may be used.

Regulation of NF-κB can also be determined as described in Example 1 infra. Briefly, mammalian cells may be transfected with a nucleic acid encoding a fusion protein comprising SEQ ID NO: 3 and a protein tag and a nucleic acid encoding NF-κB luciferase. After 24 hours, cells can be treated with a bioinert photocaged precursor to a candidate small molecule electrophile which may bind to the protein tag component of the fusion protein. The cells can then be light activated to release the candidate small molecule electrophile and allow for potential binding of the candidate electrophile to cysteines on the fusion protein component comprising SEQ ID NO: 3. Any resulting NF-κB activation that occurs is then measured via luciferase assay.

In one embodiment, the protein comprises the amino acid sequence of IYSLKIECGPKYPEAPPFVR (SEQ ID NO: 4).

In certain embodiments, the identified compound is suitable for treating conditions selected from the group consisting of cancer, autoimmune diseases, inflammatory diseases, and neurological diseases.

EXAMPLES

The following examples are provided to illustrate embodiments of the present invention but they are by no means intended to limit its scope.

Example 1—Ube2V2 is a Rosetta Stone Bridging Redox and Ubiquitin Codes, Coordinating DDR Responses Materials and Methods
General Materials and Methods.

All procedures related to zebrafish studies conform to the National Institutes of Health guidelines regarding animal experimentation and were approved by Cornell University's Institutional Animal Care and Use committees. All primers were from IDT. Phusion HotStart II polymerase was from Thermo Scientific. All restriction enzymes were from NEB. Complete EDTA free protease inhibitor was from Roche. 1×RIPA buffer was from Santa Cruz biotech. 1× Bradford dye was from BioRad. Pre-HNE and HaloTag-targetable photocaged precursor HNE alkyne (Ht-PreHNE) were synthesized as described previously (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137: 10-13 (2015), which are hereby incorporated by reference in their entirety). Cyanine5 (Cy5)-azide and Cu(TBTA) were from Lumiprobe. Dithiothreitol (DTT), streptomycin sulfate, isopropyl 3-D-1-thio-galactopyranoside (IPTG), TCEP-HCl, Coelenterazine, and D-Luciferin were from Goldbio Biotechnology. Conenzyme A was from Avanti Polar lipids. trans-1,2-Diaminocyclohexane-N,N,N',N'-tetraacetic acid monohydrate (CDTA) was from Alfa Aesar. EdU (5-ethynyl-2'-deoxyuridine) and BrdU (5-Bromo-2'-deoxyuridine) were from Chem-Impex. Adenosine triphosphate disodium salt hydrate (ATP) was from Fisher. Biotin-dPEG®$_{11}$-azide was from Quanta Biodesign. Streptavidin sepharose beads were from GE Healthcare. ANTI-FLAG® M2 affinity gel (A2220) and monoclonal anti-HA-agarose, clone HA-7 (A2095) were from Sigma-Aldrich. Bovine Serum Albumin (BSA) powder was from Thermo Scientific. All other chemicals were from Sigma. BL21 (DE3)-RIL codon plus cells were from Stratagene. The plasmid for recombinant expression of TEV protease (pRK793, Addgene #8827), ubiquitin-conjugating enzyme E2 variant 1 (Addgene #31429), ubiquitin-conjugating enzyme E2 variant 2 (Addgene #31430), ubiquitin-conjugating enzyme E2N (Addgene #12461), histone H2A (Addgene #63560) and the empty pCS2+8 vector (Addgene #34931) were from Addgene. HA-Ubiquitin plasmid was a gift from Prof. Ling Qi (Cornell University). Myc-MCM6 was a gift from Prof. John Schimenti (Cornell University). 3×FLAG peptide was from APEXBIO (A6001). HEK 293T cells were from American Type Culture Collection (ATCC). 1×DPBS, 1× Trypsin (TrypLe), 100× NEAA, 100× sodium pyruvate, 100× Penicillin-Streptomycin and 1×MEM+ Glutamax media were from Life Technologies. Fetal Bovine Serum (FBS) was from Sigma (F2442). TransIT 2020 transfection reagent was from Mirus Bio LLC. Polyethylenimine, linear, MW 25,000 (PEI, 23966-1) was from Polysciences, Inc. 365 nm UV lights were from Spectroline (for handheld size, ENF240C and if larger surface area is needed, XX15N). For T-REX™ delivery experiments, the lamps were positioned above confluent monolayer of cells or zebrafish embryos in 6-well plates such that the power of UV irradiation was ~5 mW/cm$^2$ (as measured by a hand-held power sensor (Spectroline, XDS-1000). For all confocal imaging experiments, a Zeiss LSM710 confocal microscope was used. Quantitation of fluorescence intensity was performed using Image-J software (NIH, version 1.50 g). In-gel fluorescence analysis and imaging of western blots and Coomassie stained gel were performed using BioRad Chemi-Doc MP Imaging system. Densitometric quantitation was performed using BioRad Image Lab software (version 4.1). Cy5 excitation source was epi illumination and 695/55 emission filter was used. Cell counting was done by Countess II FL (A25750). His$_6$-TEV S219V protease was recombinantly expressed and purified from BL21(DE3)-RIL cells using TALON resin. Dual luciferase assay was performed using a BioTek Cytation™ 3 Cell Imaging Multi-mode reader with dual reagent injectors. Proteomics data from G-REX™ profiling and SILAC-T-REX™ delivery experiments are provided as Table 1, below.

TABLE 1

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q15819 | Ubiquitin-conjugating enzyme E2 variant 2 OS = Homo sapiens GN = UBE2V2 PE = 1 SV = 4 - [UB2V2_HUMAN] | 345.27 | 67.59 | 6 | 6 | 11 | 137 | 145 | 16.4 | 8.09 | 1 | 3.19 |
| A8K486 | Peptidyl-prolyl cis-trans isomerase OS = Homo sapiens PE = 2 SV = 1 - [A8K486_HUMAN] | 233.60 | 75.15 | 8 | 11 | 12 | 88 | 165 | 18.0 | 6.90 | 4 | 3.63 |
| P61204 | ADP-ribosylation factor 3 OS = Homo sapiens GN = ARF3 PE = 1 SV = 2 - [ARF3_HUMAN] | 201.80 | 59.67 | 10 | 7 | 13 | 73 | 181 | 20.6 | 7.43 | 1 | 3.982 |
| Q13404 | Ubiquitin-conjugating enzyme E2 variant 1 OS = Homo sapiens GN = UBE2V1 PE = 1 SV = 2 - [UB2V1_HUMAN] | 161.06 | 60.54 | 6 | 4 | 9 | 70 | 147 | 16.5 | 7.93 | 2 | 3.234 |
| P30050 | 60S ribosomal protein L12 OS = Homo sapiens GN = RPL12 PE = 1 SV = 1 - [RL12_HUMAN] | 153.80 | 58.79 | 3 | 7 | 8 | 55 | 165 | 17.8 | 9.42 | 3 | 3.63 |
| G3V1A4 | Cofilin 1 (Non-muscle), isoform CRA_a OS = Homo sapiens GN = CFL1 PE = 1 SV = 1 - [G3V1A4_HUMAN] | 153.55 | 69.80 | 8 | 9 | 12 | 49 | 149 | 16.8 | 8.35 | 4 | 3.278 |
| Q32Q12 | Nucleoside diphosphate kinase OS = Homo sapiens GN = NME1-NME2 PE = 1 SV = 1 - [Q32Q12_HUMAN] | 149.92 | 63.36 | 8 | 4 | 11 | 58 | 292 | 32.6 | 8.48 | 5 | 6.424 |
| P08708 | 40S ribosomal protein S17 OS = Homo sapiens GN = RPS17 PE = 1 SV = 2 - [RS17_HUMAN] | 142.89 | 54.81 | 4 | 9 | 9 | 59 | 135 | 15.5 | 9.85 | 1 | 2.97 |
| H3BUX2 | Cytochrome b5 type B OS = Homo sapiens GN = CYB5B PE = 1 SV = 1 - [H3BUX2_HUMAN] | 124.84 | 65.00 | 6 | 9 | 9 | 37 | 140 | 15.7 | 6.10 | 3 | 3.08 |
| P18085 | ADP-ribosylation factor 4 OS = Homo sapiens GN = ARF4 PE = 1 SV = 3 - [ARF4_HUMAN] | 121.93 | 51.67 | 3 | 3 | 8 | 46 | 180 | 20.5 | 7.14 | 2 | 3.96 |
| C9J1Z8 | ADP-ribosylation factor 5 (Fragment) OS = Homo sapiens GN = ARF5 PE = 1 SV = 1 - [C9J1Z8_HUMAN] | 120.93 | 52.67 | 3 | 1 | 7 | 45 | 150 | 17.1 | 7.34 | 1 | 3.3 |
| P62263 | 40S ribosomal protein S14 OS = Homo sapiens GN = RPS14 PE = 1 SV = 3 - [RS14_HUMAN] | 118.03 | 68.87 | 3 | 9 | 9 | 38 | 151 | 16.3 | 10.05 | 1 | 3.322 |
| P35268 | 60S ribosomal protein L22 OS = Homo sapiens GN = RPL22 PE = 1 SV = 2 - [RL22_HUMAN] | 111.65 | 68.75 | 8 | 9 | 9 | 47 | 128 | 14.8 | 9.19 | 1 | 2.816 |
| E9PJK1 | Tetraspanin OS = Homo sapiens GN = CD81 PE = 1 SV = 1 - [E9PJK1_HUMAN] | 111.44 | 35.76 | 7 | 3 | 3 | 42 | 165 | 18.0 | 5.00 | 10 | 3.63 |
| V9HWC6 | Peptidyl-prolyl cis-trans isomerase OS = Homo sapiens GN = HEL-S-39 PE = 2 SV = 1 - [V9HWC6_HUMAN] | 104.48 | 53.37 | 2 | 13 | 13 | 40 | 208 | 22.7 | 9.32 | 1 | 4.576 |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| O60830 | Mitochondrial import inner membrane translocase subunit Tim17-B OS = Homo sapiens GN = TIMM17B PE = 1 SV = 1 - [TI17B_HUMAN] | 102.71 | 61.63 | 3 | 8 | 8 | 36 | 172 | 18.3 | 9.03 | 3 | 3.784 |
| H0YNW5 | Deoxyuridine 5'-triphosphate nucleotidohydrolase, mitochondrial OS = Homo sapiens GN = DUT PE = 1 SV = 1 - [H0YNW5_HUMAN] | 97.30 | 64.67 | 8 | 8 | 8 | 28 | 167 | 17.8 | 7.28 | 2 | 3.674 |
| P15531 | Nucleoside diphosphate kinase A OS = Homo sapiens GN = NME1 PE = 1 SV = 1 - [NDKA_HUMAN] | 93.80 | 59.21 | 4 | 1 | 8 | 42 | 152 | 17.1 | 6.19 | 3 | 3.344 |
| O43447 | Peptidyl-prolyl cis-trans isomerase H OS = Homo sapiens GN = PPIH PE = 1 SV = 1 - [PPIH_HUMAN] | 82.66 | 55.37 | 4 | 7 | 7 | 24 | 177 | 19.2 | 8.07 | 5 | 3.894 |
| P04075 | Fructose-bisphosphate aldolase A OS = Homo sapiens GN = ALDOA PE = 1 SV = 2 - [ALDOA_HUMAN] | 74.87 | 40.38 | 11 | 8 | 8 | 22 | 364 | 39.4 | 8.09 | | |
| P07737 | Profilin-1 OS = Homo sapiens GN = PFN1 PE = 1 SV = 2 - [PROF1_HUMAN] | 72.72 | 59.29 | 3 | 7 | 7 | 24 | 140 | 15.0 | 8.27 | | |
| P49755 | Transmembrane emp24 domain-containing protein 10 OS = Homo sapiens GN = TMED10 PE = 1 SV = 2 - [TMEDA_HUMAN] | 67.87 | 41.55 | 5 | 10 | 10 | 22 | 219 | 25.0 | 7.44 | | |
| P63241 | Eukaryotic translation initiation factor 5A-1 OS = Homo sapiens GN = EIF5A PE = 1 SV = 2 - [IF5A1_HUMAN] | 67.18 | 66.23 | 8 | 10 | 10 | 27 | 154 | 16.8 | 5.24 | | |
| E5RI99 | 60S ribosomal protein L30 (Fragment) OS = Homo sapiens GN = RPL30 PE = 1 SV = 1 - [E5RI99_HUMAN] | 65.53 | 51.75 | 3 | 5 | 5 | 25 | 114 | 12.6 | 9.55 | | |
| P07437 | Tubulin beta chain OS = Homo sapiens GN = TUBB PE = 1 SV = 2 - [TBB5_HUMAN] | 63.20 | 44.82 | 49 | 4 | 15 | 24 | 444 | 49.6 | 4.89 | | |
| A8K4W8 | cDNA FLJ77917, highly similar to Homo sapiens ubiquitin-conjugating enzyme E2L 3 (UBE2L3), transcript variant 1, mRNA OS = Homo sapiens PE = 2 SV = 1 - [A8K4W8_HUMAN] | 57.53 | 67.53 | 2 | 6 | 6 | 29 | 154 | 17.8 | 8.75 | | |
| Q07812 | Apoptosis regulator BAX OS = Homo sapiens GN = BAX PE = 1 SV = 1 - [BAX_HUMAN] | 56.20 | 44.27 | 8 | 8 | 8 | 19 | 192 | 21.2 | 5.22 | | |
| P28074 | Proteasome subunit beta type-5 OS = Homo sapiens GN = PSMB5 PE = 1 SV = 3 - [PSB5_HUMAN] | 55.73 | 45.25 | 2 | 8 | 8 | 18 | 263 | 28.5 | 6.92 | | |
| O14880 | Microsomal glutathione S-transferase 3 OS = Homo sapiens GN = MGST3 PE = 1 SV = 1 - [MGST3_HUMAN] | 55.57 | 50.66 | 4 | 6 | 6 | 21 | 152 | 16.5 | 9.38 | | |
| P24666 | Low molecular weight phosphotyrosine protein phosphatase OS = Homo sapiens GN = ACP1 PE = 1 SV = 3 - [PPAC_HUMAN] | 55.41 | 62.66 | 5 | 8 | 8 | 17 | 158 | 18.0 | 6.74 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q8N4V1 | Membrane magnesium transporter 1 OS = Homo sapiens GN = MMGT1 PE = 1 SV = 1 - [MMGT1_HUMAN] | 55.05 | 26.72 | 1 | 2 | 2 | 22 | 131 | 14.7 | 9.16 | | |
| Q9Y3E5 | Peptidyl-tRNA hydrolase 2, mitochondrial OS = Homo sapiens GN = PTRH2 PE = 1 SV = 1 - [PTH2_HUMAN] | 54.85 | 66.48 | 3 | 9 | 9 | 19 | 179 | 19.2 | 8.73 | | |
| P68371 | Tubulin beta-4B chain OS = Homo sapiens GN = TUBB4B PE = 1 SV = 1 - [TBB4B_HUMAN] | 54.52 | 35.28 | 35 | 1 | 12 | 21 | 445 | 49.8 | 4.89 | | |
| Q9NRV9 | Heme-binding protein 1 OS = Homo sapiens GN = HEBP1 PE = 1 SV = 1 - [HEBP1_HUMAN] | 53.13 | 61.90 | 3 | 8 | 8 | 15 | 189 | 21.1 | 5.80 | | |
| P62244 | 40S ribosomal protein S15a OS = Homo sapiens GN = RPS15A PE = 1 SV = 2 - [RS15A_HUMAN] | 52.57 | 53.85 | 5 | 5 | 8 | 18 | 130 | 14.8 | 10.13 | | |
| B3KT06 | cDNA FLJ37398 fis, clone BRAMY2027467, highly similar to Tubulin alpha-ubiquitous chain OS = Homo sapiens PE = 2 SV = 1 - [B3KT06_HUMAN] | 51.27 | 39.90 | 30 | 10 | 10 | 18 | 416 | 46.3 | 5.14 | | |
| B4DVQ0 | cDNA FLJ58286, highly similar to Actin, cytoplasmic 2 OS = Homo sapiens PE = 2 SV = 1 - [B4DVQ0_HUMAN] | 50.17 | 30.03 | 46 | 3 | 6 | 16 | 333 | 37.3 | 5.71 | | |
| B2R6X6 | Peptidyl-prolyl cis-trans isomerase OS = Homo sapiens PE = 2 SV = 1 - [B2R6X6_HUMAN] | 49.54 | 46.86 | 4 | 6 | 6 | 18 | 207 | 22.0 | 9.50 | | |
| F8W7Q4 | Protein FAM162A OS = Homo sapiens GN = FAM162A PE = 1 SV = 1 - [F8W7Q4_HUMAN] | 49.51 | 40.97 | 4 | 9 | 9 | 23 | 144 | 16.5 | 9.77 | | |
| Q9BTQ7 | Similar to ribosomal protein L23 (Fragment) OS = Homo sapiens PE = 2 SV = 1 - [Q9BTQ7_HUMAN] | 49.05 | 35.07 | 5 | 6 | 6 | 19 | 134 | 14.1 | 10.26 | | |
| H3BN98 | Uncharacterized protein (Fragment) OS = Homo sapiens PE = 4 SV = 2 - [H3BN98_HUMAN] | 48.72 | 35.02 | 6 | 3 | 6 | 18 | 237 | 27.2 | 9.55 | | |
| O75223 | Gamma-glutamylcyclotransferase OS = Homo sapiens GN = GGCT PE = 1 SV = 1 - [GGCT_HUMAN] | 48.36 | 72.34 | 6 | 10 | 10 | 20 | 188 | 21.0 | 5.14 | | |
| P61586 | Transforming protein RhoA OS = Homo sapiens GN = RHOA PE = 1 SV = 1 - [RHOA_HUMAN] | 47.82 | 67.36 | 17 | 8 | 8 | 16 | 193 | 21.8 | 6.10 | | |
| V9HW35 | Epididymis secretory protein Li 55 OS = Homo sapiens GN = HEL-S-55 PE = 2 SV = 1 - [V9HW35_HUMAN] | 47.50 | 72.84 | 2 | 9 | 9 | 16 | 162 | 17.0 | 7.24 | | |
| Q9ULC4 | Malignant T-cell-amplified sequence 1 OS = Homo sapiens GN = MCTS1 PE = 1 SV = 1 - [MCTS1_HUMAN] | 47.48 | 53.04 | 1 | 7 | 7 | 16 | 181 | 20.5 | 8.82 | | |
| B3KSE0 | cDNA FLJ36069 fis, clone TEST12019406, highly similar to HEME OXYGENASE 2 (EC 1.14.99.3) OS = Homo sapiens PE = 2 SV = 1 - [B3KSE0_HUMAN] | 47.42 | 25.00 | 9 | 6 | 6 | 20 | 316 | 35.9 | 5.50 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| B8ZZU8 | Transcription elongation factor B (SIII), polypeptide 2 (18 kDa, elongin B), isoform CRA_b OS = Homo sapiens GN = TCEB2 PE = 1 SV = 1 - [B8ZZU8_HUMAN] | 46.86 | 72.57 | 3 | 5 | 5 | 19 | 113 | 12.5 | 4.97 | | |
| P30048 | Thioredoxin-dependent peroxide reductase, mitochondrial OS = Homo sapiens GN = PRDX3 PE = 1 SV = 3 - [PRDX3_HUMAN] | 45.51 | 41.41 | 2 | 7 | 7 | 18 | 256 | 27.7 | 7.78 | | |
| X6RJP6 | Transgelin-2 (Fragment) OS = Homo sapiens GN = TAGLN2 PE = 1 SV = 1 - [X6RJP6_HUMAN] | 45.50 | 58.29 | 2 | 9 | 9 | 15 | 187 | 21.1 | 7.81 | | |
| P62316 | Small nuclear ribonucleoprotein Sm D2 OS = Homo sapiens GN = SNRPD2 PE = 1 SV = 1 - [SMD2_HUMAN] | 44.85 | 59.32 | 2 | 7 | 7 | 17 | 118 | 13.5 | 9.91 | | |
| O96000 | NADH dehydrogenase [ubiquinone] 1 beta subcomplex subunit 10 OS = Homo sapiens GN = NDUFB10 PE = 1 SV = 3 - [NDUBA_HUMAN] | 42.72 | 40.12 | 4 | 7 | 7 | 14 | 172 | 20.8 | 8.48 | | |
| M0R3D6 | 60S ribosomal protein L18a (Fragment) OS = Homo sapiens GN = RPL18A PE = 1 SV = 1 - [M0R3D6_HUMAN] | 42.31 | 41.84 | 11 | 6 | 6 | 13 | 141 | 16.7 | 10.77 | | |
| Q9NRC8 | NAD-dependent protein deacetylase sirtuin-7 OS = Homo sapiens GN = SIRT7 PE = 1 SV = 1 - [SIR7_HUMAN] | 42.29 | 14.25 | 1 | 3 | 3 | 12 | 400 | 44.9 | 9.74 | | |
| E9PGT6 | COP9 signalosome complex subunit 8 OS = Homo sapiens GN = COPS8 PE = 1 SV = 1 - [E9PGT6_HUMAN] | 42.13 | 73.99 | 5 | 6 | 6 | 15 | 173 | 19.3 | 5.53 | | |
| P57105 | Synaptojanin-2-binding protein OS = Homo sapiens GN = SYNJ2BP PE = 1 SV = 2 - [SYJ2B_HUMAN] | 41.54 | 48.28 | 4 | 5 | 5 | 19 | 145 | 15.9 | 6.30 | | |
| P07741 | Adenine phosphoribosyltransferase OS = Homo sapiens GN = APRT PE = 1 SV = 2 - [APT_HUMAN] | 41.47 | 63.89 | 5 | 8 | 8 | 14 | 180 | 19.6 | 6.02 | | |
| P09211 | Glutathione S-transferase P OS = Homo sapiens GN = GSTP1 PE = 1 SV = 2 - [GSTP1_HUMAN] | 41.34 | 55.71 | 4 | 4 | 7 | 19 | 210 | 23.3 | 5.64 | | |
| A0A0S2Z4G7 | Nucleophosmin (Nucleolar phosphoprotein B23, numatrin), isoform CRA_f (Fragment) OS = Homo sapiens GN = NPM1 PE = 2 SV = 1 - [A0A0S2Z4G7_HUMAN] | 41.00 | 31.70 | 4 | 4 | 4 | 13 | 265 | 29.4 | 4.61 | | |
| P61326 | Protein mago nashi homolog OS = Homo sapiens GN = MAGOH PE = 1 SV = 1 - [MGN_HUMAN] | 40.73 | 53.42 | 3 | 7 | 7 | 21 | 146 | 17.2 | 6.11 | | |
| B7Z9M9 | cDNA, FLJ78893, highly similar to Destrin OS = Homo sapiens PE = 2 SV = 1 - [B7Z9M9_HUMAN] | 40.73 | 39.86 | | 6 | 6 | 19 | 148 | 16.5 | 8.50 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| O15511 | Actin-related protein 2/3 complex subunit 5 OS = Homo sapiens GN = ARPC5 PE = 1 SV = 3 - [ARPC5_HUMAN] | 40.36 | 49.67 | 3 | 5 | 5 | 12 | 151 | 16.3 | 5.67 | | |
| P19105 | Myosin regulatory light chain 12A OS = Homo sapiens GN = MYL12A PE = 1 SV = 2 - [ML12A_HUMAN] | 39.26 | 46.20 | 9 | 6 | 6 | 14 | 171 | 19.8 | 4.81 | | |
| Q9NUF9 | Nucleoside diphosphate kinase (Fragment) OS = Homo sapiens GN = c371H6.2 PE = 3 SV = 1 - [Q9NUF9_HUMAN] | 39.17 | 59.48 | 3 | 7 | 7 | 12 | 153 | 17.3 | 7.91 | | |
| E9PM92 | Small acidic protein OS = Homo sapiens GN = C11orf58 PE = 1 SV = 2 - [E9PM92_HUMAN] | 38.18 | 29.30 | 3 | 3 | 3 | 14 | 157 | 17.6 | 9.66 | | |
| O00264 | Membrane-associated progesterone receptor component 1 OS = Homo sapiens GN = PGRMC1 PE = 1 SV = 3 - [PGRC1_HUMAN] | 37.73 | 24.10 | 1 | 3 | 4 | 11 | 195 | 21.7 | 4.70 | | |
| P12277 | Creatine kinase B-type OS = Homo sapiens GN = CKB PE = 1 SV = 1 - [KCRB_HUMAN] | 37.73 | 28.61 | 5 | 8 | 8 | 11 | 381 | 42.6 | 5.59 | | |
| Q8WY15 | Protein kinase C inhibitor-2 OS = Homo sapiens PE = 2 SV = 1 - [Q8WY15_HUMAN] | 37.70 | 54.69 | 3 | 4 | 4 | 15 | 128 | 13.9 | 7.05 | | |
| A0A0K0K1J6 | Epididymis secretory protein Li 96 (Fragment) OS = Homo sapiens GN = HEL-S-96 PE = 2 SV = 1 - [A0A0K0K1J6_HUMAN] | 37.67 | 48.57 | 4 | 5 | 5 | 11 | 140 | 16.0 | 8.69 | | |
| B4DZZ0 | cDNA FLJ52128, highly similar to PRA1 family protein 3 OS = Homo sapiens PE = 2 SV = 1 - [B4DZZ0_HUMAN] | 37.66 | 18.18 | 3 | 2 | 2 | 11 | 165 | 19.2 | 9.77 | | |
| P46778 | 60S ribosomal protein L21 OS = Homo sapiens GN = RPL21 PE = 1 SV = 2 - [RL21_HUMAN] | 37.45 | 36.88 | 4 | 4 | 4 | 13 | 160 | 18.6 | 10.49 | | |
| P63244 | Receptor of activated protein C kinase 1 OS = Homo sapiens GN = RACK1 PE = 1 SV = 3 - [RACK1_HUMAN] | 37.38 | 44.48 | 20 | 10 | 10 | 15 | 317 | 35.1 | 7.69 | | |
| P25398 | 40S ribosomal protein S12 OS = Homo sapiens GN = RPS12 PE = 1 SV = 3 - [RS12_HUMAN] | 36.98 | 53.03 | 1 | 6 | 6 | 15 | 132 | 14.5 | 7.21 | | |
| Q9Y281 | Cofilin-2 OS = Homo sapiens GN = CFL2 PE = 1 SV = 1 - [COF2_HUMAN] | 36.70 | 47.59 | 1 | 3 | 6 | 13 | 166 | 18.7 | 7.88 | | |
| B3KN29 | cDNA FLJ13371 fis, clone PLACE1000656, highly similar to PRA1 family protein 2 OS = Homo sapiens PE = 2 SV = 1 - [B3KN29_HUMAN] | 35.91 | 30.34 | 5 | 7 | 7 | 12 | 178 | 19.3 | 9.19 | | |
| P62280 | 40S ribosomal protein S11 OS = Homo sapiens GN = RPS11 PE = 1 SV = 3 - [RS11_HUMAN] | 35.23 | 37.97 | 3 | 9 | 9 | 14 | 158 | 18.4 | 10.30 | | |
| Q99471 | Prefoldin subunit 5 OS = Homo sapiens GN = PFDN5 PE = 1 SV = 2 - [PFD5_HUMAN] | 34.92 | 44.16 | 3 | 5 | 5 | 12 | 154 | 17.3 | 6.33 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| O95169 | NADH dehydrogenase [ubiquinone] 1 beta subcomplex subunit 8, mitochondrial OS = Homo sapiens GN = NDUFB8 PE = 1 SV = 1 - [NDUB8_HUMAN] | 34.55 | 32.80 | 3 | 6 | 6 | 11 | 186 | 21.8 | 6.80 | | |
| Q9NX14 | NADH dehydrogenase [ubiquinone] 1 beta subcomplex subunit 11, mitochondrial OS = Homo sapiens GN = NDUFB11 PE = 1 SV = 1 - [NDUBB_HUMAN] | 34.53 | 27.45 | 2 | 3 | 3 | 12 | 153 | 17.3 | 5.22 | | |
| P68104 | Elongation factor 1-alpha 1 OS = Homo sapiens GN = EEF1A1 PE = 1 SV = 1 - [EF1A1_HUMAN] | 34.45 | 19.05 | 36 | 6 | 6 | 13 | 462 | 50.1 | 9.01 | | |
| F8WCA0 | Vesicle-associated membrane protein 2 OS = Homo sapiens GN = VAMP2 PE = 4 SV = 1 - [F8WCA0_HUMAN] | 33.69 | 59.32 | 6 | 3 | 5 | 12 | 118 | 12.9 | 8.13 | | |
| A0A0S2Z469 | MpV17 mitochondrial inner membrane protein isoform 3 (Fragment) OS = Homo sapiens GN = MPV17 PE = 2 SV = 1 - [A0A0S2Z469_HUMAN] | 33.65 | 29.93 | 4 | 2 | 2 | 13 | 147 | 16.0 | 8.79 | | |
| P02533 | Keratin, type I cytoskeletal 14 OS = Homo sapiens GN = KRT14 PE = 1 SV = 4 - [K1C14_HUMAN] | 33.57 | 20.97 | 13 | 3 | 7 | 11 | 472 | 51.5 | 5.16 | | |
| Q9Y5S9 | RNA-binding protein 8A OS = Homo sapiens GN = RBM8A PE = 1 SV = 1 - [RBM8A_HUMAN] | 33.46 | 17.24 | 1 | 3 | 3 | 11 | 174 | 19.9 | 5.72 | | |
| P61224 | Ras-related protein Rap-1b OS = Homo sapiens GN = RAP1B PE = 1 SV = 1 - [RAP1B_HUMAN] | 33.44 | 53.80 | 22 | 3 | 7 | 10 | 184 | 20.8 | 5.78 | | |
| Q9Y3U8 | 60S ribosomal protein L36 OS = Homo sapiens GN = RPL36 PE = 1 SV = 3 - [RL36_HUMAN] | 33.25 | 30.48 | 2 | 5 | 5 | 13 | 105 | 12.2 | 11.59 | | |
| P32119 | Peroxiredoxin-2 OS = Homo sapiens GN = PRDX2 PE = 1 SV = 5 - [PRDX2_HUMAN] | 33.09 | 61.62 | 3 | 9 | 10 | 13 | 198 | 21.9 | 5.97 | | |
| P62851 | 40S ribosomal protein S25 OS = Homo sapiens GN = RPS25 PE = 1 SV = 1 - [RS25_HUMAN] | 33.02 | 46.40 | 1 | 8 | 8 | 14 | 125 | 13.7 | 10.11 | | |
| A0A0P0C1B5 | Cytochrome c oxidase subunit 2 OS = Homo sapiens GN = COX2 PE = 3 SV = 1 - [A0A0P0C1B5_HUMAN] | 32.60 | 44.93 | 43 | 1 | 6 | 15 | 227 | 25.5 | 4.89 | | |
| F8VPF3 | Myosin light polypeptide 6 (Fragment) OS = Homo sapiens GN = MYL6 PE = 1 SV = 1 - [F8VPF3_HUMAN] | 32.38 | 54.62 | 14 | 5 | 5 | 13 | 130 | 14.4 | 4.51 | | |
| B7Z6B3 | Receptor expression-enhancing protein OS = Homo sapiens PE = 2 SV = 1 - [B7Z6B3_HUMAN] | 32.27 | 37.82 | 5 | 6 | 6 | 13 | 156 | 17.7 | 8.65 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q15388 | Mitochondrial import receptor subunit TOM20 homolog OS = Homo sapiens GN = TOMM20 PE = 1 SV = 1 - [TOM20_HUMAN] | 32.06 | 31.03 | 1 | 3 | 3 | 9 | 145 | 16.3 | 8.60 | | |
| Q9Y6C9 | Mitochondrial carrier homolog 2 OS = Homo sapiens GN = MTCH2 PE = 1 SV = 1 - [MTCH2_HUMAN] | 31.98 | 24.09 | 3 | 5 | 5 | 11 | 303 | 33.3 | 7.97 | | |
| E5RIW3 | Tubulin-specific chaperone A OS = Homo sapiens GN = TBCA PE = 1 SV = 1 - [E5RIW3_HUMAN] | 31.81 | 46.43 | 4 | 5 | 5 | 11 | 84 | 10.1 | 4.63 | | |
| P08779 | Keratin, type I cytoskeletal 16 OS = Homo sapiens GN = KRT16 PE = 1 SV = 4 - [K1C16_HUMAN] | 31.60 | 21.78 | 13 | 3 | 7 | 13 | 473 | 51.2 | 5.05 | | |
| B7Z8T5 | cDNA FLJ53003, highly similar to Presenilin-1 (EC 3.4.23.—) OS = Homo sapiens PE = 2 SV = 1 - [B7Z8T5_HUMAN] | 30.68 | 18.56 | 5 | 3 | 3 | 8 | 264 | 29.5 | 4.81 | | |
| O14925 | Mitochondrial import inner membrane translocase subunit Tim23 OS = Homo sapiens GN = TIMM23 PE = 1 SV = 1 - [TIM23_HUMAN] | 30.36 | 43.06 | 7 | 5 | 5 | 10 | 209 | 21.9 | 8.60 | | |
| P62249 | 40S ribosomal protein S16 OS = Homo sapiens GN = RPS16 PE = 1 SV = 2 - [RS16_HUMAN] | 30.08 | 50.68 | 7 | 9 | 9 | 20 | 146 | 16.4 | 10.21 | | |
| A0A0A0MR02 | Voltage-dependent anion-selective channel protein 2 (Fragment) OS = Homo sapiens GN = VDAC2 PE = 1 SV = 1 - [A0A0A0MR02_HUMAN] | 29.96 | 44.68 | 7 | 9 | 9 | 13 | 282 | 30.3 | 7.81 | | |
| Q9BQQ5 | Ribosomal protein L27a OS = Homo sapiens GN = L27a PE = 3 SV = 1 - [Q9BQQ5_HUMAN] | 29.23 | 43.40 | 5 | 5 | 5 | 13 | 106 | 12.0 | 11.46 | | |
| P05386 | 60S acidic ribosomal protein P1 OS = Homo sapiens GN = RPLP1 PE = 1 SV = 1 - [RLA1_HUMAN] | 29.19 | 66.67 | 3 | 3 | 3 | 10 | 114 | 11.5 | 4.32 | | |
| P61077 | Ubiquitin-conjugating enzyme E2 D3 OS = Homo sapiens GN = UBE2D3 PE = 1 SV = 1 - [UB2D3_HUMAN] | 28.50 | 42.86 | 9 | 4 | 4 | 9 | 147 | 16.7 | 7.80 | | |
| J3QSY4 | H/ACA ribonucleoprotein complex subunit 2 OS = Homo sapiens GN = NHP2 PE = 1 SV = 1 - [J3QSY4_HUMAN] | 28.48 | 42.22 | 4 | 3 | 3 | 10 | 90 | 10.1 | 10.01 | | |
| V9HWK1 | Triosephosphate isomerase OS = Homo sapiens GN = HEL-S-49 PE = 2 SV = 1 - [V9HWK1_HUMAN] | 28.45 | 53.82 | 8 | 9 | 9 | 10 | 249 | 26.7 | 6.90 | | |
| P62258 | 14-3-3 protein epsilon OS = Homo sapiens GN = YWHAE PE = 1 SV = 1 - [1433E_HUMAN] | 28.28 | 37.65 | 9 | 5 | 6 | 10 | 255 | 29.2 | 4.74 | | |
| Q15185 | Prostaglandin E synthase 3 OS = Homo sapiens GN = PTGES3 PE = 1 SV = 1 - [TEBP_HUMAN] | 28.15 | 28.75 | 3 | 5 | 5 | 10 | 160 | 18.7 | 4.54 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| P62266 | 40S ribosomal protein S23 OS = Homo sapiens GN = RPS23 PE = 1 SV = 3 - [RS23_HUMAN] | 28.06 | 35.66 | 2 | 4 | 4 | 14 | 143 | 15.8 | 10.49 | | |
| O60888 | Protein CutA OS = Homo sapiens GN = CUTA PE = 1 SV = 2 - [CUTA_HUMAN] | 28.04 | 40.78 | 2 | 5 | 5 | 10 | 179 | 19.1 | 5.50 | | |
| Q99497 | Protein deglycase DJ-1 OS = Homo sapiens GN = PARK7 PE = 1 SV = 2 - [PARK7_HUMAN] | 27.80 | 34.92 | 3 | 5 | 5 | 13 | 189 | 19.9 | 6.79 | | |
| Q16527 | Cysteine and glycine-rich protein 2 OS = Homo sapiens GN = CSRP2 PE = 1 SV = 3 - [CSRP2_HUMAN] | 27.73 | 44.56 | 3 | 6 | 6 | 12 | 193 | 20.9 | 8.62 | | |
| B3KQJ0 | cDNA FLJ90530 fis, clone NT2RP4002187, highly similar to Homo sapiens hydroxysteroid (17-beta) dehydrogenase 12 (HSD17B12), mRNA OS = Homo sapiens PE = 2 SV = 1 - [B3KQJ0_HUMAN] | 27.56 | 35.58 | 4 | 6 | 6 | 9 | 312 | 34.3 | 9.26 | | |
| O95295 | SNARE-associated protein Snapin OS = Homo sapiens GN = SNAPIN PE = 1 SV = 1 - [SNAPN_HUMAN] | 27.47 | 38.24 | 1 | 5 | 5 | 8 | 136 | 14.9 | 9.31 | | |
| Q96EK6 | Glucosamine 6-phosphate N-acetyltransferase OS = Homo sapiens GN = GNPNAT1 PE = 1 SV = 1 - [GNA1_HUMAN] | 27.39 | 58.15 | 3 | 7 | 7 | 13 | 184 | 20.7 | 7.99 | | |
| P63279 | SUMO-conjugating enzyme UBC9 OS = Homo sapiens GN = UBE2I PE = 1 SV = 1 - [UBC9_HUMAN] | 26.57 | 48.10 | 6 | 6 | 6 | 13 | 158 | 18.0 | 8.66 | | |
| A0A0S2Z4Q3 | CCHC-type zinc finger nucleic acid binding protein isoform 1 (Fragment) OS = Homo sapiens GN = CNBP PE = 2 SV = 1 - [A0A0S2Z4Q3_HUMAN] | 26.43 | 34.71 | 2 | 5 | 5 | 10 | 170 | 18.7 | 7.71 | | |
| P09132 | Signal recognition particle 19 kDa protein OS = Homo sapiens GN = SRP19 PE = 1 SV = 3 - [SRP19_HUMAN] | 26.36 | 38.89 | 3 | 5 | 5 | 8 | 144 | 16.1 | 9.85 | | |
| Q13185 | Chromobox protein homolog 3 OS = Homo sapiens GN = CBX3 PE = 1 SV = 4 - [CBX3_HUMAN] | 26.25 | 37.16 | 4 | 6 | 6 | 9 | 183 | 20.8 | 5.33 | | |
| O43143 | Pre-mRNA-splicing factor ATP-dependent RNA helicase DHX15 OS = Homo sapiens GN = DHX15 PE = 1 SV = 2 - [DHX15_HUMAN] | 25.74 | 8.55 | 2 | 6 | 6 | 10 | 795 | 90.9 | 7.46 | | |
| Q9BYD1 | 39S ribosomal protein L13, mitochondrial OS = Homo sapiens GN = MRPL13 PE = 1 SV = 1 - [RM13_HUMAN] | 25.64 | 28.09 | 3 | 4 | 4 | 9 | 178 | 20.7 | 9.16 | | |
| P36404 | ADP-ribosylation factor-like protein 2 OS = Homo sapiens GN = ARL2 PE = 1 SV = 4 - [ARL2_HUMAN] | 25.56 | 49.46 | 3 | 7 | 7 | 9 | 184 | 20.9 | 6.34 | | |
| Q6IAA8 | Ragulator complex protein LAMTOR1 OS = Homo sapiens GN = LAMTOR1 PE = 1 SV = 2 - [LTOR1_HUMAN] | 25.55 | 59.63 | 6 | 5 | 5 | 12 | 161 | 17.7 | 5.15 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q8TC12 | Retinol dehydrogenase 11 OS = Homo sapiens GN = RDH11 PE = 1 SV = 2 - [RDH11_HUMAN] | 25.54 | 24.21 | 6 | 6 | 6 | 8 | 318 | 35.4 | 8.82 | | |
| O95881 | Thioredoxin domain-containing protein 12 OS = Homo sapiens GN = TXNDC12 PE = 1 SV = 1 - [TXD12_HUMAN] | 25.52 | 53.49 | 1 | 5 | 5 | 10 | 172 | 19.2 | 5.40 | | |
| C9JXB8 | 60S ribosomal protein L24 OS = Homo sapiens GN = RPL24 PE = 1 SV = 1 - [C9JXB8_HUMAN] | 25.20 | 34.71 | 3 | 5 | 5 | 10 | 121 | 14.4 | 11.31 | | |
| A0A024R5C4 | Reticulon OS = Homo sapiens GN = RTN3 PE = 4 SV = 1 - [A0A024R5C4_HUMAN] | 25.16 | 15.25 | 6 | 4 | 4 | 10 | 236 | 25.6 | 8.51 | | |
| Q8N5K1 | CDGSH iron-sulfur domain-containing protein 2 OS = Homo sapiens GN = CISD2 PE = 1 SV = 1 - [CISD2_HUMAN] | 25.10 | 39.26 | 3 | 5 | 5 | 8 | 135 | 15.3 | 9.61 | | |
| A4D2P2 | Ras-related C3 botulinum toxin substrate 1 (Rho family, small GTP binding protein Rac1) OS = Homo sapiens GN = RAC1 PE = 3 SV = 1 - [A4D2P2_HUMAN] | 25.09 | 39.86 | 8 | 4 | 6 | 12 | 148 | 16.8 | 8.91 | | |
| Q9GZP4 | PITH domain-containing protein 1 OS = Homo sapiens GN = PITHD1 PE = 1 SV = 1 - [PITH1_HUMAN] | 25.06 | 37.91 | 3 | 6 | 6 | 10 | 211 | 24.2 | 5.74 | | |
| Q7Z2W9 | 39S ribosomal protein L21, mitochondrial OS = Homo sapiens GN = MRPL21 PE = 1 SV = 2 - [RM21_HUMAN] | 25.02 | 35.61 | 5 | 5 | 5 | 8 | 205 | 22.8 | 9.89 | | |
| Q06830 | Peroxiredoxin-1 OS = Homo sapiens GN = PRDX1 PE = 1 SV = 1 - [PRDX1_HUMAN] | 24.79 | 30.65 | 4 | 5 | 6 | 9 | 199 | 22.1 | 8.13 | | |
| B4DDB9 | cDNA FLJ56339, highly similar to Signal peptidase complex subunit 2 (EC 3.4.—.—) OS = Homo sapiens PE = 2 SV = 1 - [B4DDB9_HUMAN] | 24.69 | 29.20 | 7 | 7 | 7 | 9 | 226 | 25.0 | 8.47 | | |
| O43598 | 2′-deoxynucleoside 5′-phosphate N-hydrolase 1 OS = Homo sapiens GN = DNPH1 PE = 1 SV = 1 - [DNPH1_HUMAN] | 24.66 | 58.05 | 2 | 6 | 6 | 8 | 174 | 19.1 | 5.05 | | |
| Q9H773 | dCTP pyrophosphatase 1 OS = Homo sapiens GN = DCTPP1 PE = 1 SV = 1 - [DCTP1_HUMAN] | 24.64 | 36.47 | 3 | 4 | 4 | 8 | 170 | 18.7 | 5.03 | | |
| P07195 | L-lactate dehydrogenase B chain OS = Homo sapiens GN = LDHB PE = 1 SV = 2 - [LDHB_HUMAN] | 24.59 | 28.44 | 4 | 6 | 7 | 10 | 334 | 36.6 | 6.05 | | |
| P62487 | DNA-directed RNA polymerase II subunit RPB7 OS = Homo sapiens GN = POLR2G PE = 1 SV = 1 - [RPB7_HUMAN] | 24.52 | 36.63 | 1 | 4 | 4 | 10 | 172 | 19.3 | 5.54 | | |
| O15173 | Membrane-associated progesterone receptor component 2 OS = Homo sapiens GN = PGRMC2 PE = 1 SV = 1 - [PGRC2_HUMAN] | 24.41 | 33.63 | 2 | 5 | 6 | 9 | 223 | 23.8 | 4.88 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| P42771 | Cyclin-dependent kinase inhibitor 2A OS = Homo sapiens GN = CDKN2A PE = 1 SV = 2 - [CDN2A_HUMAN] | 24.04 | 39.74 | 9 | 6 | 6 | 8 | 156 | 16.5 | 5.81 | | |
| Q86XN0 | MRPL43 protein (Fragment) OS = Homo sapiens GN = MRPL43 PE = 2 SV = 1 - [Q86XN0_HUMAN] | 23.71 | 48.97 | 3 | 1 | 5 | 8 | 145 | 16.0 | 8.66 | | |
| C7DJS2 | Glutathione S-transferase pi (Fragment) OS = Homo sapiens GN = GSTP1 PE = 2 SV = 1 - [C7DJS2_HUMAN] | 23.53 | 42.38 | 2 | 1 | 4 | 7 | 151 | 16.7 | 5.10 | | |
| P51149 | Ras-related protein Rab-7a OS = Homo sapiens GN = RAB7A PE = 1 SV = 1 - [RAB7A_HUMAN] | 23.47 | 49.28 | 8 | 7 | 7 | 9 | 207 | 23.5 | 6.70 | | |
| Q6FIE5 | PHP14 protein OS = Homo sapiens GN = PHP14 PE = 2 SV = 1 - [Q6FIE5_HUMAN] | 23.42 | 43.20 | 2 | 3 | 3 | 8 | 125 | 13.8 | 6.07 | | |
| Q15365 | Poly(rC)-binding protein 1 OS = Homo sapiens GN = PCBP1 PE = 1 SV = 2 - [PCBP1_HUMAN] | 23.25 | 14.61 | 12 | 3 | 3 | 9 | 356 | 37.5 | 7.09 | | |
| A0A087WXM6 | 60S ribosomal protein L17 (Fragment) OS = Homo sapiens GN = RPL17 PE = 3 SV = 1 - [A0A087WXM6_HUMAN] | 23.15 | 46.15 | 11 | 8 | 8 | 11 | 169 | 19.6 | 10.04 | | |
| P06733 | Alpha-enolase OS = Homo sapiens GN = ENO1 PE = 1 SV = 2 - [ENOA_HUMAN] | 23.14 | 14.98 | 3 | 5 | 5 | 9 | 434 | 47.1 | 7.39 | | |
| P48047 | ATP synthase subunit O, mitochondrial OS = Homo sapiens GN = ATP5O PE = 1 SV = 1 - [ATPO_HUMAN] | 22.99 | 35.21 | 4 | 6 | 6 | 9 | 213 | 23.3 | 9.96 | | |
| Q08ES8 | Cell growth-inhibiting protein 34 OS = Homo sapiens PE = 2 SV = 1 - [Q08ES8_HUMAN] | 22.91 | 20.90 | 4 | 4 | 4 | 8 | 177 | 20.1 | 9.60 | | |
| Q86YZ3 | Hornerin OS = Homo sapiens GN = HRNR PE = 1 SV = 2 - [HORN_HUMAN] | 22.87 | 10.70 | 1 | 4 | 4 | 18 | 2850 | 282.2 | 10.04 | | |
| P49721 | Proteasome subunit beta type-2 OS = Homo sapiens GN = PSMB2 PE = 1 SV = 1 - [PSB2_HUMAN] | 22.86 | 46.77 | 4 | 6 | 6 | 7 | 201 | 22.8 | 7.02 | | |
| P61019 | Ras-related protein Rab-2A OS = Homo sapiens GN = RAB2A PE = 1 SV = 1 - [RAB2A_HUMAN] | 22.74 | 20.28 | 2 | 2 | 3 | 8 | 212 | 23.5 | 6.54 | | |
| Q9P0I0 | NADH dehydrogenase [ubiquinone] 1 alpha subcomplex subunit 13 OS = Homo sapiens GN = NDUFA13 PE = 1 SV = 3 - [NDUAD_HUMAN] | 22.65 | 41.67 | 5 | 5 | 5 | 9 | 144 | 16.7 | 8.43 | | |
| H7BYV1 | Interferon-induced transmembrane protein 2 (Fragment) OS = Homo sapiens GN = IFITM2 PE = 4 SV = 1 - [H7BYV1_HUMAN] | 22.51 | 22.97 | 11 | 2 | 2 | 6 | 74 | 8.2 | 9.55 | | |
| P62834 | Ras-related protein Rap-1A OS = Homo sapiens GN = RAP1A PE = 1 SV = 1 - [RAP1A_HUMAN] | 22.44 | 60.33 | 7 | 3 | 7 | 8 | 184 | 21.0 | 6.67 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q9BY32 | Inosine triphosphate pyrophosphatase OS = Homo sapiens GN = ITPA PE = 1 SV = 2 - [ITPA_HUMAN] | 22.43 | 39.18 | 2 | 4 | 4 | 8 | 194 | 21.4 | 5.66 | | |
| Q9NPB0 | SAYSvFN domain-containing protein 1 OS = Homo sapiens GN = SAYSD1 PE = 2 SV = 1 - [SMDC1_HUMAN] | 22.37 | 24.04 | 2 | 2 | 2 | 9 | 183 | 20.2 | 8.81 | | |
| X1WI28 | 60S ribosomal protein L10 (Fragment) OS = Homo sapiens GN = RPL10 PE = 1 SV = 6 - [X1WI28_HUMAN] | 22.25 | 25.87 | 6 | 4 | 4 | 7 | 201 | 23.1 | 10.01 | | |
| P84095 | Rho-related GTP-binding protein RhoG OS = Homo sapiens GN = RHOG PE = 1 SV = 1 - [RHOG_HUMAN] | 22.06 | 26.70 | 1 | 4 | 4 | 10 | 191 | 21.3 | 8.12 | | |
| P60866 | 40S ribosomal protein S20 OS = Homo sapiens GN = RPS20 PE = 1 SV = 1 - [RS20_HUMAN] | 22.02 | 23.53 | 4 | 4 | 4 | 11 | 119 | 13.4 | 9.94 | | |
| V9HW62 | Lactoylglutathione lyase OS = Homo sapiens GN = HEL-S-74 PE = 2 SV = 1 - [V9HW62_HUMAN] | 22.00 | 44.02 | 2 | 6 | 6 | 14 | 184 | 20.7 | 5.47 | | |
| P46783 | 40S ribosomal protein S10 OS = Homo sapiens GN = RPS10 PE = 1 SV = 1 - [RS10_HUMAN] | 21.86 | 18.79 | 3 | 3 | 3 | 7 | 165 | 18.9 | 10.15 | | |
| Q9UHV9 | Prefoldin subunit 2 OS = Homo sapiens GN = PFDN2 PE = 1 SV = 1 - [PFD2_HUMAN] | 21.69 | 35.06 | 1 | 4 | 4 | 8 | 154 | 16.6 | 6.58 | | |
| E5RJR5 | S-phase kinase-associated protein 1 OS = Homo sapiens GN = SKP1 PE = 1 SV = 1 - [E5RJR5_HUMAN] | 21.55 | 46.63 | 5 | 5 | 5 | 11 | 163 | 18.7 | 4.70 | | |
| Q6RW13 | Type-1 angiotensin II receptor-associated protein OS = Homo sapiens GN = AGTRAP PE = 1 SV = 1 - [ATRAP_HUMAN] | 21.41 | 24.53 | 2 | 2 | 2 | 6 | 159 | 17.4 | 6.14 | | |
| Q9NQE9 | Histidine triad nucleotide-binding protein 3 OS = Homo sapiens GN = HINT3 PE = 1 SV = 1 - [HINT3_HUMAN] | 21.23 | 37.91 | 1 | 5 | 5 | 7 | 182 | 20.3 | 6.60 | | |
| Q15836 | Vesicle-associated membrane protein 3 OS = Homo sapiens GN = VAMP3 PE = 1 SV = 3 - [VAMP3_HUMAN] | 20.84 | 40.00 | 3 | 1 | 3 | 9 | 100 | 11.3 | 8.79 | | |
| B4DWU6 | cDNA FLJ51361, highly similar to Keratin, type II cytoskeletal 6A OS = Homo sapiens PE = 2 SV = 1 - [B4DWU6_HUMAN] | 20.71 | 17.50 | 10 | 4 | 7 | 7 | 520 | 55.8 | 6.48 | | |
| H7BZ50 | Mitotic-spindle organizing protein 2B (Fragment) OS = Homo sapiens GN = MZT2B PE = 1 SV = 1 - [H7BZ50_HUMAN] | 20.71 | 40.50 | 6 | 3 | 3 | 6 | 121 | 12.4 | 10.61 | | |
| M0R1F6 | NAD-dependent protein deacetylase sirtuin-6 (Fragment) OS = Homo sapiens GN = SIRT6 PE = 1 SV = 1 - [M0R1F6_HUMAN] | 20.70 | 36.56 | 8 | 4 | 4 | 8 | 186 | 20.2 | 8.07 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| P23396 | 40S ribosomal protein S3 OS = Homo sapiens GN = RPS3 PE = 1 SV = 2 - [RS3_HUMAN] | 20.64 | 30.04 | 13 | 6 | 6 | 8 | 243 | 26.7 | 9.66 | | |
| Q9H061 | Transmembrane protein 126A OS = Homo sapiens GN = TMEM126A PE = 1 SV = 1 - [T126A_HUMAN] | 20.57 | 46.67 | 2 | 5 | 5 | 9 | 195 | 21.5 | 9.26 | | |
| M0R3D4 | Prenylated Rab acceptor protein 1 OS = Homo sapiens GN = RABAC1 PE = 1 SV = 1 - [M0R3D4_HUMAN] | 20.56 | 22.52 | 4 | 4 | 4 | 8 | 151 | 17.0 | 7.24 | | |
| P56377 | AP-1 complex subunit sigma-2 OS = Homo sapiens GN = AP1S2 PE = 1 SV = 1 - [AP1S2_HUMAN] | 20.55 | 26.75 | 10 | 3 | 4 | 8 | 157 | 18.6 | 5.47 | | |
| B5BU8 | Dual specificity phosphatase 3 (Fragment) OS = Homo sapiens GN = DUSP3 PE = 2 SV = 1 - [B5BU8_HUMAN] | 20.47 | 43.78 | 4 | 6 | 6 | 7 | 185 | 20.6 | 8.15 | | |
| N0BMC4 | Cytochrome c oxidase subunit 2 OS = Homo sapiens GN = COX2 PE = 3 SV = 1 - [N0BMC4_HUMAN] | 20.44 | 44.93 | 41 | 1 | 6 | 11 | 227 | 25.6 | 4.89 | | |
| H0Y6Y8 | 39S ribosomal protein L43, mitochondrial (Fragment) OS = Homo sapiens GN = MRPL43 PE = 1 SV = 1 - [H0Y6Y8_HUMAN] | 20.30 | 41.42 | 4 | 1 | 5 | 8 | 169 | 18.8 | 8.51 | | |
| P61966 | AP-1 complex subunit sigma-1A OS = Homo sapiens GN = AP1S1 PE = 1 SV = 1 - [AP1S1_HUMAN] | 20.22 | 32.91 | 2 | 3 | 4 | 6 | 158 | 18.7 | 5.73 | | |
| Q8WVJ2 | NudC domain-containing protein 2 OS = Homo sapiens GN = NUDCD2 PE = 1 SV = 1 - [NUDC2_HUMAN] | 20.15 | 28.66 | 2 | 3 | 3 | 6 | 157 | 17.7 | 5.07 | | |
| P37108 | Signal recognition particle 14 kDa protein OS = Homo sapiens GN = SRP14 PE = 1 SV = 2 - [SRP14_HUMAN] | 20.09 | 30.88 | 2 | 5 | 5 | 9 | 136 | 14.6 | 10.04 | | |
| M0R0F0 | 40S ribosomal protein S5 (Fragment) OS = Homo sapiens GN = RPS5 PE = 1 SV = 1 - [M0R0F0_HUMAN] | 20.04 | 24.50 | 5 | 4 | 4 | 7 | 200 | 22.4 | 9.55 | | |
| Q9BU61 | NADH dehydrogenase [ubiquinone] 1 alpha subcomplex assembly factor 3 OS = Homo sapiens GN = NDUFAF3 PE = 1 SV = 1 - [NDUF3_HUMAN] | 19.41 | 15.22 | 3 | 3 | 3 | 7 | 184 | 20.3 | 8.22 | | |
| P98172 | Ephrin-B1 OS = Homo sapiens GN = EFNB1 PE = 1 SV = 1 - [EFNB1_HUMAN] | 19.40 | 22.54 | 1 | 4 | 4 | 6 | 346 | 38.0 | 8.94 | | |
| O75251 | NADH dehydrogenase [ubiquinone] iron-sulfur protein 7, mitochondrial OS = Homo sapiens GN = NDUFS7 PE = 1 SV = 3 - [NDUS7_HUMAN] | 19.33 | 24.88 | 11 | 4 | 4 | 8 | 213 | 23.5 | 9.99 | | |
| A8K690 | cDNA FLJ76863, highly similar to Homo sapiens stress-induced-phosphoprotein 1 (Hsp70/Hsp90-organizing protein) (STIP1), mRNA OS = Homo sapiens PE = 2 SV = 1 - [A8K690_HUMAN] | 19.20 | 9.39 | 3 | 4 | 4 | 8 | 543 | 62.6 | 6.80 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q13526 | Peptidyl-prolyl cis-trans isomerase NIMA-interacting 1 OS = Homo sapiens GN = PIN1 PE = 1 SV = 1 - [PIN1_HUMAN] | 19.06 | 46.01 | 4 | 4 | 4 | 8 | 163 | 18.2 | 8.82 | | |
| Q07065 | Cytoskeleton-associated protein 4 OS = Homo sapiens GN = CKAP4 PE = 1 SV = 2 - [CKAP4_HUMAN] | 18.92 | 12.79 | 4 | 4 | 4 | 6 | 602 | 66.0 | 5.92 | | |
| Q96E16 | Small integral membrane protein 19 OS = Homo sapiens GN = SMIM19 PE = 3 SV = 2 - [SMI19_HUMAN] | 18.62 | 28.97 | 1 | 2 | 2 | 5 | 107 | 12.4 | 5.45 | | |
| H7C1U8 | MICOS complex subunit (Fragment) OS = Homo sapiens GN = APOO PE = 1 SV = 1 - [H7C1U8_HUMAN] | 18.41 | 28.09 | 3 | 4 | 4 | 6 | 178 | 20.1 | 8.62 | | |
| Q9Y2R5 | 28S ribosomal protein S17, mitochondrial OS = Homo sapiens GN = MRPS17 PE = 1 SV = 1 - [RT17_HUMAN] | 18.40 | 40.00 | 4 | 4 | 4 | 6 | 130 | 14.5 | 9.85 | | |
| P11441 | Ubiquitin-like protein 4A OS = Homo sapiens GN = UBL4A PE = 1 SV = 1 - [UBL4A_HUMAN] | 18.28 | 35.67 | 2 | 5 | 5 | 8 | 157 | 17.8 | 8.66 | | |
| P00492 | Hypoxanthine-guanine phosphoribosyltransferase OS = Homo sapiens GN = HPRT1 PE = 1 SV = 2 - [HPRT_HUMAN] | 18.22 | 36.70 | 2 | 5 | 5 | 7 | 218 | 24.6 | 6.68 | | |
| Q9NRF9 | DNA polymerase epsilon subunit 3 OS = Homo sapiens GN = POLE3 PE = 1 SV = 1 - [DPOE3_HUMAN] | 18.00 | 29.93 | 1 | 2 | 2 | 6 | 147 | 16.8 | 4.74 | | |
| Q9Y3C6 | Peptidyl-prolyl cis-trans isomerase-like 1 OS = Homo sapiens GN = PPIL1 PE = 1 SV = 1 - [PPIL1_HUMAN] | 17.95 | 20.48 | 1 | 3 | 3 | 5 | 166 | 18.2 | 7.99 | | |
| Q8N5L8 | Ribonuclease P protein subunit p25-like protein OS = Homo sapiens GN = RP25L PE = 1 SV = 1 - [RP25L_HUMAN] | 17.95 | 46.63 | 1 | 3 | 3 | 6 | 163 | 17.6 | 10.30 | | |
| A0A087X2I2 | Glutathione peroxidase OS = Homo sapiens GN = GPX4 PE = 1 SV = 1 - [A0A087X2I2_HUMAN] | 17.93 | 41.33 | 11 | 8 | 8 | 9 | 196 | 22.0 | 8.37 | | |
| A0A0B7NXV1 | MHC class I antigen OS = Homo sapiens GN = HLA-C PE = 3 SV = 1 - [A0A0B7NXV1_HUMAN] | 17.76 | 20.77 | 31 | 1 | 4 | 6 | 366 | 40.6 | 5.72 | | |
| F5GYT8 | Methylcrotonoyl-CoA carboxylase subunit alpha, mitochondrial OS = Homo sapiens GN = MCCC1 PE = 1 SV = 2 - [F5GYT8_HUMAN] | 17.71 | 9.39 | 4 | 3 | 3 | 5 | 575 | 64.0 | 6.90 | | |
| A0A0B4J2A2 | Peptidyl-prolyl cis-trans isomerase A-like 4C OS = Homo sapiens GN = PPIAL4C PE = 2 SV = 1 - [PAL4C_HUMAN] | 17.60 | 20.73 | 2 | 1 | 2 | 5 | 164 | 18.1 | 9.22 | | |
| K7ELS0 | Uncharacterized protein C19orf43 OS = Homo sapiens GN = C19orf43 PE = 1 SV = 1 - [K7ELS0_HUMAN] | 17.58 | 20.45 | 5 | 3 | 3 | 10 | 132 | 13.5 | 4.91 | | |
| A0PJ74 | TIMM17A protein (Fragment) OS = Homo sapiens GN = TIMM17A PE = 2 SV = 1 - [A0PJ74_HUMAN] | 17.51 | 41.04 | 3 | 2 | 2 | 4 | 134 | 13.9 | 8.97 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q9H840 | Gem-associated protein 7 OS = Homo sapiens GN = GEMIN7 PE = 1 SV = 1 - [GEMI7_HUMAN] | 17.44 | 45.04 | 1 | 2 | 2 | 7 | 131 | 14.5 | 7.40 | | |
| Q8N4Q1 | Mitochondrial intermembrane space import and assembly protein 40 OS = Homo sapiens GN = CHCHD4 PE = 1 SV = 1 - [MIA40_HUMAN] | 17.35 | 35.21 | 2 | 4 | 4 | 7 | 142 | 16.0 | 4.31 | | |
| Q12974 | Protein tyrosine phosphatase type IVA 2 OS = Homo sapiens GN = PTP4A2 PE = 1 SV = 1 - [TP4A2_HUMAN] | 17.27 | 38.92 | 5 | 2 | 4 | 6 | 167 | 19.1 | 8.37 | | |
| Q5T8U5 | Surfeit 4 OS = Homo sapiens GN = SURF4 PE = 1 SV = 1 - [Q5T8U5_HUMAN] | 17.22 | 25.81 | 7 | 4 | 4 | 7 | 186 | 21.1 | 6.52 | | |
| B7Z6P1 | cDNA FLJ53662, highly similar to Actin, alpha skeletal muscle OS = Homo sapiens PE = 2 SV = 1 - [B7Z6P1_HUMAN] | 17.20 | 15.74 | 15 | 1 | 4 | 7 | 343 | 38.6 | 5.38 | | |
| B7Z597 | cDNA FLJ54373, highly similar to 60 kDa heat shock protein, mitochondrial OS = Homo sapiens PE = 2 SV = 1 - [B7Z597_HUMAN] | 16.76 | 6.56 | 3 | 2 | 2 | 5 | 564 | 60.0 | 5.74 | | |
| Q76P68 | C1CK0721Q.2 (60S Ribosomal Protein L12 LIKE protein) OS = Homo sapiens GN = cICK0721Q.2 PE = 3 SV = 1 - [Q76P68_HUMAN] | 16.59 | 14.55 | 1 | 1 | 2 | 8 | 165 | 17.9 | 9.52 | | |
| O75947 | ATP synthase subunit d, mitochondrial OS = Homo sapiens GN = ATP5H PE = 1 SV = 3 - [ATP5H_HUMAN] | 16.43 | 63.98 | 3 | 7 | 7 | 8 | 161 | 18.5 | 5.30 | | |
| P82912 | 28S ribosomal protein S11, mitochondrial OS = Homo sapiens GN = MRPS11 PE = 1 SV = 2 - [RT11_HUMAN] | 16.31 | 23.71 | 3 | 3 | 3 | 9 | 194 | 20.6 | 10.81 | | |
| Q9BUH6 | Protein PAXX OS = Homo sapiens GN = C9orf142 PE = 1 SV = 2 - [PAXX_HUMAN] | 16.12 | 21.08 | 1 | 3 | 3 | 7 | 204 | 21.6 | 5.48 | | |
| P61081 | NEDD8-conjugating enzyme Ubc12 OS = Homo sapiens GN = UBE2M PE = 1 SV = 1 - [UBC12_HUMAN] | 16.01 | 31.69 | 1 | 6 | 6 | 7 | 183 | 20.9 | 7.69 | | |
| P13647 | Keratin, type II cytoskeletal 5 OS = Homo sapiens GN = KRT5 PE = 1 SV = 3 - [K2C5_HUMAN] | 16.00 | 9.83 | 6 | 3 | 5 | 6 | 590 | 62.3 | 7.74 | | |
| P62277 | 40S ribosomal protein S13 OS = Homo sapiens GN = RPS13 PE = 1 SV = 2 - [RS13_HUMAN] | 15.94 | 37.09 | 3 | 5 | 5 | 7 | 151 | 17.2 | 10.54 | | |
| P51571 | Translocon-associated protein subunit delta OS = Homo sapiens GN = SSR4 PE = 1 SV = 1 - [SSRD_HUMAN] | 15.89 | 30.64 | 2 | 4 | 4 | 5 | 173 | 19.0 | 6.15 | | |
| P0DMV8 | Heat shock 70 kDa protein 1A OS = Homo sapiens GN = HSPA1A PE = 1 SV = 1 - [HS71A_HUMAN] | 15.77 | 10.45 | 22 | 4 | 5 | 6 | 641 | 70.0 | 5.66 | | |
| P50990 | T-complex protein 1 subunit theta OS = Homo sapiens GN = CCT8 PE = 1 SV = 4 - [TCPQ_HUMAN] | 15.68 | 9.67 | 4 | 5 | 5 | 6 | 548 | 59.6 | 5.60 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q567V2 | Mpv17-like protein 2 OS = Homo sapiens GN = MPV17L2 PE = 1 SV = 2 - [M17L2_HUMAN] | 15.65 | 24.76 | 1 | 4 | 4 | 5 | 206 | 23.2 | 9.25 | | |
| E7EUT5 | Glyceraldehyde-3-phosphate dehydrogenase OS = Homo sapiens GN = GAPDH PE = 1 SV = 1 - [E7EUT5_HUMAN] | 15.63 | 23.08 | 6 | 4 | 4 | 6 | 260 | 27.9 | 6.95 | | |
| B4DMA2 | cDNA FLJ54023, highly similar to Heat shock protein HSP 90-beta OS = Homo sapiens PE = 2 SV = 1 - [B4DMA2_HUMAN] | 15.61 | 9.62 | 10 | 1 | 5 | 6 | 686 | 79.1 | 5.02 | | |
| Q5R3B4 | Mitochondrial pyruvate carrier 2 (Fragment) OS = Homo sapiens GN = MPC2 PE = 1 SV = 1 - [Q5R3B4_HUMAN] | 15.49 | 38.10 | 3 | 3 | 3 | 6 | 105 | 11.7 | 10.20 | | |
| Q6FIG4 | RAB1B protein OS = Homo sapiens GN = RAB1B PE = 2 SV = 1 - [Q6FIG4_HUMAN] | 15.46 | 27.36 | 19 | 1 | 4 | 6 | 201 | 22.2 | 5.73 | | |
| P62820 | Ras-related protein Rab-1A OS = Homo sapiens GN = RAB1A PE = 1 SV = 3 - [RAB1A_HUMAN] | 15.17 | 26.83 | 19 | 1 | 4 | 8 | 205 | 22.7 | 6.21 | | |
| Q71DI3 | Histone H3.2 OS = Homo sapiens GN = HIST2H3A PE = 1 SV = 3 - [H32_HUMAN] | 15.09 | 28.68 | 1 | 1 | 2 | 4 | 136 | 15.4 | 11.27 | | |
| A0A0S4XQQ0 | MHC Class I Antigen OS = Homo sapiens GN = HLA-A PE = 3 SV = 1 - [A0A0S4XQQ0_HUMAN] | 15.02 | 21.92 | 166 | 2 | 5 | 6 | 365 | 41.0 | 6.99 | | |
| O96008 | Mitochondrial import receptor subunit TOM40 homolog OS = Homo sapiens GN = TOMM40 PE = 1 SV = 1 - [TOM40_HUMAN] | 14.95 | 17.45 | 1 | 3 | 3 | 4 | 361 | 37.9 | 7.25 | | |
| Q58I9 | Vesicle transport protein SFT2C OS = Homo sapiens GN = SFT2D3 PE = 2 SV = 1 - [SFT2C_HUMAN] | 14.78 | 26.98 | 1 | 4 | 4 | 6 | 215 | 21.8 | 9.89 | | |
| O43175 | D-3-phosphoglycerate dehydrogenase OS = Homo sapiens GN = PHGDH PE = 1 SV = 4 - [SERA_HUMAN] | 14.74 | 12.01 | 4 | 6 | 6 | 6 | 533 | 56.6 | 6.71 | | |
| P10620 | Microsomal glutathione S-transferase 1 OS = Homo sapiens GN = MGST1 PE = 1 SV = 1 - [MGST1_HUMAN] | 14.67 | 30.32 | 4 | 4 | 4 | 5 | 155 | 17.6 | 9.39 | | |
| H3BMT0 | Hematological and neurological-expressed 1-like protein (Fragment) OS = Homo sapiens GN = HN1L PE = 1 SV = 1 - [H3BMT0_HUMAN] | 14.56 | 61.74 | 3 | 1 | 4 | 6 | 115 | 12.2 | 8.19 | | |
| B2R4U3 | cDNA, FLJ92217, highly similar to Homo sapiens ubiquitin-conjugating enzyme E2C (UBE2C), mRNA OS = Homo sapiens PE = 2 SV = 1 - [B2R4U3_HUMAN] | 14.40 | 17.32 | 2 | 2 | 2 | 8 | 179 | 19.6 | 7.37 | | |
| P26373 | 60S ribosomal protein L13 OS = Homo sapiens GN = RPL13 PE = 1 SV = 4 - [RL13_HUMAN] | 14.39 | 24.17 | 3 | 5 | 5 | 7 | 211 | 24.2 | 11.65 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| H0YNG3 | Signal peptidase complex catalytic subunit SEC11 OS = Homo sapiens GN = SEC11A PE = 1 SV = 1 - [H0YNG3_HUMAN] | 14.34 | 37.42 | 6 | 5 | 5 | 6 | 163 | 18.6 | 9.55 | | |
| P52758 | Ribonuclease UK114 OS = Homo sapiens GN = HRSP12 PE = 1 SV = 1 - [UK114_HUMAN] | 14.32 | 32.85 | 3 | 3 | 3 | 6 | 137 | 14.5 | 8.68 | | |
| E9PH64 | NADH dehydrogenase [ubiquinone] 1 beta subcomplex subunit 9 OS = Homo sapiens GN = NDUFB9 PE = 1 SV = 1 - [E9PH64_HUMAN] | 14.26 | 33.93 | 6 | 4 | 4 | 7 | 168 | 20.4 | 7.88 | | |
| Q9Y277 | Voltage-dependent anion-selective channel protein 3 OS = Homo sapiens GN = VDAC3 PE = 1 SV = 1 - [VDAC3_HUMAN] | 14.21 | 21.55 | 4 | 4 | 4 | 9 | 283 | 30.6 | 8.66 | | |
| Q7Z5G4 | Golgin subfamily A member 7 OS = Homo sapiens GN = GOLGA7 PE = 1 SV = 2 - [GOGA7_HUMAN] | 14.15 | 34.31 | 1 | 4 | 4 | 5 | 137 | 15.8 | 7.05 | | |
| F5H018 | GTP-binding nuclear protein Ran (Fragment) OS = Homo sapiens GN = RAN PE = 1 SV = 7 - [F5H018_HUMAN] | 14.06 | 28.64 | 6 | 4 | 4 | 5 | 199 | 22.5 | 8.73 | | |
| P56537 | Eukaryotic translation initiation factor 6 OS = Homo sapiens GN = EIF6 PE = 1 SV = 1 - [IF6_HUMAN] | 14.03 | 22.86 | 2 | 4 | 4 | 7 | 245 | 26.6 | 4.68 | | |
| O75607 | Nucleoplasmin-3 OS = Homo sapiens GN = NPM3 PE = 1 SV = 3 - [NPM3_HUMAN] | 13.97 | 38.20 | 1 | 4 | 4 | 7 | 178 | 19.3 | 4.63 | | |
| P55957 | BH3-interacting domain death agonist OS = Homo sapiens GN = BID PE = 1 SV = 1 - [BID_HUMAN] | 13.88 | 21.03 | 2 | 2 | 2 | 5 | 195 | 22.0 | 5.44 | | |
| Q9NS69 | Mitochondrial import receptor subunit TOM22 homolog OS = Homo sapiens GN = TOMM22 PE = 1 SV = 3 - [TOM22_HUMAN] | 13.77 | 35.21 | 1 | 2 | 2 | 4 | 142 | 15.5 | 4.34 | | |
| Q9NX00 | Transmembrane protein 160 OS = Homo sapiens GN = TMEM160 PE = 1 SV = 1 - [TM160_HUMAN] | 13.75 | 17.55 | 1 | 2 | 2 | 6 | 188 | 19.6 | 8.03 | | |
| G3V203 | 60S ribosomal protein L18 OS = Homo sapiens GN = RPL18 PE = 1 SV = 1 - [G3V203_HUMAN] | 13.69 | 29.27 | 9 | 4 | 4 | 5 | 164 | 18.7 | 11.59 | | |
| P62854 | 40S ribosomal protein S26 OS = Homo sapiens GN = RPS26 PE = 1 SV = 3 - [RS26_HUMAN] | 13.58 | 36.52 | 2 | 3 | 3 | 8 | 115 | 13.0 | 11.00 | | |
| P61923 | Coatomer subunit zeta-1 OS = Homo sapiens GN = COPZ1 PE = 1 SV = 1 - [COPZ1_HUMAN] | 13.56 | 30.51 | 10 | 5 | 5 | 5 | 177 | 20.2 | 4.81 | | |
| Q9NZ45 | CDGSH iron-sulfur domain-containing protein 1 OS = Homo sapiens GN = CISD1 PE = 1 SV = 1 - [CISD1_HUMAN] | 13.45 | 25.93 | 1 | 2 | 2 | 5 | 108 | 12.2 | 9.09 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| S4R329 | ER membrane protein complex subunit 4 OS = Homo sapiens GN = EMC4 PE = 1 SV = 1 - [S4R329_HUMAN] | 13.36 | 40.28 | 6 | 2 | 2 | 4 | 72 | 7.8 | 9.82 | | |
| O43324 | Eukaryotic translation elongation factor 1 epsilon-1 OS = Homo sapiens GN = EEF1E1 PE = 1 SV = 1 - [MCA3_HUMAN] | 13.36 | 25.86 | 4 | 3 | 3 | 9 | 174 | 19.8 | 8.54 | | |
| I6L8B7 | Fatty acid-binding protein, epidermal OS = Homo sapiens GN = FABP5 PE = 1 SV = 1 - [I6L8B7_HUMAN] | 13.30 | 40.59 | 2 | 2 | 2 | 7 | 101 | 11.2 | 6.07 | | |
| B2R548 | Prefoldin subunit 4 OS = Homo sapiens PE = 2 SV = 1 - [B2R548_HUMAN] | 13.28 | 29.10 | 3 | 3 | 3 | 5 | 134 | 15.3 | 4.53 | | |
| B4DEF7 | cDNA FLJ60062, highly similar to 78 kDa glucose-regulated protein OS = Homo sapiens PE = 2 SV = 1 - [B4DEF7_HUMAN] | 13.25 | 26.26 | 2 | 5 | 5 | 5 | 278 | 30.4 | 6.05 | | |
| P18077 | 60S ribosomal protein L35a OS = Homo sapiens GN = RPL35A PE = 1 SV = 2 - [RL35A_HUMAN] | 13.19 | 30.91 | 4 | 7 | 7 | 8 | 110 | 12.5 | 11.06 | | |
| O95989 | Diphosphoinositol polyphosphate phosphohydrolase 1 OS = Homo sapiens GN = NUDT3 PE = 1 SV = 1 - [NUDT3_HUMAN] | 13.16 | 34.30 | 1 | 3 | 3 | 4 | 172 | 19.5 | 6.34 | | |
| A0A0D9SGK2 | Protein tyrosine phosphatase type IVA 1 OS = Homo sapiens GN = PTP4A1 PE = 1 SV = 1 - [A0A0D9SGK2_HUMAN] | 12.97 | 23.65 | 7 | 1 | 3 | 5 | 148 | 17.1 | 9.16 | | |
| R4GNH9 | Exosome complex component CSL4 OS = Homo sapiens GN = EXOSC1 PE = 1 SV = 1 - [R4GNH9_HUMAN] | 12.95 | 42.45 | 6 | 4 | 4 | 5 | 139 | 15.1 | 9.55 | | |
| B4DJI1 | L-lactate dehydrogenase OS = Homo sapiens PE = 2 SV = 1 - [B4DJI1_HUMAN] | 12.89 | 21.97 | 4 | 5 | 6 | 7 | 305 | 33.6 | 8.46 | | |
| E7EQ69 | N-alpha-acetyltransferase 50 OS = Homo sapiens GN = NAA50 PE = 1 SV = 1 - [E7EQ69_HUMAN] | 12.88 | 36.90 | 8 | 5 | 5 | 5 | 168 | 19.3 | 8.81 | | |
| Q4G0I0 | Protein CCSMST1 OS = Homo sapiens GN = CCSMST1 PE = 2 SV = 1 - [CSMT1_HUMAN] | 12.85 | 34.85 | 2 | 5 | 5 | 5 | 132 | 15.0 | 7.02 | | |
| C9JLU1 | DNA-directed RNA polymerases I, II, and III subunit RPABC3 (Fragment) OS = Homo sapiens GN = POLR2H PE = 1 SV = 7 - [C9JLU1_HUMAN] | 12.82 | 46.98 | 2 | 4 | 4 | 5 | 149 | 17.0 | 4.68 | | |
| Q53G19 | Mitochondrial ribosomal protein L11 isoform a variant (Fragment) OS = Homo sapiens PE = 2 SV = 1 - [Q53G19_HUMAN] | 12.80 | 29.17 | 3 | 4 | 4 | 6 | 192 | 20.6 | 9.91 | | |
| P63104 | 14-3-3 protein zeta/delta OS = Homo sapiens GN = YWHAZ PE = 1 SV = 1 - [1433Z_HUMAN] | 12.80 | 16.33 | 8 | 2 | 3 | 7 | 245 | 27.7 | 4.79 | | |
| P07900 | Heat shock protein HSP 90-alpha OS = Homo sapiens GN = HSP90AA1 PE = 1 SV = 5 - [HS90A_HUMAN] | 12.79 | 7.38 | 8 | 1 | 4 | 5 | 732 | 84.6 | 5.02 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q8NFP7 | Diphosphoinositol polyphosphate phosphohydrolase 3-alpha OS = Homo sapiens GN = NUDT10 PE = 1 SV = 1 - [NUD10_HUMAN] | 12.77 | 33.54 | 2 | 3 | 3 | 7 | 164 | 18.5 | 5.68 | | |
| E9PQQ4 | Heat shock cognate 71 kDa protein (Fragment) OS = Homo sapiens GN = HSPA8 PE = 1 SV = 1 - [E9PQQ4_HUMAN] | 12.76 | 35.67 | 16 | 4 | 5 | 6 | 171 | 18.7 | 8.09 | | |
| A6NGP5 | Hematological and neurological-expressed 1-like protein OS = Homo sapiens GN = HN1L PE = 1 SV = 2 - [A6NGP5_HUMAN] | 12.74 | 40.45 | 7 | 1 | 4 | 4 | 178 | 18.9 | 9.45 | | |
| P20618 | Proteasome subunit beta type-1 OS = Homo sapiens GN = PSMB1 PE = 1 SV = 2 - [PSB1_HUMAN] | 12.74 | 21.99 | 2 | 4 | 4 | 7 | 241 | 26.5 | 8.13 | | |
| J3QQY2 | Transmembrane and coiled-coil domain-containing protein 1 OS = Homo sapiens GN = TMCO1 PE = 1 SV = 1 - [J3QQY2_HUMAN] | 12.73 | 35.58 | 4 | 3 | 3 | 5 | 104 | 11.4 | 9.66 | | |
| Q9Y3D5 | 28S ribosomal protein S18c, mitochondrial OS = Homo sapiens GN = MRPS18C PE = 1 SV = 1 - [RT18C_HUMAN] | 12.65 | 21.83 | 1 | 2 | 2 | 3 | 142 | 15.8 | 9.55 | | |
| Q9BWH2 | FUN14 domain-containing protein 2 OS = Homo sapiens GN = FUNDC2 PE = 1 SV = 2 - [FUND2_HUMAN] | 12.60 | 33.33 | 1 | 5 | 5 | 7 | 189 | 20.7 | 9.73 | | |
| Q99536 | Synaptic vesicle membrane protein VAT-1 homolog OS = Homo sapiens GN = VAT1 PE = 1 SV = 2 - [VAT1_HUMAN] | 12.55 | 19.08 | 5 | 5 | 5 | 5 | 393 | 41.9 | 6.29 | | |
| B2R7M3 | cDNA, FLJ93510, highly similar to Homo sapiens JTV1 gene (JTV1), mRNA OS = Homo sapiens PE = 2 SV = 1 - [B2R7M3_HUMAN] | 12.54 | 17.19 | 4 | 3 | 3 | 5 | 320 | 35.4 | 8.41 | | |
| Q9BW83 | Intraflagellar transport protein 27 homolog OS = Homo sapiens GN = IFT27 PE = 1 SV = 1 - [IFT27_HUMAN] | 12.51 | 35.48 | 5 | 4 | 4 | 4 | 186 | 20.5 | 5.41 | | |
| B8ZZK5 | Phosphodiesterase 6D, cGMP-specific, rod, delta, isoform CRA_a OS = Homo sapiens GN = PDE6D PE = 1 SV = 1 - [B8ZZK5_HUMAN] | 12.42 | 40.86 | 3 | 3 | 3 | 5 | 93 | 10.8 | 8.85 | | |
| Q9U130 | Multifunctional methyltransferase subunit TRM112-like protein OS = Homo sapiens GN = TRMT112 PE = 1 SV = 1 - [TR112_HUMAN] | 12.41 | 33.60 | 3 | 4 | 4 | 5 | 125 | 14.2 | 5.26 | | |
| P52815 | 39S ribosomal protein L12, mitochondrial OS = Homo sapiens GN = MRPL12 PE = 1 SV = 2 - [RM12_HUMAN] | 12.39 | 28.79 | 3 | 3 | 3 | 5 | 198 | 21.3 | 8.87 | | |
| P52298 | Nuclear cap-binding protein subunit 2 OS = Homo sapiens GN = NCBP2 PE = 1 SV = 1 - [NCBP2_HUMAN] | 12.37 | 23.72 | 5 | 4 | 4 | 5 | 156 | 18.0 | 8.21 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q9Y3D0 | Mitotic spindle-associated MMXD complex subunit MIP18 OS = Homo sapiens GN = FAM96B PE = 1 SV = 1 - [MIP18_HUMAN] | 12.36 | 25.77 | 1 | 2 | 2 | 3 | 163 | 17.7 | 5.19 | | |
| P12004 | Proliferating cell nuclear antigen OS = Homo sapiens GN = PCNA PE = 1 SV = 1 - [PCNA_HUMAN] | 12.33 | 17.24 | 3 | 2 | 3 | 6 | 261 | 28.8 | 4.69 | | |
| P62318 | Small nuclear ribonucleoprotein Sm D3 OS = Homo sapiens GN = SNRPD3 PE = 1 SV = 1 - [SMD3_HUMAN] | 12.32 | 40.48 | 2 | 3 | 3 | 5 | 126 | 13.9 | 10.32 | | |
| B7Z587 | cDNA FLJ51273, highly similar to Transmembrane protein 11 OS = Homo sapiens PE = 2 SV = 1 - [B7Z587_HUMAN] | 12.24 | 27.91 | 2 | 4 | 4 | 7 | 172 | 19.5 | 6.25 | | |
| E9PCY7 | Heterogeneous nuclear ribonucleoprotein H OS = Homo sapiens GN = HNRNPH1 PE = 1 SV = 1 - [E9PCY7_HUMAN] | 12.24 | 13.29 | 14 | 2 | 4 | 6 | 429 | 47.1 | 6.34 | | |
| B2RDN9 | cDNA, FLJ96699, highly similar to Homo sapiens thyroid autoantigen 70 kDa (Ku antigen) (G22P1), mRNA OS = Homo sapiens PE = 2 SV = 1 - [B2RDN9_HUMAN] | 12.19 | 5.91 | 2 | 2 | 2 | 4 | 609 | 69.7 | 6.70 | | |
| Q9HD33 | 39S ribosomal protein L47, mitochondrial OS = Homo sapiens GN = MRPL47 PE = 1 SV = 2 - [RM47_HUMAN] | 12.19 | 10.00 | 1 | 4 | 4 | 5 | 250 | 29.4 | 10.37 | | |
| P61106 | Ras-related protein Rab-14 OS = Homo sapiens GN = RAB14 PE = 1 SV = 4 - [RAB14_HUMAN] | 12.18 | 25.58 | 2 | 3 | 4 | 6 | 215 | 23.9 | 6.21 | | |
| F8VVM2 | Phosphate carrier protein, mitochondrial OS = Homo sapiens GN = SLC25A3 PE = 1 SV = 1 - [F8VVM2_HUMAN] | 12.16 | 36.28 | 6 | 2 | 2 | 4 | 324 | 36.1 | 9.26 | | |
| F8WDD7 | Actin-related protein 2/3 complex subunit 4 OS = Homo sapiens GN = ARPC4 PE = 4 SV = 1 - [F8WDD7_HUMAN] | 12.16 | 36.28 | 6 | 3 | 3 | 6 | 113 | 13.0 | 9.51 | | |
| C9JQB1 | Nucleoside diphosphate kinase OS = Homo sapiens GN = NME6 PE = 1 SV = 1 - [C9JQB1_HUMAN] | 12.13 | 41.13 | 4 | 4 | 4 | 4 | 141 | 16.2 | 7.46 | | |
| O75396 | Vesicle-trafficking protein SEC22b OS = Homo sapiens GN = SEC22B PE = 1 SV = 4 - [SC22B_HUMAN] | 12.11 | 20.00 | 1 | 3 | 3 | 6 | 215 | 24.6 | 6.92 | | |
| Q8TA90 | Similar to Elongation factor 2b (Fragment) OS = Homo sapiens PE = 2 SV = 1 - [Q8TA90_HUMAN] | 12.11 | 13.93 | 3 | 4 | 4 | 4 | 517 | 57.5 | 6.93 | | |
| Q9BRG1 | Vacuolar protein-sorting-associated protein 25 OS = Homo sapiens GN = VPS25 PE = 1 SV = 1 - [VPS25_HUMAN] | 12.05 | 26.70 | 2 | 3 | 3 | 5 | 176 | 20.7 | 6.34 | | |
| P60520 | Gamma-aminobutyric acid receptor-associated protein-like 2 OS = Homo sapiens GN = GABARAPL2 PE = 1 SV = 1 - [GBRL2_HUMAN] | 12.03 | 47.86 | 2 | 4 | 4 | 5 | 117 | 13.7 | 8.10 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q14691 | DNA replication complex GINS protein PSF1 OS = Homo sapiens GN = GINS1 PE = 1 SV = 1 - [PSF1_HUMAN] | 12.02 | 26.53 | 2 | 5 | 5 | 7 | 196 | 23.0 | 7.39 | | |
| J3KSC4 | Ras-related C3 botulinum toxin substrate 3 (Fragment) OS = Homo sapiens GN = RAC3 PE = 1 SV = 1 - [J3KSC4_HUMAN] | 11.96 | 35.38 | 3 | 2 | 4 | 6 | 130 | 14.8 | 7.34 | | |
| B7Z4B7 | cDNA FLJ52561, highly similar to Four and a half LIM domains protein 1 OS = Homo sapiens PE = 2 SV = 1 - [B7Z4B7_HUMAN] | 11.93 | 17.34 | 9 | 3 | 3 | 4 | 248 | 28.1 | 8.31 | | |
| O95182 | NADH dehydrogenase [ubiquinone] 1 alpha subcomplex subunit 7 OS = Homo sapiens GN = NDUFA7 PE = 1 SV = 3 - [NDUA7_HUMAN] | 11.80 | 27.43 | 4 | 2 | 2 | 6 | 113 | 12.5 | 10.18 | | |
| B3KSW0 | CDP-diacylglycerol--inositol 3-phosphatidyltransferase (Phosphatidylinositol synthase), isoform CRA_b OS = Homo sapiens GN = CDIPT PE = 2 SV = 1 - [B3KSW0_HUMAN] | 11.75 | 25.95 | 5 | 4 | 4 | 4 | 185 | 20.2 | 8.28 | | |
| B4DQT8 | cDNA FLJ61158, highly similar to ADP-ribosylation factor-like protein 8B OS = Homo sapiens PE = 2 SV = 1 - [B4DQT8_HUMAN] | 11.73 | 23.73 | 4 | 3 | 3 | 4 | 177 | 20.6 | 7.78 | | |
| B4DE96 | cDNA FLJ53762, highly similar to Synaptobrevin-like protein 1 OS = Homo sapiens PE = 2 SV = 1 - [B4DE96_HUMAN] | 11.62 | 32.68 | 6 | 3 | 3 | 6 | 153 | 17.4 | 9.29 | | |
| Q9BSW5 | RPS2 protein (Fragment) OS = Homo sapiens GN = RPS2 PE = 2 SV = 2 - [Q9BSW5_HUMAN] | 11.61 | 27.84 | 11 | 3 | 3 | 4 | 97 | 10.5 | 9.17 | | |
| C9J0K6 | Sorcin OS = Homo sapiens GN = SRI PE = 1 SV = 1 - [C9J0K6_HUMAN] | 11.60 | 40.65 | 3 | 4 | 4 | 4 | 155 | 17.6 | 5.60 | | |
| B4DNK4 | Pyruvate kinase OS = Homo sapiens GN = PKM PE = 1 SV = 1 - [B4DNK4_HUMAN] | 11.55 | 12.04 | 12 | 4 | 4 | 4 | 457 | 49.9 | 7.83 | | |
| Q9GZN8 | UPF0687 protein C20orf27 OS = Homo sapiens GN = C20orf27 PE = 1 SV = 3 - [CT027_HUMAN] | 11.46 | 29.31 | 1 | 4 | 4 | 4 | 174 | 19.3 | 6.84 | | |
| Q9Y3D6 | Mitochondrial fission 1 protein OS = Homo sapiens GN = FIS1 PE = 1 SV = 2 - [FIS1_HUMAN] | 11.37 | 23.68 | 1 | 3 | 3 | 4 | 152 | 16.9 | 8.79 | | |
| O15155 | BET1 homolog OS = Homo sapiens GN = BET1 PE = 1 SV = 1 - [BET1_HUMAN] | 11.37 | 24.58 | 2 | 2 | 2 | 3 | 118 | 13.3 | 9.06 | | |
| B5MC22 | Mitochondrial fission process protein 1 OS = Homo sapiens GN = MTFP1 PE = 1 SV = 1 - [B5MC22_HUMAN] | 11.36 | 39.86 | 4 | 4 | 4 | 4 | 143 | 15.5 | 9.31 | | |
| A8MZB2 | N-acetyltransferase 5 (ARD1 homolog, S. cerevisiae), isoform CRA_a OS = Homo sapiens GN = NAA20 PE = 1 SV = 1 - [A8MZB2_HUMAN] | 11.31 | 24.10 | 2 | 4 | 4 | 5 | 166 | 18.8 | 5.00 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| P62753 | 40S ribosomal protein S6 OS = *Homo sapiens* GN = RPS6 PE = 1 SV = 1 - [RS6_HUMAN] | 11.30 | 22.09 | 4 | 4 | 4 | 4 | 249 | 28.7 | 10.84 | | |
| Q9Y3B4 | Splicing factor 3B subunit 6 OS = *Homo sapiens* GN = SF3B6 PE = 1 SV = 1 - [SF3B6_HUMAN] | 11.29 | 29.60 | 1 | 3 | 3 | 4 | 125 | 14.6 | 9.38 | | |
| Q8N5N7 | 39S ribosomal protein L50, mitochondrial OS = *Homo sapiens* GN = MRPL50 PE = 1 SV = 2 - [RM50_HUMAN] | 11.23 | 20.89 | 1 | 2 | 2 | 5 | 158 | 18.3 | 7.88 | | |
| Q9NWU5 | 39S ribosomal protein L22, mitochondrial OS = *Homo sapiens* GN = MRPL22 PE = 1 SV = 1 - [RM22_HUMAN] | 11.17 | 17.96 | 4 | 3 | 3 | 3 | 206 | 23.6 | 9.94 | | |
| P26641 | Elongation factor 1-gamma OS = *Homo sapiens* GN = EEF1G PE = 1 SV = 3 - [EF1G_HUMAN] | 11.05 | 13.73 | 2 | 4 | 4 | 4 | 437 | 50.1 | 6.67 | | |
| P61088 | Ubiquitin-conjugating enzyme E2 N OS = *Homo sapiens* GN = UBE2N PE = 1 SV = 1 - [UBE2N_HUMAN] | 10.86 | 30.26 | 6 | 4 | 4 | 4 | 152 | 17.1 | 6.57 | | |
| Q96F25 | UDP-N-acetylglucosamine transferase subunit ALG14 homolog OS = *Homo sapiens* GN = ALG14 PE = 1 SV = 1 - [ALG14_HUMAN] | 10.81 | 15.74 | 1 | 3 | 3 | 5 | 216 | 24.1 | 8.94 | | |
| P01111 | GTPase NRas OS = *Homo sapiens* GN = NRAS PE = 1 SV = 1 - [RASN_HUMAN] | 10.75 | 20.11 | 2 | 4 | 4 | 5 | 189 | 21.2 | 5.17 | | |
| Q5T7C4 | High mobility group protein B1 OS = *Homo sapiens* GN = HMGB1 PE = 1 SV = 1 - [Q5T7C4_HUMAN] | 10.73 | 29.75 | 5 | 3 | 3 | 4 | 158 | 18.3 | 9.70 | | |
| Q9NRP0 | Oligosaccharyltransferase complex subunit OSTC OS = *Homo sapiens* GN = OSTC PE = 1 SV = 1 - [OSTC_HUMAN] | 10.71 | 14.09 | 1 | 2 | 2 | 4 | 149 | 16.8 | 9.13 | | |
| Q92520 | Protein FAM3C OS = *Homo sapiens* GN = FAM3C PE = 1 SV = 1 - [FAM3C_HUMAN] | 10.69 | 14.10 | 1 | 2 | 2 | 3 | 227 | 24.7 | 8.29 | | |
| C9JP0 | Ubiquitin-conjugating enzyme E2 E1 (Fragment) OS = *Homo sapiens* GN = UBE2E1 PE = 1 SV = 1 - [C9JP0_HUMAN] | 10.68 | 25.17 | 4 | 2 | 3 | 4 | 147 | 16.2 | 8.56 | | |
| A0A0S2Z359 | Solute carrier family 25 member 4 isoform 3 (Fragment) OS = *Homo sapiens* GN = SLC25A4 PE = 2 SV = 1 - [A0A0S2Z359_HUMAN] | 10.63 | 25.00 | 6 | 1 | 2 | 3 | 156 | 17.5 | 9.82 | | |
| C9JE12 | Transmembrane and ubiquitin-like domain-containing protein 1 (Fragment) OS = *Homo sapiens* GN = TMUB1 PE = 1 SV = 1 - [C9JE12_HUMAN] | 10.60 | 20.39 | 3 | 2 | 2 | 4 | 152 | 16.1 | 4.91 | | |
| A0A087WTB8 | Ubiquitin carboxyl-terminal hydrolase OS = *Homo sapiens* GN = UCHL3 PE = 1 SV = 1 - [A0A087WTB8_HUMAN] | 10.46 | 18.56 | 3 | 3 | 3 | 4 | 194 | 21.9 | 4.93 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q96AB3 | Isochorismatase domain-containing protein 2 OS = Homo sapiens GN = ISOC2 PE = 1 SV = 1 - [ISOC2_HUMAN] | 10.46 | 35.12 | 3 | 3 | 3 | 4 | 205 | 22.3 | 7.77 | | |
| A0A096LNT6 | Tail-anchored protein insertion receptor WRB OS = Homo sapiens GN = WRB PE = 1 SV = 1 - [A0A096LNT6_HUMAN] | 10.42 | 30.43 | 7 | 3 | 3 | 4 | 69 | 8.1 | 8.54 | | |
| Q04695 | Keratin, type I cytoskeletal 17 OS = Homo sapiens GN = KRT17 PE = 1 SV = 2 - [K1C17_HUMAN] | 10.41 | 9.49 | 7 | 2 | 2 | 4 | 432 | 48.1 | 5.02 | | |
| Q9Y5M8 | Signal recognition particle receptor subunit beta OS = Homo sapiens GN = SRPRB PE = 1 SV = 3 - [SRPRB_HUMAN] | 10.37 | 12.18 | 1 | 1 | 2 | 4 | 271 | 29.7 | 9.04 | | |
| G3V4P8 | Glia maturation factor beta (Fragment) OS = Homo sapiens GN = GMFB PE = 1 SV = 1 - [G3V4P8_HUMAN] | 10.21 | 33.33 | 2 | 2 | 3 | 3 | 150 | 17.5 | 5.31 | | |
| Q9Y6H1 | Coiled-coil-helix-coiled-coil-helix domain-containing protein 2 OS = Homo sapiens GN = CHCHD2 PE = 1 SV = 1 - [CHCH2_HUMAN] | 10.07 | 25.17 | 1 | 2 | 2 | 3 | 151 | 15.5 | 9.22 | | |
| C9JOI7 | Profilin-2 OS = Homo sapiens GN = PFN2 PE = 1 SV = 1 - [C9JOI7_HUMAN] | 10.04 | 30.77 | 8 | 2 | 2 | 3 | 91 | 9.8 | 9.17 | | |
| J3KS15 | Peptidyl-tRNA hydrolase ICT1, mitochondrial (Fragment) OS = Homo sapiens GN = ICT1 PE = 1 SV = 1 - [J3KS15_HUMAN] | 10.00 | 16.67 | 2 | 2 | 2 | 3 | 192 | 21.9 | 9.72 | | |
| D3YTB1 | 60S ribosomal protein L32 (Fragment) OS = Homo sapiens GN = RPL32 PE = 1 SV = 1 - [D3YTB1_HUMAN] | 9.92 | 30.08 | 3 | 4 | 4 | 4 | 133 | 15.6 | 11.44 | | |
| Q8WUX2 | Putative glutathione-specific gamma-glutamylcyclotransferase 2 OS = Homo sapiens GN = CHAC2 PE = 2 SV = 1 - [CHAC2_HUMAN] | 9.79 | 21.74 | 1 | 3 | 3 | 3 | 184 | 20.9 | 5.43 | | |
| Q9BRT2 | Ubiquinol-cytochrome-c reductase complex assembly factor 2 OS = Homo sapiens GN = UQCC2 PE = 1 SV = 1 - [UQCC2_HUMAN] | 9.77 | 33.33 | 3 | 3 | 3 | 4 | 126 | 14.9 | 7.37 | | |
| L0R5D5 | Alternative protein TMEM70 OS = Homo sapiens GN = TMEM70 PE = 4 SV = 1 - [L0R5D5_HUMAN] | 9.69 | 37.17 | 2 | 3 | 3 | 4 | 113 | 13.2 | 6.52 | | |
| Q8WUY1 | Protein THEM6 OS = Homo sapiens GN = THEM6 PE = 1 SV = 2 - [THEM6_HUMAN] | 9.63 | 22.60 | 2 | 5 | 5 | 5 | 208 | 23.8 | 9.55 | | |
| P17858 | ATP-dependent 6-phosphofructokinase, liver type OS = Homo sapiens GN = PFKL PE = 1 SV = 6 - [PFKAL_HUMAN] | 9.62 | 4.74 | 1 | 2 | 2 | 4 | 780 | 85.0 | 7.50 | | |
| Q9NR33 | DNA polymerase epsilon subunit 4 OS = Homo sapiens GN = POLE4 PE = 1 SV = 2 - [DPOE4_HUMAN] | 9.60 | 29.91 | 1 | 2 | 2 | 4 | 117 | 12.2 | 4.92 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| G3V3I1 | Proteasome subunit alpha type OS = Homo sapiens GN = PSMA6 PE = 1 SV = 1 - [G3V3I1_HUMAN] | 9.55 | 20.27 | 4 | 2 | 2 | 3 | 148 | 16.6 | 8.63 | | |
| A6ND22 | 28S ribosomal protein S16, mitochondrial OS = Homo sapiens GN = MRPS16 PE = 1 SV = 1 - [A6ND22_HUMAN] | 9.54 | 41.41 | 2 | 3 | 3 | 6 | 99 | 11.1 | 9.69 | | |
| B7Z7E5 | cDNA FLJ58703, highly similar to Homo sapiens lung cancer-related protein 8 (HLC-8), mRNA OS = Homo sapiens PE = 2 SV = 1 - [B7Z7E5_HUMAN] | 9.51 | 6.58 | 4 | 2 | 2 | 4 | 547 | 60.7 | 9.14 | | |
| K7ELQ9 | Transmembrane protein 205 (Fragment) OS = Homo sapiens GN = TMEM205 PE = 1 SV = 1 - [K7ELQ9_HUMAN] | 9.45 | 24.71 | 4 | 3 | 3 | 4 | 170 | 19.3 | 8.97 | | |
| J3QL15 | Ribosomal protein L19 (Fragment) OS = Homo sapiens GN = RPL19 PE = 1 SV = 1 - [J3QL15_HUMAN] | 9.38 | 14.06 | 6 | 2 | 2 | 5 | 128 | 15.0 | 11.97 | | |
| F5H4N4 | Peroxisomal membrane protein 2 OS = Homo sapiens GN = PXMP2 PE = 1 SV = 1 - [F5H4N4_HUMAN] | 9.35 | 20.00 | 2 | 2 | 2 | 4 | 160 | 17.5 | 8.60 | | |
| P13073 | Cytochrome c oxidase subunit 4 isoform 1, mitochondrial OS = Homo sapiens GN = COX4I1 PE = 1 SV = 1 - [COX41_HUMAN] | 9.29 | 25.44 | 3 | 4 | 4 | 4 | 169 | 19.6 | 9.51 | | |
| E7EX90 | Dynactin subunit 1 OS = Homo sapiens GN = DCTN1 PE = 1 SV = 1 - [E7EX90_HUMAN] | 9.28 | 4.46 | 4 | 3 | 3 | 6 | 1256 | 139.0 | 5.67 | | |
| Q8N8J7 | Uncharacterized protein C4orf32 OS = Homo sapiens GN = C4orf32 PE = 2 SV = 2 - [CD032_HUMAN] | 9.27 | 24.24 | 1 | 3 | 3 | 12 | 132 | 14.6 | 4.70 | | |
| B5MCT8 | 40S ribosomal protein S9 OS = Homo sapiens GN = RPS9 PE = 1 SV = 1 - [B5MCT8_HUMAN] | 9.18 | 24.46 | 5 | 4 | 4 | 4 | 139 | 16.6 | 11.06 | | |
| J3KTJ8 | 60S ribosomal protein L26 (Fragment) OS = Homo sapiens GN = RPL26 PE = 4 SV = 7 - [J3KTJ8_HUMAN] | 9.17 | 18.56 | 12 | 3 | 3 | 6 | 97 | 11.6 | 10.90 | | |
| F5GXW6 | Brain protein I3 OS = Homo sapiens GN = BRI3 PE = 1 SV = 1 - [F5GXW6_HUMAN] | 9.07 | 20.41 | 2 | 2 | 2 | 3 | 98 | 10.9 | 8.78 | | |
| F5GWF6 | T-complex protein 1 subunit beta OS = Homo sapiens GN = CCT2 PE = 1 SV = 2 - [F5GWF6_HUMAN] | 9.06 | 12.26 | 5 | 4 | 4 | 4 | 530 | 56.8 | 6.44 | | |
| Q9NP J3 | Acyl-coenzyme A thioesterase 13 OS = Homo sapiens GN = ACOT13 PE = 1 SV = 1 - [ACO13_HUMAN] | 9.05 | 21.43 | 1 | 2 | 2 | 3 | 140 | 15.0 | 9.14 | | |
| B1AJY7 | 26S proteasome non-ATPase regulatory subunit 10 OS = Homo sapiens GN = PSMD10 PE = 1 SV = 1 - [B1AJY7_HUMAN] | 8.98 | 26.94 | 4 | 3 | 3 | 4 | 193 | 20.8 | 6.64 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| F5H265 | Polyubiquitin-C (Fragment) OS = Homo sapiens GN = UBC PE = 1 SV = 1 - [F5H265_HUMAN] | 8.84 | 33.56 | 31 | 2 | 2 | 3 | 149 | 16.8 | 6.58 | | |
| Q04837 | Single-stranded DNA-binding protein, mitochondrial OS = Homo sapiens GN = SSBP1 PE = 1 SV = 1 - [SSBP_HUMAN] | 8.83 | 22.30 | 2 | 2 | 2 | 3 | 148 | 17.2 | 9.60 | | |
| Q5RI15 | Cytochrome c oxidase protein 20 homolog OS = Homo sapiens GN = COX20 PE = 1 SV = 2 - [COX20_HUMAN] | 8.79 | 22.88 | 1 | 2 | 2 | 3 | 118 | 13.3 | 8.76 | | |
| Q86TW5 | Full-length cDNA clone CS0DC006YI13 of Neuroblastoma of Homo sapiens (human) (Fragment) OS = Homo sapiens PE = 2 SV = 1 - [Q86TW5_HUMAN] | 8.55 | 17.27 | 2 | 2 | 2 | 4 | 139 | 15.7 | 9.83 | | |
| Q5T092 | Protein RER1 (Fragment) OS = Homo sapiens GN = RER1 PE = 1 SV = 1 - [Q5T092_HUMAN] | 8.51 | 18.35 | 5 | 2 | 2 | 3 | 158 | 18.4 | 7.43 | | |
| K7ES31 | Eukaryotic translation initiation factor 3 subunit K OS = Homo sapiens GN = EIF3K PE = 1 SV = 1 - [K7ES31_HUMAN] | 8.50 | 10.95 | 4 | 2 | 2 | 3 | 137 | 15.9 | 6.74 | | |
| B4DIQ8 | cDNA FLJ55694, highly similar to Dipeptidyl-peptidase 1 (EC 3.4.14.1) OS = Homo sapiens PE = 2 SV = 1 - [B4DIQ8_HUMAN] | 8.41 | 7.85 | 2 | 2 | 2 | 3 | 446 | 50.1 | 6.99 | | |
| Q14442 | Phosphatidylinositol N-acetylglucosaminyltransferase subunit H OS = Homo sapiens GN = PIGH PE = 1 SV = 1 - [PIGH_HUMAN] | 8.37 | 12.23 | 1 | 2 | 2 | 3 | 188 | 21.1 | 6.73 | | |
| Q9Y3D2 | Methionine-R-sulfoxide reductase B2, mitochondrial OS = Homo sapiens GN = MSRB2 PE = 1 SV = 2 - [MSRB2_HUMAN] | 8.35 | 32.42 | 2 | 3 | 3 | 3 | 182 | 19.5 | 8.63 | | |
| O95168 | NADH dehydrogenase [ubiquinone] 1 beta subcomplex subunit 4 OS = Homo sapiens GN = NDUFB4 PE = 1 SV = 3 - [NDUB4_HUMAN] | 8.34 | 21.71 | 1 | 2 | 2 | 3 | 129 | 15.2 | 9.85 | | |
| B0AZV0 | cDNA, FLJ79540, highly similar to Serine-threonine kinase receptor-associatedprotein OS = Homo sapiens PE = 2 SV = 1 - [B0AZV0_HUMAN] | 8.29 | 19.14 | 3 | 3 | 3 | 3 | 256 | 28.5 | 4.91 | | |
| P00918 | Carbonic anhydrase 2 OS = Homo sapiens GN = CA2 PE = 1 SV = 2 - [CAH2_HUMAN] | 8.26 | 14.62 | 2 | 3 | 3 | 3 | 260 | 29.2 | 7.40 | | |
| Q15126 | Phosphomevalonate kinase OS = Homo sapiens GN = PMVK PE = 1 SV = 3 - [PMVK_HUMAN] | 8.20 | 17.71 | 1 | 3 | 3 | 3 | 192 | 22.0 | 5.73 | | |
| B5BU24 | 14-3-3 protein beta/alpha OS = Homo sapiens GN = YWHAB PE = 2 SV = 1 - [B5BU24_HUMAN] | | 17.48 | 8 | 2 | 3 | 7 | 246 | 28.1 | 4.83 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| P54886 | Delta-1-pyrroline-5-carboxylate synthase OS = Homo sapiens GN = ALDH18A1 PE = 1 SV = 2 - [P5CS_HUMAN] | 8.14 | 4.91 | 1 | 3 | 3 | 3 | 795 | 87.2 | 7.12 | | |
| J3KTF8 | Rho GDP-dissociation inhibitor 1 (Fragment) OS = Homo sapiens GN = ARHGDIA PE = 1 SV = 7 - [J3KTF8_HUMAN] | 8.14 | 23.71 | 4 | 3 | 3 | 4 | 194 | 21.6 | 5.49 | | |
| P62424 | 60S ribosomal protein L7a OS = Homo sapiens GN = RPL7A PE = 1 SV = 2 - [RL7A_HUMAN] | 8.12 | 16.92 | 4 | 3 | 3 | 3 | 266 | 30.0 | 10.61 | | |
| Q05D40 | CYP51A1 protein (Fragment) OS = Homo sapiens GN = CYP51A1 PE = 2 SV = 1 - [Q05D40_HUMAN] | 8.08 | 13.33 | 4 | 2 | 2 | 3 | 180 | 19.5 | 9.45 | | |
| Q02413 | Desmoglein-1 OS = Homo sapiens GN = DSG1 PE = 1 SV = 2 - [DSG1_HUMAN] | 8.07 | 4.39 | 1 | 3 | 3 | 5 | 1049 | 113.7 | 5.03 | | |
| Q9HBL7 | Plasminogen receptor (KT) OS = Homo sapiens GN = PLGRKT PE = 1 SV = 1 - [PLRKT_HUMAN] | 8.07 | 15.65 | 1 | 2 | 2 | 3 | 147 | 17.2 | 9.58 | | |
| A0A087WY88 | Protein jagunal homolog 1 OS = Homo sapiens GN = JAGN1 PE = 1 SV = 1 - [A0A087WY88_HUMAN] | 8.04 | 7.73 | 3 | 3 | 3 | 3 | 181 | 20.8 | 9.57 | | |
| A8K2Z3 | cDNA FLJ76092, highly similar to Homo sapiens 5'-nucleotidase, cytosolic II-like 1 (NT5C2L1), mRNA OS = Homo sapiens PE = 2 SV = 1 - [A8K2Z3_HUMAN] | 7.94 | 11.43 | 3 | 3 | 3 | 4 | 455 | 51.8 | 6.35 | | |
| Q86W20 | Protease serine 1 (Fragment) OS = Homo sapiens GN = PRSS1 PE = 3 SV = 1 - [Q86W20_HUMAN] | 7.91 | 23.81 | 6 | 2 | 2 | 3 | 84 | 9.2 | 10.27 | | |
| P04080 | Cystatin-B OS = Homo sapiens GN = CSTB PE = 1 SV = 2 - [CYTB_HUMAN] | 7.90 | 45.92 | 1 | 3 | 3 | 3 | 98 | 11.1 | 7.56 | | |
| B3KQA0 | cDNA FLJ90015 fis, clone HEMBA1000634, highly similar to Homo sapiens Mof4 family associated protein 1 (MRFAP1), mRNA OS = Homo sapiens PE = 2 SV = 1 - [B3KQA0_HUMAN] | 7.87 | 26.77 | 2 | 2 | 2 | 4 | 127 | 14.5 | 4.64 | | |
| E7EX53 | Ribosomal protein L15 (Fragment) OS = Homo sapiens GN = RPL15 PE = 1 SV = 1 - [E7EX53_HUMAN] | 7.87 | 15.79 | 4 | 2 | 2 | 3 | 133 | 15.7 | 11.00 | | |
| A8K7F6 | cDNA FLJ78244, highly similar to Homo sapiens eukaryotic translation initiation factor 4A, isoform 1 (EIF4A1), mRNA OS = Homo sapiens PE = 2 SV = 1 - [A8K7F6_HUMAN] | 7.85 | 19.21 | 21 | 5 | 5 | 5 | 406 | 46.1 | 5.48 | | |
| A0A087WUL2 | Proteasome subunit beta type-3 (Fragment) OS = Homo sapiens GN = PSMB3 PE = 1 SV = 1 - [A0A087WUL2_HUMAN] | 7.76 | 20.69 | 2 | 2 | 2 | 3 | 145 | 16.2 | 8.43 | | |
| A0A087WVA1 | Selenoprotein T OS = Homo sapiens GN = SELT PE = 1 SV = 1 - [A0A087WVA1_HUMAN] | 7.71 | 15.38 | 2 | 3 | 3 | 4 | 195 | 22.3 | 8.78 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| F5H282 | T-complex protein 1 subunit alpha OS = Homo sapiens GN = TCP1 PE = 1 SV = 1 - [F5H282_HUMAN] | 7.63 | 9.94 | 3 | 2 | 2 | 4 | 332 | 36.4 | 7.02 | | |
| B4DUR8 | T-complex protein 1 subunit gamma OS = Homo sapiens GN = CCT3 PE = 1 SV = 1 - [B4DUR8_HUMAN] | 7.56 | 6.60 | 5 | 3 | 3 | 3 | 500 | 55.6 | 5.64 | | |
| A2VC08 | MHC class I antigen (Fragment) OS = Homo sapiens GN = HLA-B PE = 3 SV = 1 - [A2VC08_HUMAN] | 7.51 | 18.68 | 124 | 1 | 3 | 3 | 273 | 31.7 | 6.39 | | |
| K7EP07 | Tubulin-folding cofactor B (Fragment) OS = Homo sapiens GN = TBCB PE = 1 SV = 7 - [K7EP07_HUMAN] | 7.48 | 18.82 | 3 | 3 | 3 | 3 | 170 | 19.3 | 5.34 | | |
| B3KTM1 | Malate dehydrogenase OS = Homo sapiens PE = 2 SV = 1 - [B3KTM1_HUMAN] | 7.47 | 14.29 | 6 | 2 | 2 | 3 | 231 | 24.6 | 7.99 | | |
| Q99735 | Microsomal glutathione S-transferase 2 OS = Homo sapiens GN = MGST2 PE = 1 SV = 1 - [MGST2_HUMAN] | 7.47 | 19.05 | 1 | 3 | 3 | 3 | 147 | 16.6 | 9.55 | | |
| Q6ZVI6 | NADH-cytochrome b5 reductase OS = Homo sapiens PE = 2 SV = 1 - [Q6ZVI6_HUMAN] | 7.46 | 11.67 | 3 | 2 | 2 | 3 | 257 | 28.9 | 6.99 | | |
| D3DP46 | Signal peptidase complex subunit 3 homolog (S. cerevisiae), isoform CRA_a OS = Homo sapiens GN = SPCS3 PE = 4 SV = 1 - [D3DP46_HUMAN] | 7.43 | 12.78 | 2 | 2 | 2 | 3 | 180 | 20.3 | 8.97 | | |
| B4DGK8 | cDNA FLJ57723, moderately similar to Protein-tyrosine phosphatase mitochondrial 1, mitochondrial (EC 3.1.3.48) OS = Homo sapiens PE = 2 SV = 1 - [B4DGK8_HUMAN] | 7.43 | 18.25 | 2 | 2 | 2 | 3 | 137 | 15.8 | 9.70 | | |
| Q5VZR0 | Golgi-associated plant pathogenesis-related protein 1 OS = Homo sapiens GN = GLIPR2 PE = 1 SV = 1 - [Q5VZR0_HUMAN] | 7.43 | 20.31 | 3 | 2 | 2 | 2 | 128 | 14.2 | 9.51 | | |
| Q9BYC9 | 39S ribosomal protein L20, mitochondrial OS = Homo sapiens GN = MRPL20 PE = 1 SV = 1 - [RM20_HUMAN] | 7.41 | 21.48 | 1 | 3 | 3 | 3 | 149 | 17.4 | 10.86 | | |
| Q59F34 | Ribosomal protein L28 variant (Fragment) OS = Homo sapiens PE = 2 SV = 1 - [Q59F34_HUMAN] | 7.40 | 38.95 | 5 | 3 | 3 | 6 | 95 | 10.7 | 10.42 | | |
| Q9BW61 | DET1- and DDB1-associated protein 1 OS = Homo sapiens GN = DDA1 PE = 1 SV = 1 - [DDA1_HUMAN] | 7.36 | 27.45 | 1 | 2 | 2 | 3 | 102 | 11.8 | 8.68 | | |
| O14828 | Secretory carrier-associated membrane protein 3 OS = Homo sapiens GN = SCAMP3 PE = 1 SV = 3 - [SCAM3_HUMAN] | 7.35 | 9.22 | 2 | 2 | 2 | 2 | 347 | 38.3 | 7.64 | | |
| P08727 | Keratin, type I cytoskeletal 19 OS = Homo sapiens GN = KRT19 PE = 1 SV = 4 - [K1C19_HUMAN] | 7.33 | 7.50 | 2 | 1 | 3 | 3 | 400 | 44.1 | 5.14 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| B4DIZ6 | cDNA FLJ57941, highly similar to Nucleoside diphosphate-linked moiety X motif 6 (EC 3.6.1.—) OS = Homo sapiens PE = 2 SV = 1 - [B4DIZ6_HUMAN] | 7.32 | 36.24 | 2 | 3 | 3 | 3 | 149 | 16.3 | 6.09 | | |
| Q6PI78 | Transmembrane protein 65 OS = Homo sapiens GN = TMEM65 PE = 1 SV = 2 - [TMM65_HUMAN] | 7.30 | 20.00 | 1 | 4 | 4 | 4 | 240 | 25.5 | 8.60 | | |
| P62314 | Small nuclear ribonucleoprotein Sm D1 OS = Homo sapiens GN = SNRPD1 PE = 1 SV = 1 - [SMD1_HUMAN] | 7.28 | 43.70 | 2 | 3 | 3 | 3 | 119 | 13.3 | 11.56 | | |
| Q5JR95 | 40S ribosomal protein S8 OS = Homo sapiens GN = RPS8 PE = 1 SV = 1 - [Q5JR95_HUMAN] | 7.28 | 14.89 | 2 | 2 | 2 | 2 | 188 | 21.9 | 10.36 | | |
| P61026 | Ras-related protein Rab-10 OS = Homo sapiens GN = RAB10 PE = 1 SV = 1 - [RAB10_HUMAN] | 7.27 | 23.00 | 17 | 1 | 3 | 3 | 200 | 22.5 | 8.38 | | |
| M0R2L9 | 40S ribosomal protein S19 (Fragment) OS = Homo sapiens GN = RPS19 PE = 1 SV = 1 - [M0R2L9_HUMAN] | 7.27 | 57.75 | 4 | 1 | 4 | 4 | 71 | 8.2 | 8.88 | | |
| Q9Y6A4 | Cilia- and flagella-associated protein 20 OS = Homo sapiens GN = CFAP20 PE = 1 SV = 1 - [CFA20_HUMAN] | 7.23 | 12.44 | 2 | 3 | 3 | 3 | 193 | 22.8 | 9.76 | | |
| P60953 | Cell division control protein 42 homolog OS = Homo sapiens GN = CDC42 PE = 1 SV = 2 - [CDC42_HUMAN] | 7.22 | 21.99 | 7 | 3 | 3 | 3 | 191 | 21.2 | 6.55 | | |
| A0A0D9SG71 | Ubiquitin-conjugating enzyme E2 A OS = Homo sapiens GN = UBE2A PE = 1 SV = 1 - [A0A0D9SG71_HUMAN] | 7.21 | 24.37 | 6 | 3 | 3 | 3 | 119 | 13.6 | 4.75 | | |
| Q9Y3D9 | 28S ribosomal protein S23, mitochondrial OS = Homo sapiens GN = MRPS23 PE = 1 SV = 2 - [RT23_HUMAN] | 7.16 | 18.95 | 1 | 2 | 2 | 3 | 190 | 21.8 | 8.90 | | |
| Q9BVV7 | Mitochondrial import inner membrane translocase subunit Tim21 OS = Homo sapiens GN = TIMM21 PE = 1 SV = 1 - [TIM21_HUMAN] | 7.12 | 14.11 | 2 | 3 | 3 | 3 | 248 | 28.2 | 9.70 | | |
| O43402 | ER membrane protein complex subunit 8 OS = Homo sapiens GN = EMC8 PE = 1 SV = 1 - [EMC8_HUMAN] | 7.08 | 14.76 | 1 | 2 | 2 | 2 | 210 | 23.8 | 6.40 | | |
| P27348 | 14-3-3 protein theta OS = Homo sapiens GN = YWHAQ PE = 1 SV = 1 - [1433T_HUMAN] | 7.05 | 16.33 | 3 | 2 | 3 | 3 | 245 | 27.7 | 4.78 | | |
| D6RAN8 | 39S ribosomal protein L27, mitochondrial OS = Homo sapiens GN = MRPL27 PE = 1 SV = 1 - [D6RAN8_HUMAN] | 7.01 | 44.09 | 3 | 3 | 3 | 3 | 93 | 10.5 | 9.54 | | |
| E7ETK0 | 40S ribosomal protein S24 OS = Homo sapiens GN = RPS24 PE = 1 SV = 1 - [E7ETK0_HUMAN] | 6.95 | 20.61 | 3 | 2 | 2 | 3 | 131 | 15.2 | 10.89 | | |
| J3JS69 | 40S ribosomal protein S18 OS = Homo sapiens GN = RPS18 PE = 1 SV = 1 - [J3JS69_HUMAN] | 6.93 | 24.39 | 2 | 2 | 2 | 3 | 82 | 9.8 | 11.41 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| B3KP47 | cDNA FLJ31151 fis, clone IMR322001541, highly similar to Probable ribosome biogenesis protein RLP24 OS = Homo sapiens PE = 2 SV = 1 - [B3KP47_HUMAN] | 6.92 | 16.56 | 2 | 2 | 2 | 3 | 163 | 19.6 | 9.86 | | |
| Q02790 | Peptidyl-prolyl cis-trans isomerase FKBP4 OS = Homo sapiens GN = FKBP4 PE = 1 SV = 3 - [FKBP4_HUMAN] | 6.84 | 7.84 | 1 | 2 | 2 | 2 | 459 | 51.8 | 5.43 | | |
| P39019 | 40S ribosomal protein S19 OS = Homo sapiens GN = RPS19 PE = 1 SV = 2 - [RS19_HUMAN] | 6.83 | 40.00 | 6 | 2 | 5 | 5 | 145 | 16.1 | 10.32 | | |
| Q9Y5J6 | Mitochondrial import inner membrane translocase subunit Tim10 B OS = Homo sapiens GN = TIMM10B PE = 1 SV = 1 - [T10B_HUMAN] | 6.83 | 39.81 | 1 | 2 | 2 | 3 | 103 | 11.6 | 7.43 | | |
| C9IZF9 | Programmed cell death 6-interacting protein (Fragment) OS = Homo sapiens GN = PDCD6IP PE = 1 SV = 1 - [C9IZF9_HUMAN] | 6.69 | 18.95 | 3 | 2 | 2 | 4 | 153 | 17.1 | 5.90 | | |
| P62380 | TATA box-binding protein-like protein 1 OS = Homo sapiens GN = TBPL1 PE = 1 SV = 1 - [TBPL1_HUMAN] | 6.65 | 19.35 | 1 | 2 | 2 | 2 | 186 | 20.9 | 9.54 | | |
| Q9BRX8 | Redox-regulatory protein FAM213A OS = Homo sapiens GN = FAM213A PE = 1 SV = 3 - [F213A_HUMAN] | 6.61 | 13.10 | 1 | 2 | 2 | 2 | 229 | 25.7 | 8.84 | | |
| Q9UFW8 | CGG triplet repeat-binding protein 1 OS = Homo sapiens GN = CGGBP1 PE = 1 SV = 2 - [CGBP1_HUMAN] | 6.57 | 23.35 | 2 | 3 | 3 | 3 | 167 | 18.8 | 8.95 | | |
| B4DKS8 | cDNA FLJ57121, highly similar to Heterogeneous nuclear ribonucleoprotein F OS = Homo sapiens PE = 2 SV = 1 - [B4DKS8_HUMAN] | 6.56 | 14.20 | 6 | 1 | 3 | 3 | 338 | 37.2 | 6.05 | | |
| B4DS97 | cDNA FLJ57579, highly similar to Dynactin subunit 5 OS = Homo sapiens PE = 2 SV = 1 - [B4DS97_HUMAN] | 6.54 | 18.66 | 3 | 2 | 2 | 4 | 134 | 14.9 | 9.00 | | |
| F5H702 | 39S ribosomal protein L48, mitochondrial OS = Homo sapiens GN = MRPL48 PE = 1 SV = 1 - [F5H702_HUMAN] | 6.53 | 34.51 | 2 | 3 | 3 | 3 | 113 | 12.8 | 5.24 | | |
| P51970 | NADH dehydrogenase [ubiquinone] 1 alpha subcomplex subunit 8 OS = Homo sapiens GN = NDUFA8 PE = 1 SV = 3 - [NDUA8_HUMAN] | 6.52 | 33.14 | 1 | 3 | 3 | 3 | 172 | 20.1 | 7.65 | | |
| Q05DH1 | Proteasome subunit alpha type (Fragment) OS = Homo sapiens GN = PSMA7 PE = 2 SV = 1 - [Q05DH1_HUMAN] | 6.36 | 10.92 | 2 | 2 | 2 | 2 | 238 | 26.7 | 8.87 | | |
| C9JXG8 | Ran-specific GTPase-activating protein (Fragment) OS = Homo sapiens GN = RANBP1 PE = 1 SV = 2 - [C9JXG8_HUMAN] | 6.35 | 22.07 | 8 | 2 | 2 | 2 | 145 | 16.9 | 8.53 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| A0A024RB27 | HCG24991, isoform CRA_a OS = Homo sapiens GN = hCG_24991 PE = 3 SV = 1 - [A0A024RB27_HUMAN] | 6.32 | 17.73 | 4 | 2 | 3 | 3 | 203 | 22.7 | 8.79 | | |
| E4W6B6 | RPL27/NME2 fusion protein (Fragment) OS = Homo sapiens GN = RPL27 PE = 2 SV = 1 - [E4W6B6_HUMAN] | 6.31 | 30.16 | 4 | 3 | 3 | 3 | 126 | 14.2 | 10.46 | | |
| B1AKZ5 | Astrocytic phosphoprotein PEA-15 OS = Homo sapiens GN = PEA15 PE = 1 SV = 1 - [B1AKZ5_HUMAN] | 6.25 | 23.15 | 3 | 2 | 2 | 2 | 108 | 12.5 | 5.17 | | |
| P24390 | ER lumen protein-retaining receptor 1 OS = Homo sapiens GN = KDELR1 PE = 1 SV = 1 - [ERD21_HUMAN] | 6.24 | 16.98 | 1 | 2 | 2 | 2 | 212 | 24.5 | 8.62 | | |
| Q9UQ80 | Proliferation-associated protein 2G4 OS = Homo sapiens GN = PA2G4 PE = 1 SV = 3 - [PA2G4_HUMAN] | 6.22 | 8.88 | 1 | 2 | 2 | 3 | 394 | 43.8 | 6.55 | | |
| Q9NVP2 | Histone chaperone ASF1B OS = Homo sapiens GN = ASF1B PE = 1 SV = 1 - [ASF1B_HUMAN] | 6.21 | 14.36 | 1 | 2 | 2 | 2 | 202 | 22.4 | 4.56 | | |
| P68431 | Histone H3.1 OS = Homo sapiens GN = HIST1H3A PE = 1 SV = 2 - [H31_HUMAN] | 6.17 | 28.68 | 1 | 1 | 2 | 2 | 136 | 15.4 | 11.12 | | |
| Q6P1X6 | UPF0598 protein C8orf82 OS = Homo sapiens GN = C8orf82 PE = 1 SV = 2 - [CH082_HUMAN] | 6.15 | 16.20 | 2 | 2 | 2 | 2 | 216 | 23.9 | 9.14 | | |
| H0YJH7 | Lamina-associated polypeptide 2, isoforms beta/gamma (Fragment) OS = Homo sapiens GN = TMPO PE = 1 SV = 1 - [H0YJH7_HUMAN] | 6.12 | 14.35 | 3 | 2 | 2 | 2 | 237 | 26.9 | 9.31 | | |
| Q14484 | Beta-globin (Fragment) OS = Homo sapiens GN = HBB PE = 3 SV = 1 - [Q14484_HUMAN] | 6.11 | 52.46 | 23 | 2 | 2 | 2 | 61 | 6.7 | 4.88 | | |
| Q9Y584 | Mitochondrial import inner membrane translocase subunit Tim22 OS = Homo sapiens GN = TIMM22 PE = 1 SV = 2 - [TIM22_HUMAN] | 6.10 | 15.98 | 1 | 2 | 2 | 2 | 194 | 20.0 | 7.59 | | |
| Q6NSF2 | RPLP0 protein OS = Homo sapiens GN = RPLP0 PE = 2 SV = 1 - [Q6NSF2_HUMAN] | 6.00 | 20.87 | 7 | 2 | 2 | 2 | 254 | 27.3 | 8.22 | | |
| J3QLL0 | Importin subunit alpha-1 (Fragment) OS = Homo sapiens GN = KPNA2 PE = 1 SV = 1 - [J3QLL0_HUMAN] | 5.99 | 26.12 | 6 | 2 | 2 | 2 | 134 | 15.2 | 10.21 | | |
| Q9NWH2 | Transmembrane protein 242 OS = Homo sapiens GN = TMEM242 PE = 1 SV = 1 - [TM242_HUMAN] | 5.97 | 21.99 | 1 | 2 | 2 | 2 | 141 | 14.7 | 9.11 | | |
| Q96KK5 | Histone H2A type 1-H OS = Homo sapiens GN = HIST1H2AH PE = 1 SV = 3 - [H2A1H_HUMAN] | 5.95 | 21.88 | 13 | 2 | 2 | 2 | 128 | 13.9 | 10.89 | | |
| F5H3C5 | Superoxide dismutase (Fragment) OS = Homo sapiens GN = SOD2 PE = 1 SV = 1 - [F5H3C5_HUMAN] | 5.93 | 32.43 | 10 | 2 | 2 | 2 | 111 | 12.1 | 8.46 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q0VDC6 | Peptidyl-prolyl cis-trans isomerase OS = Homo sapiens GN = FKBP1A PE = 1 SV = 1 - [Q0VDC6_HUMAN] | 5.88 | 23.45 | 1 | 2 | 2 | 2 | 145 | 15.7 | 9.17 | | |
| P22695 | Cytochrome b-c1 complex subunit 2, mitochondrial OS = Homo sapiens GN = UQCRC2 PE = 1 SV = 3 - [QCR2_HUMAN] | 5.87 | 7.28 | 1 | 2 | 2 | 2 | 453 | 48.4 | 8.63 | | |
| A6YPU5 | Oral cancer overexpressed protein 1-A OS = Homo sapiens GN = ORAOV1 PE = 1 SV = 1 - [A6YPU5_HUMAN] | 5.82 | 31.43 | 5 | 2 | 2 | 2 | 70 | 7.7 | 4.59 | | |
| B2R418 | cDNA, FLJ92106, highly similar to Homo sapiens adaptor-related protein complex 3, sigma 1 subunit(AP3S1), mRNA OS = Homo sapiens PE = 2 SV = 1 - [B2R418_HUMAN] | 5.79 | 12.44 | 2 | 2 | 2 | 3 | 193 | 21.7 | 5.39 | | |
| H0YM70 | Proteasome activator complex subunit 2 OS = Homo sapiens GN = PSME2 PE = 1 SV = 1 - [H0YM70_HUMAN] | 5.77 | 12.72 | 4 | 2 | 2 | 2 | 228 | 26.0 | 5.92 | | |
| B4DUD4 | cDNA FLJ59988, highly similar to Ras-related protein Rab-2B OS = Homo sapiens PE = 2 SV = 1 - [B4DUD4_HUMAN] | 5.77 | 18.24 | 2 | 1 | 2 | 2 | 170 | 19.0 | 7.42 | | |
| F8VR50 | Actin-related protein 2/3 complex subunit 3 (Fragment) OS = Homo sapiens GN = ARPC3 PE = 1 SV = 1 - [F8VR50_HUMAN] | 5.73 | 28.57 | 6 | 2 | 2 | 2 | 84 | 9.7 | 7.93 | | |
| B4DGX3 | cDNA FLJ54607, highly similar to Multifunctional protein ADE2 OS = Homo sapiens PE = 2 SV = 1 - [B4DGX3_HUMAN] | 5.73 | 10.36 | 3 | 2 | 2 | 2 | 280 | 31.5 | 6.06 | | |
| Q9BSD7 | Cancer-related nucleoside-triphosphatase OS = Homo sapiens GN = NTPCR PE = 1 SV = 1 - [NTPCR_HUMAN] | 5.73 | 20.00 | 2 | 3 | 3 | 3 | 190 | 20.7 | 9.54 | | |
| A0A087X1K9 | Acyl-protein thioesterase 1 OS = Homo sapiens GN = LYPLA1 PE = 1 SV = 1 - [A0A087X1K9_HUMAN] | 5.72 | 28.31 | 4 | 3 | 3 | 3 | 166 | 18.0 | 5.06 | | |
| A8K005 | cDNA FLJ77896, highly similar to Homo sapiens Ras homolog enriched in brain (RHEB), mRNA OS = Homo sapiens PE = 2 SV = 1 - [A8K005_HUMAN] | 5.64 | 12.50 | 3 | 2 | 2 | 2 | 184 | 20.5 | 5.92 | | |
| Q9NX76 | CKLF-like MARVEL transmembrane domain-containing protein 6 OS = Homo sapiens GN = CMTM6 PE = 1 SV = 1 - [CKLF6_HUMAN] | 5.62 | 11.48 | 1 | 2 | 2 | 2 | 183 | 20.4 | 5.29 | | |
| Q8NCS4 | Uncharacterized protein ZMYM6NB OS = Homo sapiens GN = ZMYM6NB PE = 1 SV = 1 - [ZMYNB_HUMAN] | 5.61 | 17.53 | 1 | 2 | 2 | 2 | 154 | 16.9 | 9.17 | | |
| B3KUZ8 | Aspartate aminotransferase OS = Homo sapiens PE = 2 SV = 1 - [B3KUZ8_HUMAN] | 5.56 | 7.82 | 3 | 2 | 2 | 2 | 371 | 41.3 | 8.84 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| B8XPJ7 | Soluble catechol-O-methyltransferase OS = Homo sapiens GN = COMT PE = 2 SV = 1 - [B8XPJ7_HUMAN] | 5.48 | 14.03 | 4 | 2 | 2 | 2 | 221 | 24.5 | 5.45 | | |
| K7EMA7 | 60S ribosomal protein L23a OS = Homo sapiens GN = RPL23A PE = 1 SV = 1 - [K7EMA7_HUMAN] | 5.46 | 30.00 | 6 | 2 | 2 | 2 | 70 | 7.9 | 9.23 | | |
| O75348 | V-type proton ATPase subunit G 1 OS = Homo sapiens GN = ATP6V1G1 PE = 1 SV = 3 - [VATG1_HUMAN] | 5.36 | 11.86 | 1 | 2 | 2 | 3 | 118 | 13.7 | 8.79 | | |
| Q96D05 | Uncharacterized protein C10orf35 OS = Homo sapiens GN = C10orf35 PE = 1 SV = 1 - [CJ035_HUMAN] | 5.35 | 22.31 | 1 | 2 | 2 | 3 | 121 | 13.2 | 11.58 | | |
| Q96KR6 | Protein FAM210B OS = Homo sapiens GN = FAM210B PE = 1 SV = 2 - [F210B_HUMAN] | 5.35 | 15.10 | 1 | 2 | 2 | 2 | 192 | 20.4 | 10.43 | | |
| P82663 | 28S ribosomal protein S25, mitochondrial OS = Homo sapiens GN = MRPS25 PE = 1 SV = 1 - [RT25_HUMAN] | 5.35 | 21.39 | 1 | 2 | 2 | 2 | 173 | 20.1 | 8.82 | | |
| P16152 | Carbonyl reductase [NADPH] 1 OS = Homo sapiens GN = CBR1 PE = 1 SV = 3 - [CBR1_HUMAN] | 5.32 | 9.75 | 1 | 2 | 2 | 2 | 277 | 30.4 | 8.32 | | |
| P30041 | Peroxiredoxin-6 OS = Homo sapiens GN = PRDX6 PE = 1 SV = 3 - [PRDX6_HUMAN] | 5.30 | 10.71 | 1 | 2 | 2 | 3 | 224 | 25.0 | 6.38 | | |
| H0Y9R4 | 60S ribosomal protein L9 (Fragment) OS = Homo sapiens GN = RPL9 PE = 1 SV = 1 - [H0Y9R4_HUMAN] | 5.30 | 12.09 | 5 | 2 | 2 | 2 | 91 | 10.1 | 7.12 | | |
| B4DPY0 | Glutathione peroxidase OS = Homo sapiens PE = 2 SV = 1 - [B4DPY0_HUMAN] | 5.29 | 13.92 | 3 | 2 | 2 | 3 | 158 | 18.1 | 8.81 | | |
| Q9UBB4 | Ataxin-10 OS = Homo sapiens GN = ATXN10 PE = 1 SV = 1 - [ATX10_HUMAN] | 5.23 | 6.11 | 1 | 2 | 2 | 2 | 475 | 53.5 | 5.25 | | |
| P25786 | Proteasome subunit alpha type-1 OS = Homo sapiens GN = PSMA1 PE = 1 SV = 1 - [PSA1_HUMAN] | 5.19 | 14.83 | 4 | 3 | 3 | 3 | 263 | 29.5 | 6.61 | | |
| H3BTP7 | 60S ribosomal protein L4 (Fragment) OS = Homo sapiens GN = RPL4 PE = 1 SV = 1 - [H3BTP7_HUMAN] | 5.17 | 24.12 | 5 | 2 | 2 | 2 | 170 | 18.8 | 10.77 | | |
| D6RBK0 | Prohibitin (Fragment) OS = Homo sapiens GN = PHB PE = 1 SV = 1 - [D6RBK0_HUMAN] | 5.16 | 17.74 | 9 | 3 | 3 | 3 | 124 | 13.7 | 9.36 | | |
| J3QS48 | Mannose-P-dolichol utilization defect 1 protein OS = Homo sapiens GN = MPDU1 PE = 1 SV = 1 - [J3QS48_HUMAN] | 5.14 | 23.76 | 16 | 2 | 2 | 2 | 101 | 11.0 | 8.48 | | |
| K7ESP4 | Dephospho-CoA kinase domain-containing protein (Fragment) OS = Homo sapiens GN = DCAKD PE = 1 SV = 1 - [K7ESP4_HUMAN] | 5.11 | 11.48 | 2 | 2 | 2 | 2 | 209 | 24.2 | 9.67 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| G3V2V8 | Epididymal secretory protein E1 (Fragment) OS = Homo sapiens GN = NPC2 PE = 1 SV = 1 - [G3V2V8_HUMAN] | 5.10 | 23.77 | 9 | 2 | 2 | 2 | 122 | 13.1 | 8.34 | | |
| Q9BV57 | 1,2-dihydroxy-3-keto-5-methylthiopentene dioxygenase OS = Homo sapiens GN = ADI1 PE = 1 SV = 1 - [MTND_HUMAN] | 5.10 | 15.64 | 1 | 2 | 2 | 2 | 179 | 21.5 | 5.68 | | |
| H3BUT5 | Nuclear envelope phosphatase-regulatory subunit 1 OS = Homo sapiens GN = CNEP1R1 PE = 1 SV = 1 - [H3BUT5_HUMAN] | 5.05 | 26.88 | 3 | 2 | 2 | 2 | 93 | 10.4 | 8.54 | | |
| P14174 | Macrophage migration inhibitory factor OS = Homo sapiens GN = MIF PE = 1 SV = 4 - [MIF_HUMAN] | 5.04 | 26.09 | 1 | 2 | 2 | 2 | 115 | 12.5 | 7.88 | | |
| P62081 | 40S ribosomal protein S7 OS = Homo sapiens GN = RPS7 PE = 1 SV = 1 - [RS7_HUMAN] | 5.00 | 19.07 | 1 | 2 | 2 | 2 | 194 | 22.1 | 10.10 | | |
| P10599 | Thioredoxin OS = Homo sapiens GN = TXN PE = 1 SV = 3 - [THIO_HUMAN] | 4.99 | 21.90 | 1 | 2 | 2 | 2 | 105 | 11.7 | 4.92 | | |
| Q96IR1 | RPS4X protein (Fragment) OS = Homo sapiens GN = RPS4X PE = 2 SV = 2 - [Q96IR1_HUMAN] | 4.97 | 13.99 | 3 | 2 | 2 | 2 | 243 | 27.2 | 9.94 | | |
| A0A087WTV6 | Pyrroline-5-carboxylate reductase 2 OS = Homo sapiens GN = PYCR2 PE = 1 SV = 1 - [A0A087WTV6_HUMAN] | 4.97 | 14.23 | 2 | 2 | 2 | 2 | 246 | 25.9 | 9.26 | | |
| Q96EL2 | 28S ribosomal protein S24, mitochondrial OS = Homo sapiens GN = MRPS24 PE = 1 SV = 1 - [RT24_HUMAN] | 4.95 | 17.96 | 1 | 3 | 3 | 3 | 167 | 19.0 | 9.38 | | |
| Q7RTV0 | PHD finger-like domain-containing protein 5A OS = Homo sapiens GN = PHF5A PE = 1 SV = 1 - [PHF5A_HUMAN] | 4.90 | 26.36 | 1 | 2 | 2 | 2 | 110 | 12.4 | 8.41 | | |
| B4DQX3 | cDNA FLJ58927, highly similar to Endoplasmin (Heat shock protein 90 kDa beta member 1) OS = Homo sapiens PE = 2 SV = 1 - [B4DQX3_HUMAN] | 4.85 | 12.88 | 5 | 1 | 2 | 2 | 163 | 18.5 | 5.20 | | |
| A0A087WZX2 | NADH dehydrogenase [ubiquinone] 1 beta subcomplex subunit 6 OS = Homo sapiens GN = NDUFB6 PE = 1 SV = 1 - [A0A087WZX2_HUMAN] | 4.81 | 28.87 | 2 | 2 | 2 | 2 | 97 | 11.7 | 9.48 | | |
| A0A087WUN7 | SRA stem-loop-interacting RNA-binding protein, mitochondrial OS = Homo sapiens GN = SLIRP PE = 1 SV = 1 - [A0A087WUN7_HUMAN] | 4.81 | 26.09 | 5 | 2 | 2 | 2 | 92 | 10.3 | 10.23 | | |
| O60493 | Sorting nexin-3 OS = Homo sapiens GN = SNX3 PE = 1 SV = 3 - [SNX3_HUMAN] | 4.79 | 6.17 | 1 | 2 | 2 | 2 | 162 | 18.8 | 8.66 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| E9PN66 | Tumor protein p53-inducible protein 11 (Fragment) OS = Homo sapiens GN = TP53I11 PE = 1 SV = 1 - [E9PN66_HUMAN] | 4.76 | 41.94 | 12 | 2 | 2 | 2 | 62 | 6.9 | 9.60 | | |
| Q1RMG2 | Adenosylhomocysteinase OS = Homo sapiens GN = AHCY PE = 2 SV = 1 - [Q1RMG2_HUMAN] | 4.72 | 8.82 | 2 | 2 | 2 | 2 | 306 | 33.8 | 6.61 | | |
| Q86WX3 | Active regulator of SIRT1 OS = Homo sapiens GN = RPS19BP1 PE = 1 SV = 1 - [AROS_HUMAN] | 4.72 | 25.00 | 1 | 2 | 2 | 2 | 136 | 15.4 | 10.74 | | |
| F2Z393 | Transaldolase OS = Homo sapiens GN = TALDO1 PE = 1 SV = 1 - [F2Z393_HUMAN] | 4.71 | 6.92 | 2 | 2 | 2 | 2 | 318 | 35.3 | 8.97 | | |
| H7C3I1 | Hsc70-interacting protein (Fragment) OS = Homo sapiens GN = ST13 PE = 1 SV = 1 - [H7C3I1_HUMAN] | 4.71 | 18.49 | 10 | 2 | 2 | 2 | 146 | 16.3 | 4.88 | | |
| A8K9X0 | Protein YIPF OS = Homo sapiens PE = 2 SV = 1 - [A8K9X0_HUMAN] | 4.70 | 5.93 | 2 | 2 | 2 | 2 | 236 | 26.2 | 6.18 | | |
| A0A0A0MRS4 | Transmembrane protein 38B, isoform CRA_b OS = Homo sapiens GN = TMEM38B PE = 1 SV = 1 - [A0A0A0MRS4_HUMAN] | 4.68 | 14.35 | 2 | 2 | 2 | 2 | 237 | 26.4 | 9.10 | | |
| Q9UBK9 | Protein UXT OS = Homo sapiens GN = UXT PE = 1 SV = 1 - [UXT_HUMAN] | 4.64 | 15.92 | 2 | 2 | 2 | 3 | 157 | 18.2 | 7.59 | | |
| E5RIU6 | Cyclin-dependent kinase 1 (Fragment) OS = Homo sapiens GN = CDK1 PE = 1 SV = 2 - [E5RIU6_HUMAN] | 4.63 | 12.70 | 6 | 2 | 2 | 2 | 189 | 21.7 | 8.51 | | |
| Q5W0J0 | Ras-related protein Rab-18 OS = Homo sapiens GN = RAB18 PE = 1 SV = 1 - [Q5W0J0_HUMAN] | 4.61 | 16.15 | 4 | 2 | 2 | 2 | 161 | 18.0 | 4.88 | | |
| P00441 | Superoxide dismutase [Cu—Zn] OS = Homo sapiens GN = SOD1 PE = 1 SV = 2 - [SODC_HUMAN] | 4.60 | 15.58 | 1 | 2 | 2 | 2 | 154 | 15.9 | 6.13 | | |
| Q6NSD4 | Glutathione peroxidase OS = Homo sapiens GN = GPX1 PE = 2 SV = 1 - [Q6NSD4_HUMAN] | 4.58 | 18.62 | 3 | 2 | 2 | 2 | 145 | 16.2 | 5.54 | | |
| B2R761 | cDNA, FLJ93299, highly similar to Homo sapiens sterol carrier protein 2 (SCP2), mRNA OS = Homo sapiens PE = 2 SV = 1 - [B2R761_HUMAN] | 4.55 | 4.02 | 2 | 2 | 2 | 2 | 547 | 59.0 | 7.05 | | |
| B2R8A2 | cDNA, FLJ93804, highly similar to Homo sapiens gp25L2 protein (HSGP25L2G), mRNA OS = Homo sapiens PE = 2 SV = 1 - [B2R8A2_HUMAN] | 4.55 | 7.94 | 2 | 2 | 2 | 3 | 214 | 25.1 | 7.18 | | |
| Q9BSQ6 | RPL13A protein (Fragment) OS = Homo sapiens GN = RPL13A PE = 2 SV = 2 - [Q9BSQ6_HUMAN] | 4.54 | 11.44 | 5 | 2 | 2 | 2 | 201 | 23.4 | 10.93 | | |
| E9PNN3 | 6-pyruvoyl tetrahydrobiopterin synthase OS = Homo sapiens GN = PTS PE = 1 SV = 1 - [E9PNN3_HUMAN] | 4.53 | 35.06 | 2 | 2 | 2 | 2 | 77 | 8.9 | 4.72 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| P05141 | ADP/ATP translocase 2 OS = Homo sapiens GN = SLC25A5 PE = 1 SV = 7 - [ADT2_HUMAN] | 4.51 | 7.72 | 2 | 1 | 2 | 2 | 298 | 32.8 | 9.69 | | |
| P11498 | Pyruvate carboxylase, mitochondrial OS = Homo sapiens GN = PC PE = 1 SV = 2 - [PYC_HUMAN] | 4.50 | 1.87 | 1 | 2 | 2 | 2 | 1178 | 129.6 | 6.84 | | |
| E7EQ72 | Transmembrane emp24 domain-containing protein 2 (Fragment) OS = Homo sapiens GN = TMED2 PE = 1 SV = 2 - [E7EQ72_HUMAN] | 4.42 | 15.06 | 3 | 2 | 2 | 2 | 166 | 18.5 | 4.79 | | |
| Q9BVS9 | IPO5 protein (Fragment) OS = Homo sapiens GN = IPO5 PE = 2 SV = 1 - [Q9BVS9_HUMAN] | 4.37 | 5.48 | 5 | 2 | 2 | 2 | 310 | 35.5 | 4.84 | | |
| E9PKZ0 | 60S ribosomal protein L8 (Fragment) OS = Homo sapiens GN = RPL8 PE = 1 SV = 1 - [E9PKZ0_HUMAN] | 4.34 | 11.22 | 3 | 2 | 2 | 2 | 205 | 22.4 | 10.76 | | |
| E9PIB8 | Selenoprotein S OS = Homo sapiens GN = VIMP PE = 1 SV = 1 - [E9PIB8_HUMAN] | 4.32 | 27.71 | 4 | 3 | 3 | 4 | 166 | 18.5 | 9.79 | | |
| C9JAX1 | Frataxin, mitochondrial OS = Homo sapiens GN = FXN PE = 1 SV = 1 - [C9JAX1_HUMAN] | 4.32 | 21.48 | 2 | 2 | 2 | 2 | 135 | 14.9 | 5.14 | | |
| Q8TCC3 | 39S ribosomal protein L30, mitochondrial OS = Homo sapiens GN = MRPL30 PE = 1 SV = 1 - [RM30_HUMAN] | 4.27 | 29.81 | 2 | 3 | 3 | 3 | 161 | 18.5 | 9.99 | | |
| A6NLJ7 | Ubiquitin carboxyl-terminal hydrolase OS = Homo sapiens GN = UCHL1 PE = 2 SV = 1 - [A6NU7_HUMAN] | 4.27 | 19.01 | 4 | 2 | 2 | 2 | 142 | 15.7 | 5.35 | | |
| B3KTN4 | Citrate synthase OS = Homo sapiens PE = 2 SV = 1 - [B3KTN4_HUMAN] | 4.19 | 6.41 | 3 | 2 | 2 | 2 | 421 | 47.0 | 7.24 | | |
| D6RBE9 | Annexin OS = Homo sapiens GN = ANXA5 PE = 1 SV = 1 - [D6RBE9_HUMAN] | 3.93 | 10.45 | 2 | 2 | 2 | 2 | 220 | 24.7 | 4.89 | | |
| A8YXX5 | Cell proliferation-inducing protein 60 OS = Homo sapiens GN = PIG60 PE = 2 SV = 1 - [A8YXX5_HUMAN] | 3.88 | 5.93 | 8 | 2 | 2 | 2 | 354 | 38.2 | 9.55 | | |
| P14868 | Aspartate-tRNA ligase, cytoplasmic OS = Homo sapiens GN = DARS PE = 1 SV = 2 - [SYDC_HUMAN] | 3.79 | 6.59 | 1 | 2 | 2 | 2 | 501 | 57.1 | 6.55 | | |
| J3QRU7 | Biogenesis of lysosome-related organelles complex 1 subunit 2 (Fragment) OS = Homo sapiens GN = BLOC1S2 PE = 1 SV = 1 - [J3QRU7_HUMAN] | 3.29 | 25.64 | 2 | 2 | 2 | 2 | 117 | 13.5 | 7.84 | | |
| Q5JPE4 | Vacuolar protein sorting-associated protein 29 OS = Homo sapiens GN = DKFZp667O202 PE = 3 SV = 1 - [Q5JPE4_HUMAN] | 3.07 | 14.36 | 3 | 2 | 2 | 2 | 181 | 20.4 | 6.79 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| H3BND3 | Cleavage and polyadenylation-specificity factor subunit 5 (Fragment) OS = Homo sapiens GN = NUDT21 PE = 1 SV = 7 - [H3BND3_HUMAN] | 2.93 | 18.00 | 3 | 2 | 2 | 2 | 150 | 17.2 | 6.38 | | |
| B2R959 | cDNA, FLJ94229, highly similar to Homo sapiens heterogeneous nuclear ribonucleoprotein L (HNRPL), mRNA OS = Homo sapiens PE = 2 SV = 1 - [B2R959_HUMAN] | 2.92 | 11.29 | 1 | 2 | 2 | 3 | 558 | 60.2 | 7.11 | | |
| H0Y4T6 | Peptidyl-prolyl cis-trans isomerase NIMA-interacting 4 (Fragment) OS = Homo sapiens GN = PIN4 PE = 1 SV = 1 - [H0Y4T6_HUMAN] | 2.75 | 15.38 | 5 | 2 | 2 | 2 | 91 | 9.5 | 10.17 | | |
| H0Y4R1 | Inosine-5'-monophosphate dehydrogenase 2 (Fragment) OS = Homo sapiens GN = IMPDH2 PE = 1 SV = 1 - [H0Y4R1_HUMAN] | 2.73 | 6.60 | 2 | 2 | 2 | 2 | 470 | 51.0 | 8.18 | | |
| B2RDE0 | cDNA, FLJ96567, highly similar to Homo sapiens propionyl Coenzyme A carboxylase, alpha polypeptide(PCCA), mRNA OS = Homo sapiens PE = 2 SV = 1 - [B2RDE0_HUMAN] | 2.47 | 5.12 | 2 | 2 | 2 | 2 | 703 | 77.4 | 7.06 | | |
| P18669 | Phosphoglycerate mutase 1 OS = Homo sapiens GN = PGAM1 PE = 1 SV = 2 - [PGAM1_HUMAN] | 2.33 | 7.48 | 4 | 2 | 2 | 2 | 254 | 28.8 | 7.18 | | |
| Q59F44 | Cytochrome b-5 isoform 1 variant (Fragment) OS = Homo sapiens PE = 2 SV = 1 - [Q59F44_HUMAN] | 2.25 | 25.76 | 2 | 2 | 2 | 2 | 132 | 14.6 | 5.72 | | |
| P09234 | U1 small nuclear ribonucleoprotein C OS = Homo sapiens GN = SNRPC PE = 1 SV = 1 - [RU1C_HUMAN] | 2.14 | 18.87 | 3 | 2 | 2 | 2 | 159 | 17.4 | 9.67 | | |
| Q5QNZ2 | ATP synthase F(0) complex subunit B1, mitochondrial OS = Homo sapiens GN = ATP5F1 PE = 1 SV = 1 - [Q5QNZ2_HUMAN] | 2.13 | 12.82 | 4 | 2 | 2 | 2 | 195 | 22.3 | 9.26 | | |
| Q1JQ76 | Ribosomal protein (Fragment) OS = Homo sapiens GN = RPL10A PE = 2 SV = 1 - [Q1JQ76_HUMAN] | 2.12 | 14.56 | 2 | 2 | 2 | 2 | 206 | 23.5 | 10.07 | | |
| A0A024RBI3 | NifU-like N-terminal domain containing, isoform CRA_c OS = Homo sapiens GN = NIFUN PE = 3 SV = 1 - [A0A024RBI3_HUMAN] | 2.10 | 26.76 | 7 | 3 | 3 | 3 | 142 | 15.3 | 7.21 | | |

TABLE 1-continued

| Accession | Description | Score | Coverage | # Proteins | # Unique Peptides | # Peptides | # PSMs | # AAs | MW [kDa] | calc. pI | # of cysteines | expected number of cysteines |
|---|---|---|---|---|---|---|---|---|---|---|---|---|
| Q9Y3C8 | Ubiquitin-fold modifier-conjugating enzyme 1 OS = Homo sapiens GN = UFC1 PE = 1 SV = 3 - [UFC1_HUMAN] | 2.05 | 14.37 | 1 | 2 | 2 | 2 | 167 | 19.4 | 7.40 | | |
| Q9BUE6 | Iron-sulfur cluster assembly 1 homolog, mitochondrial OS = Homo sapiens GN = ISCA1 PE = 1 SV = 1 - [ISCA1_HUMAN] | 2.03 | 20.93 | 1 | 2 | 2 | 2 | 129 | 14.2 | 9.07 | | |
| P31689 | DnaJ homolog subfamily A member 1 OS = Homo sapiens GN = DNAJA1 PE = 1 SV = 2 - [DNJA1_HUMAN] | 1.83 | 6.55 | 1 | 2 | 2 | 2 | 397 | 44.8 | 7.08 | | |
| V9GYJ7 | Rab GDP dissociation inhibitor beta (Fragment) OS = Homo sapiens GN = GDI2 PE = 1 SV = 7 - [V9GYJ7_HUMAN] | 1.79 | 17.46 | 6 | 2 | 2 | 2 | 126 | 14.2 | 9.61 | | |
| P07099 | Epoxide hydrolase 1 OS = Homo sapiens GN = EPHX1 PE = 1 SV = 1 - [HYEP_HUMAN] | 1.78 | 7.03 | 2 | 2 | 2 | 3 | 455 | 52.9 | 7.25 | | |
| Q9HDC9 | Adipocyte plasma membrane-associated protein OS = Homo sapiens GN = APMAP PE = 1 SV = 2 - [APMAP_HUMAN] | 1.75 | 6.73 | 1 | 2 | 2 | 3 | 416 | 46.5 | 6.16 | | |

Figure 3C:
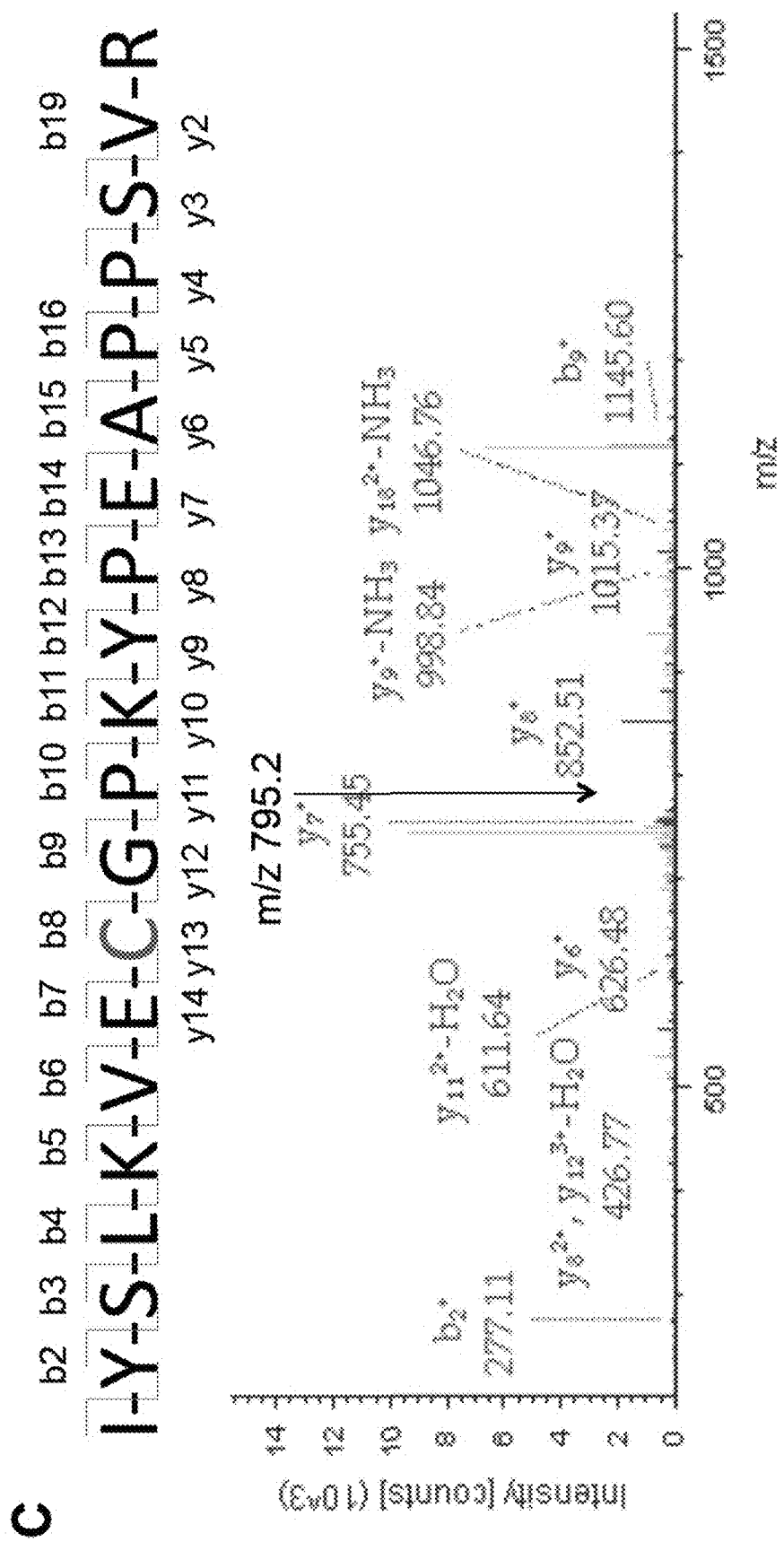
Figures 3D, 3E, 3F:
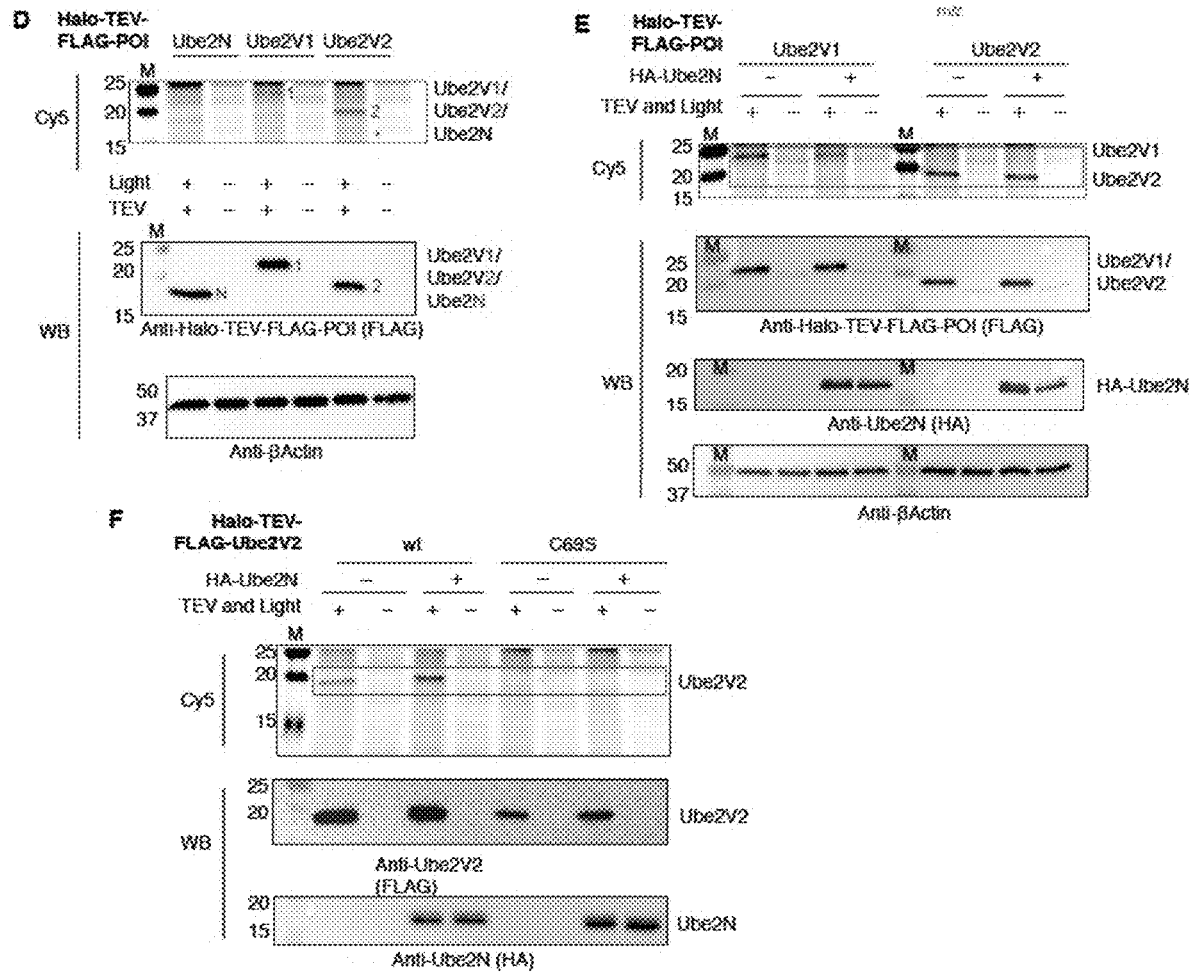

MS analysis of the site of modification is provided as FIG. 32 (also see FIG. 3C). Data in Table 1 and FIG. 3C suggest Structure A is the most likely adduct among the three commonly observed HNEylated cysteines in cellular context (Lin et al., "A Generalizable Platform for Interrogating Target- and Signal-Specific Consequences of Electrophilic Modifications in Redox-Dependent Cell Signaling," *Journal of the American Chemical Society* 137:6232-6244 (2015); Parvez et al., "T-REX on-demand redox targeting in live cells," *Nature Protocols* 11:2328-2356 (2016); Parvez et al., "Substoichiometric Hydroxynonenylation of a Single Protein Recapitulates Whole-Cell-Stimulated Antioxidant Response," *Journal of the American Chemical Society* 137: 10-13 (2015), which are hereby incorporated by reference in their entirety).

TABLE 2

Primers used for the construction of human Halo-TEV-Flag-Ube2V2-wt Halo-TEV-Flag-Ube2V2-C69S, Flag2-Ube2V2-wt, Flag2-Ube2V2-C69S, Halo-TEV-Flag-Ube2V1-wt, T7-Ube2N, NF-kB-Luciferase, Myc-H2A, T7-H2A, and HA-H2A in either pFN21a or pCS2+8 vector.

(a) List of primers for cloning of the gene of interest into pFN21a vector

| Entry | Plasmid | Primers |
|---|---|---|
| (1) | Halo-TEV-Flag-Ube2V2-wt | Fwd-1 AGCGATAACGCGATCGCCGACTACAAGG ATGACGACGATAAGATGGCGGTCTCCACA GGA (SEQ ID NO: 17) Fwd-2 GATTTCCGGCGAGCCAACCACTGAGGATC TGTACTTTCAGAGCGATAACGCGATCGCC (SEQ ID NO: 18) Rev-1 TAGAGGATCCCCGGGTACCGAGCCCGAAT TCGTTTAATTGTTGTATGTTTGTCCTTCTG G (SEQ ID NO: 19) Rev-2 TGTTAGCAGCCGGATCAGCTTGCATGCCT GCAGGTCGACTCTAGAGGATCCCCGGGTA CC (SEQ ID NO: 20) |
| (2) | Halo-TEV-Flag-Ube2V2-C69S | Fwd-1 GAAAACAGAATATATAGCCTGAAAGTAG AAAGTGGACCTAAATACCCAGAAGCTCCT CC (SEQ ID NO: 21) Rev-1 GGAGGAGCTTCTGGGTATTTAGGTCCACT TTCTACTTTCAGGCTATATATTCTGTTTTC (SEQ ID NO: 22) |
| (3) | Flag2-Ube2V2-wt | Fwd-1 TGACGACGATAAGGACTACAAGGATGAC GACGATAAGATGGCGGTCTCCACAGGA (SEQ ID NO: 23) Fwd-2 ATAGGGCTAGCAAAGCCACCATGGATTAC AAGGATGACGACGATAAGGACTACAAGG AT (SEQ ID NO: 24) Rev-1 TAGAGGATCCCCGGGTACC GAGCCCGAATTCGTTTAATTGTTGTATGTT TGTCCTTCTGG (SEQ ID NO: 25) Rev-2 TGTTAGCAGCCGGATCAGCTTGCATGCCT GCAGGTCGACTCTAGAGGATCCCCGGGTA CC (SEQ ID NO: 26) |
| (4) | Flag2-Ube2V2-C69S | Fwd-1 GAAAACAGAATATATAGCCTGAAAGTAG AAAGTGGACCTAAATACCCAGAAGCTCCT CC (SEQ ID NO: 27) Rev-1 GGAGGAGCTTCTGGGTATTTAGGTCCACT TTCTACTTTCAGGCTATATATTCTGTTTTC (SEQ ID NO: 28) |

TABLE 2-continued

Primers used for the construction of human Halo-TEV-Flag-Ube2V2-wt Halo-TEV-Flag-Ube2V2-C69S, Flag2-Ube2V2-wt, Flag2-Ube2V2-C69S, Halo-TEV-Flag-Ube2V1-wt, T7-Ube2N, NF-kB-Luciferase, Myc-H2A, T7-H2A, and HA-H2A in either pFN21a or pCS2+8 vector.

(5) Halo-TEV-Flag-Ube2V1-wt
Fwd-1
AGCGATAACGCGATCGCCGACTACAAGG
ATGACGACGATAAG
ATGCCAGGAGAGGTTCAA (SEQ ID NO: 29)
Fwd-2
GATTTCCGGCGAGCCAACCACTGAGGATC
TGTACTTTCAGAGCGATAACGCGATCGCC
(SEQ ID NO: 30)
Rev-1
TAGAGGATCCCCGGGTACC
GAGCCCGAATTCGTTTAATTGCTGTAACA
CTGTCCTTCG (SEQ ID NO: 31)
Rev-2
TGTTAGCAGCCGGATCAGCTTGCATGCCT
GCAGGTCGACTCTAGAGGATCCCCGGGTA
CC (SEQ ID NO: 32)

(6) T7-Ube2N
Fwd-1
GCAAAGCCACCATGGCCAGCATGACCGG
CGGCCAGCAGATGGGCATGGCCGGGCTG
CCCC (SEQ ID NO: 33)
Fwd-2
AGCTCTTAAGGCTAGAGTATTAATACGAC
TCACTATAGGGCTAGCAAAGCCACCATGG
CC (SEQ ID NO: 34)
Rev-1
TAGAGGATCCCCGGGTACCGAGCCCGAAT
TCGTTTAATTGTTGTATGTTTGTCCTTCTG
G (SEQ ID NO: 35)
Rev-2
TGTTAGCAGCCGGATCAGCTTGCATGCCT
GCAGGTCGACTCTAGAGGATCCCCGGGTA
CC (SEQ ID NO: 36)

(7) NF-kB-Luciferase
Fwd-1
GAGCTCGCTAGCGGGAATTTCCGGGGACT
TTCCGGGAATTTCCGG (SEQ ID NO: 37)
Fwd-2
TGGCCGGTACCTGAGCTCGCTAGCGGGAA
(SEQ ID NO: 38)
Fwd-3
AAGTCCCCGGAAATTCCCGCTAGCGAGCT
CAGGTACCGGCCA (SEQ ID NO: 39)
Rev-1
CGAGGCCAGATCTGGAAATTCCCGGAAA
GTCCCCGGAAATTCCCGGAAAG (SEQ ID
NO: 40)
Rev-2
TGGCCGCCGAGGCCAGATCTGGAAATT
(SEQ ID NO: 41)
Rev-3
AGATCTGGCCTCGGCGGCCAAGCTTAGAC
ACTAGAGGGTAT (SEQ ID NO: 42)

(8) HA-H2AX
Fwd-1
CTACCCATACGACGTCCCAGACTACGCTG
TACCTAGGATCCAGTCGGGAC (SEQ ID
NO: 43)
Fwd-2
CTAGAGTATTAATACGACTCACTATAGGG
CTAGCAAAGCCACCTACCCATACGACGTC
CC (SEQ ID NO: 44)
Rev-1
TCGACTCTAGAGGATCCCCGGGTACCGAG
CCCGAATTCGTCTACTTGCCCTTGGCCTTG
T (SEQ ID NO: 45)
Rev-2
GGGCTTTGTTAGCAGCCGGATCAGCTTGC
ATGCCTGCAGGTCGACTCTAGAGGATCCC
CG (SEQ ID NO: 46)

TABLE 2-continued

Primers used for the construction of human Halo-TEV-Flag-Ube2V2-wt Halo-TEV-Flag-Ube2V2-C69S, Flag2-Ube2V2-wt, Flag2-Ube2V2-C69S, Halo-TEV-Flag-Ube2V1-wt, T7-Ube2N, NF-kB-Luciferase, Myc-H2A, T7-H2A, and HA-H2A in either pFN21a or pCS2+8 vector.

| | | |
|---|---|---|
| (9) | Myc-H2AX | Fwd-1<br>ACAAAAACTCATCTCAGAAGAGGATCTGG<br>TACCTAGGATCCAGTCGGGAC (SEQ ID<br>NO: 47)<br>Fwd-2<br>TAATACGACTCACTATAGGGCTAGCAAAG<br>CCACCGAACAAAAACTCATCTCAGAAGA<br>GGA (SEQ ID NO: 48)<br>Rev-1<br>TCGACTCTAGAGGATCCCCGGGTACCGAG<br>CCCGAATTCGTCTACTTGCCCTTGGCCTTG<br>T (SEQ ID NO: 49)<br>Rev-2<br>GGGCTTTGTTAGCAGCCGGATCAGCTTGC<br>ATGCCTGCAGGTCGACTCTAGAGGATCCC<br>CG (SEQ ID NO: 50) |
| (10) | T7-H2AX | Fwd-1<br>CCAGCATGACCGGCGCCAGCAGATGGG<br>CGTACCTAGGATCCAGTCGGGAC (SEQ ID<br>NO: 51)<br>Fwd-2<br>AGAGTATTAATACGACTCACTATAGGGCT<br>AGCAAAGCCACCATGGCCAGCATGACCG<br>GCG (SEQ ID NO: 52)<br>Rev-1<br>TCGACTCTAGAGGATCCCCGGGTACCGAG<br>CCCGAATTCGTCTACTTGCCCTTGGCCTTG<br>T (SEQ ID NO: 53)<br>Rev-2<br>GGGCTTTGTTAGCAGCCGGATCAGCTTGC<br>ATGCCTGCAGGTCGACTCTAGAGGATCCC<br>CG (SEQ ID NO: 54) |

(b) List of primers for cloning of the gene of interest into PC S2+8 vector

| Entry | Plasmid | Primers |
|---|---|---|
| (1) | Halo-TEV-Flag-Ube2V2-wt | Fwd-1<br>TAATTAAAGGCCGGCCAGCGATCGCCGGA<br>CATGGCAGAAATCGGTACTGG (SEQ ID<br>NO: 55)<br>Fwd-2<br>GCTACTTGTTCTTTTTGCAGGATCCACTAG<br>TGGCGCGCCATTAATTAAAGGCCGGCCAG<br>C (SEQ ID NO: 56)<br>Rev-1<br>TTCTAGAGGCTCGAGAGGCCT<br>TCATGTCTGCTCGAAGCG (SEQ ID NO: 57)<br>Rev-2<br>CTTATCATGTCTGGATCTACGTAATACGA<br>CTCACTATAGTTCTAGAGGCTCGAGAGGC<br>CT (SEQ ID NO: 58) |
| (2) | Halo-TEV-Flag-Ube2V2-C69S | The same as entry 1 |
| (3) | HA-Ubiquitin | Fwd-1<br>TAATTAAAGGCCGGCCAGCGATCGCCGGA<br>CTACCCATACGACGTCCCAG (SEQ ID NO: 59)<br>Fwd-2<br>GCTACTTGTTCTTTTTGCAGGATCCACTAG<br>TGGCGCGCCATTAATTAAAGGCCGGCCAG<br>C (SEQ ID NO: 60)<br>Rev-1<br>TTCTAGAGGCTCGAGAGGCCTCCTCTAGA<br>TGCATGCTCGAG (SEQ ID NO: 61) |

TABLE 2-continued

Primers used for the construction of human Halo-TEV-Flag-Ube2V2-wt Halo-TEV-Flag-Ube2V2-C69S, Flag2-Ube2V2-wt, Flag2-Ube2V2-C69S, Halo-TEV-Flag-Ube2V1-wt, T7-Ube2N, NF-kB-Luciferase, Myc-H2A, T7-H2A, and HA-H2A in either pFN21a or pCS2+8 vector.

```
                    Rev-2
                    CTTATCATGTCTGGATCTACGTAATACGA
                    CTCACTATAGTTCTAGAGGCTCGAGAGGC
                    CT (SEQ ID NO: 62)

(4)    HA-UBE2N     The same as entry 3.
```

TABLE 3 shRNA sequences
The following shRNA sequences were used in pLKO1 vector. For details, see lentivirus production and infection method sections.

| Entry | Plasmid | Sequences |
|---|---|---|
| (1) | shUbe2N-#16 | CCGGCCATAGAAACAGCTAGAGCATCTCG AGATGCTCTAGCTGTTTCTATGGTTTTG (SEQ ID NO: 63) |
| (2) | shUbe2N-#17 | CCGGAGACAAGTTGGGAAGAATATGCTC GAGCATATTCTTCCCAACTTGTCTTTTTG (SEQ ID NO: 64) |
| (3) | shUbe2N-#18 | CCGGGCTGAGGCATTTGTGAGTCTTCTCG AGAAGACTCACAAATGCCTCAGCTTTTT (SEQ ID NO: 65) |
| (4) | shLac Z (shRNA control)-D11 | CGCGATCGTAATCACCCGAGT (SEQ ID NO: 66) |

TABLE 4

Summary of antibodies

| Antibody | Application | Catalog number; Supplier | Dilution |
|---|---|---|---|
| Mouse monoclonal anti-β-Actin-HRP | WB | A4700; Sigma Aldrich | 1:30000 |
| Rabbit polyclonal anti-Halo | WB | G9281; Promega | 1:1000 |
| Rabbit anti-Ubiquitin | WB | Ab7780, Abcam | 1:500 |
| Mouse monoclonal anti-mono- and polyubiquitinylated conjugates FK2 | WB | BML-PW8810-0100, Enzo Life Sciences | 1:500 |
| Monoclonal anti-gapdh- peroxidase | WB | G92296; Sigma | 1:30000 |
| Anti-ubiquitin, Lys63-Specific, clone Apu3, rabbit monoclonal | WB | 05-1308, Merck Millipore | 1:500 |
| Anti-ubiquitin, Lys-48-specific, clone Apu2, rabbit monoclonal | WB | 05-1307, Merck Millipore | 1:7000 |
| Rabbit polyclonal anti-FLAG | WB | PA1-984B, Fisher | 1:3000 |
|  | IF | Pierce | 1:300 |
| Rabbit polyclonal anti-53bp1 | IF | Sc-22760, Santa Cruz | 1:300 |
| Goat polyclonal anti-FLAG | IF | Ab1257, Abcam | 1:300 |
| Rat monoclonal anti-HA | WB | 11867423001, Sigma Aldrich | 1:3000 |
|  | IF |  | 1:300 |
| Rabbit polyclonal anti PCNA | ELISA | Sc-7907, Santa Cruz | 1:1000 |
| Goat polyclonal anti-myc tag | WB | Ab 9132, Abcam | 1:2000 |
| Mouse monoclonal anti BrdU, MoBU-1 | IF | B35128, ThermoFisher | 1:500 |
| Rat monoclonal anti BrdU, BU1/75 (ICR1) | IF | Ab6326, Abcam | 1:1000 |
| Anti-phospho-Histone H2A.X (Ser139) Antibody, mouse monoclonal | IF | 05-636, Merck Millipore | 1:300 |
| Secondary antibody to rabbit IgG, HRP linked | WB | 7074; Cell Signaling Technology | 1:5000 |
| Secondary antibody to mouse, HRP linked | WB | Ab6789; Abcam | 1:5000 |
| Donkey Anti-rabbit IgG AlexaFluor® 647 | IF | Ab 150075; Abcam | 1:1000 |
| Goat Anti-Rat IgG H&L AlexaFluor® 568 | IF | Ab 175710; Abcam | 1:1000 |
| Goat Anti-rabbit AlexaFluor® 488 | IF | A11008; Invitrogen | 1:1000 |
| Goat Anti-Mouse Ig, Human ads-FITC | IF | 1010-02, Southern Biotech | 1:1000 |

All sterile cell culture plastic-ware was from CellTreat, except for glass-bottomed dishes used for imaging that were from In Vitro Scientific.

Validation of Antibodies.

Many of the antibodies were themselves used to show knockdown of proteins using multiple shRNAs. The antibody specificities of the transgenes of interest were independently verified using targeted siRNA knockdowns. In addition, for many experiments, results were replicated by detecting ectopic expression of an epitope-tagged version (where the gene of interest from both non-transfected and transfected cells can be viewed in the same frame, validating the specificity of the antibody). By this metric, that the data for ectopically-overexpressed proteins are consistent with the immunofluorescence (IF) data for the endogenous protein was confirmed. Wherever possible, anti-FLAG/myc/HA were used to detect the ectopic proteins, thereby eliminating doubts about antibody specificity. Halo protein was confirmed to be expressed ubiquitously throughout the transfected cells and that the photocaged small-molecule probe (Ht-PreHNE) co-localized with Halo; for instance, when Halo was fused to nuclear localization signal sequence.

G-REX™ Profiling in Mammalian Cells.

HEK 293T cells were maintained in 1×MEM+ Glutamax™ media supplemented with 10% FBS, 1×NEAA, 1× sodium pyruvate and 1× Pen-Strep. Cells were grown in a humidified, 5% $CO_2$ incubator at 37° C. 24 h later, cells were transfected with pfN21a-Halo plasmid using TransIT-2020 transfection reagent per the manufacturer's recommendation. Subsequent steps were performed under dim light. 24-36 h post transfection, monolayer of cells were treated with 25 µM Ht-PreHNE in serum-free media and incubated for 2.5 h. Cells were gently rinsed with serum-free media three times every 30 min over the next 1.5 h. UV lamps were turned on 10 min prior to use. (Light source: 365 nm, 0.3 mW/cm² hand-held UV-lamp placed 1 inch above samples). For samples designated as "samples exposed to light", lids were removed from the culture dishes and cells were placed under 365 nm UV light for 5-8 min. The cells were harvested, washed two times with ice-cold PBS and frozen in liquid nitrogen. After cell lysis (lysis procedure varies depending on assay methods), click with Biotin-azide (as described in Biotin/streptavidin pulldown procedure), and pull down enrichment by Streptavidin, the protein enriched would be eluted by 2× Laemmeli dye containing 6% βME at 98° C. for 10 min. The sample was subjected to SDS-PAGE followed by Coomassie stain and the gel band(s) corresponding to specific region(s) of interest is excised (in this scenario, a gel band between 15-25-kDa region) and sent for MS identification (see detailed methods regarding In-gel trypsin digestion of SDS gel bands, Protein Identification by nano LC/MS/MS Analysis, and LC-MS/MS data analysis reported elsewhere in the methods section).

Construction of Plasmids.

Ligase-free cloning method was used to clone various plasmids (Table 2, above) for expression in mammalian cells and in zebrafish. In order to clone any desired fusion genes in any vector of choice, the gene of interest (GOI) was PCR-amplified out from the original plasmid using the indicated forward (fwd-1) and reverse primers (rev-1) in Table 2a and 2b. The resultant PCR product was extended using the indicated fwd-2, and rev-2 primers. The resultant "megaprimer" was inserted into the destination vector of interest that had been linearized with an appropriate restriction enzyme (NEB) using PCR. The plasmid was verified by sequencing the entire gene at the genomics facility of Cornell Institute of Biotechnology. Plasmids were purified using EZ-10 spin column plasmid DNA miniprep kits (Bio Basic, BS614).

Cell Growth and Culture Maintenance.

HEK 293T cells were maintained in 1×MEM+ Glutamax™ media supplemented with 10% FBS, 1×NEAA, 1× sodium pyruvate and 1× Pen-Strep. Cells were grown in humidified, 5% $CO_2$ incubator at 37° C. All cell lines were tested negative for *mycoplasma* [testing was performed every 3 months using LookOut® *Mycoplasma* PCR Detection Kit (Sigma)]. For SILAC-T-REX™ delivery protocol, SILAC HEK 293T cells were cultured and passaged at least five times (more than two weeks) using, in final concentrations, SILAC drop-off media 1×DMEM (ThermoFisher #89985) supplemented with 10% dialyzed FBS (Sigma Aldrich #F0392), the corresponding light/heavy amino acids, light amino acids: 146 µg/mL of L-lysine (Sigma Aldrich #L8662) and 84 µg/mL of L-arginine (Sigma Aldrich #A8094) or the same concentration of heavy amino acids: L-lysine-$^{13}C_6$, $^{15}N_2$ hydrochloride (Sigma Aldrich #608041) and L-arginine-$^{13}C_6$, $^{15}N_4$ hydrochloride (Sigma Aldrich #608033) respectively, 1× sodium pyruvate and 1× Pen-Strep. Cells were maintained in a humidified, 5% $CO_2$ incubator at 37° C.

Generation of Lentiviral-Based Knockdown Lines.

HEK293T packaging cells were seeded and grown overnight in antibiotic free media in 6 well plates. At 80% confluence, each well was transfected with packaging plasmid (pCMV-R8.74psPAX2, 500 ng), envelope plasmid (pCMV-VSV-G, 50 ng) and pLKO vector (500 ng) using TransIT.LT1 as per the manufacturer's protocol. After 18 h, media were removed and replaced with 20% serum containing media. After 24 h, media containing viruses were collected, spun down and passed through a 0.6 micron filter and stored at −80° C. or used directly.

Cells in log phase were treated with 0.6 ml of virus supernatant (from above) in 8 µg/ml polybrene in a total of 6 ml of media in a 6-well plate. After 24 h, media were removed and replaced with media containing 2 µg/ml puromycin (which was completely toxic to all lines used in this study). Cells were cultured until the plate was confluent, then cells were split and moved to a 10 cm dish in 2 µg/ml puromycin containing media and grown again until reaching confluence. At this, the line was considered to be "selected", and target gene expression was analyzed by western blot and compared to shRNA controls. Cells up to passage 5 were used for assays and they were typically grown in 1.5 µg/ml puromycin.

T-REX™ Delivery in Mammalian Cells.

HEK 293T cells were maintained in 1×MEM+ Glutamax™ media supplemented with 10% FBS, 1×NEAA, 1× sodium pyruvate and 1× Pen-Strep. Cells were grown in a humidified, 5% $CO_2$ incubator at 37° C. For in-gel fluorescence analysis and western blot, ~0.7-0.8×10⁶ HEK 293T cells were seeded in 8 cm² tissue culture dishes. 24 h later, cells were transfected using TransIT-2020 transfection reagent per the manufacturer's recommendation. Subsequent steps were performed under dim light. 24-36 h post transfection, monolayer of cells were treated with 25 µM Ht-PreHNE in serum-free media and incubated for 2.5 h. Cells were gently rinsed with serum-free media three times every 30 min over the next 1.5 h. Meanwhile, UV lamps were turned on 10 min prior to UV irradiation time. For samples designated for light exposure, lids were removed from the dishes and cells were placed under 365 nm UV light for 5-8 min. The cells were harvested, washed two times with ice-cold PBS and frozen in liquid nitrogen. See FIG. 21.

Western Blotting.

Cells were lysed in 1×RIPA buffer containing in final concentrations 1× Protease inhibitor, 1 mM sodium orthovanadate and 1 mM PMSF, by rapid freeze-thaw (×3). Cell debris was removed and the supernatant was collected after centrifugation at 18,000×g for 20 min at 4° C. Protein concentration was determined using Bradford assay. 30-50 µg of total lysates were subjected to SDS-PAGE and the gel was transferred onto a PVDF membrane at 100 V for 1 h at 4° C. or at 40 V overnight at 4° C. Membrane was blocked with 10% milk and probed with various antibodies at the indicated dilutions (Table 4, above).

In-Gel Fluorescence Assay.

All steps were performed in dark or under dim light. Cells from 8 cm² plates were lysed in 30 µL buffer containing 50 mM HEPES (pH 7.6), 150 mM NaCl, 1% Nonidet P-40, 1× Roche cOmplete, mini, EDTA-free protease inhibitor cocktail, and 0.3 mM TCEP by rapid freeze-thaw (×3). Cells debris was removed by centrifugation at 18,000×g for 20 min at 4° C. Protein concentration of the clarified lysate was determined using Bradford assay. A portion of the lysate protein was made up to 22 µL final volume containing, in final concentrations, 50 mM HEPES (pH 7.6), 150 mM NaCl, 1.0 mg/mL lysate protein, 0.3 mM TCEP, and 0.2 mg/mL TEV protease. The sample was incubated at 37° C. for 45 min, and subsequently subjected to Click reaction. In a final volume of 27 µL, the click reaction mix consisted of 1.7 mM TCEP, 5% t-BuOH, 1% SDS, 1 mM $CuSO_4$, 0.1 mM Cu(TBTA), 10 µM Cy5 azide and the lysate from above. The samples were incubated at 37° C. for 30 min and subsequently quenched with 5 µL 4× Laemmeli dye containing 6% βME. After additional 5-min incubation at 37° C., 25 µL of the lysate was subjected to SDS-PAGE. After electrophoresis, the gel was rinsed 3× with $ddH_2O$ with 5-min each rinse on a shaker and imaged on a Biorad Chemi-doc-MP Imager. Where applicable, the gel was transferred to a PVDF membrane for western blot analysis.

Biotin Azide Pull Down for Mammalian Lysate.

HEK 293T cells were seeded in 60 $cm^2$ plate. After the cells reached 60% confluence (~18-24 h), the old media were replaced with fresh 8 mL complete media. Cells were transfected with 7.5 µg of the designated plasmids encoding the HaloTag fusion gene and 30 µL PEI (1 mg/mL) in 600 µL in Opti-MEM media for 24-36 h after which the cells were treated with 25 µM Ht-PreHNE or without alkyne (control) for 2.5 h. Rinsing and light shining protocol were as described above. Cells were harvested, washed twice with chilled 1× DPBS and flash frozen.

Mammalian cell lysis was performed in 200 µL of lysis buffer containing in final concentrations 50 mM HEPES (pH 7.6), 150 mM NaCl, 1% Nonidet P-40 and 1× Roche cOmplete, mini, EDTA-free protease inhibitor cocktail by rapid freeze-thaw (×3). Lysate was clarified by centrifugation at 18,000×g for 30 min at 4° C.

Zebrafish cell lysis was performed with similar procedure as mammalian cells: 50 mM HEPES (pH 7.6), 150 mM NaCl, 1% Nonidet P-40, 0.2 mg/ml soybean protease inhibitor (Sigma), and 3× Roche cOmplete, mini, EDTA-free protease inhibitor cocktail by rapid freeze-thaw and votexing with zirconia beads (Bio spec 0.7 mm beads; 11079107zx).

Total protein concentration from either mammalian cell lysate or zebrafish lysate was determined using Bradford assay with BSA as standard. The lysate was subsequently diluted to 2 mg/mL with a buffer made up of 50 mM HEPES (pH 7.6) and 0.3 mM TCEP, and subjected to Click reaction with biotin azide for 30 min at 37° C. The final concentrations of each components were: 1% SDS, 5% t-BuOH, 200 µM Biotin azide, 2 mM TCEP, 0.9 mM $CuSO_4$ and 0.1 mM Cu(TBTA). The lysate proteins were precipitated by adding 4 volumes of EtOH pre-chilled at −20° C. (EtOH final concentration is 80%). The sample was vortexed and incubated at −80° C. overnight (or at least 4 h) to facilitate precipitation. The precipitant was collected by centrifugation at 21,000×g for 120 min at 4° C. and washed twice with pre-chilled MeOH, once with pre-chilled acetone. The pellet was air-dried, then redissolved in 20-50 µL 50 mM HEPES (pH 7.6), 4% LDS and 0.5 µM EDTA and dissolved by vortexing and heating at 42° C. for 5 min. LDS was diluted to a final concentration of 0.5% with 350 L of 50 mM HEPES (pH 7.6) and added to 50 µL bed volume of Streptavidin sepharose beads pre-equilibrated with 50 mM HEPES (pH 7.6) and 0.5% LDS. The sample was incubated with beads for 2-3 h at room temperature by end-over-end rotation after which time the supernatant was removed by centrifugation at 500×g for 3 min. The beads were washed three times with 500 µL of 50 mM HEPES (pH 7.6) with 0.5% LDS with end-over-end rotation at room temperature for 30 min during each wash. The bound protein was eluted by boiling the beads at 98° C. for 10 min with 30 µL of 2× Laemmeli dye containing 6% βME. The sample was subjected to SDS-PAGE followed by Coomassie stain or transferred to a PVDF membrane for western blot analysis.

Anti-FLAG and Anti-HA Pull Down from Mammalian Lysate.

HEK 293T cells were seeded in 2×60 $cm^2$ plates. After the cells reached 60% confluence (~18-24 h), the old media was replaced with 8 mL of fresh complete media. Cells were transfected with 7.5 µg of the designated Halo clone and 30 µL PEI (1 mg/mL) in 600 µL in Opti-MEM media for 24-36 h after which the cells were treated with 25 µM Ht-PreHNE for 2.5 h. Rinsing and light shining protocol were as described above. Cells were harvested, pooled, washed twice with chilled 1×DPBS and flash frozen. Cell lysis was performed in 100-200 µL per $1.5×10^6$ cells of either: lysis buffer [containing in final concentrations 50 mM HEPES (pH 7.6), 150 mM NaCl, 1% Nonidet P-40 and 1× Roche cOmplete, mini, EDTA-free protease inhibitor cocktail] for Flag pull down; or RIPA buffer [containing in final concentrations 50 mM HEPES (pH 7.6), 150 mM NaCl, 1% Nonidet P-40, 0.1% SDS, 0.25% sodium deoxycholate, and 1× Roche cOmplete, mini, EDTA-free protease inhibitor cocktail] for HA pull down, followed by rapid freeze-thaw cycles (×3). Lysate was clarified by centrifugation at 18,000×g for 10 min at 4° C. Total protein concentration was determined using Bradford assay with BSA as standard. The lysate was subsequently diluted to 2 mg/mL with binding buffer containing in final concentrations 50 mM HEPES (pH 7.6), 150 mM NaCl, 1× Roche cOmplete, mini, EDTA-free protease inhibitor cocktail, and 0.1% Tween-20. This diluted lysate was subjected to either 50-100 µL bed volume of ANTI-FLAG® M2 affinity gel (A2220, Sigma) or monoclonal anti-HA-agarose (clone HA-7, A2095, Sigma) that had been pre-equilibrated with the binding buffer above. The sample was incubated with beads for 2-3 h at 4° C. by end-over-end rotation after which time the supernatant was removed post-centrifugation at 1000×g (anti-FLAG pull down) or 5000×g (anti-HA pull down) for 3 min. The beads were washed three times at 4° C. with 500 µL wash buffer containing in final concentrations 50 mM HEPES (pH 7.6), 150 mM NaCl, 1× Roche cOmplete, mini, EDTA-free protease inhibitor cocktail, and 0.1% Tween-20, using end-over-end rotation over 10 min during each wash. The bound protein was eluted by either incubating with 0.15 mg/mL 3× flag peptide for 2 h at 4° C. (anti-Flag pull down) or by boiling the beads at 98° C. for 10 min with 30 µL of 3× Laemmeli dye containing 6% βME (anti-HA pull down). The sample was subjected to SDS-PAGE and transferred to a PVDF membrane for western blot analysis described above.

For hydroxylamine treated FLAG eluent assay, after eluting with 3× FLAG-peptide, the eluent was boiled with Laemmeli dye containing 6% βME and 100 mM freshly prepared hydroxylamine for 10 min followed by SDS-PAGE and Western Blot analysis.

Isolation Procedure for Ubiquitylated Proteins from Mammalian Cell Lysates: K63-Linked with K63-TUBE (Biotin).

Cells were grown and transfected as described above. After T-REX™ delivery, cells were harvested and lysed in 100-200 µL (~$1.5×10^6$ cells) of lysis buffer [containing in final concentrations 50 mM HEPES (pH 7.6), 300 nM Biotin K63-TUBE, 150 mM NaCl, 5 mM EDTA, 3 mM 1,10-phenanthroline, 5 mM NEM, 20 µM PR-619, 1% Nonidet P-40 and 1× Roche cOmplete, mini, EDTA-free protease inhibitor cocktail] according to manufactures' manual (Biotin K63 TUBE, Lifesensors). Lysate was clarified by centrifugation at 18,000×g for 10 min at 4° C. Total protein concentration was determined using Bradford assay using BSA as standard. The lysate was subsequently diluted to 5-10 fold with binding buffer containing in final concentrations 50 mM HEPES (pH 7.6), 150 mM NaCl, 5 mM EDTA, 0.1% NP-40, 1× Roche cOmplete, mini, EDTA-free protease inhibitor cocktail, and 0.05% Triton-X 100 while adjusting the concentration of Biotin K63-TUBE and all inhibitors accordingly. This diluted lysate was treated with 100 µL bed volume streptavidin sepharose beads that had been pre-equilibrated with the binding buffer (vide supra). Upon incubation by end-over-end rotation at 4° C. for 3-5 h, supernatant was removed post-centrifugation at 500×g for 1 min. The beads were washed three times with 500 µL of 50 mM HEPES (pH 7.6), 150 mM NaCl, 5 mM EDTA, 0.1% NP-40, 1× Roche cOmplete, mini, EDTA-free protease inhibitor cocktail, and 0.05% Triton-X 100 with end-over-end rotation at 4° C. for 20 min during each wash. Bound protein was eluted by boiling the beads at 98° C. for 10 min with 30 µL of 2× Laemmeli dye containing 6% βME. The sample was subjected to SDS-PAGE and transferred to a PVDF membrane for western blot analysis.

Luciferase Assay (for NF-κB-Reporter Assay).

$1.5-1.6 \times 10^5$ HEK 293T cells were seeded in each well of a 48-well plate. 24 h later, the cells were transfected with 120 ng of the designated HaloTag fusion gene plasmid and 120 ng of NF-kB-Firefly luciferase: pCMV-Renilla luciferase (40:1) mix, using TransIT-2020 transfection agent. 24 h post-transfection, cells were treated with 25 µM Ht-PreHNE or vehicle (corresponding volume of DMSO alone) for 2.5 h, rinsed three times and irradiated with 365 nm UV light for 10 min. The cells were incubated for a further 8 h. For dual luciferase assay, cells in each well were gently washed with 1×DPBS and lysed in 65 µL of 1× passive lysis buffer containing in final concentrations 25 mM Tris (pH 7.8), 2 mM 1,2-CDTA, 2 mM DTT, 1 mg/mL BSA, 1% Triton X-100, and 10% Glycerol. 20 µL of the lysate was transferred to a white opaque 96-well plate (Corning). Firefly luciferase was read after adding 50 µL Firefly substrate (75 mM HEPES pH 8.0, 4 mM $MgSO_4$, 20 mM DTT, 0.1 mM EDTA, 0.53 mM ATP, 0.27 mM Coenzyme-A, 0.47 mM D-Luciferin Firefly). Subsequently, 50 µL of Stop and Glow substrate (7.5 mM sodium acetate pH 5.0, 400 mM sodium sulfate, 10 mM CDTA, 15 mM sodium pyrophosphate, 0.025 mM APMBT, 5.5 µM Coelenterazine) was added and Renilla luciferase activity was measured.

In-Gel Trypsin Digestion of SDS Gel Bands.

The enriched Halo-Ube2V2 protein band from the SDS-PAGE gel above from anti-Flag pull down was cut and subjected to in-gel digestion with reconstituted Arg-C(Promega) followed by extraction of the peptides as previously reported (Yang et al, "Development of an Integrated Approach for Evaluation of 2-D gel Image Analysis: Impact of Multiple Proteins in Single Spots on Comparative Proteomics in Conventional 2-D gel/MALDI Workflow,". *Electrophoresis* 28:2080-2094 (2007), which is hereby incorporated by reference in its entirety). The excised gel pieces were washed consecutively in 200 µL distilled water, 100 mM ammonium bicarbonate (Ambic, pH 7.8)/acetonitrile (1:1) and acetonitrile (ACN). The gel pieces were reduced with 70 µL 5 mM TCEP in 50 mM Ambic solution (pH 7.8) for 45 min at room temperature and alkylated with 100 µL of 55 mM Iodoacetamide in 100 mM Ambic at room temperature in dark for 60 min. After wash steps as described above, the gel slices were dried and rehydrated with 50 µL Arg-C in 50 mM Ambic, 10% ACN (20 ng/µL) at 37° C. for 16 hrs. The digested peptides were extracted twice with 70 µL of 50% ACN, 5% formic acid (FA) and once with 70 µL of 90% ACN, 5% FA. Extracts from each sample were combined and lyophilized.

Protein Identification by Nano LC/MS/MS Analysis.

The in-gel tryptic digests were reconstituted in 20 µL of 0.5% FA for nanoLC-ESI-MS/MS analysis, which was carried out by an Orbitrap Fusion mass spectrometer (Thermo-Fisher Scientific, San Jose, Calif.) equipped with a "CorConneX" nano ion source device (CorSolutions LLC, Ithaca, N.Y.). The Orbitrap was interfaced with a Dionex UltiMate3000RSLCnano system (Thermo, Sunnyvale, Calif.). The gel extracted peptide samples (5 µL) were injected onto a PepMap C18 trap column-nano Viper (5 µm, 100 µm×2 cm, Thermo) at 20 µL/min flow rate for on-line desalting and then separated on a PepMap C18 RP nano column (3 µm, 75 µm×25 cm, Thermo) which was installed in the nano device with a 10-µm spray emitter (NewObjective, Woburn, Mass.). The Orbitrap calibration and nanoLC-MS/MS operation were as described previously (Yang et al., "Evaluation of Different Multidimensional LC-MS/MS Pipelines for Isobaric Tags for Relative and Absolute Quantitation (iTRAQ)-based Proteomic Analysis of Potato Tubers in Response to Cold Storage," *J Proteome Res* 10:4647-4660 (2011), which is hereby incorporated by reference in its entirety). Peptides were eluted with a 90-min gradient of 5% to 38% ACN in 0.1% FA at a flow rate of 300 nL/min, followed by a 5-min ramping to 95% ACN-0.1% FA and a 7-min hold at 95% ACN-0.1% FA. The Orbitrap Elite was operated in positive ion mode with nano spray voltage set at 1.5 kV and source temperature at 250° C.

The instrument was operated in parallel data-dependent acquisition (DDA) under FT-IT mode using FT mass analyzer for one MS survey scan from m/z 375 to 1800 with a resolving power of 120,000 (fwhm at m/z 400) followed by MS/MS scans on top 15 most intensive peaks with multiple charged ions above a threshold ion count of 10,000 in FT mass analyzer. External calibration using Ultramark 1621 for both FT mass analyzer and IT mass analyzer is performed. Dynamic exclusion parameters and normalized collisional energy were set same as previously (Yang et al., "Evaluation of Different Multidimensional LC-MS/MS Pipelines for Isobaric Tags for Relative and Absolute Quantitation (iTRAQ)-based Proteomic Analysis of Potato Tubers in Response to Cold Storage," *J Proteome Res* 10:4647-4660 (2011); Hochrainer et al., "Monoubiquitination of Nuclear RelA Negatively Regulates NF-kappaB Activity Independent of Proteasomal Degradation," *Cell Mol Life Sci* 69:2057-2073 (2012), which are hereby incorporated in their entirety). All data were acquired under Xcalibur 2.2 operation software (Thermo-Fisher Scientific).

LC-MS/MS Data Analysis.

The DDA raw files for CID MS/MS only were subjected to database searches using Proteome Discoverer (PD) 1.4 software (Thermo Fisher Scientific, Bremen, Germany) with the Sequest HT algorithm. The database search was conducted against a human UniProt database containing 160, 672 entries with two-missed Arg-C cleavage sites allowed. The peptide precursor tolerance was set to 10 ppm and fragment ion tolerance was set to 0.6 Da. Variable modification of cysteine carboxymethylation, methionine oxidation, N-terminal acetylation and deamidation of asparagine/glutamine were set along with HNE alkyne (152.08 Da) and reduced HNE alkyne (154.10 Da) as well as their dehydrated HNE alkyne (134.07 Da) and dehydrated and reduced HNE alkyne (136.09 Da) on cysteine and all of these modifications also on histidine and lysine residues. Only high confidence peptides defined by Sequest HT with a 1% FDR by Percolator were considered for the peptide identification. All MS/MS spectra for identified Cam and HNE Cys modified peptides from initial database searching were manually inspected and validated using Xcalibur 2.2. Results are shown in FIG. 32 and FIG. 3C.

Immunofluorescence (IF).

Cells were grown to 70% confluence in 35 mm glass-bottomed dishes and transfected with HaloTagged plasmids. T-REX™ delivery was performed as mentioned above. 3 h post irradiation by UV light, cells were fixed by adding −20° C. pre-chilled MeOH and incubating at 4° C. for 20 min. The fixative was aspirated and the cells washed three times with 1×DPBS with 5-min incubation at room temperature. Blocking and permeabilization was performed in one-step by incubation at 37° C. for 1 h in 1×DPBS containing 3% BSA and 0.2% Triton X-100. Cells were subsequently incubated with primary antibody (1:300, Table 4) in incubation buffer (1% BSA, 0.02% Triton X-100 in 1×DPBS) for 2 h at room temperature. Cells were rinsed 3 times with 1×DPBS with 5 min incubation for each wash and subsequently incubated in dark for 1 h at room temperature with corresponding second antibody (1:1000, Table 4) in incubation buffer. Cells were rinsed 3 times with 1×DPBS with 5 min incubation for each rinse. DAPI (Sigma) was freshly prepared in 1×DPBS from 2 mg/mL wt./v stock solution in water and added to the wells at the final concentration of 0.2 µg/mL. The samples were incubated in dark for 1 min and washed once with 1×DPBS and stored at 4° C. in dark till images were taken using a Zeiss LSM 710 meta confocal fluorescence microscope. Image analysis was performed using Image-J (NIH).

Measurement of DNA-Replication Efficiency by BrdU/EdU Staining (in Fixed Cells).

$4.8 \times 10^5$ cells were plated in glass-bottomed dishes (In Vitro Scientific) and allowed to grow for 24 h. Cells were transfected with the indicated plasmid and allowed to grow for another 24 h. Cells were then treated with 3 µM Ht-PreHNE no alkyne for 2.5 h followed by two rinses with serum-free medium. After this time, 20 µM EdU (final concentration) was added into cell culture media for 30 min before the $3^{rd}$ rinse. The cells were rinsed another two times before light shining. 2.5 h post light irradiation, cells were treated with 50 µM BrdU for 30 min at 37° C. Then the cells were fixed with −20° C. pre-chilled MeOH for 20 min and then carried on to immunofluorescence assay as described elsewhere.

Histone Extractions.

HEK 293T cells were grown, transfected with either wt-Halo-Flag-Ube2V2 or C69S-Halo-Flag-Ube2V2, and subjected to T-REX™ delivery protocols and controls as described above. The conventional histone acid extraction method (Shechter et al., "Extraction, Purification and Analysis of Histones," *Nature Protocols* 2:1445-1457 (2007), which is hereby incorporated by reference in its entirety) was used for all samples. Generally, cells were lysed by 1 mL of hypotonic buffer (final concentration: 10 mM Tris pH 8.0, 1 mM KCl, 1.5 mM $MgCl_2$ and 1 mM TCEP) 30 min on an end-to-end rotor at 4° C. After clearance by centrifugation at 10,000×g, 4° C. for 10 min. Discard the supernatant and treat the debris with 0.4 N sulfuric acid at 4° C. overnight. After the solution were cleared again by centrifugation at 16,000×g, 4° C. for 10 min, the proteins in the supernatant were precipitated by treatment with 100% trichloroacetic acid overnight 4° C. The pellet were collected by centrifugation at 16,000×g, 4° C. for 10 min and redissolved in 1 M Tris pH 8.0 buffer. The protein concentration from resolubilization was determined using Bradford assay with BSA as standard. 30-50 µg of total lysates were subjected to SDS-PAGE and the gel was either stained by Coomassie or transferred onto a PVDF membrane at 100 V for 1 h at 4° C. or at 40 V overnight at 4° C.

ELISA.

Antibody was bound to the plate at the stated concentration (1-3 µg/mL) in sodium bicarbonate buffer pH 9.6 for at least 24 h in a 96 well white plate (80 µL per plate) at 4° C. Maximum incubation time was 2 days. Next, incubation buffer was removed, washed once with TBS-Tween (100 mM Tris, 150 mM NaCl, 0.03% Tween-20) and then blocked in 5% BSA in TBS-Tween (280 µL per plate) for 3-5 h at rt. Then BSA was washed away twice using TBS-Tween, and wells were filled with 150 µL blocking buffer (1.1% BSA, 5 mM sodium orthovanadate, 20 mM NaF). Cells were lysed in 50 mM HEPES pH 7.6, 1% NP-40, 5 mM sodium orthovanadate, 20 mM NaF and 2×ROCHE complete minus EDTA protease inhibitors. 30 µg each lysate (quantified by Bradford relative to BSA) was added to each well (approximately 30 µL lysate, but always equal amounts of total lysate buffer was added for each set). For selected samples (usually those yielding the most protein), the amount of lysate loaded was doubled in separate wells and the value recorded was ultimately compared to the value obtained for 1× lysate. This gave equal signal (proving saturation conditions, meaning that the amount of ubiquitinated protein detected reflects the ratio of ubiquitinated to non-ubiquitinated protein in the lysate). This was incubated at 4° C. overnight. Next, wells were washed with TBS-Tween 3 times, then primary antibody was added in 1.1% BSA in TBS-Tween overnight at 4° C. Then, wells were washed and HRP-conjugated secondary antibody was added in 1% milk in TBS-Tween. After 1 h at r.t., wells were washed 3 times with TBS-Tween, for 15 min, then one time with TBS for 20 min after which time 50 µL TBS was added to each well. HRP was detected using a Biotek cytation 3 plate reader. Femto ELISA substrate was used, injecting 50 µL Femto ELISA substrates 1 and 2 per well. Signals were calculated relative to well coated in antibody and treated with untransfected lysate.

In Vitro Transcription.

All genes were cloned into pCS2+8 vector using the primers in Table 2, above. Prior to in-vitro transcription, the genes were PCR amplified using RNA fwd and rev primers. In vitro transcription was performed using the mMessage mMachine SP6 transcription kit according to manufacturer's suggestion.

Fish Injection and T-REX™ Delivery.

All procedures conform to the National Institutes of Health guidelines regarding animal experimentation and were approved by Cornell University's Institutional Animal Care and Use committees.

Fertilized eggs at the 1-2 cell stage from casper zebrafish were injected with mRNA (1.6 mg/ml) into the yolk sack. Immediately after injection, embryos were pooled, and separated into two petri dishes (10 cm) filled with 30 mL 10% Hank's salt solution with methylene blue and penicillin (100 U/mL)/streptomycin (100 µg/ml). To one set was added the HaloTag-targetable photocaged precursor to HNE (Ht-PreHNE, hereafter) (<15 µM) and the other DMSO in the dark. Embryos were maintained at 28° C. in the dark for 28 h then they were washed in 10% Hank's solution with no methylene blue/antibiotic (3 times for 30 min each). Embryos were moved to 6-well plates. Half of the embryos (Ht-preHNE-treated or -untreated) were irradiated with UV light (5 min), and the other half of each set was not irradiated. Embryos were left for 8 h at which point they were euthanized, washed with cold 1×DPBS and dechorionated (and deyolked if protein analysis was to be undertaken).

Statistical Analysis.

n for imaging experiments represents the number of single cells or zebrafish cells quantified from at least ten fields of view on at least three independent plates. n for western blot represents the number of lanes on western blots under identical experimental conditions and each lane is derived from a separate culture plate. FIG. 7A, n=3 independent sets of biological replicates at different passages; each set of replicates consists of independent triplicates. FIG. 8C, at least four independent sets of biological replicates at different passages were performed, n=9 for wt-Halo-(FLAG) Ube2V2, including T-REX™ delivery and controls; n=4 for C69S-mutant, including T-REX™ delivery and controls. FIG. 8D, at least three independent sets of biological replicates at different passages were performed, for wt-Halo-(FLAG)Ube2V2, n=5 (T-REX™ delivery), n=6 (light alone), n=6 (Ht-PreHNE alone), n=6 (DMSO); for C69S-mutant, n=3 (T-REX™ delivery), n=3 (light alone), n=3 (Ht-PreHNE alone), n=2 (DMSO). FIG. 8G, Two independent replicates were performed. In total, n=3 for shUbe2N-#16, n=2 for shUbe2N-#17, n=4 for shUbe2N-#18, n=2 for sh-LacZ-D11 controls. FIG. 10C, n=3 independent sets of biological replicates at different passages. FIG. 12E, two independent replicates were performed. For each set of cells transfected with wt-Halo-(FLAG)-Ube2V2, n=3 (T-REX™ delivery); n=3 (Light alone), n=3 (Ht-PreHNE alone), n=3 (DMSO); for cells transfected with C69S-Halo-(FLAG)-Ube2V2, n=3 (T-REX™ delivery), n=3 (DMSO). FIG. 12H, for wt-Halo-(FLAG)-Ube2V2, n=648 (0 h), n=624 (1 h), n=634 (3 h), n=571 (6 h), n=542 (18 h); for C69S-Halo-(FLAG)-Ube2V2, n=585 (0 h), n=615 (1 h), n=644 (3 h), n=649 (6 h), n=646 (18 h). FIG. 12I, for shUbe2N-#16, n=379 (T-REX™ delivery), n=297 (Light alone), n=342 (Ht-PreHNE alone), n=402 (DMSO), n=241 (Mitomycin-C); for shLacZ-D11, n=434 (T-REX™ delivery), n=390 (Light alone), n=483 (Ht-PreHNE alone), n=434 (DMSO), n=445 (Mitomycin-C). FIG. 12J, for wt-Halo-(FLAG)-Ube2V2, n=339 (T-REX™ delivery), n=375 (Light alone), n=300 (Ht-PreHNE alone), n=465 (DMSO), n=280 (Mitomycin-C), for C69S-Halo-(FLAG)-Ube2V2, n=266 (T-REX™ delivery), n=212 (Light alone), n=283 (Ht-PreHNE alone), n=312 (DMSO), n=305 (Mitomycin-C). FIG. 14C, n=69 (T-REX™ delivery), n=74 (Light alone), n=64 (Ht-PreHNE alone), n=69 (DMSO). FIG. 13A, for wt-Halo-(FLAG)-Ube2V2, n=50 (T-REX™ delivery), n=50 (Light alone), n=50 (PreHNE alone), n=50 (DMSO), n=180 (Mitomycin-C); for C69S-Halo-(FLAG)-Ube2V2, n=95 (T-REX™ delivery), n=59 (Light alone), n=55 (Ht-PreHNE alone), n=55 (DMSO), n=55 (Mitomycin-C). FIG. 13B, for wt-Halo-(FLAG)-Ube2V2, n=143 (0 h), n=137 (3 h), n=172 (24 h); for C69S-Halo-(FLAG)-Ube2V2, n=164 (0 h), n=138 (3 h), n=156 (24 h). FIG. 13F, for shUbe2N-#16, n=66 (T-REX™ delivery), n=186 (Light alone), n 15=270 (Ht-PreHNE alone), n=240 (DMSO); for shLacZ-D11, n=185 (T-REX™ delivery), n=247 (Light alone), n=233 (Ht-PreHNE alone), n=234 (DMSO).

Results

G-REX™ Profiling: An Unbiased Method to Profile Privileged Innate Electrophile Sensors.

Figure 4A:
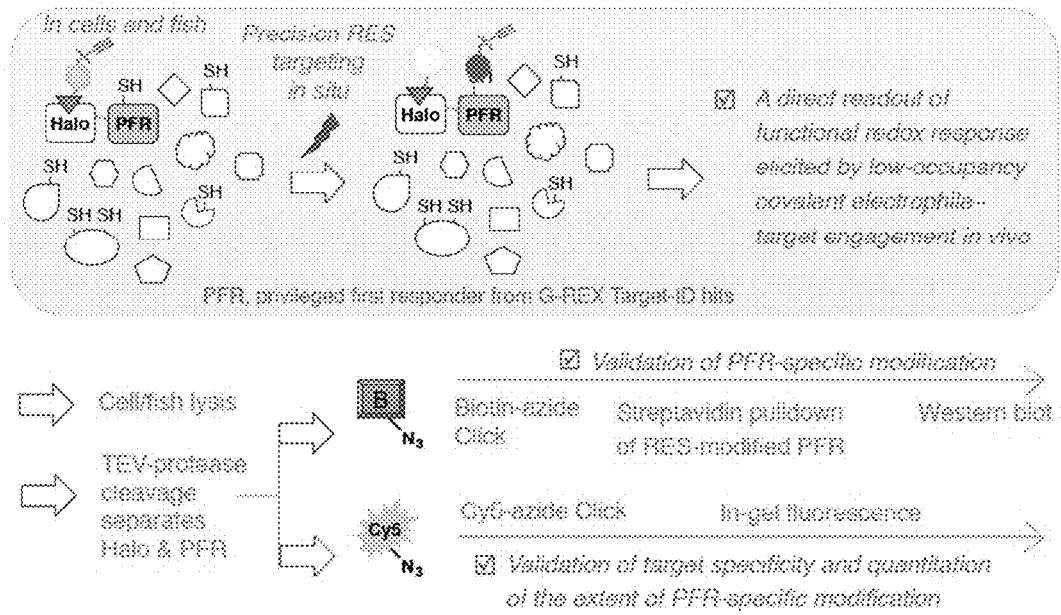
FIGS. 4A-4F demonstrates that G-REX™ profiling identifies privileged first-responding redox-sensor cysteines genome-wide.
Figure 4B:
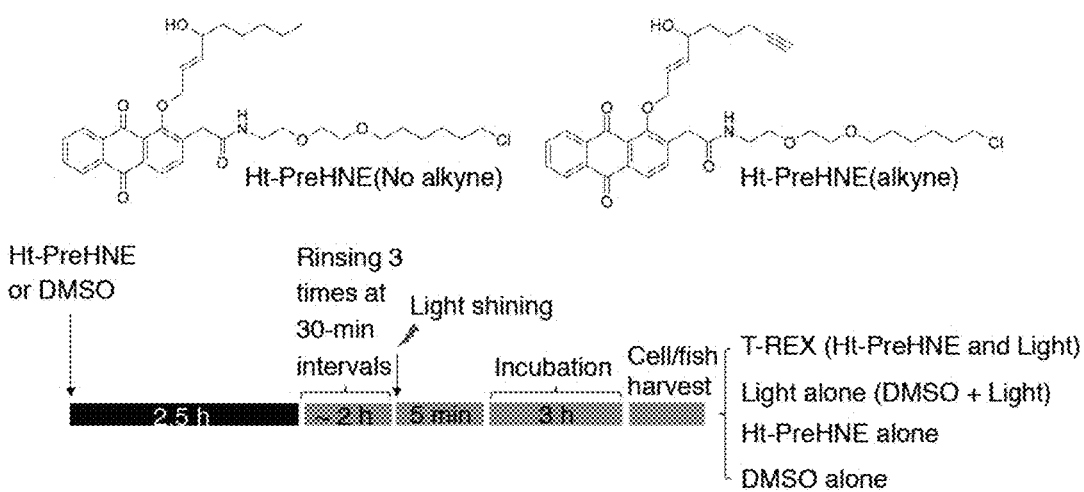

To gain a first-time ability to directly assay downstream ramifications of these non-enzymatic redox-modification events at single-protein-target resolution and obtain mechanistic information about precision RES-signaling, "T-REX™ delivery" (targetable reactive gletrophiles and oxidants) was recently developed (Parvez et al., "T-REX On-Demand Redox Targeting in Live Cells," *Nat. Protocols* 11:2328-56 (2016), which is hereby incorporated by reference in its entirety) (FIGS. 4A-4B). While T-REX™ delivery has provided the previously-inaccessible ability to directly read-out functional consequences of target-specific RES-modifications in vivo (cells and fish) in the backdrop of an otherwise unperturbed proteome, it has the following limitations: (1) T-REX™ delivery relies on ectopic overexpression of Halo-fusion proteins, in which HaloTagged is fused to individual select targets; (2) one thus has to have some prior knowledge about which targets could potentially bear functionally-responsive cysteines [i.e., privileged first responders (PFRs)]. To that end, potential PFRs for a medium-throughput T-REX™ delivery screen need to be cherry-picked from previously published hits obtained from profiling methods built on bulk-RES-introduction from outside the cell, and (3) T-REX™ delivery is a one-target-at-a-time, low/medium-throughput gel-based screen.

To strive for a functional high-throughput screen at the whole-genome scale to target-ID PFRs, a new platform was devised, G-REX™ profiling, that captures PFR-cysteines directly in vivo, at a specific user-defined time (FIG. 3A). Technical aspects regarding exploitation of HaloTag and biocompatible photocaging chemistry of bioinert photocaged small-molecule RES-precursors overlay exactly between G-REX™ profiling and T-REX™ delivery. However, G-REX™ profiling (1) requires no reliance on ectopic overexpression of the target protein of interest (i.e., HaloTag is expressed alone in cells with no transgene fused to it); (2) G-REX™ profiling is thus "casting a net" for innate PFRs at the whole-genome scale in a high-throughput manner, at the user-defined time/dose/duration/locale; (3) in that capacity, G-REX™ profiling is the first-time method to deliver a native RES signal of choice in situ; and (4) it selectively captures targets specifically under RES-limited conditions (thus targets likely represent those that undergo low-stoichiometric RES-modifications, i.e., likely to be PFRs), as opposed to ID of targets labeled by RES following bulk introduction of reactive signals from outside of cells/animals, which often is non-discriminating in all parameters (time, locale, target, and extent of RES-occupancy on individual targets).

Specifically herein, G-REX™ profiling identifies PFR-cysteines via instantaneous release of a minimal amount of specific endogenous electrophile [e.g., 4-hydroxynonenal (HNE)—a known signalling messenger that is cytotoxic and mutagenic at high concentrations (Schopfer et al., "Formation and Signaling Actions of Electrophilic Lipids," *Chem. Rev.* 111:5997-6021 (2011); Jacobs et al., "Systems Analysis of Protein Modification and Cellular Responses Induced by Electrophile Stress," *Acc. Chem. Res.* 43:673-83 (2010); Long et al., "The Die Is Cast: Precision Electrophilic Modifications Contribute to Cellular Decision Making," *Chem. Res. Toxicol.* 30(8): 1599-1608 (2016), which are hereby incorporated by reference in their entirety)] in a cell (FIG. 3A and FIG. 4B). Because the amount of electrophile is low and release is rapid ($t_{1/2}$<1-2 min), only the most sensitive cysteines can react before HNE metabolism (true $k_{cat}/K_m$-type conditions). The G-REX™ profiling system—when directly coupled to T-REX™ delivery single-protein-redox targeting (Parvez et al., "T-REX On-Demand Redox Targeting in Live Cells," *Nat. Protocols* 11:2328-56 (2016), which is hereby incorporated by reference in its entirety) (FIG. 4A)—presents a previously-inaccessible two-in-one capability, simultaneously enabling (1) proteome-wide profiling, and (2) target-specific functional validations of novel sensors and phenotypically-dominant responses specifically triggered as a direct result of low-occupancy on-target RES-modifications under electrophile-limited conditions in situ (FIG. 3A and FIGS. 4A-4B). Using this G-REX™ profiling-T-REX™ delivery double-tap strategy, a novel privileged cysteine was identified of conserved importance present in two proteins that acts as a redox-Ub signalling shunt modulating two disparate signaling pathways.

Figures 4C, 4D, 4E, 4F:
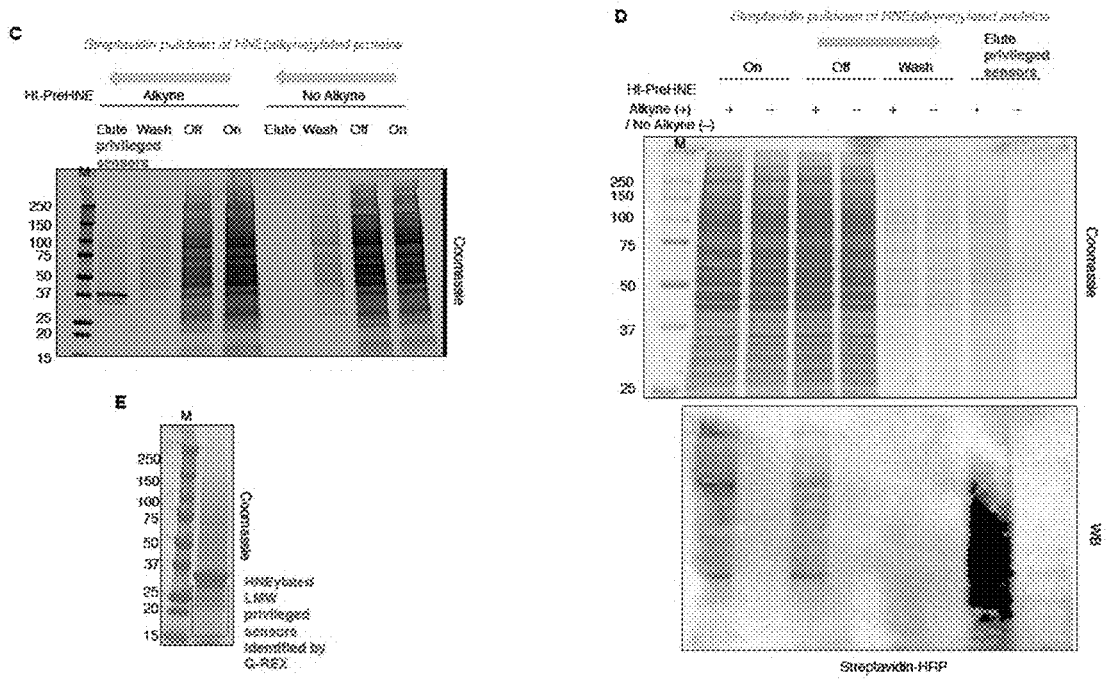

Gel-based analysis coupled with streptavidin blot verified successful labeling of proteins from G-REX™ profiling (FIG. 3A and FIGS. 4C-4D). Many redox-sensing proteins, such as Keap1, are unusually cysteine (Cys) rich. These proteins likely use mass action to improve their odds of being HNEylated and trigger downstream signaling. In addition, for Keap1, many Cys's are functional sensors (Parvez et al., "Substoichiometric Hydroxynonenylation of a Single Protein Recapitulates Whole-Cell-Stimulated Antioxidant Response," *J. Amer. Chem. Soc.* 137:10-13 (2015), which is hereby incorporated by reference in its entirety). Recent findings make a strong case that sensing ability is not necessarily correlated with the number of Cys's: applicants have found some HNE-sensing proteins/enzymes—such as Akt3 (Long et al., "Akt3 is a Privileged First Responder in Isozyme-Specific Electrophile Response," *Nat. Chem. Biol.* 13:333-8 (2017), which is hereby incorporated by reference in its entirety) and small heat shock protein (Parvez et al., "T-REX On-Demand Redox Targeting in Live Cells," *Nat. Protocols* 11:2328-56 (2016), which is hereby incorporated by reference in its entirety)—contain unique sensor Cys's and rely mostly upon kinetic privilege to sense endogenous RES such as HNE. To increase the odds of finding highly-reactive yet cysteine-poor sensors, the low-molecular-weight (LMW) protein pool was focused on (FIG. 4E). A 15-25-kDa region of the resultant gel (FIG. 4E) was thus cut and HNE-labeled proteins identified by MS. The top hit from this pool was Ube2V2 (Mms2 (Hofmann et al., "Noncanonical MMS2-Encoded Ubiquitin-Conjugating Enzyme Functions in Assembly of Novel Polyubiquitin Chains for DNA Repair," *Cell* 96:645-53 (1999), which is hereby incorporated by reference in its entirety))—a Ub-conjugating protein-variant with a poorly-understood role in DNA damage. Human Ube2V2 bears only one cysteine (C69) (FIG. 5). A homologous protein, Ube2V1 (Uev1 (Deng et al., "Activation of the IkappaB Kinase Complex by TRAF6 Requires a Dimeric Ubiquitin-Conjugating Enzyme Complex and a Unique Polyubiquitin Chain," *Cell* 103:351-61 (2000), which is hereby incorporated by reference in its entirety)) was the fourth highest confidence hit (FIG. 4F and Table 1).

Ube2V1 bears three cysteines, one of which (C94) is analogous to C69 in Ube2V1 (FIG. 5) (Michelle et al., "What was the Set of Ubiquitin and Ubiquitin-Like Conjugating Enzymes in the Eukaryote Common Ancestor?" *J. Mol. Evol.* 68:616-28 (2009), which is hereby incorporated by reference in its entirety). Although neither of these proteins is reportedly redox-sensitive, remarkably, five other hits in the top ten [peptidyl-prolyl cis-trans isomerase (Aluise et al., "Peptidyl-Prolyl Cis/Trans-Isomerase A1 (Pin1) is a Target for Modification by Lipid Electrophiles," *Chem. Res. Toxicol.* 26:270-9 (2013), which is hereby incorporated by reference in its entirety), ADP-ribosylation factor-3 (Chacko et al., "Pleiotropic Effects of 4-Hydroxynonenal on Oxidative Burst and Phagocytosis in Neutrophils," *Redox Biology* 9:57-66 (2016), which is hereby incorporated by reference in its entirety) and -4 (Chacko et al., "Pleiotropic Effects of 4-Hydroxynonenal on Oxidative Burst and Phagocytosis in Neutrophils," *Redox Biology* 9:57-66 (2016), which is hereby incorporated by reference in its entirety), nucleoside diphosphate kinase (Mano et al., "Identification of Oxidatively Modified Proteins in Salt-Stressed *Arabidopsis*: A Carbonyl-Targeted Proteomics Approach," *Plant Cell Physiol.* 55:1233-44 (2014), which is hereby incorporated by reference in its entirety), and cofilin-1 (Chavez et al., "Site-Specific Protein Adducts of 4-Hydroxy-2(E)-Nonenal in Human THP-1 Monocytic Cells: Protein Carbonylation Is Diminished by Ascorbic Acid," *Chem. Res. Toxicol.* 23:37-47 (2010), which is hereby incorporated by reference in its entirety)] were known HNE-sensors. This evidence underscores G-REX™ profiling as a sensitive method to identify first-responding sensor proteins.

G-REX™ Profiling Identifies a Novel Conserved Cysteine Present in Two Privileged Sensors in Humans, Ube2V1 and Ube2V2.

Because Ube2V2 that contains only one cysteine (C69) was the top hit and it was also found together with a homologous protein Ube2V1 containing a similar cysteine, it was hypothesized that Ube2V2(C69)/[Ube2V1(C94)] (FIG. 5A) are privileged sensors. Alignments of human Ube2V1 and Ube2V2 with other vertebrate counterparts showed that C69 and C94 are both conserved from humans to yeast (FIGS. 5B-5D). Neither cysteine is implicated in electrophile sensing. The analogous cysteine in *Saccharomyces cerevisiae* Ube2V2 (Mms2) is also not required for activity (Hofmann et al., "In Vitro Assembly and Recognition of Lys-63 Polyubiquitin Chains," *J. Biol. Chem.* 276: 27936-43 (2001), which is hereby incorporated by reference in its entirety). The longest isoform of human Ube2V1 has two other cysteines, one of which is not conserved beyond chimpanzees, whereas the other is conserved to frogs (FIG. 5B). Interestingly, both Ube-2V1 and -2V2 modulate ubiquitination activity of Ube2N (a low confidence hit in the G-REX data). Ube2N is an established Ub-conjugating E2-ligase that assembles K63-linked ubiquitin on target proteins (Hofmann et al., "Noncanonical MMS2-Encoded Ubiquitin-Conjugating Enzyme Functions in Assembly of Novel Polyubiquitin Chains for DNA Repair," *Cell* 96:645-53 (1999); Deng et al., "Activation of the IkappaB Kinase Complex by TRAF6 Requires a Dimeric Ubiquitin-Conjugating Enzyme Complex and a Unique Polyubiquitin Chain," *Cell* 103:351-61 (2000), which are hereby incorporated by reference in their entirety). As opposed to proteasomal targeting, K63-linked ubiquitination plays a role in cell signaling, including NF-κB signaling (Iwai, K., "Diverse Ubiquitin Signaling in NF-κB Activation," *Trends Cell Biol.* 22:355-64 (2012), which is hereby incorporated by reference in its entirety) and the DNA damage response (DDR) (Mailand et al., "RNF8 Ubiquitylates Histones at DNA Double-Strand Breaks and Promotes Assembly of Repair Proteins," *Cell* 131:887-900 (2007); Doil et al., "RNF168 Binds and Amplifies Ubiquitin Conjugates on Damaged Chromosomes to Allow Accumulation of Repair Proteins," *Cell* 136:435-46 (2009); Silva et al., "63 Polyubiquitination is a New Modulator of the Oxidative Stress Response," *Nat. Struct. Mol. Biol.* 22:116-23 (2015), which are hereby incorporated by reference in their entirety). Intriguingly, Ube2V2/Ube2V1 both lack a catalytic cysteine required for E2-activity, whereas Ube2N houses a catalytically-essential nucleophilic Cys(C87) required for E2-catalytic function. Indeed, Ube2N(C87) has also proven susceptible to various electrophilic inhibitors (Hodge et al., "Covalent Inhibition of Ubc13 Affects Ubiquitin Signaling and Reveals Active Site Elements Important for Targeting," *ACS Chem. Biol.* 10:1718-28 (2015), which is hereby incorporated by reference in its entirety). The findings from G-REX™ profiling thus raise the tantalizing possibility that Ube2V1/2 serve as novel signaling shunts bridging the human redoxome and ubiquitome, enabling 'signal exchange' between a non-canonical redox signal (HNE) and a canonical enzyme-catalyzed signal (Ub).

The on-target HNE-labeling of C69 within Ube2V2 was verified using the single-protein redox-targeting method, T-REX™ delivery, in live cells (FIGS. 4A-4B) (Parvez et al., "T-REX On-Demand Redox Targeting in Live Cells," *Nat. Protocols* 11:2328-56 (2016), which is hereby incorporated by reference in its entirety), followed by LC-MS/MS on Ube2V2 enriched from extracts (FIGS. 3B-3C and FIG. 32). These data underscore the capability of G-REX™ profiling-T-REX™ delivery coupled platform to identify bona fide HNE-sensors at the proteome scale and subsequently interrogate the consequences of on-target electrophilic modification under conditions that mimic endogenous signaling. From recent unbiased screens, approximately 10% of proteins can react with HNE under T-REX™ delivery (Long et al., "Akt3 is a Privileged First Responder in Isozyme-Specific Electrophile Response," *Nat. Chem. Biol.* 13:333-8 (2017); Parvez et al., "T-REX On-Demand Redox Targeting in Live Cells," *Nat. Protocols* 11:2328-56 (2016), which are hereby incorporated by reference in their entirety). Because T-REX™ delivery is built on a quasi-intramolecular delivery (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety), the efficiency of this targeting process is not affected by protein expression (Long et al., "Akt3 is a Privileged First Responder in Isozyme-Specific Electrophile Response," *Nat. Chem. Biol.* 13:333-8 (2017); Parvez et al., "T-REX On-Demand Redox Targeting in Live Cells," *Nat. Protocols* 11:2328-56 (2016); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety). Regardless, expression of Ube2N, and Ube2V2/Ube2V1 proteins was similar in the experiments (FIGS. 3D-3E, FIGS. 6A-6B). T-REX™ delivery-targeted delivery efficiencies (Parvez et al., "T-REX On-Demand Redox Targeting in Live Cells," *Nat. Protocols* 11:2328-56 (2016), which is hereby incorporated by reference in its entirety) independently measured for Ube2V2, Ube2V1, and Ube2N were 15±6%, 5±2%, and <2%, respectively. Delivery to Ube2V1/2V2 was unaffected by Ube2N-co-overexpression (FIG. 3B, 3E, 3F, and FIGS. 6B-6D). Ube2V1(C94S) and Ube2V2(C69S) both showed significantly-reduced targeting relative to WT counterparts (FIG. 3F and FIGS. 6C-6E). Furthermore, affinity capture of any proteins non-specifically adducted by adventitious HNE released during T-REX™ delivery-targeted delivery to Ube2V2, showed that there was no detectable HNEylation of Ube2N (FIG. 6F). This finding is consistent with Ube2N being a low-confidence hit in G-REX™ profiling (FIG. 4G and FIG. 32).

Aside from documenting the power of G-REX™ profiling to identify novel HNE sensors, the finding that Ube2V1/2 are privileged HNE-sensors is significant for several reasons. First, the relative HNE-sensitivity of these similar proteins does not correlate with the number of Cys's they contain. Second, in this series, HNE-sensing ability does not correlate with enzymatic function: catalytically-inactive E2-variants (Ube2V1/2) are much better HNE-sensors than catalytically-active E2-ligase (Ube2N). Third, although HNE released under G-REX™ profiling labeled many proteins, it has been shown that only 1-8% of free HNE in cells labels proteins (Ullrich et al., "Intracellular Metabolism of 4-Hydroxynonenal in Primary Cultures of Rabbit Synovial Fibroblasts," *Free Radic. Biol. Med.* 22:1153-57 (1997), which is hereby incorporated by reference in its entirety). Thus, the 15% Ube2v2(C69)-specific labeling above represents a huge enrichment over these background proteins—a result consistent with there being no labeling of the C69S-mutant.

Target- and Cys-Site-Specific RES-Sensing by Ube2V1 and Ube2V2 Triggers Specific Pathway Activation.

Functional responses brought about by on-target HNEylation of Ube2V1 and Ube2V2 separately were next evaluated. Ube2N-Ube2V2 heterodimer (FIG. 3B) is implicated to be important in DNA damage response (DDR), whereas Ube2N-Ube2V1 regulates NF-κB inflammatory signaling (Deng et al., "Activation of the IkappaB Kinase Complex by TRAF6 Requires a Dimeric Ubiquitin-Conjugating Enzyme Complex and a Unique Polyubiquitin Chain," *Cell* 103:351-61 (2000); Andersen et al., "Distinct Regulation of Ubc13 Functions by the Two Ubiquitin-Conjugating Enzyme Variants Mms2 and Uev1A," *J. Cell Biol.* 170:745-55 (2005), which are hereby incorporated by reference in their entirety). Consistent with previous data, subsequent to T-REX™ delivery-targeted HNEylation of Ube2V1 (with coexpression of Ube2N), a 3-fold upregulation in NF-κB-signaling was measured relative to all controls. Replicating this experiment with Ube2V2 in place of Ube2V1 did not result in NF-κB-pathway activation (FIG. 7A), confirming that HNE-induced NF-κB signaling upregulation was Ube2V1-specific. These data further demonstrate that G-REX™ profiling can identify functional first responders.

By contrast to the established position of Ube2V1 in NF-κB-directed inflammatory signaling, the precise biological mechanisms underlying the role of Ube2V2 in DDR are unclear. To elucidate how Ube2V2's HNE-sensing function fits into the DDR program, the ramifications of Ube2V2-specific HNEylation relative to Ube2V2(C69S)—a mutant unable to undergo HNEylation but otherwise similar to wild-type (wt)-Ube2V2 were studied. Briefly, Ube2N co-precipitated with Ube2V2(C69S) as efficiently as wt-Ube2V2 (FIGS. 8A-8B). PR-619—a deubiquitinating-enzyme inhibitor (one of the few inhibitor classes that elevate K63-linked Ub-pools (Altun et al., "Activity-Based Chemical Proteomics Accelerates Inhibitor Development for Deubiquitylating Enzymes," *Chem. Biol.* 18:1401-12 (2011), which is hereby incorporated by reference in its entirety))—was able to promote ubiquitination of Ube2V2 (C69S) as efficiently as wt-Ube2V2 (FIG. 7B).

Ube2V2-Ube2N-heterodimer catalyzes the synthesis of non-canonical K63-linked poly-ubiquitin chains with various functional roles in cell signaling (Hofmann et al., "Noncanonical MMS2-Encoded Ubiquitin-Conjugating Enzyme Functions in Assembly of Novel Polyubiquitin Chains for DNA Repair," *Cell* 96:645-53 (1999); Xia et al., "Direct Activation of Protein Kinases by Unanchored Polyubiquitin Chains," *Nature* 461:114-19 (2009); Broomfield et al., "MMS2, Encoding a Ubiquitin-Conjugating-Enzyme-Like Protein, is a Member of the Yeast Error-Free Postreplication Repair Pathway," *Proc. Nat'l. Acad. Sci.* 95:5678-5683 (1998), which are hereby incorporated by reference in their entirety). It was found that Ube2V2-specific HNEylation enabled by T-REX™ delivery, did not alter K63-linked total cellular Ub pools (FIG. 7C, 'input'), whereas treatment with PR-619 promoted elevation of K63-ubiquitination as expected (FIG. 7B). In addition, there was also no effect on pan- (FIG. 8B, compare 'input' lanes) or K48-linked- (FIG. 7D) cellular poly-Ub-pools as a consequence of Ube2V2-specific HNEylation. Two different proteasome inhibitors—bortezomib and MG132—elevated pan-Ub-pools as expected (FIG. 9A, 'input'; FIG. 9B, dotted box in 'input').

Unexpectedly, however, upon assessment of Ube2v2 enriched subsequent to T-REX™ delivery, it was discovered that C69-selective-HNEylation is accompanied by Ube2V2-specific-ubiquitination (FIG. 7C, 7E, FIG. 8B, FIG. 9C, IP-panels). Importantly, the effect was suppressed in Ube2V2(C69S), indicating that HNEylation of Ube2V2 is a trigger for its selective ubiquitination (FIG. 7C, 7E, and FIGS. 8B-8C, FIG. 9C). A band (~150 kDa) was observed in IP samples for both wt and C69S-mutant upon T-REX™ delivery (e.g., FIG. 7C, top blot in IP). This is likely due to cross-linking induced by the compound; however, as shown below this has no bearing on downstream signaling as C69S mutant is hyopmorphic for all downstream events.

The nature of the Ub-linkages formed selectively on Ube2V2 was next ascertained. Bortezomib and MG132 had no effect on the amount of ubiquitinated-Ube2V2 formed upon targeted-HNEylation [FIGS. 9A-9B (treated/untreated conditions within IP-panel and IP-lanes, respectively)]. Thus, the high-molecular weight (HMW)-ubiquitinated Ube2V2 was not primed for proteasomal degradation, and hence unlikely contains K48-linked-Ub—the canonical proteasome-targeting signal. As a corollary, very little upregulation in K48-linked-Ub post targeted-HNEylation was found (FIG. 7D). By contrast, K63-linked ubiquitination of Ube2V2 was significantly upregulated upon T-REX™ delivery, only in cells expressing wt, and not in cells expressing HNE-sensing-defective-C69S-mutant (FIG. 7C, FIG. 8D). This outcome was further verified using affinity capture of K63-linked-Ub using a tandem Ub-binding protein (TUBE) that showed an increase in Ube2V2 only upon T-REX™ delivery (FIG. 8E). Overexpression of HA-Ub(K63R) reduced the amount of Ube2V2(wt) in the poly-ubiquitin pool (FIG. 9D).

Since Ube2N is an established E2-ligase promoting K63-linked ubiquitination (Hofinann et al., "Noncanonical MMS2-Encoded Ubiquitin-Conjugating Enzyme Functions in Assembly of Novel Polyubiquitin Chains for DNA Repair," Cell 96:645-53 (1999); Andersen et al., "Distinct Regulation of Ubc13 Functions by the Two Ubiquitin-Conjugating Enzyme Variants Mms2 and Uev1A," J. Cell Biol. 170:745-55 (2005), which are hereby incorporated by reference in their entirety), it was hypothesized that Ube2N was responsible for elevated Ube2V2-ubiquitination. Overexpression of Ube2N had no significant effect on HNEylation-driven Ube2V2-poly-ubiquitination (FIG. 10A). Ube2V2-HNEylation also did not alter Ube2N-levels (FIGS. 3E-3F and FIGS. 6B-6D). This is not unexpected since RNF4 (Branigan et al., "Structural Basis for the RING-Catalyzed Synthesis of K63-Linked Ubiquitin Chains," Nat. Struct. Mol. Biol. 22:597-602 (2015), which is hereby incorporated by reference in its entirety)/RNF8/168 (Campbell et al., "Molecular Insights Into the Function of RING Finger (RNF)-Containing Proteins hRNF8 and hRNF168 in Ubc13/Mms2-Dependent Ubiquitylation," J. Biol. Chem. 287: 23900-10 (2012); Hodge et al., "RNF8 E3 Ubiquitin Ligase Stimulates Ubc13 E2 Conjugating Activity That Is Essential for DNA Double Strand Break Signaling and BRCA1 Tumor Suppressor Recruitment," J. Biol. Chem. 291:9396-410 (2016), which are hereby incorporated by reference in their entirety)—both Ub-E3 ligases—are also required for Ube2N-Ub discharge, thus factors other than Ube2N could limit this process, rendering overexpression of Ube2N alone ineffective. However, it was consistently found on Ube2N that had been enriched by IP of wt-Ube2V2 from native cells, a minor band of MW equivalent to monoubiquitinated-Ube2N. The same band was detected when Ube2N bearing either a T7 (detected using rabbit-secondary-HRP; FIG. 11A) or an HA tag (detected using a rat-HRP conjugated primary; FIG. 11B) was used, ruling out non-specific binding. Intriguingly, this band was selectively lost only when T-REX™ delivery was carried out in wt-Ube2V2, but not in the HNE-insensitive C69S-hypomorph-expressing cells (FIGS. 10B-10C, FIG. 8B). This putative monoubiquitinated-Ube2N band was removed upon addition of hydroxylamine to the loading buffer (FIG. 10B, 'IP') (Pickart et al., "Mechanism of Ubiquitin Carboxyl-Terminal Hydrolase. Borohydride and Hydroxylamine Inactivate in the Presence of Ubiquitin," J. Biol. Chem. 261:210-17 (1986), which is hereby incorporated by reference in its entirety), and depleted by proteasome-inhibitor treatment (conditions known to deplete labile/exchangeable Ub-pool) (FIG. 9A and FIG. 11B) (Xu et al., "Bortezomib Rapidly Suppresses Ubiquitin Thiolesterification to Ubiquitin-Conjugating Enzymes and Inhibits Ubiquitination of Histones and Type I Inositol 1,4,5-Trisphosphate Receptor," Mol. Cancer Ther. 3:1263-9 (2004), which is hereby incorporated by reference in its entirety). These results are characteristic of a non-amide linkage between Ube2N and Ub, likely the active Ub-thioester bond that serves as a Ub-donor to downstream targets during the catalytic cycle. In addition, no HMW-ubiquitination of Ube2N was observed under both native and SDS-/sonication-induced denatured conditions (FIG. 9A and FIG. 11B).

Loss of the active intermediate, mono-Ub-Ube2N, coupled with the upregulation in Ube2V2-ubiquitination, is consistent with HNEylation of Ube2V2 stimulating Ub-release from Ube2N. It further suggests that Ube2V2 is likely a target of Ube2N itself. To evaluate this hypothesis, cell lines expressing different shRNAs targeting Ube2N were prepared. Two of these shRNAs gave >50% reduction in Ube2N levels (#16,#17) relative to both wt-lines and lines expressing non-targeted shRNAs and a third shRNA (#18) gave weaker knockdown (FIGS. 8F-8G). Ube2N-knockdown lines did not show perturbation in poly-Ub-pools [FIG. 8F, Anti-Ub (endogenous) blot]. Lines with higher knockdown-efficiencies (#16,#17) showed significantly reduced HMW-ubiquitination of Ube2V2 following T-REX™ delivery-assisted HNEylation (FIG. 12A, FIGS. 11C-11D). Line-#18 showed weak suppression of polyubiquitination, consistent with Ube2N-dose-dependent regulation of Ube2V2-polyubiquitination (FIG. 12B). These data—in conjunction with Ube2V2(C69S) hypomorphism—establish that Ube2V2(C69)-specific electrophilic modification stimulates Ube2N-enzymatic activity.

Ube2V2-(C69)HNEylation-Controlled Ube2N Stimulation Drives DDR Signaling.

The physiologic ramification of this HNEylation event was further tracked by mapping, at the proteome-scale, perturbations in Ube2V2-interactome in response to Ube2V2-specific electrophilic modification using SILAC-T-REX™ delivery. SILAC—in contrast to standard pulldown-proteomics—was deployed to eliminate false-positives and bias toward abundant targets, and avoid missing low-affinity interactions (Mann, M., "Functional and Quantitative Proteomics Using SILAC," Nat. Rev. Mol. Cell Biol. 7:952-8 (2006), which is hereby incorporated by reference in its entirety). Briefly, T-REX™ delivery was executed independently in cells cultured in heavy or light arginine/lysine, expressing either HaloTagged-wt-Ube2V2 (heavy) or -(C69S)-mutant (light). A 1:1 mixture of these cells was lysed, IP-ed for Ube2V2, and heavy:light ratio was analyzed following trypsin-digest and LC-MS/MS (FIG. 12C). Ub was significantly enriched in the heavy (wt) fraction, consistent with enhanced Ube2V2-polyubiquitination upon HNEylation. The heavy fraction was also enriched in Ube2N-binding proteins known to be involved in DDR: p53 (Kastan et al., "Participation of p53 Protein in the Cellular Response to DNA Damage," Cancer Res. 51:6304-11 (1991), which is hereby incorporated by reference in its entirety) and H2A (Ikura et al., "DNA Damage-Dependent Acetylation and Ubiquitination of H2AX Enhances Chromatin Dynamics," Mol. Cell. Biol. 27:7028-40 (2007); Weake et al., "Histone Ubiquitination," in Bradshaw, eds., REGULATION OF ORGANELLE AND CELL COMPARTMENT SIGNALING, Academic Press, pp. 167-78 (2011); Bergink et al., "Principles of Ubiquitin and SUMO Modifications in DNA Repair," Nature 458:461-7 (2009); Messick et al., "The Ubiquitin Landscape at DNA Double-Strand Breaks," J. Cell. Biol. 187:319-26 (2009), which are hereby incorporated by reference in their entirety). MCM6 (Bell et al., "DNA Replication in Eukaryotic Cells," Annu. Rev. Biochem. 71:333-74 (2002), which is hereby incorporated by reference in its entirety)—a previously unknown binder of Ube2V2/Ube2N was also found. Altogether these data indicate that HNEylation of Ube2V2 promotes Ube2N to bind its client proteins with higher affinity, offering an elegant explanation for the observed loss of Ube2N-monoUb accompanying Ube2V2(C69)-specific HNEylation (FIGS. 10B-10C; FIG. 9A, FIG. 11B), and consequent increased ubiquitination of downstream targets.

The hypothesis that 'Ube2V2-specific HNEylation stimulates Ube2N activity' would predict increased ubiquitination of known Ube2N-binders and novel interactors, especially those enriched in the SILAC-T-REX™ delivery. MCM6 was co-overexpressed with either wt-Halo-Ube2V2 or the HNE-sensing-defective C69S-mutant. Upregulated ubiquitination of MCM6 upon T-REX™ delivery was only observed in cells expressing wt-Ube2V2 (FIG. 12D). Thus, Mcm6 is likely a target of Ube2N-catalyzed ubiquitination, validating that T-REX™ delivery coupled with SILAC can identify novel regulatory intersections. Increased ubiquitination of endogenous PCNA was also detected by ELISA (FIG. 12E), a known downstream target of Ube2N (Hoege et al., "RAD6-Dependent DNA Repair is Linked to Modification of PCNA by Ubiquitin and SUMO," Nature 419:135-41 (2002), which is hereby incorporated by reference in its entirety) and a low confidence hit in the SILAC data.

Finally, the electrophile-sensing effect of Ube2V2 on ubiquitination of H2A was investigated; specifically, H2AX that has essential signaling roles in DDR (Maze et al., "Every Amino Acid Matters: Essential Contributions of Histone Variants to Mammalian Development and Disease," Nat. Rev. Genet. 15:259-71 (2014); Celeste et al., "Genomic Instability in Mice Lacking Histone H2AX," Science 296:922-7 (2002), which are hereby incorporated by reference in their entirety). The findings below suggest a model in which Ube2V2(C69)-specific HNEylation-driven amplification of Ube2N activity upregulates downstream DDR pathways, priming cells to protect against DNA damage. Ubiquitination of H2A and its variants is a key epigenetic marker in DDR (Bergink et al., "Principles of Ubiquitin and SUMO Modifications in DNA Repair," Nature 458:461-7 (2009), which is hereby incorporated by reference in its entirety). However, the identity of specific ubiquitin ligases involved for specific H2A-variants (or other targets) remains unclear, with redundancy likely playing a role (Weake et al., "Histone Ubiquitination," in Bradshaw, eds., REGULATION OF ORGANELLE AND CELL COMPARTMENT SIGNALING, Academic Press, pp. 167-78 (2011), which is hereby incorporated by reference in its entirety), and whether Ube2N-assisted H2AX-ubiquitination and H2AX-phosphorylation (γ-H2AX)—a key, early signaling event in the DDR pathway-coordinate also remains difficult to be determined. Furthermore, upstream signals and surveillance mechanisms that elicit this Ube2N-dependent innate DDR are to date unresolved. A conventional histone isolation procedure (Shechter et al., "Extraction, Purification and Analysis of Histones," Nat. Protoc. 2:1445-57 (2007), which is hereby incorporated by reference in its entirety) was used, subsequent to T-REX™ delivery in cells expressing either Halo-Ube2V2 [wt or (C69S)]. Only wt-Ube2V2-but not the hypomorph-expressing cells upregulated ubiquitination of endogenous-H2AX (FIG. 12F). This response was ablated selectively in Ube2N-knockdown cells (FIG. 12G).

A recent report suggests that (BMI1)-(RNF2) E2-E3 ligase complex mediates H2AX-monoubiquitnation that is required for γ-H2AX formation in DDR initiation (Pan et al., "Monoubiquitination of H2AX Protein Regulates DNA Damage Response Signaling," J. Biol. Chem. 286:28599-607 (2011), which is hereby incorporated by reference in its entirety). This observation, along with the established role of the (Ube2N/Ube2V2)-(RNF8/168) E2-E3 ligase pair in H2A(X)-ubiquitination (Weake et al., "Histone Ubiquitination," in Bradshaw, eds., REGULATION OF ORGANELLE AND CELL COMPARTMENT SIGNALING, Academic Press, pp. 167-78 (2011); Messick et al., "The Ubiquitin Landscape at DNA Double-Strand Breaks," J. Cell. Biol. 187:319-26 (2009), which are hereby incorporated by reference in their entirety), made a hypothesis that a similar cascade is at play for the Ube2V2 (C69)-specific HNEylation-driven DDR. Thus, changes in γ-H2AX following T-REX™ delivery-directed Ube2V2 (C69)-HNEylation were assayed. Indeed, an approximately two-fold increase in cellular γ-H2AX was observed following Ube2V2(C69)-targeted-HNEylation (FIG. 12H; FIGS. 13A-13C). γ-H2AX upregulation was transient: increased γ-H2AX could be measured up to 18-h post light-induced HNE targeting, but γ-H2AX reduced to basal after 24 h (FIG. 12H, FIG. 13B). This behavior is consistent with a signalling/preconditioning response. Mitomycin-C upregulated γ-H2AX-upregulation by 3-4-fold (FIG. 12I; FIGS. 13A, 13C) (Meyer et al., "Clustered DNA Damage Induces Pan-Nuclear H2AX Phosphorylation Mediated by ATM and DNA-PK," Nucleic Acids Res. 41:6109-18 (2013); Stiff et al., "ATR-Dependent Phosphorylation and Activation of ATM in Response to UV Treatment or Replication Fork Stalling," Embo J. 25:5775-82 (2006), which are hereby incorporated by reference in their entirety), validating the assay and showing that the effect of HNEylation is biologically—as well as statistically—significant. γ-H2AX-upregulation required both Ube2v2(C69) and Ube2N because (1) no significant γ-H2AX upregulation was measured in cells expressing Ube2V2-C69S-mutant at any point over the time course (18-h) post T-REX™ delivery (FIG. 12G, FIG. 13B); and (2) notably, wt-Ube2V2-specific HNEylation was amorphic for γ-H2AX-upregulation in Ube2N-depleted background (FIG. 12I). However, both backgrounds hypomorphic for T-REX™ delivery-specific γ-H2AX-upregulation (i.e., Ube2V2-C69S-mutant-expressing cells and cells deficient of Ube2N) still upregulated γ-H2AX upon mitomycin-C treatment (FIG. 12I; FIGS. 13A, 13C).

The role of γ-H2AX in DNA-damage checkpoint remains enigmatic, although evidence exists that H2AX is required to initiate several DNA-damage checkpoints. In light of the reported increase in ubiquitination of other proteins during DNA damage (such as PCNA), it was postulated that HNEylation, specifically of Ube2V2, and subsequent increase in ubiquitination of downstream targets of Ube2N, serves to promote DDR-like responses. Although preconditioning is a common mechanism whereby RES-signals elicit beneficial cytoprotective responses to defend against or adapt to cellular stress, triggering of DDR is not one of the pathways known to function through this mechanism.

Whether DNA-synthesis stall (that occurs in response to many DNA damage events) accompanies C69-specific Ube2V2-HNEylation was investigated. A dual-pulse assay was used, which involves sequential, timed pulsing with two orthogonal DNA-labeling agents (EdU, followed by BrdU) that can be detected by fluorescence imaging (FIG. 13D). This assay is very accurate, because DNA-synthesis is measured over a defined time range, allowing a good estimate of synthesis-rate to be determined. In cells expressing wt-Ube2V2, the extent of DNA-synthesis stall was similar to that observed under mitomycin-C treatment, whereas corresponding cells expressing Ube2V2(C69S) exhibited a normal DNA-synthesis rate post T-REX™ delivery (FIG. 13J and FIG. 13E). This DNA-synthesis stall did not occur in Ube2N-depleted cells (FIG. 13F).

DDR preconditioning occurs in zebrafish embryos. To examine the relevance of this functional signal exchange in a whole-vertebrate system, these experiments were extended to zebrafish (*Danio rerio*) (MacRae et al., "Zebrafish as Tools for Drug Discovery," *Nat. Rev. Drug. Discov.* 14:721-31 (2015), which is hereby incorporated by reference in its entirety). Phylogenetic analysis indicated that zebrafish Ube2V2 possess a cysteine analogous to C69 in humans (FIG. 5C, 5D). It was first demonstrated that ectopic human Ube2V2 senses bioactive electrophiles such as HNE in zebrafish. Human HaloTagged-Ube2V2 was expressed in zebrafish by injecting embryos at the 1-cell stage with in vitro transcribed mRNA, incubating embryos with Ht-PreHNE (1 µM) for 1 day in the dark, then washing away excess probe, exposing the live specimens to light (5 min, 365 nm at 0.3 mW/cm$^2$). A portion of these samples was subjected to biotin-mediated enrichment of in-situ HNEylated proteins. The remaining portion was incubated for 3 h post light exposure. Subsequently, the fish were fixed and γ-H2AX levels were measured using whole-mount immunofluorescence.

Ube2V2 was significantly HNEylated following T-REX™ delivery in zebrafish (FIG. 14A). Targeted HNEylation led to detectable levels of UMW HNEylated-Ube2V2 that was poly-ubiquitinated (FIG. 14A). As in cell culture, global ubiquitin pools were unchanged (FIG. 15A). These results are consistent with sequence alignments that showed conservation of the sensor cysteine (C69) from humans to fish (FIG. 5C, 5D).

Furthermore, T-REX™ delivery-treated fish selectively showed upregulation in γ-H2AX (FIGS. 14B-14C). On the other hand, treatment of embryos with mitomycin-C led to a high level of γ-H2AX-expression relative to untreated fish, but these fish were severely deformed or died during treatment (FIGS. 14B-14C; FIG. 15B). Although latencies and other confounding factors make the comparison between mitomycin-C treatment and T-REX™ delivery indirect, this result at least suggests that RES-targeting of Ube2V2 could constitute a non-invasive method to prime DDR, without eliciting severe genotoxic stress.

Example 2—T-REX™ On-Demand Redox Targeting: A Toolset for Functional Discoveries and Validations Materials and Methods for Example 2
Reagents for Chemical Synthesis.
Required reagents include ethylenediamine (Sigma-Aldrich, cat. no. E26266), sodium hydride (Fisher, cat. no. S318 10), 3-Heptyn-1-ol (Sigma-Aldrich, cat. no. 630845), 1N HCl (Sigma-Aldrich, cat. no. 38283 Fluka), magnesium sulfate anhydrous (JT Baker, cat. no. J41620), hexanes (Sigma-Aldrich, cat. no. 227064), ethyl acetate (EtOAc) (Sigma-Aldrich, cat. no. 270989), diethyl ether (Et$_2$O) (Sigma-Aldrich, cat. no. 673811), dichloromethane (DCM, CH$_2$C$_{12}$) (Sigma-Aldrich, cat. no. 270997), pyridinium chlorochromate (PCC) (Sigma-Aldrich, cat. no. 190144), 1-Hydroxyanthraquinone (TCI-America, cat. no. H0354), 2-Propenal (Sigma-Aldrich, cat. no. 01680), 2-(2-(6-chlorohexyloxy)ethoxy)ethanamine (Promega, cat. no. P6711), sodium thiosulfate (Na$_2$S$_2$O$_4$) (Sigma-Aldrich, cat no. 72049), calcium chloride (CaCl$_2$) (Sigma-Aldrich, cat no. C1016), sulfuric acid (H$_2$SO$_4$) (Sigma-Aldrich, cat. no. 339741), Celite® (Sigma-Aldrich, cat. no. 22140), piperidine (Sigma-Aldrich, cat. no. 411027), methyl-2-sulfinylacetate (Sigma-Aldrich, cat. no. 237582), acetonitrile (Sigma-Aldrich, cat. no. 271004), dihydropyran (DHP) (Sigma-Aldrich, cat. no. D106208), pyridinium p-Toluenesulfonate (PPTS) (Alfa-Aesar, cat. no. A15708), sodium bicarbonate (NaHCO$_3$) (Sigma-Aldrich, cat. no. S6014), sodium sulfate (Sigma-Aldrich, cat. no. S9627), toluene (Sigma-Aldrich, cat. no. 244511), DIBAL-H (Sigma-Aldrich, cat. no. 256811), tetrabromomethane (CBr$_4$) (Sigma-Aldrich, cat. no. C11081), triphenyl phosphine (PPh$_3$) (Sigma-Aldrich, cat. no. 93092), P-Toluenesulfonic acid (p-TsOH) monohydrate (Sigma-Aldrich, cat. no. 402885), methanol (MeOH) (Sigma-Aldrich, cat. no. 322415), benzyl bromide (Sigma-Aldrich, cat. no. B17905), potassium carbonate (K$_2$CO$_3$) (Sigma-Aldrich, cat. no. P5833), potassium iodide (KI) (Sigma-Aldrich, cat. no. P2963), acetone (Sigma-Aldrich, cat. no. 34850), dimethyl sulfide (Me$_2$S) (Sigma-Aldrich, cat. no. 274380), 2-methyl-2-butene (Sigma-Aldrich, cat. no. 86262), tert-butanol (t-BuOH) (Sigma-Aldrich, cat. no. 471712), sodium phosphate monohydrate (NaH$_2$PO$_4$.H$_2$O) (Sigma-Aldrich, cat. no. S9638), sodium chlorite (NaClO$_2$) (Sigma-Aldrich, cat. no. 71388), hydroxybenzotriazole (HOBt) (Sigma-Aldrich, cat. no. 157260), N, N-Diisopropylethyleneamine (DIEA) (Sigma-Aldrich, cat. no. D125806), 1-ethyl-3-(3-dimethylaminopropyl) carbodiimide (EDCI) (Sigma-Aldrich, cat. no. E6383), palladium on Carbon (Pd/C) (Sigma-Aldrich, cat. no. 205699), tetra-n-butylammonium fluoride (TBAF) (Sigma-Aldrich, cat. no. 241512), tetrahydrofuran (THF) (Sigma-Aldrich, cat. no. 401757), diethylformamide (DMF) (Sigma-Aldrich, cat. no. 227056), potassium permanganate (KMNO$_4$) (Sigma-Aldrich, cat. no. 223468), silica gel (Silicycle; cat. no. SiliaFlash P60), and dry ice.

Reagents for T-REX™ Delivery Experiments in *E. coli*.
pet28a-Halo-Keap plasmid *E. coli* BL21 Codon plus (DE3) RIL competent cells (Agilent, cat. no. 230245), Luria-broth (LB) media (10 g NaCl, 10 g tryptone, 5 g yeast extract per liter. Add 15 g agar for LB agar). Chloramphenicol (Goldbio, cat. no. C-105-5), kanamycin (Goldbio, cat. no. K-120-5), LB-KAN agar plates (Kanamycin 50 µg/mL), Isopropyl-beta-D-galactopyranoside (IPTG) (Gold Biotechnology, cat. no. I12481C), TCEP-HCl (Goldbio, cat. no. TCEP1), sulfo-Cy5 azide (Lumiprobe, cat. no. B3330), copper Tris[(1-benzyl-1H-1,2,3-triazol-4-yl)methyl]amine (Cu-TBTA) (Lumiprobe, cat. no. 21050), HaloTag-targetable precursor to HNE(alkyne) (also known as Ht-PreHNE or HtPHA) (FIG. 29) (See synthesis and reagent setup), HNE(alkyne) (FIG. 29) (See synthesis and reagent setup), HEPES, OmniPur Lysozyme from Egg white (EMD Millipore, cat. no. 5950), Dnase-I from bovine pancrease (EMD Millipore, cat. no. 260913), DMSO, t-Butanol, Sodium-dodecyl sulfate (SDS), copper sulfate pentahydrate, β-mercaptoethanol (BME) (Sigma-Aldrich, cat. no. M6250), TEV protease (see TEV protease purification protocol), and standard reagents for protein gel electrophoresis.

Additional Reagents and Equipment for Recombinant Proteins Expression in E. coli.

Streptomycin B sulfate (Goldbio, cat. no. S-150-100), Econo column (Biorad, cat. no. 7374251), TALON metal affinity resin (Clontech, cat. no. 635502), Amicon ultra-15, MWCO 10 kDa (Millipore, cat. no. UFC901024), GE Healthcare Hiload™ 26/60 Superdex™ 200 prep grade column (ID No. 0823027), Äkta FPLC system (GE Healthcare).

Reagents for T-REX™ Delivery Experiments in Cultured Mammalian Cells.

pMIR-DsRed-IRES-His6-Halo-Keap1 plasmid, available from Addgene (ID number 58240), Halo-ORF clone library in pFN21a vector, available from Promega pcDNA3.1 myc3 Nrf2 plasmid, available from Addgene (ID number 21555), eGFP-Nrf2, available from Addgene (ID number 21549), pMIR-Halo-PTEN plasmid, available from Addgene (ID number 58241), pcDNA3 InPAkt plasmid (materials transfer from Professor Jin Zhang, UCSD), HEK-293 cells (ATCC, cat. no. CRL-1573), TransIT-2020 (Mirus, cat. no MIR5400), Polyethyleneimine (PEI, Polyscience Inc., cat. no. 23966-2) (See reagent setup), Standard media for cell culture, HaloTag TMR ligand (Promega, cat. no. G8251), HaloTag targetable photocaged precursor to HNE(alkyne) (also known as Ht-PreHNE or HtPHA) (FIG. 29) (See synthesis and reagent setup), HNE(alkyne) (FIG. 29) (See synthesis and reagent setup), Quickstart™ Bradford 1× dye (Bio-Rad, cat. no. 5000205), bovine serum albumin (BSA) as standard 2 mg/mL (Pierce, cat. no. 23209), TCEP-HCl (Goldbio, cat. no. TCEP1), Sulfo-Cy5 azide (Lumiprobe, cat. no. B3330), cCopper Tris[(1-benzyl-1H-1,2,3-triazol-4-yl)methyl]amine (Cu-TBTA, Lumiprobe, cat. no. 21050), DMSO, t-Butanol, sodium-dodecyl sulfate (SDS), copper sulfate pentahydrate, TEV protease (see TEV protease purification protocol), ammonium bicarbonate (Sigma-Aldrich, cat. no. 09830), formic acid (Sigma-Aldrich, cat. no. F0507), iodoacetamide (Sigma-Aldrich, cat. no. I1149), sequencing grade modified trypsin (Promega, cat. no. V5113), standard reagents for protein gel electrophoresis, standard reagents for western blotting, milk for PVDF membrane blocking (Walmart, great value non-fat instant dry milk), mouse monoclonal anti-Keap1 primary antibody (Abcam, cat. no. Ab119403, 1:5000), rabbit polyclonal anti-HaloTag primary antibody (Promega, cat. no. 9281, 1:2000), rabbit polyclonal anti-RRM1 primary antibody (Abcam, cat. no. Ab81085, 1:2000), mouse monoclonal anti-phosphatidylinositol 3,4,5-triphosphate (PIP3) (Echelon Biosciences, cat. no. Z-P345, 1:500), goat anti-rabbit IgG Alexa Flour® 647 preadsorbed (Abcam, cat. no. Ab150083, 1:1000), Goat anti-mouse Ig, Human ads-FITC (Southern Biotech, cat. no. 1010-02, 1:1000), 4,6-Diamidino-2-phenylindole dihydrochloride (DAPI) (Sigma, cat. no. D9542), rabbit polyclonal anti-GFP primary antibody (Santa Cruz, cat. no. sc-8334, 1:1000), mouse monoclonal anti-actin (Sigma-Aldrich, cat. no. A4700, 1:30000), secondary antibody to mouse (Abcam, cat. no. Ab6789, 1:5000), secondary antibody to rabbit (Abcam, cat. no. Ab97051, 1:8000).

Reagents for Making Firefly and Renilla Luciferase Substrates (Optional).

HEPES (Fisher, cat no. BP310-1), magnesium sulfate (JT Baker, cat. no. J41620), dithiothreitol (DTT) (Goldbio, DTT100), ethylenediaminetetraacetic acid (EDTA) (Fisher, cat. no. BP120-1), adenosine triphosphate disodium salt hydrate (ATP) (Fisher, cat. no. AC102080500), coenzyme A (Avanti, cat. no. 870700P), D-luciferin Firefly (Goldbio, cat. no. L-123-250), Tris base (Fisher, cat. no. BP152 10), trans-1,2-Diaminocyclohexane-N,N,N',N'-tetraacetic acid monohydrate (CDTA) (Alfa Aesar, cat. no. B22928-14), bovine serum albumin (BSA) (Fisher, cat. no. BP9703-100), goat Serum (Sigma, cat. no. G9023), Triton X-100 (Fisher, cat. no. BP-151-100), glycerol (Fisher, cat. no. BP229 4), sodium acetate anhydrous (USB, cat. no. 21608), sodium sulfate (Sigma-Aldrich, cat. no. S9627), sodium pyrophosphate (Fisher, S390-500), 2-(4-aminophenyl)-6-methylbenzothiazole (APMBT) (Enamine, cat. no. EN300-17374), methanol anhydrous (Sigma-Aldrich, cat. no. 322415), coelenterazine (Goldbio, cat. no. CZ2.5).

Equipment for Chemical Synthesis.

Fume hood, weighing balance, weighing paper, spatulae, round-bottomed flasks, separatory funnel, graduated cylinders, pasteur pipettes, tweezers, magnetic stir plate, syringes and needles, magnetic stir bars, glass-backed thin layer silica chromatography plates, 365 nm UV lamp Spectroline™ E-Series, column for flash chromatography, vacuum pump, rotary evaporator, ozonator, nitrogen and argon gas, Schlenk line.

Equipment for T-REX™ Delivery Experiments in E. coli.

Standard equipment for E. coli cell culture, Standard equipment for protein gel electrophoresis, cell density meter for optical density (OD) measurement, centrifuge capable of spinning culture tubes, microcentrifuge tubes, temperature adjustable shaker-Incubator, handheld UV-lamp with 365 nm light (Spectroline ENF 240C), ChemiDoc-MP imaging system (Bio-Rad).

Equipment for T-REX™ Delivery in Cultured Mammalian Cells.

Standard equipment for mammalian cell culture, handheld UV-lamp with 365 nm light (Spectroline ENF 240C), sterile 48-well cell culture plates, white, opaque, flat-bottomed 96-well plate for luminescence measurement (Corning), glass-bottom dishes for imaging (In Vitro Scientific, 1.5N, D35-20-1), confocal microscope with appropriate filters, plate reader for measuring luminescence (Biotek Cytation3 in our case), flow cytometer with appropriate lasers and filters (BD LSRII, for example), Biosafety level 2 hood, ChemiDoc-MP imaging system (Bio-Rad).

Chemical Compounds Set Up.

HaloTag-targetable precursor to HNE(alkyne) (also known as Ht-PreHNE or HtPHA): Make a stock of 150-200 mM HtPHA in DMSO. Determine concentration using UV-Vis spectrophotometer (At 25° C., ε366=3950 M-1 cm-1). One-shot aliquots can be stored protected from light in −80° C. for >6 months. HNE(alkyne): Make a stock of 150-200 mM HNE(alkyne) in DMSO. Determine concentration using UV-Vis spectrophotometer (At 25° C., ε225=16900 M-1 cm-). One-shot aliquots can be stored in −80° C. for >6 months. CuSO$_4$ solution: Make a 100 mM CuSO$_4$. 5H$_2$O solution in double-distilled water (ddH$_2$O). The solution can be stored >1 year at 4° C. TCEP solution: Make a 100 mM TCEP-HCl solution in 50 mM HEPES (pH 7.6). Aliquots can be stored in −20° C. for up to 6 months. Avoid freeze-thaw. Cy5 azide: Make a 0.5 mM Cy5 azide solution in DMSO. Aliquot and store in −20° C. for >6 months protected from light as one-shot aliquots. 20% SDS: Dissolve 10 g SDS in 50 mL ddH$_2$O. Vortex to dissolve.

Biological Reagents Set Up.

Kanamycin: Dissolve Kanamycin at 50 mg/mL in autoclaved ddH$_2$O (1000×) and filter sterilize (0.22 μm filter).

Aliquots can be stored at −20° C. for >6 months. Chloramphenicol: Dissolve Chloramphenicol at 30 mg/mL in 200-proof ethanol (1000×). Aliquots can be stored at −20° C. for >6 months. IPTG: Make a 1 M solution of IPTG (1000×) in autoclaved ddH2O, filter sterilize (0.22 µm filter) before use. Polyethyleneimine (PEI, 25000 MW linear chain): Dissolve PEI to 1 mg/mL in autoclaved ddH$_2$O by heating at 80° C. Let the solution cool to room temperature. Neutralize to pH 7.0. Filter sterilize (0.22 µm filter). Aliquot can be stored at −20° C. for >6 months. Avoid multiple freeze-thaw. Blocking buffer: Add 20 µL Triton X-100 in 9.5 mL 50 mM HEPES pH 7.6. Vortex to mix. Add 0.5 mL goat serum and mix well. Incubation buffer: Add 20 µL Triton X-100 in 100 mL 50 mM HEPES pH 7.6. Vortex to mix. Add 1 mL goat serum and mix well. DAPI: Make a 5 mg/mL stock DAPI solution in DMSO. 5× Passive Lysis Buffer (PLB)100: Dilute 125 mM Tris pH 7.8, 10 mM 1,2-CDTA 10 mM DTT, 5 mg/mL BSA, 5% Triton X-100, 50% Glycerol. 5×PLB can be stored in −20° C. for at least 2 months. 1× Firefly luciferase Substrate100: Dilute 75 mM HEPES pH 8.0, 4 mM MgSO$_4$, 20 mM DTT, 0.1 mM EDTA, 0.53 mM ATP, 0.27 mM Coenzyme A, 0.47 mM D-Luciferin Firefly. Aliquot the substrate in amber tubes. The substrate can be stored in −80° C. for at least 2 months. 1× Renilla Luciferase Buffer101: Dissolve 7.5 mM sodium acetate pH 5.0, 400 mM sodium sulfate, 10 mM CDTA, 15 mM sodium pyrophosphate, 0.025 mM APMBT. Aliquot the buffer in microcentrifuge tubes. The substrate can be stored in −20° C. for at least 3 months. 100× Renilla Luciferase Substrate101: Dilute coelenterazine to ~0.5 mg/mL in anhydrous methanol immediately upon receipt. Determine the concentration of the substrate using UV-VIS spectrophotometer. Blank the spectrophotometer with dry methanol. Measure A345. At 25° C., ε345=9800 M-1 cm-1 in methanol. Calculate concentration. Further dilute the stock in dry methanol to make a final concentration of 0.55 mM Coelenterazine. Aliquots of stock Renilla luciferase substrate can be stored in −80° C. for at least 3 months. Note: Pre-made substrates for Luciferase Assay are also available commercially (Dual-Luciferase Reporter Assay System, Promega, cat. no. E1910) Moisture can lead to decay of coelenterazine; e.g., avoid wet methanol.

ChemiDoc-MP Imaging System Setup for Cy5 Florescent Gel Imaging.

Set Cy5 excitation source as red epi illumination and emission filter as 695/55 filter.

Plate Reader Automated Protocol for Luciferase Reporter Assays for AR Pathway Activation.

Set up the plate reader with the following commands: Inject 50 µL Firefly substrate; shake plate for 2 s; pause for 2 s; read Luminescence for 10 s. Subsequently, run the protocol. Repeat the protocol except inject 50 µL of 1× Renilla substrate in Renilla luciferase buffer. The gain for the detector will need to be optimized based on the signal intensity.

Flow Cytometer Settings for GFP Reporter Assays for AR Pathway Activation.

Run calibration and cleaning based on the manufacturer's instruction. On the BD LSR-II, GFP is detected in the 488-1 channel with 488 nm excitation laser, 525/50 filter, and 505LP mirror for all of the experiments.

LC-MS/MS Setup for the Identification of LDE Modified Sites on POI.

For the LC step, separate the peptides on a CapLC system (Waters Co. Milford, Mass., USA) coupled to a QSTAR XL (ABSCIEX, Framingham Mass.). Desalt onto an Everest C18 (5 µm, 500 µm ID×15 mm, Grace, Deerfield, Ill.) with solvent A (97:3 H$_2$O:ACN with 0.1% vol/vol formic acid and 0.01% vol/vol TFA) at 40 µL/min. After a 6-min wash, separate the peptides on a Jupiter C18 (3 µm, 100 µm ID×150 mm, Phenomenex, Torrance, Calif.) using a 40-min linear gradient of 10%0/to 40% solvent B (85% ACN/10/o isopropanol+0.1% vol/vol formic acid+0.0075% vol/vol TFA) at 250 nL/min. For the MS/MS step, MS data acquisition was performed using Analyst QS 1.1 software (AB-Sciex) in positive ion mode for information dependent acquisition (IDA) analysis. Set the nanospray voltage to 2.1 kV for all experiments in a positive ion mode. Use nitrogen as the curtain (value of 20) with heated interface at 130° C. Set the declustering potential at 80 eV and Gas1 as 5 (arbitrary unit). In IDA analysis, full scan MS data are acquired after each survey scan from m/z 350 to m/z 1300. The three highest intensity ions above the predefined threshold of 28 cps with multiple charge states (+2 and +3) are selected for tandem MS (MS/MS) with rolling collision energy applied for detected ions based on different charge states and m/z values. Each MS/MS acquisition is completed and switched back to survey scan when the precursor intensity falls below a predefined threshold or after a maximum of 65 s acquisition.

Section 1: Chemical Syntheses of HNE(Alkyne) and HaloTag-Targetable Photocaged Precursor to HNE(Alkyne) (Also Known as Ht-PreHNE or HtPHA) TIMING: 4 Days.

All chemical reactions in this section are conducted in oven-dried glassware under an atmosphere of nitrogen unless otherwise stated. Concentration involves removal of solvents by means of a rotary-evaporator (equipped with a 37-40° C. water bath) attached to a diaphragm pump (15-60 Torr) followed by removal of residual solvents at <1 Torr with a vacuum pump. Flash chromatography is performed on silica gel 60 (230-400 mesh): a typical purification procedure for 5 g of crude product uses 50 g of silica gel in a 4×30 cm (diameter×length) column and 10-ml fractions are collected.

Synthesis of HNE(Alkyne) (FIG. 17 Inset and FIG. 29).
1. Add 2.76 g NaH (69 mmol) to 26.8 mL ethylenediamine (40 mmol) at 0° C. under an atmosphere of nitrogen. Stir for 1 h at room temperature (15-22° C.) and then for another hour at 60° C. NaH releases a flammable gas (hydrogen) on contact with water and other protic solvents. Keep away from naked flames and use in a fume hood.
2. Cool the reaction to 45° C. and add 2 mL of 1 (16.4 mmol). Heat the reaction back to 60° C. and stir for 1 h.
3. Slowly add 20 mL 1 N HCl at 0° C., extract with ether 50 mL×3 and dry with magnesium sulfate 200 mg or more until the newly added powder no longer clumps upon swirling.
4. Purify the residue after concentration in vacuo by using flash chromatography with hexanes. EtOAc (2:1 v/v) as eluent to obtain alcohol 2. (Rf=0.5 hexanes:EtOAC 2:1). Alcohol 2 can be stored in a sealed glass vial in a −20° C. freezer for minimally 6 months.
5. Dissolve 1.44 g of the product 2 (28 mmol) in 40 mL CH$_2$Cl$_2$. Add 5.53 g PCC (56 mmol) and stir at room temperature for 1 h.
6. Filter the reaction mix through Celite® (~10 g).
7. Concentrate the filtrate and isolate the aldehyde 3 after separation via flash chromatography using hexanes: Et2O (2:1 v/v) as eluent. (Rf=0.8 hexanes:EtOAc 2:1). Aldehyde 3 is best used immediately. If pausing is needed, 3 should be stored strictly under air-free conditions with minimal exposure to moisture.

8. Add 1.16 g of aldehyde 3 (10.5 mmol) add 1.73 mL piperidine (17.6 mmol) to a solution of 1.74 g methyl 2-phenylsulfinylacetate (8.78 mmol) in 40 mL $CH_3CN$.
9. Stir the reaction overnight at room temperature. Add aqueous ammonium chloride and extract with $CH_2Cl_2$.
10. Collect the organic layer, dry, concentrate and isolate ester 4 using flash chromatography with hexanes: EtOAc (10:1 v/v) as eluent. (Rf=0.5 hexanes:EtOAc 10:1; stain $KMnO_4$; impurity at 0.95 red under UV). Ester 4 can be stored in a sealed glass vial in a −20° C. freezer for minimally 6 months
11. Compound 4 can be used to prepare either HNE (alkyne) or compound 8 by following the steps in options A and B respectively.

(A) Preparation of HNE(Alkyne)

(i) HNE(alkyne) can be prepared from 4 by reduction of ester with DIBAL-H (steps 11-xx). To do this, dissolve 0.4 g ester 4 (2.2 mmol) in 20 mL $CH_2Cl_2$. Cool the reaction to −80° C.

(ii) Dissolve 4.45 mL DIBAL-H (2 M in hexane, 4.4 mmol) in 20 mL $CH_2Cl_2$ and add dropwise to the reaction. Stir for 1 h.

(iii) Add 24.7 mL 1 N HCl, extract with diethyl ether, dry and concentrate in vacuo.

(iv) Isolate the pure product via flash chromatography using hexanes: Et20 (4:1 v/v) as eluent (Rf=0.5 in hexanes: Et2O 4:1). HNE(alkyne) is highly unstable to air-oxidation and polymerization. The purified material should be characterized promptly and during this time may be stored under Ar at room temperature. For long-term storage, HNE (alkyne) should be stored as one-shot aliquots in DMSO at −80° C. and must be used immediately once thawed.

(B) Preparation of Compound 8

(i) To 0.4 g of the ester 4 (2 mmol), add 1.1 mL dihydropyran (12 mmol) and 0.08 g pyridinium p-toluene-sulfonate (0.32 mmol). Stir the reaction for 24 h at room temperature under argon.

(ii) Add saturated 5 mL $NaHCO_3$, extract with O1 mL DCM×3. Wash twice with O1 mL water, followed by once with O1 mL brine and dry with $Na_2SO_4$ (40 mg or more until the newly added powder no longer clumps upon swirling) to obtain 5. 5 can be stored in a sealed glass vial in a −20° C. freezer for minimally 6 months.

(iii) Dissolve 0.5 g of the protected ester 5 (1.8 mmol) in 20 mL toluene. Cool the reaction to −80° C.

(iv) Add 2 equivalents DIBAL-H (2 M in Hexane) dropwise to the reaction. Stir for 1 h and then add 0.5 mL 3M NaOH.

(v) Purify the desired product using flash chromatography with hexanes:EtOAc (1:1 v/v) as eluent to obtain 6. 6 can be stored in a sealed vial in a −20° C. freezer for 1 month.

(vi) Brominate 0.35 g of the resulting alcohol 6 (1.4 mmol) by adding 0.5 g $CBr_4$ (1.54 mmol), 0.44 g PPh3 (1.68 mmol) in distilled 20 mL DCM at 0° C. Stir the reaction for 15 min.

(vii) Add saturated $NaHCO_3$ (50 mL), extract with DCM (40 mL×3), dry with $Na_2SO_4$ (200 mg or more until the newly added powder no longer clumps upon swirling) and concentrate.

(viii) Isolate the desired product 7 after flash chromatography using hexanes:EtOAc (6:1 v/v) as eluent. 7 is promptly forwarded to the subsequent step. Temporary storage (<1 week) is possible in moisture-free conditions and at low temperature (≤−20° C.).

(ix) To deprotect the THP group, weigh out 0.26 g of 7 (0.87 mmol) add 0.66 g pTsOH (0.35 mmol) and 25 mL MeOH. Stir the reaction overnight.

(x) Add $NaHCO_3$ (50 mL), and extract with EtOAc (40 mL×3). Wash with water (40 mL) and concentrate in vacuo.

(xi) Isolate the desired product 8 after flash chromatography using hexanes:EtOAc (4:1 v/v) as eluent. 8 is immediately carried onto the subsequent step. Temporary storage (<2 days) is possible under air- and moisture-free conditions at low temperature (≤−20° C.).

Synthesis of Anthrahydroquinone Cage (FIG. 29) TIMING: 3 Days.

12. Weigh out 1 g of 1-hydroxyanthraquinone 9 (4.46 mmol). Dissolve in 100 mL 5% NaOH in 1:1 MeOH: $ddH_2O$ under argon.

13. Add 4.3 g Na2S2O4. Heat mixture to 70-75° C. for 10 min and then add 3.0 mL 2-propenal (44.6 mmol). Heat reaction mix and reflux overnight.

14. Let the reaction mix cool and then add it to cold 200 mL solution of 2.5% $H_2SO_4$. Extract with 3×50 mL $CH_2Cl_2$, combine, dry over 10 g $CaCl_2$ for 48 h.

15. Concentrate the sample in vacuo and purify the residue via flash chromatography using 2:1 hexanes: $CH_2Cl_2$ to obtain 10 (Blankespoor et al., "Photochemistry of 1-Alkoxy- and 1-(Benzyloxy)-9,10-Anthraquinones in Methanol: A Facile Process for the Preparation of Aldehydes and Ketones," *J. Org. Chem.* 60:6852-9 (1995), which is hereby incorporated by reference in its entirety).

16. Weigh out 0.2 g of 10 (0.76 mmol) and dissolve in 10 mL DMF.

17. Add 0.27 mL of Benzyl bromide, 0.628 g of potassium carbonate and 0.038 g of potassium iodide. Stir the reaction for 1 h at 65° C. and subsequently cool it to room temperature. A color change from dark purple to orange is observed as reaction progresses.

18. Dilute the reaction with 50 mL water and extract organic layer using 50 mL EtOAc.

19. Wash organic layer with 50 mL water, 50 mL brine and 50 mL 1N HCl. Dry and concentrate in vacuo to yield 11 as a yellow solid (Rf=0.1 hexanes:EtOAc 30:1; benzyl bromide 0.8). 11 can be stored in a sealed glass vial in a −20° C. freezer for minimally 6 months.

20. Dissolve 0.23 g of compound 11 (0.65 mmol) in 50 mL $CH_2Cl_2$. Cool to −78° C. in an ice bath made using acetone and dry ice.

21. Bubble $O_3$ using an ozonator for 15 min followed by the addition of 4.5 mL $Me_2S$. Allow the reaction to warm up to room temperature and let it stir for 10 h. $Me_2S$ has a pungent stench and must be used in a fume hood.

22. Concentrate the reaction mix in vacuo. Dilute the reaction mix with 50 mL EtOAc and wash with 50 mL water.

23. Collect the organic layer, dry with $Na_2SO_4$ (100 mg or more until the newly added powder no longer clumps upon swirling and concentrate to yield 12. (Rf=0.6 hexanes:EtOAc 3:1). 12 should ideally be carried on to the subsequent step promptly. If pausing is required, the purified material should be stored at −80° C. in a moisture-free Ar atmosphere.

24. Dissolve 0.23 g of 12 (0.645 mmol) and 9 mL 2-methyl-2-butene in 37.5 mL t-BuOH and cooled to 0° C. Add a solution of 0.633 g $NaH_2PO_4.H_2O$ (4.59 mmol) and 0.524 g $NaClO_2$ (5.79 mmol) in water dropwise to the reaction mix.

25. Warm up the resulting mix at room temperature and let it stir overnight.

26. Add 150 mL 0.1 N HCl and extract with EtOAc (200 mL×3). Wash the organic extract with water (200 mL)

and brine (200 mL), dry with Na$_2$SO$_4$ (200 mg or more until the newly added powder no longer clumps upon swirling) in vacuo and concentrate in vacuo to yield 13 as a yellow solid. (Rf=0.05 hexanes:EtOAc 3:1). 13 can be stored in a sealed glass vial in a −20° C. freezer for minimally 1 year.

Coupling of Halo Linker and Anthrahydroquinone Cage (FIG. 29) TIMING 1 Day.

27. Dissolve 0.24 g 13 (0.65 mmol) and 0.14 g 2-(2-(6-chlorohexyloxy)ethoxy)ethanamine (0.65 mmol) in 15 mL CH$_2$Cl$_2$ and cool the mix to 0° C.
28. Sequentially add 0.13 g of HOBt (0.78 mmol), 0.22 mL DIEA (1.95 mmol) and 0.14 g EDCI (0.91 mmol). Let the reaction warm to room temperature and stir overnight.
29. Add water (20 mL) and then CH$_2$Cl$_2$ (20 mL). Extract organic layer with CH$_2$Cl$_2$ (20 mL×3) and concentrate.
30. Purify the residue via flash chromatography using hexanes: EtOAc (1:2 v/v) as eluent to yield amide 14 as a yellow oil (Rf=0.3 hexanes:EtOAc 1:2). 14 can be stored in a sealed glass vial in a −20° C. freezer for minimally 2 years.

Synthesis of HaloTag-Targetable Precursor to HNE (Alkyne) (Also Known as Ht-PreHNE or HtPHA) (FIG. 29) TIMING: 1 Day.

31. To remove the benzyl protecting group, dissolve 0.16 g 14 (0.277 mmol) in 21 mL EtOAc and add 10%/Pd/C (0.028 g, 0.028 mmol) in a round-bottomed flask
32. Degas the mixture by sequential vacuum exposure, then purging with nitrogen (three times), refill with hydrogen gas (1 atm) at room temperature and let stir for 1 h. Rigorously degassed solvent must be used to expel dissolved oxygen.
33. Filter the reaction mixture through Celite®, and concentrate to yield 15 as yellow solid; (Rf=0.5 hexanes:EtOAc 1:6). Activated Pd/C is pyrophoric, do not let the powder completely dry out when filtering (chase with excess EtOAc) and store waste in a dedicated container that is wetted with water.
34. Dissolve 0.1 g (0.2 mmol) phenol 15 and 0.112 g TBAF (0.4 mmol) in 2 mL THF and 2 mL DMF.
35. Add 0.177 g bromide 8 (0.6 mmol) to the mixture and stir at room temperature overnight.
36. Add 10 mL water, extract organic layer with ethyl acetate (20 mL×3).
37. After concentration in vacuo, purify the residue via flash chromatography using hexanes: EtOAc (1:5 v/v) as eluent to yield HtPHA as yellow solid (Rf=0.6 hexanes:EtOAc 1:6). HtPHA should be stored as one-shot aliquots in DMSO in −80° C. for 6 months protected from light, used immediately once thawed, and handled in dim light.

Box 1: Live Imaging: Assessing Complete HaloTag Conjugation (i.e., Blocking Experiment with Halo-TMR Ligand) TIMING: 2 Days.

Transient transfection using TransIT-2020
(i) Split HEK-293 cells in two 35 mm glass-bottom dishes. For each dish, seeding ~4×10$^5$ cells in 2.0 mL total cell culture medium should result in cells that are ~40-50% confluent after 24 h, which is optimal. Too low and too high cell density may result in excessive cell death or poor transfection efficiency, respectively. Higher cell density is also not optimal for imaging.
(ii) Transfect cells with HaloTag-conjugated POI using TransIT-2020 according to the manufacturer's protocol.
(iii) The subsequent steps are performed 24-36 h post-transfection.

Blocking with Halo-TMR ligand and imaging. The following steps are performed under dim light.
(i) Treat the cells in one dish with HtPHA in 2 mL serum-free media. The protocol for treating with T-REX™ delivery photocaged precursor is identical to that in Step 2A 39A (i-ii) below.
(ii) Treat the second dish with serum-free media containing DMSO instead.
(iii) Rinsing protocol is same as in Step 39A (iii) 2A below.
(iv) After the 3rd rinse cycle, remove the rinse media from both dishes and replace with 1.52 mL serum-free media containing 3 µM Halo-TMR ligand for both dishes. Make sure Halo-TMR ligand is thoroughly mixed by pipetting up and down at least 8-10 times.
(v) Incubate the cells for 1-2 h.
(vi) Rinse 3× with 1.5 mL serum-free media.
(vii) Image cells using a confocal microscope according to the instruments protocol [for example, Zeiss 710 may be used for image acquisition. Images were analyzed using ImageJ software (NIH)].

Box 2: Functional Assay for Halo-Keap1 Binding to Nrf2. TIMING: 2 Days.

Transient transfection using TransIT-2020
(i) Split HEK-293 cells in two 35 mm glass-bottom dishes. For each dish, seeding ~4×10$^5$ cells in 2.0 mL total cell culture medium should result in cells that are ~40-50% confluent after 24 h, which represents optimal cell density. Too low and too high cell density may result in excessive cell death or poor transfection efficiency respectively. Higher cell density is also not optimal for imaging.
(ii) Transfect one plate with 1500 ng of eGFP-Nrf2 plasmids and the second plate with 750 ng of eGFP-Nrf2 and 750 ng of pMIR-DsRed-IRES-Halo-Keap1. Transfect with TransiT-2020 following the manufacturer's protocol.
(iii) Incubate at 37° C. for 24-36 h in a humidified incubator in the presence of 5% CO2 atmosphere, then proceed for imaging and data analysis.

Imaging and data analysis
(i) Image cells using a confocal microscope according to the instruments protocol (for example, Zeiss 710 may be used for image acquisition).
ii) Images were analyzed using ImageJ software (NIH). Briefly, the average green fluorescence intensity in the nucleus ($F_{nucleus}$) was quantitated by tracing a freehand circle around the nucleus. Next, the average green florescence intensity of the cytosol was measured by tracing a freehand circle around the cytosol excluding the nucleus. The ratio of nuclear to cytosolic green fluorescence was subsequently calculated. To get reliable results, it is important to collect images from at least 100 individual cells per condition.

Section 2: T-REX™ Delivery in Live Mammalian Cells or in *E. coli*.

The two steps of this section are transfection (step 38) and the T-REX™ delivery experiment (step 39). For both steps, option A will give instructions for mammalian cells and option B will give instructions for *E. coli*.

Step 38: Express HaloTagged POIs in the cells following the steps in option A for transfecting the mammalian cells and option B for transforming the *E. coli* cells. Halo-Keap1 with TEV cleavage site between Halo and Keap1 is used as an example of Halo fusion protein in this protocol. A hexa-histidine tag is placed before HaloTag (Parvez et al., "Substoichiometric Hydroxynonenylation of a Single Protein Recapitulates Whole-Cell-Stimulated Antioxidant Response," J. Am. Chem. Soc. 137:10-13 (2015), which is hereby incorporated by reference in its entirety). Option A1 is carried out using HEK-293 cells cultured in 8 cm$^2$ adherent culture dish in a humidified atmosphere of 5% $CO_2$ at 37° C. The amounts of reagents used in this procedure can be scaled up or down according to the size of adherent culture dish that is used in experiments.

A) Transient Transfection of Mammalian Cells with Polyethylenimine (PEI). TIMING: 1 Hour.

(i) Allow cells to reach 60-70% confluence at the point of transfection.

(ii) Mix 6 μL of 1 mg/mL PEI stock solution (with 1.5 μg of plasmid DNA (pMIR-CMV-Dsred-IRES-Halo-Keap1) in 150 μL of antibiotic-free, serum-free media in a microcentrifuge tube. Incubate this solution for 15 min at room temperature. This step will need to be modified depending on the requirements of the experiment. For LC-MS/MS analysis experiments (See Section 3, Step X40B), the experiment is done in 4×21 cm$^2$ adherent culture dish. For each 21 cm$^2$ dish, mix 12 μL of 1 mg/mL PEI stock solution with 6.0 μg of plasmid DNA (pMIR-CMV-Dsred-IRES-His6-Halo-Keap1) in 200 μL of antibiotic-free, serum-free media.

(iii) Meanwhile, aspirate the old media from the dishes and replace with fresh 1.5 mL media. If using 21 cm$^2$ dishes, replace the medium with 3 ml fresh medium.

(iv) Subsequent to a 15-min incubation period, add the plasmid DNA solution dropwise on the cells.

(v) Subsequent experiments are performed 24 h post transfection. To do this, proceed to Step 39A.

B) Transformation and Cell Growth of *E. coli* Cells for T-REX™ Delivery. TIMING: 2 Hours.

(i) Transform chemically competent BL21 codon plus (DE3) RIL cells with pet28a-Halo-Keap1, and plate it on LB-kanamycin plate. Incubate the plate overnight at 37° C.

(ii) Pick one colony from the plate and inoculate it into 5 mL of LB-kanamycin-chloramphenicol media (50 μg/mL of Kanamycin, 30 μg/mL chloramphenicol). Shake the flask at 200 rpm at 37° C. overnight.

(iii) Dilute the 5 mL overnight culture into another 5 mL LB-kanamycin media to a final OD of 0.1-0.2. Shake the culture flask at 200 rpm at 37° C. until the OD value reaches 0.6-0.8.

(iv) Induce the culture with IPTG to 0.5 mM final concentration at 19° C. Shake the culture at 19° C. overnight at 200 rpm. It is important to induce expression when the OD is 0.6-0.8

(v) Proceed to step 39B.

Step 39: Perform the T-REX™ delivery experiment by performing the steps in option A for mammalian cells and option B for *E. coli*.

A) Treatment of Mammalian Cells with T-REX™ Delivery Photocaged Precursor, Photo-Uncaging and Harvest of Cells. TIMING: 4 Hours.

The subsequent steps are done under dim light.

(i) Treat the cells with HtPHA at a final concentration of 25 μM for 2.5 h in 1-5 mL serum-free media. Remove the old media. Media that contains serum affects the uptake of T-REX™ delivery photocaged precursors by cells and thus should be avoided. The solubility of T-REX™ delivery photocaged precursor is low therefore vigorous mixing during dilution of the compound from DMSO stock aliquot into 37° C. serum-free media is required to make sure the solution is homogeneous.

(ii) Rinse three times (each time with 1-5 mL of serum-free media) every 30 min over 1.5 h. Media should be added slowly along the sidewall of dish to prevent cells from detaching. Adding and removing media should be as gentle as possible to avoid cells detaching from the culture dish and as efficiently as possible to avoid cells being dried out at the same time. Marking the point of the plate where you will add and aspirate media and performing all operations at that point minimizes loss of cells.

(iii) For the samples designated for light exposure, remove lids from the plates and irradiate mono-layered adherent cultures with 365 nm UV light for 20 min at room temperature (see FIG. 18), and subsequently re-incubate at 37° C. for a further 5 min. Wear UV-protective safety eyeglasses while shining light.

(iv) Trypsinize the cells with 500 μL trypsin, transfer into microcentrifuge tubes, and harvest by centrifugation at 500×g for 8 min at room temperature.

(v) Wash the cell pellets twice with 1×PBS. Flash-freeze the cell pellets in liquid $N_2$. The cell pellets can be stored at −80° C. for up to 3 days.

B) Treatment of Bacterial Cells with T-REX™ Delivery Photocaged Precursor, Photo-Uncaging, and Harvest of Cells. TIMING: 4 Hours.

The subsequent steps are done in dim light.

(i) After overnight growth, dilute the cells to OD of 0.3-0.4 in LB-kanamycin media.

(ii) Treat cells with 25 μM HtPHA for 2 h while shaking at 200 rpm at 19° C.

(iii) Take out 1 mL of cell suspension and transfer into a microcentrifuge tube. Centrifuge at 5,000×g for 5 min. Discard supernatant. Wash the cell pellet by resuspending in 1 mL PBS and centrifuging to collect the pellet.

(iv) Repeat the wash step four additional times.

(v) After the fifth rinse, resuspend the cells in 500 μL PBS and irradiate by placing the samples under 365 nm UV light source for 30 min at room temperature, while constantly shaking the samples at 80-100 rpm. The microcentrifuge tubes must be uncapped during irradiation. Wear UV-protective safety eyeglasses while shining light.

(vi) Incubate for additional 10 min post light shining at room temperature.

(vii) Harvest cells by centrifugation at 5,000×g, for 5 min. Cell pellets can be stored at −80° C. for up to 3 days.

Section 3: Downstream Analyses.

Step 40: The nature of downstream analyses used will depend on the objectives of the experiment. Using Nrf2-AR signaling as a model response pathway, here, six different methods to analyze the effects of protein-specific modification with LDEs are described. Option A describes how to quantify targeting efficiency using Click coupling; the first step in this process is to lyse the cells (mammalian or bacterial) obtained at the end of Step 39.

Option B describes steps for liquid chromatography-coupled tandem mass spectrometry (LC-MS/MS) analysis to determine which residue(s) on the POI are modified by HNE(alkyne). His$_6$-Halo-Keap1 with TEV cleavage site between Halo and Keap1 is used as an example of Halo fusion protein that contains cysteines to be modified in this protocol. The following protocol is carried out with HEK-293 cells in 4×21 cm$^2$ adherent culture dish. The amounts of reagents used in this protocol can be scaled up or down according to the size of adherent culture dish used.

Options C and D describe how to evaluate the extent of downstream transcriptional activation as a consequence of targeted redox modification on a specific sensor POI upstream, either by dual luciferase reporter assays with the use of a plate reader detecting bioluminescence in cell lysates (Option C) or by GFP reporter assays with the use of a flow cytometer detecting GFP fluorescence in live cells (Option D). In both cases, the Nrf2-AR transcriptional activation is used as an example readout as a result of Keap1-targeted HNEylation.

Options E and F describe how to probe the functional downstream impact on endogenous biological entities triggered by targeted redox modification of an upstream sensor POI either by antibody staining of the endogenous species in fixed cells (Option E) or by FRET-based biosensor readout reporting their cellular levels directly in live cells (Option F). The measurement of changes in endogenous PIP3 phosphoinositides is used as an example as a result of targeted HNEylation of PTEN lipid phosphatase that is coupled to accumulation of cellular PIP3 levels.

(A) Quantitating Targeting Efficiency by Click Coupling. TIMING: 6 Hours.

(i) For mammalian cells, add 15 µL freshly prepared lysis buffer (50 mM Hepes pH 7.6, 0.3 mM TCEP and 1% Nonidet p-40) to mammalian cell pellets from Step 2A above and subject to 3 cycles of freeze-thaw. For *E. coli* cells, resuspend cell pellet in 100 µL lysis buffer consisting of 50 mM HEPES pH 7.6, 2 mM TCEP, 1% Nonidet p-40, 150 µg/mL Lysozyme, 5 µg/mL DNAse-I. Incubate for 20 min at room temperature with agitation. For mammalian cells make sure the cells are resuspended well in lysis buffer. For *E. coli* cells, do not vortex after adding lysozyme or DNAse-I.

(ii) Remove debris by centrifugation (18,000×g, 8 min) at 4° C.

(iii) Measure lysate concentration by Bradford assay relative to BSA as standard.

(iv) Dilute a portion of the clarified lysate to 1 mg/mL in a final volume of ~25 µL containing 50 mM Hepes pH 7.6, 0.3 mM TCEP, and 0.2 mg/mL His6-TEV-S219V. Incubate at 37° C. for 45 min. The optimal concentration of lysate protein is ~1.0 mg/mL. High concentration of lysate protein causes failure of Click coupling. Precipitates may appear upon adding His6-TEV-S219V. Gentle resuspension is necessary to ensure the success of Click coupling. For sample without light exposure, His6-TEV-S219V is omitted.

(v) For Click coupling in a final volume of ~30 µL, add the following reagents to a final concentration of 1.7 mM TCEP, 5% v/v t-BuOH, 1% wt/v SDS, 1 mM CuSO$_4$, 0.1 mM TBTA, 10 µM Cy5 azide, and TEV-protease-treated lysate above. Incubate the resulting mixture at 37° C. for 30 min. All the concentrations above are critical to the success of Click coupling. Mix well to make sure that the solution is homogeneous. Generally, SDS is needed to obtain good results.

(vi) Quench with 5 µL of 4× Laemmli buffer that contains 6% (vol/vol) BME and further incubate for 5 min at 37° C. Load 20 µL into each well of 10% (wt/vol) polyacrylamide gel, and resolve by electrophoresis. 4× Laemmli buffer should be warmed in advance to ensure homogeneity. Fresh SDS-PAGE buffer should be used to reduce background signal. It is recommended to rinse the wells of polyacrylamide gel (remove buffer in the wells using a P-200 pipettman with a loading tip, repeat for 4-5 times) before loading the samples with fresh SDS-PAGE buffer to enhance signal/noise ratio.

(vii) Upon completion of the gel-electrophoresis, rinse the gel with ddH$_2$O 20 mL (×2, 5 min) and analyze for Cy5 signal using a ChemiDoc-MP imaging system (Bio-Rad) (see Equipment Setup). Any alternative fluorescence gel imager platforms can be used in this step. Rinsing reduces the background signal. It is recommended to rinse the gel several times and analyze the gel between each rinse to obtain the optimal result with highest signal/noise ratio.

(viii) Transfer the gel to a PVDF membrane for western blot analysis. After transfer is complete, block membrane with 10% (vol/vol) milk, then probe with anti-Keap1 and anti-actin antibodies (see materials list for dilutions).

(ix) Use the following equation to calculate targeting efficiency:

$$[(Cy5_x/WB_x)/((Cy5_y)-(Cy5_{Halo}))/(WB_y))] \times 100\%$$

Cy5$_x$: Amount of Cy5 signal on target protein in the sample exposed to light

WB$_x$: Amount of western blot signal on target protein in the sample exposed to light Cy5$_y$: Amount of Cy5 signal on Halo-fusion protein in the sample not exposed to light Cy5$_{Halo}$: Amount of Cy5 signal on Halo protein in the sample exposed to light WB$_y$: Amount of western blot signal on Halo-fusion protein in the sample not exposed to light (x) Bio-Rad Image Lab™ software is used to quantitate the intensities of Cy5 signal and western blot signal. If using this software: Open the Cy5 image or western blot using the software. From the "Analysis Tool Box", pick "Volume Tools" followed by "Rectangle". Draw rectangles of the same sizes around each of the desired bands. Draw another rectangle of the same size in an area without any bands and use this for background subtraction. (Designate this rectangle as the background by double clicking and choosing "background"). Under "Subtraction Method" menu chose "Global". Click on "Analysis table" to generate the quantitated signal intensities corresponding to selected bands. Export the analysis table to Excel. Use the "Adjusted volume" values as the signal intensities of the desired bands.

B) LC-MS/MS Analysis of Modified Cysteines. TIMING: 2-3 Days.

The starting material for Option B is prepared as described in Steps 38A and 39A.

(i) Enrichment of (His-tagged) protein from mammalian cells. Harvest confluent monolayer cultures of cells from 4×21 cm$^2$ cultured plates. While immediate lysing is recommended since HNE modifications are unstable, if pausing is needed, the cell pellets can be flash frozen in liquid N$_2$ and stored at −80° C. for up to 3 days. The pellets were pooled and lysed in 100 µL lysis buffer A (50 mM Hepes pH 7.6, 5 mM Imidazole, 5 mM BME) by 3 cycles of rapid freeze-thaw. Make sure the cells are resuspended well in lysis buffer A.

(ii) Remove debris by centrifugation at 18,000×g for 8 min at 4° C.

(iii) Equilibrate 20 µL bed volume of TALON resin by washing 3× with 500 µL buffer A.

(iv) Determine lysate concentration using Bradford assay with BSA as standard.

(v) Dilute lysate to 1.0 mg/mL with lysis buffer A, and add to the TALON resin in a 1.7 mL centrifuge tube. Incubate the suspension in dark at 4° C. for 1.5 h with end-over-end rotation. High concentration of lysate protein enhances non-specific binding therefore brings in impurities in the final pulled down Keap1. A portion of clarified lysate prior to treatment with TALON resin (typically 5-10 µL) should be saved to confirm the modification of cysteines by electrophiles using Click coupling. See Step 3, Step 40A above.

(vi) Centrifuge the sample at 500×g for 3 min at 4° C. Remove the supernatant and add 360 µL wash buffer B (50 mM Hepes pH 7.6, 100 mM NaCl, 10 mM Imidazole, 5 mM BME) to the resin. Incubate the suspension in dark at 4° C. for 3 min with end-over-end rotation. Do not remove any resin in this step and subsequent steps.

(vii) Remove the supernatant after centrifugation at 500×g for 3 min at 4° C. Add 240 µL wash buffer C (50 mM Hepes, 100 mM NaCl, 20 mM Imidazole, 5 mM BME, pH 7.6) followed by incubation in the dark at 4° C. for 3 min with end-over-end rotation.

(viii) Repeat step vii above.

(ix) Remove wash buffer after centrifugation at 500×g for 3 min at 4° C. Add 25 µL elution buffer (50 mM Hepes pH 7.6, 100 mM NaCl, 200 mM Imidazole, 5 mM BME) and incubate resin in the dark at 4° C. for 5 min with end-over-end rotation. CRITICAL STEP: The supernatant from the wash step should be removed thoroughly to maximize the yield of His6-Halo-Keap1 in the elution.

(x) Collect the eluent after centrifugation at 18000×g for 3 min at 4° C. Mix eluent with 4× Laemmli buffer with 6% (v/v) BME, incubate for 5 min at 37° C., and resolve on a 10% SDS-PAGE gel. Stain the gel with Coomassie R-250 stain (or freshly prepared Colloidal Coomassie G-250 stain for enhanced sensitivity) for 24-48 h until desired sensitivity is achieved.

(xi) Rinse the gel with ddH$_2$O for 30 min and excise the band corresponding to His6-Halo-Keap1. The gel slices can be stored at −80° C. with 50 µL of ddH$_2$O for up to 2 weeks.

LC-MS/MS Analysis.

(i) Wash the gel pieces with 100 µL ddH$_2$O. Remove and discard water.

(ii) Add 100 µL (50:50) 100 mM NH$_4$HCO$_3$ pH 7.8: acetonitrile and let sit for 10 min. Remove and discard the liquid.

(iii) Add 50 µL acetonitrile and let the sample sit for 5 min. Remove and discard acetonitrile. Dry the gel pieces in a fume hood for 10 min.

(iv) Reduce the proteins with 5 mM TCEP in 50 mM NH$_4$HCO$_3$ solution pH 7.8 for 45 min at 37° C. and alkylate with 20 mM iodoacetamide in 50 mM NH$_4$HCO$_3$ in dark for 45 min. Use of TCEP instead of DTT is very important as DTT can reduce labeling of proteins by LDEs.

(v) Repeat steps i, ii, and iii.

(vi) Rehydrate the gel pieces by adding 60 µL (10 µg/mL solution) of trypsin in 50 mM NH$_4$HCO$_3$ pH 7.8 on ice for 30 min and then at 37° C. overnight.

(vii) To stop the enzymatic reaction, add formic acid to a final concentration of 1%. Remove and save supernatant.

(viii) Add 120 µL 50% acetonitrile containing 5% formic acid to the trypsinized gel pieces. Let the sample sit for 45 min. Sonicate for 5 min. Remove supernatant and combine with supernatant from step vii.

(ix) Repeat step viii.

(x) Add 90% acetonitrile containing 5% formic acid. Let the sample sit for 5 min. Remove and combine supernatants. Dry the supernatant under vacuum.

(xi) Re-suspend peptides in 60 µL of 0.1% vol/vol formic acid and inject into LC system described in the Equipment Setup section of the Protocol. To prevent loss of modification, ionization temperature should not be too high (in this case it is 130° C.).

(xii) After data acquisition, combine the individual MS/MS spectra acquired for each of the precursor within a single LC run, smoothen, de-isotope using an Analyst "script" mascot.dll to create a peak list, and save the peak list to a file.

(xiii) Subsequently, use the peak list file to query NCBI human sub-database and contaminations using the MASCOT 2.4 from Matrix Science (London, UK) with the following parameters: peptide mass tolerance, 0.3 Da; MS/MS ion mass tolerance, 0.3 Da; allow up to two missed cleavage; several variable modifications were applied including methionine oxidation, cysteine carbamidomethylation along with electrophile Michael adduct, reduced electrophile Michael adduct, dehydrated electrophile Michael adduct, or dehydrated electrophile (1,2)-addition adduct or electrophile Michael adduct in Schiff-based form on cysteine residues (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). Only significant scores for the peptides defined by Mascot probability analysis greater than "identity" with 95% confidence should be considered for the peptide identification and modification site determinations.

(xiv) Manually inspect and validate all MS/MS spectra for the identified peptides with HNE-type modifications.

(xiv) To approximate the extent of modifications on a given site, extract the modified peptide signal (XIC) from the chromatogram and compare with XIC of the unmodified peptide.

Box 3: Blockage of Pathway Activation by HaloTag Non-Fused Control: Analysis Using Western Blot. TIMING: 4 Days.

Transient transfection using polyethylenimine (PEI; PolyScience Inc.) TIMING: 1 day.

(i) Plate HEK-293 cells in a 35 mm (8 cm$^2$ surface area) dish. For a 35 mm dish, seeding ~7×10$^5$ cells in 1.5 mL total cell culture medium should result in cells that are ~70% confluent after 24 h, which is optimal for transfection with PEI. Too low and too high cell density may result in excessive cell death or poor transfection efficiency respectively.

(ii) Transfect the cells with 500 ng of each of the following plasmids: pMIR-Dsred-IRES-Halo-HA, pMIR-DsRed-IRES-His-Keap1 and pcDNA3.1 myc-Nrf2. For transient transfection using PEI, see Step 2A 2, Step 38A above.

Treatment of cells with T-RE delivery photocaged precursor, photo-uncaging and harvest of cells (i) Perform Section 2, Step 39A except harvest the cells 4 h post illumination.

SDS-PAGE and western blot (i) Lyse cells by adding 30 µL freshly prepared and pre-chilled lysis buffer (50 mM Hepes pH 7.6, 0.3 mM TCEP, 1% Nonidet p-40) and subjecting to 3 flash freeze-thaw cycles. Make sure the cells are resuspended well in lysis buffer.

(ii) Remove debris by centrifugation (18,000×g, 8 min) at 4° C. Determine protein concentration using Bradford Assay using BSA as standard. Analyze ~30 µg of lysate protein by SDS-PAGE and western blotting using standard protocol.

(C) Analysis Using Luciferase Reporter Assay for Evaluating AR Activation. TIMING: 3 Days.

Option C starts with a new transfection.

(i) Transient transfection using TransIT-2020. Plate HEK-293 cells in a 48-well plate (0.9 cm$^2$ surface area). For a single well, seeding ~5×10$^4$ cells in 300 µL total cell culture medium should result in cells that are 50-60% confluent after 24 h, which is optimal for transfection with TransIT-2020. It is important to have at least triplicate samples for each condition. If seeding in multiple wells, make a stock of 1.5×10$^5$ cells/mL and add 300 µL of the stock in each well after careful suspension. Too low and too high cell density may result in excessive cell death or poor transfection efficiency respectively.

(ii) Premix ARE-Firefly Luciferase plasmid and pCMV-Renilla luciferase plasmid in a 40:1 ratio by mass. Transfect the cells with the following plasmids: premixed 40:1 ARE-Firefly:pCMV Renilla luciferase plasmids, pCMV Halo-Keap1 and pcDNA3.1 myc-Nrf2.

(iii) For transient transfection of cells in a single well of a 48-well plate, in 26 µL of antibiotic-free, serum-free media add 120 ng of each plasmid (Halo-Keap1 and myc-Nrf2) and 120 ng of the ARE-Firefly:pCMV Renilla luciferase plasmid mix (360 ng total) followed by the addition of 0.78 µL of TransIT-2020. The solution is mixed gently and incubated at room temperature for 20 min. The amount of DNA and TransIT-2020 reagent may need to be optimized for different cell lines.

(iv) Subsequent to 20-min incubation, the lipoplex is added dropwise to the cells in complete media.

(v) Subsequent steps are performed 24 h post transfection.

(vi) Treatment of cells with T-REX™ delivery photocaged precursor and photo-uncaging. Treat the cells as described in Section 2, Step 39A except: Cells are treated with the T-REX™ delivery photocaged precursor at a concentration of 25 µM in 300 µL serum-free media; Rinsing is performed with 300 µL serum-free media; and Post light shining, the cells are incubated for 18 h before measuring luciferase activity.

(vii) Measuring luciferase activity (TIMING: 3 hours). To analyze the level of AR activation using Luciferase reporter assay, wash the cells with 150 µL of 1×PBS. PBS should be added dropwise along the sidewalls of the wells to prevent cells from detaching.

(viii) Lyse cells by adding 65 µL of 1×PLB and incubating at room temperature on a shaker for 15-20 min. Lysate should not be left at room temperature for longer than 1 h.

(ix) Meanwhile, thaw out the Firefly substrate and prepare 1× Renilla luciferase substrate by adding the 100× Coelenterazine stock in methanol into in 1× Renilla luciferase buffer.

(x) Pipette out 20 µL of the well-mixed lysate in a 96-well white opaque plate (Corning) for measuring chemi-luminescence. Read the Firefly Luciferase signal after adding 50 µL of Firefly Luciferase substrate on a plate-reader (for example, a BioTek Cytation 3 cell imaging multi-mode microplate reader may be used). Subsequently, read the Renilla luciferase signal after adding 50 µL of the 1× Renilla substrate. If handling multiple wells simultaneously, automated dispenser can be used to add Firefly and Renilla luciferase substrates to minimize decay of signal intensity.

(xi) Analyze data by calculating the ratio of Firefly luciferase signal intensity to Renilla luciferase signal.

(D) Analysis Using GFP Reporter Assay for Evaluating AR Activation. TIMING: 3 Days.

Option D starts with a new transfection.

(i) Transient transfection using TransIT-2020. Perform the transfection as described in Step 40 Option (C) (i). Briefly: Transfect the cells with ARE:GFP, pFN21a-Halo-Keap1, and pcDNA3.1 myc-Nrf2 in a 3:1:1 ratio by mass. For transient transfection of cells in a single well of a 48-well plate, in 26 µL of antibiotic-free, serum-free media add 156 ng of ARE:GFP, 52 ng of pFN21a-Halo-TEV-Keap1, and 52 ng of pcDNA3.1 myc-Nrf2 (260 ng total) followed by the addition of 0.78 µL of TransIT-2020. The lipoplex is mixed gently and incubated at room temperature for 20 min. It is important to use plasmids that do not express another fluorescent protein.

(ii) Subsequent to 20 min of incubation, the lipoplex is added dropwise onto the cells.

(iii) The following steps are performed 24 h post-transfection.

(iv) Treatment of cells with T-REX™ delivery photocaged precursor and photo-uncaging (TIMING: 7 hours). Treat the cells with photocaged precursor as described in Step 40C (vi).

(v) Measuring GFP fluorescence using flow cytometry. Set up the flow cytometer equipment.

(vi) Harvest the cells by adding 100 µL of trypsin TrypLE and incubating at room temperature for 1 minute. Transfer the cell solution into a FACS tube and rinse the well with another 900 µL of FACS buffer. Resuspend the culture several times to ensure a single-cell suspension before loading onto the flow cytometer.

(vii) Perform flow cytometry experiment to determine GFP signal. Measure at least 10,000 events per well.

(viii) Data Analysis. Any cytometry software could be used to process the data. Here, FlowJo (v 10) was used.

(E) Immunofluorescence Analysis. TIMING: 4 Days.

(i) Transient transfection using TransIT-2020. Split HEK-293 cells in four 35 mm glass-bottom dishes. For each dish, seeding ~4×$10^5$ cells in 2.0 mL total cell culture medium should result in cells that are ~40-50% confluent after 24 h, which represents optimal cell density. Too low and too high cell density may result in excessive cell death or poor transfection efficiency respectively. Higher cell density is also not optimal for imaging.

(ii) Transfect each plate with 2000 ng of Halo-PTEN plasmid. Transfect with TransIT-2020 following the manufacturer's protocol.

(iii) The subsequent steps are performed 24-36 h post transfection.

(iv) Treatment of cells with T-REX™ delivery photocaged precursor, photo-uncaging and cell fixing (TIMING: 8 hours). Treat the cells with photocaged precursor as described in Section 2, Step 39A.

(v) After shining light on the sample, incubate the plates at 37° C. for 10 hours.

(vi) Aspirate old media, wash once gently with 1.5 mL 1×PBS. Fix cells by adding 1.5 mL 2% formaldehyde (pre-chilled at 4° C.). Incubate the plates for 20 min at 4° C.

(vii) Aspirate formaldehyde. Add 1.5 mL 1×PBS to the plates. Fixed cells can be stored at 4° C. for up to 2 weeks.

(viii) Permeabilization of cell membrane and antibody binding. Aspirate PBS from the plates. Add 1.5 mL of blocking-permeabilization buffer to each plate. Incubate plates at 37° C. for 1 hour.

(ix) Meanwhile, prepare of antibodies to Halo (1:1000) and PIP3 (1:500) in 600 µL of incubation buffer.

(x) Remove blocking-permeabilization buffer, wash once with 50 mM HEPES pH 7.6 and add 150 µL of primary antibody solution. Add primary antibody solution only in the recessed region to minimize amount of antibody usage. Incubate for 2 hours at room temperature.

(xi) Gently remove primary antibody solution using a pipette. The solution can be stored at 4° C. and reused.

(xii) Wash with 1.5 mL 1×PBS to the plates. Incubate at 37° C. for 5 min. Aspirate the PBS and repeat the rinse step two additional times.

(xiii) Prepare 1:1000 dilutions of fluorophore conjugated secondary antibodies in 600 µL PBS with 0.02% Triton X-100. Avoid exposure of fluorophore conjugated antibodies to stray light.

(xiv) Add 150 µL of secondary antibody solution to each plate. Incubate for 1 hour at room temperature protected from light.

(xv) Remove secondary antibody solution and add 1.5 mL 1×PBS to the plates. Incubate at 37° C. for 5 min. Aspirate the PBS and repeat the rinse step two additional times.

(xvi) Prepare a 1 µg/mL dilution of DAPI in 1×PBS. Add 1.5 mL DAPI solution to the plates. Incubate for 1 min at room temperature. Aspirate and rinse plates once with 1×PBS. Cells can be imaged immediately or stored protected from light at 4° C. in 1×PBS for 1-2 days.

(xvii) Imaging and data analysis. Image cells using a confocal microscope according to the instruments protocol (for example, Zeiss 710 may be used for image acquisition).

(xviii) Images were analyzed using ImageJ software (NIH). Briefly, the average green fluorescence intensity (intensity of signal due to PIP3) for each cell was determined by drawing a free hand circle around the image. This was repeated for each condition such that 50-100 cells were analyzed each time from multiple different frames. A global average of the green fluorescence intensity was calculated for each condition, then these values were plotted and analyzed using prism. To get reliable results, it is important to collect images from at least 50 individual cells per condition.

(F) Fret Analysis. Timing: 4 Days.

Option F starts with a new transfection.

(i) Transient transfection using TransiT-2020. See Section 3, Step 40E.

(ii) Transfect each plate with 1000 ng of Halo-PTEN and 1000 ng of InPAkt reporter plasmid. Transfect with TransIT-2020 following the manufacturer's protocol.

(iii) The subsequent steps are performed 24-36 h post transfection.

(iv) Treatment of cells with T-REX™ delivery photocaged precursor, photo-uncaging and cell fixing. Treat the cells with photocaged precursor as described in Section 2, Step 39A. The amounts of reagents used should be scaled up for 4×35 mm adherent culture dish.

(v) Irradiate the cells with UV light only for 3 min. After shining light on the sample. Incubate the plates at 37° C. for 10 hours. Longer irradiation time will result in photobleaching of the FRET reporter proteins.

(vi) Imaging and data analysis. Image cells using a confocal microscope according to the previously described protocol (Ananthanarayanan et al., "Signal Propagation From Membrane Messengers to Nuclear Effectors Revealed by Reporters of Phosphoinositide Dynamics and Akt Activity," *Proc. Nat'l. Acad. Sci. U.S.A.* 102:15081-6 (2005), which is hereby incorporated by reference in its entirety). Blue laser (408 nm) is used for excitation. Record the signals in cyan channel (463-498 nm) and yellow channel (525-620 nm).

(vii) Analyse the images using ImageJ software (NIH). To do this, determine the average cyan and yellow fluorescence intensity for each cell by drawing a free hand circle around the image. Repeat this for each condition such that 150-200 cells were analyzed each time from multiple different frames. Calculate the ratio of mean yellow to mean cyan fluorescence intensity for each condition, then plot these values and analyse the results using prism. To get reliable results, it is important to collect images from at least 150 individual cells per condition.

Box 4: His6-TEV-S219V Expression and Purification.
TIMING: 4-5 Days.

Expression of His6-TEV-S219Vin *E. coli*

(i) Transform chemically competent BL21 (DE3) RIL cells with His6-TEV-S219V (Addgene, Plasmid #8827), and plate it on LB-Ampicillin (100 µg/mL) plate. Incubate the plate overnight at 37° C.

(ii) Pick a single colony from the plate and inoculate it into 5 mL of LB-ampicillin-Chloramphenicol media (100 µg/mL of Kanamycin, 30 µg/mL Chloramphenicol). Shake the flask at 200 rpm at 37° C. overnight.

(iii) Dilute the 5 mL overnight culture into 1 liter LB-kanamycin in a 2 L flask. Shake the culture flask at 200 rpm at 37° C. until the OD value reaches 0.6-0.8.

(iv) Induce the culture with IPTG to 1 mM final concentration. Shake the culture at 37° C. for 6 h at 200 rpm. CRITICAL STEP: For maximal protein yield, it is important to induce expression when the OD is 0.6-0.8

(v) Harvest the cells by centrifugation at 7,000 g for 10 min at 4° C. Discard the supernatant by decanting. Keep the cell pellet on ice. The cell pellets can be flash frozen and stored in −80° C. for at least 1 month.

Preparation of Buffers. All buffers can be prepared beforehand, filtered using a 0.22 µm filter and stored without the addition of reducing agents at 4° C. for up to 2 weeks.

(i) Preparation of Lysis buffer: Prepare His6-TEV-S219V lysis buffer by mixing 50 mM Na2HPO4 pH 8.0, 100 mM NaCl, 10 mM Imidazole, 5% glycerol, 5 mM BME. Freshly add BME just before use.

(ii) Preparation of Wash Buffer: Prepare His6-TEV-S219V wash buffer by mixing 50 mM $Na_2HPO_4$ pH 8.0, 200 mM NaCl, 25 mM Imidazole, 5% glycerol, 5 mM BME. Freshly add BME right before use.

(iii) Preparation of Elution Buffer: Prepare His6-TEV-S219V elution buffer by mixing 50 mM $Na_2HPO_4$ pH 8.0, 200 mM NaCl, 125 mM Imidazole, 5% glycerol, 5 mM BME. Freshly add BME right before use.

(iv) Preparation of Storage Buffer: Prepare His6-TEV-S219V storage buffer by mixing 50 mM Tris pH 7.5, 150 mM NaCl, 0.5 mM EDTA, 10% glycerol, 3 mM TCEP. Freshly add TCEP before use. Readjust the pH to 7.5 after adding TCEP.

Purification of His6-TEV-S219 V using a TALON cobalt-affinity column. Maintain cell pellet, cell lysate and all buffers on ice at all times to minimize loss of protein activity.

(i) Pipette out 14 mL of TALON resin [7 mL bed volume (BV)] in an Econo-column. Let the buffer flowthrough. Wash the resin with 10 BV of water followed by 5 BV of lysis buffer. Do not allow resin to dry.

(ii) Pre-equilibrate a GE Healthcare Hiload™ 26/60 Superdex™ 200 prep grade column (ID No. 0823027) with 320 mL storage buffer.

(iii) If frozen, thaw cell pellet on ice. Resuspend the cells in 5 mL of lysis buffer per gram of cell pellet. Cell pellets need to be resuspended vigorously. Pipette up and down till no clumps are visible. Clumps of cells can clog the cell disrupter.

(iv) Lyse cells by passing the cell suspension twice through the cell disrupter at 13,000 psi. Maintain the lysate on ice at all times.

(v) Centrifuge the lysate at 30,000 g for 30 min at 4° C. Collect the supernatant in a clean glassware.

(vi) To remove DNA, add streptomycin sulfate solution to a final concentration of 2%. Prepare streptomycin sulfate solution by dissolving the solid in 8-10 mL of chilled ddH$_2$O. Add streptomycin sulfate solution drop by drop while stirring the supernatant gently at 4° C. Vigorous stirring can lead to loss of protein activity. A viscous yellow DNA precipitate should be observed on adding streptomycin sulfate. Discontinue adding streptomycin sulfate if white protein precipitate is observed.
(vii) Centrifuge the supernatant at 30,000 g for 30 min at 4° C. Collect the supernatant in a clean glassware.
(viii) Resuspend the pre-equilibrated TALON resin with the supernatant and transfer to the clean glassware. Incubate the supernatant with the resin for 50 min-1 h at 4° C. while gently stirring. Long incubation time can lead to decay of protein activity. Very short incubation can result in inefficient binding and therefore reduced protein yield.
(ix) Add the cell lysate-resin mixture back to the Econo-column and let the lysate flow through. Avoid letting the column run dry.
(x) Wash the resin 3 times, each with 2 bed volumes of wash buffer.
(xi) Elute His6-TEV-S219V from the column using elution buffer. Collect 1 mL fractions and check for presence of protein by measuring A280 values. Pool the protein containing fractions. Concentrate the protein in a 10 kDa cut-off concentrator to bring the total volume to 10-12 mL. Too high a concentration can result in protein precipitation. If the starting volume is too large, protein can be loaded in two batches on the Superdex 200 column.
(xii) Load the protein on a pre-equilibrated column for buffer exchange at a flow rate of 1 mL/min.
(xiii) Collect fractions corresponding to the protein peaks. Pool the fractions. Concentrate to a final concentration of 4-5 mg/mL. Measure protein concentration using standard protein concentration measurement assays.
(xiv) Confirm the purity of His6-TEV-S219V using protein gel electrophoretic analysis. The molecular weight of His-TEV is 26 kDa.
(xv) Aliquot His6-TEV-S219V, flash freeze and store at −80° C. His6-TEV-S219V aliquots are stable at −80° C. for at least a year.

Troubleshooting.

See Table 5, below, for troubleshooting guidelines.

TABLE 5

Troubleshooting Guidelines

| Step | Problem | Possible Reason | Troubleshooting |
|---|---|---|---|
| Step 4 | Low yield of alcohol 2 | Ethylenediamine is old. Reaction interfered with O$_2$ and moisture. Product destroyed during reaction quenching | Use either redistilled or fresh out of the bottle. Make sure the reaction is protected under dry N$_2$ or Ar. The reaction quenching is exothermic, add the quencher (1N HCl) slowly and make sure the flask is well cooled. |
| Step 7 | Low yield of aldehyde 3 | Aldehyde 3 is volatile. | Volatile compound. Avoid excess heating of the rotavap water bath above 35° C. |
| Step 11A | Low yield of HNE(alkyne) | HNE(alkyne) is not stable. | Prone to air oxidation and polymerization. Carry on non-stop through steps involving reaction workup, rotavap, chromatography, to final storage. |
| Step 11B(viii) | Product 7 partially deprotected | One of the isomers of product 7 is not stable. | Product 8 (deprotected 7) can be separated from 7 by chromatography on silica gel, or can be carried through to the next step. |
| Step 30 | Low yield of 14 | Reaction yield can be reduced by adventitious O$_2$ and/or moisture. | Make sure all the solvents are dry and the reaction is protected under dry N$_2$ or Ar. Thoroughly degas solvents used. |
| Step 31 | Incomplete deprotection of 14 | Some of the catalyst (10% Pd/C) may be deactivated | Add more catalyst (10% Pd/C) and extend the reaction time. Typically, high catalyst loading can be tolerated. Ensure that the reaction is tightly sealed and that an atmosphere of hydrogen is maintained throughout. |
| Step 36 | Difficult to remove impurities from HtPHA | Polarity of impurities is close to that of HtPHA. | Run flash chromatography with gradient eluent, from 1:3 to 1:5 (v/v, hexanes: EtOAc) |
| Step 36 | Final product decomposition | Light induced photo-uncaging of the final product | During the synthesis (especially from 14 to 15, and 15 to HtPHA), protect the reaction flask from stray light. |
| Step 40A | No Cy5 signal on gel | Failure of Click coupling | Check lysate protein concentration. The concentration should be around 1.0 mg/mL. Check every reagent in Click coupling step. Make sure all of them are freshly prepared and the concentrations are correct. Mix the reaction well. Use cells treated globally with HNE(alkyne) as a positive control. |
| Step 40A | High Cy5 background | Old SDS-PAGE running buffer | Use fresh SDS-PAGE running buffer. Rinse the gel several times and analyze the gel between each rinse to obtain the optimal result with highest signal to noise ratio. Let the dye font run out completely before imaging the gel. |

TABLE 5-continued

Troubleshooting Guidelines

| Step | Problem | Possible Reason | Troubleshooting |
|---|---|---|---|
| Step 40A | Incomplete TEV cleavage | Loss of TEV activity | Use fresh aliquot. Avoid freeze thaw. Mix well after adding $His_6$-TEV-S219V. Increase TEV amount and incubation time of TEV cleavage. |
| Step 40B | Low yield of pull down protein | Affinity protein purification condition is not optimal | This protocol is optimized for $His_6$-Halo-TEV-Keap 1. Further optimization may be required for other proteins. |
| | | Protein not eluting or eluting prematurely | Monitor protein in washes through SDS-PAGE. If premature elution is observed, decrease the concentration of Imidazole in the wash buffers. Conversely, if no elution is observed, increase Imidazole concentration to 200-400 mM or elute with Laemelli buffer to validate binding. |
| | | Protein unstable after modification[103] | Add a proteasome inhibitor (bortezomib) in lysis buffer and/or to cells. |
| Step 40B | Modification not found | Targeting is not efficient. | Check modification of protein by Cy5 labeling as described in Step 3A. |
| | | Modification is reduced | Make sure TCEP is used instead of DTT in the sample preparation. |
| | | Inefficient MS conditions | Adjust ionization temperature to obtain optimal results. Low ionization temperature may lead to poor ionization and decrease sensitivity. High ionization temperature may cause loss of modification. |
| Step 40C; 40D | Low Firefly/Renilla/GFP signal intensity | Significant loss of cells during rinsing | Perform the rinsing with care. Add the media slowly along the sidewall of culture dish. Adding and removing media should be as gentle as possible but also as efficiently as possible: wash plates sequentially (2 or 3 plates at a time) to avoid drying out. Mark position on plate where cells are washed. |
| | | Excessive cell death | Use the suggested cell density for transfection. If using different transfection reagent or different cells, optimize transfection condition. |
| | | Low transfection efficiency | Optimize transfection conditions for the cell type and the reagent used. |
| | | Instrument setting is not optimal | Run a positive control. For flow cytometry, cells transfected with GFP can be used. Adjust gain (i.e. laser power) if necessary. |
| | | Response timing is not optimal | Set up a time-course for measurements (recommended time points for pilot trials: 4 h, 12 h, 18 h post T-REX ™ delivery light exposure). |
| Step 40C, 40D | Batch to batch variability in targeting/ARE results | Difference in experimental setup and execution | Count cells and seed the numbers as specified in the protocol. Transfect and perform experiments at similar confluence. Use cells at lower passage number (lower than 6-7 continuous passages). |
| Step 40C, 40D | Activation of ARE-Luciferase with light alone or with pre-HNE alone | Release of pre-HNE due to stray light | Protect photocaged-precursor-treated samples from stray light. |
| | | Stressed cells | Count cells before seeding. Too low and too high cell density can stress the cells leading to higher background. |

Timing.

Steps 1-11A, chemical synthesis of HNE(alkyne): 4 d

Steps 1-37, Chemical synthesis of HtPHA: 8-10 d

Step 38, Transfection in mammalian cells (option A) or transformation in E. coli (Option B): 1-2 h Step 39, T-REX™ delivery experiment in mammalian cells (Option A) or E. coli (Option B): 4 h Step 40, Downstream analyses—Options:
   (A) Targeting efficiency quantitation: 6 h
   (B) LC-MS/MS analysis of residue modified: 2-3 d h
      Enrichment of (his-tagged) protein from mammalian cells: 4 h
      LC-MS/MS analysis: 2-3 d
   (C) Dual luciferase reporter assays evaluating AR pathway activation: 3 d
      Transient transfection using TransIT-2020: 1 h
      Treatment of cells with T-REX™ delivery photocaged precursor and photo-uncaging: 4 h
      Measuring Luciferase activity: 2 h
   (D) Flow cytometry analysis of GFP reporter evaluating AR pathway activation: 3 d
      Transient transfection using TransIT-2020: 1 h
      Treatment of cells with T-REX™ delivery photocaged precursor and photo-uncaging: 4 h
      Measuring GFP fluorescence using flow cytometry: 2 h (E) Immunofluorescence analysis of downstream perturbation on cellular entities: 4d
Transient transfection using TransIT-2020:1 h
Treatment of cells with T-REX™ delivery photocaged precursor, photo-uncaging and cell-fixing: 4 h
Permeabilization of cell membrane and antibody binding: 6 h
Imaging and data analysis: 6 h
(F) FRET-biosensor reporting downstream perturbation on cellular entities: 4 d
Transient transfection using TransIT-2020:1 h
Treatment of cells with T-REX™ delivery photocaged precursor, photo-uncaging and cell-fixing: 4 h
Imaging and data analysis: 6 h
Anticipated Results.
Analytical Data
HNE(alkyne) (see FIG. 17 inset and FIG. 29 for chemical structure)
$^1$H-NMR (300 MHz) δ 1.50-1.76 (4H, m), 1.92 (1H, t, J=2.7 Hz), 2.19 (2H, dt, J=2.7, 6.3 Hz), 2.61 (1H, br), 4.39-4.44 (1H, m), 6.25 (H, ddd, J=1.2, 7.8, 15.9 Hz), 6.79 (1H, dd, J=4.5, 15.6 Hz), 9.50 (1H, d, J=7.5 Hz). $^{13}$C-NMR (75 MHz) δ 18.1, 24.0, 35.1, 69.1, 70.4, 83.8, 130.7, 159.2, 193.9.

HtPHA also known as Ht-PreHNE (see FIG. 29 for chemical structure)
$^1$H-NMR spectroscopy (0.02 g, 24% yield): $^1$H-NMR (300 MHz) δ 1.59-1.69 (4H, m), 1.96 (1H, t, J=2.1 Hz), 2.23-2.26 (2H, m), 3.57 (2H, d, J=6.6 Hz), 4.23-4.29 (1H, m), 4.55 (2H, d, J=5.7 Hz), 5.10-5.18 (2H, m), 5.91-6.16 (3H, m), 7.64 (1H, d, J=7.8 Hz), 7.75-7.79 (2H, m), 8.10-8.12 (1H, d, J=8.1 Hz), 8.24-8.29 (2H, m). $^{13}$C-NMR (75 MHz) δ 18.3, 24.3, 34.4, 35.9, 68.6, 71.7, 74.3, 84.2, 117.2, 123.6, 124.7, 126.2, 126.7, 127.2, 131.2, 131.4, 133.5, 134.2, 134.8, 135.6, 135.8, 137.1, 142.7, 157.2, 182.7, 183.1. LRMS (LDI) calc'd for $C_{26}H_{24}O_4$ 400.2 ($M^+$), found 400.1.

TEV Purification
The typical yield of TEV protease is 0.5 mg pure protein per gram of cell pellet.

In-Gel Fluorescence to Determine Labeling
Typical labeling results with HNE are shown in FIG. 22A, FIG. 24B and FIG. 25A and FIG. 23A. Targeting efficiency [calculated using the equation shown in Step 40A (ix)] ranges from 10-40%.

Results

Temporal Control and Target Specificity.
T-REX™ delivery (targetable reactive glectrophiles and oxidants) technology (Fang et al., "Temporally Controlled Targeting of 4-hydroxynonenal to Specific Proteins in Living Cells," J. Am. Chem. Soc. 135:14496-99 (2013); Lin et al., "A Generalizable Platform for Interrogating Target- and Signal-Specific Consequences of Electrophilic Modifications in Redox-Dependent Cell Signaling," J. Am. Chem. Soc. 137:6232-44 (2015); Parvez et al., "Substoichiometric Hydroxynonenylation of a Single Protein Recapitulates Whole-Cell-Stimulated Antioxidant Response," J. Am. Chem. Soc. 137:10-13 (2015), which are hereby incorporated by reference in their entirety) selectively modifies a specific redox-sensor protein of interest (POI), enabling the decoding of the functional consequences of specific redox events, against the backdrop of an otherwise unperturbed proteome (FIG. 17). A potential redox sensor protein is chosen based on previous lists of postulated LDE-modified proteins from global proteomics experiments, or putative redox-sensor POIs. The POI is genetically fused to a HaloTag domain. The T-REX™ delivery assay uses a small organic molecule that is made up of a photocaged LDE and a chloroalkane recognition unit. The HaloTag enzyme (Janssen D. B., "Evolving Haloalkane Dehalogenases," Curr. Opin. Chem. Biol. 8:150-59 (2004); Los et al., "The Halo Tag: A Novel Technology for Cell Imaging and Protein Analysis," Methods Mol. Biol. 356:195-208 (2007); Los et al., "HaloTag: A Novel Protein Labeling Technology for Cell Imaging and Protein Analysis," ACS Chem. Biol. 3:373-82 (2008); Ohana et al., "HaloTag7: A Genetically Engineered Tag That Enhances Bacterial Expression of Soluble Proteins and Improves Protein Purification," Protein Expr. Purif. 68:110-120 (2009), which are hereby incorporated by reference in their entirety) rapidly and specifically conjugates to the chloroalkane recognition unit, resulting in an irreversible 1:1 Halo: small-molecule complex. The 15-atom linker between the chloroalkane function and the photocaged LDE renders the inert caged motif solvent-exposed such that low-energy light illumination (0.3 mW/cm$^2$, 365 nm) (FIG. 18) unleashes ($t_{1/2}$<1-2 min) a maximum of one LDE molecule per caged precursor in vitro (Lin et al., "A Generalizable Platform for Interrogating Target- and Signal-Specific Consequences of Electrophilic Modifications in Redox-Dependent Cell Signaling," J. Am. Chem. Soc. 137: 6232-44 (2015); Parvez et al., "Substoichiometric Hydroxynonenylation of a Single Protein Recapitulates Whole-Cell-Stimulated Antioxidant Response," J. Am. Chem. Soc. 137:10-13 (2015), which are hereby incorporated by reference in their entirety) and in cells ($t_{1/2}$~0.5+0.3 min) (FIG. 20A). Proximity enhancement (Long et al., "On-Demand Targeting: Investigating Biology with Proximity-Directed Chemistry," J. Am. Chem. Soc. 138:3610-22 (2016), which is hereby incorporated by reference in its entirety) enables targeted LDE modification of the redox-sensitive POI whereas HaloTag itself does not react with the liberated LDE (FIG. 20B).

Blocking Experiments to Check for Specificity.
Pretreatment of Halo-POI-expressing cells with HaloTag-targetable photocaged LDE ("photocaged precursor" hereafter) prior to addition of TMR-dye-conjugated chloroalkane and subsequent live imaging-confirmed that the photocaged precursors saturate the Halo protein binding site within 2 hours (Fang et al., "Temporally Controlled Targeting of 4-hydroxynonenal to Specific Proteins in Living Cells," J. Am. Chem. Soc. 135:14496-99 (2013), which is hereby incorporated by reference in its entirety), consistent with HaloTag's rapid second-order reaction (Los et al., "HaloTag: A Novel Protein Labeling Technology for Cell Imaging and Protein Analysis," ACS Chem. Biol. 3:373-82 (2008), which is hereby incorporated by reference in its entirety) (Box 1). Functionality of HaloTagged POIs was also assessed (Box 2, vide infra). Both TMR-dye-conjugated chloroalkane and the photocaged precursor (FIG. 17, inset) labeled HaloTag exclusively. Hence, there is no reaction of caged precursors with other cellular targets or the POI, and the chloroalkane appendage is stable (Fang et al., "Temporally Controlled Targeting of 4-hydroxynonenal to Specific Proteins in Living Cells," J. Am. Chem. Soc. 135; 14496-99 (2013); Lin et al., "A Generalizable Platform for Interrogating Target- and Signal-Specific Consequences of Electrophilic Modifications in Redox-Dependent Cell Signaling," J. Am. Chem. Soc. 137:6232-44 (2015); Parvez et al., "Substoichiometric Hydroxynonenylation of a Single Protein Recapitulates Whole-Cell-Stimulated Antioxidant Response," J. Am. Chem. Soc. 137:10-13 (2015), which are hereby incorporated by reference in their entirety). Such a result is common because eukaryotic cells and most bacteria, including E. coli (Janssen D. B., "Evolving Haloalkane Dehalogenases,"

Curr. Opin. Chem. Biol. 8:150-59 (2004); Los et al., "The Halo Tag: A Novel Technology for Cell Imaging and Protein Analysis," *Methods Mol. Biol.* 356:195-208 (2007); Ohana et al., "HaloTag7: A Genetically Engineered Tag That Enhances Bacterial Expression of Soluble Proteins and Improves Protein Purification," *Protein Expr. Purif.* 68:110-120 (2009), which are hereby incorporated by reference in their entirety), do not express haloalkane dehydrogenases conferring excellent bioorthogonality.

Cytotoxicity.

The caged precursors were non-toxic as judged by AlamarBlue® and trypan blue viability assays (Fang et al., "Temporally Controlled Targeting of 4-hydroxynonenal to Specific Proteins in Living Cells," *J. Am. Chem. Soc.* 135:14496-99 (2013); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety). UV light exposure under T-REX™ delivery conditions also does not elicit upregulation of γ-H2AX (Rogakou et al., "DNA Double-Stranded Breaks Induce Histone H2AX Phosphorylation on Serine 139," *J. Biol. Chem.* 273:5858-68 (1998), which is hereby incorporated by reference in its entirety) and does not perturb other stress-sensitive pathways such as NF-κB (Morgan et al., "Crosstalk of Reactive Oxygen Species and NF-kappaB Signaling," *Cell. Res.* 21:103-15 (2011), which is hereby incorporated by reference in its entirety), markers for DNA damage and inflammatory signaling, respectively (FIG. 20). In T-REX™ delivery, the maximum LDE signal delivered is equal to the concentration of HaloTag fusion protein (FIG. 17). Thus, side reactions of the T-REX™ delivery-liberated LDE with proteins other than the target POI are much lower than whole-cell flooding. By contrast, global treatment with reactive LDEs induces time- and dose-dependent cytotoxicity. $EC_{50}$ of viability, for instance, even for the robust cell line HEK-293T, is ~31 µM over 18-h treatment (Delmastro-Greenwood et al., "Redox-Dependent Anti-Inflammatory Signaling Actions of Unsaturated Fatty Acids," *Annu. Rev. Physiol.* 76:79-105 (2014); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety). Because the typical concentrations used in the literature for redox signaling studies with LDEs, for instance HNE, are above 20 µM and can reach as high as 1 mM over prolonged treatment, users are encouraged to carefully evaluate the extent of loss in cell viability under these conditions and consider associated off-target responses.

Quantitating the Extent of Modification.

Alkyne functionalization enables fluorescence-based quantitation of the amount of LDE signal delivered to the POI, and that remains unliberated on the HaloTag (FIG. 17) (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). The low background signal to the overall proteome along with the fact that targeting is not achieved when the HaloTag is expressed separately with the POI (the "non-fused" system, vide infra, Box 3) (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety) collectively led to the conclusion that the majority of liberated lipid electrophile that does not hit its intended target is likely intercepted by small-molecule thiols such as glutathione (Tjalkens et al., "Formation and Export of the Glutathione Conjugate of 4-hydroxy-2, 3-E-nonenal (4-HNE) in Hepatoma Cells," *Arch. Biochem. Biophys.* 361:113-19 (1999); Volkel et al., "Glutathione Conjugates of 4-hydroxy-2(E)-nonenal as Biomarkers of Hepatic Oxidative Stress-Induced Lipid Peroxidation in Rats," *Free Radic. Biol. Med.* 38:1526-36 (2005); Banerjee, eds., REDOX BIOCHEMISTRY, Hoboken, N.J.: John Wiley and Sons (2007); Cao et al., "The Role of Chemically Induced Glutathione and Glutathione S-Transferase in Protecting Against 4-hydroxy-2-nonenal-mediated Cytotoxicity in Vascular Smooth Muscle Cells," *Cardiovasc. Toxicol.* 3:165-77 (2003), which are hereby incorporated by reference in their entirety). The percentage delivery (i.e., the amount of signal that is delivered to the POI with respect to the total initially present in the photocage) is assayed post cell lysis by a series of steps involving: TEV-protease-mediated separation of HaloTag from the POI; Click coupling (Kolb et al., "Click Chemistry: Diverse Chemical Function From a Few Good Reactions," *Angew Chem. Int. Ed Engl.* 40:2004-21 (2001), which is hereby incorporated by reference in its entirety) reaction with Cy5-azide; and in-gel fluorescence analysis (FIG. 21). Western blotting of housekeeping protein (e.g., actin), and target POI, respectively, normalizes for loading and transfection efficiency across all samples against no-light-exposed and/or no-TEV-treated controls. Subtraction of the amount of signal associated with unreacted photocage on HaloTag accounts for the true percentage of POI molecules modified in cells [see equation in Step 40A (ix)]. The value obtained from this method is broadly similar to that estimated by ion peak integration post LC/MS-MS analysis (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety).

Generality in the Scope of Targetable LDEs.

Tolerance of HaloTag to a range of sterically-demanding groups appended to chloroalkane ligands permits versatile functionalization of caged precursor (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety), making it feasible to deliver LDEs of varying chemical architectures (FIG. 17, inset). For all the LDEs studied, expressing Halo and POI as two separate proteins, in place of the Halo-POI fusion protein, resulted in no labeling of POI in cells confirming that proximity-based targeting was in operation (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137: 10-13 (2015), which are hereby incorporated by reference in their entirety). In vitro kinetic analyses (Lin et al., "A Generalizable Platform for Interrogating Target- and Signal-Specific Consequences of Electrophilic Modifications in Redox-Dependent Cell Signaling," *J. Am. Chem. Soc.* 137: 6232-44 (2015), which is hereby incorporated by reference in its entirety) suggest a two-step targeting mechanism: formation of an initial target-signal encounter complex followed by covalent Michael adduction with Cys residue(s) on the target. Labeling efficiency for a given target is governed by partitioning between the rate of covalent adduct formation and diffusion of the LDE signal out of the coordination shell of the target POI (Fang et al., "Temporally Controlled Targeting of 4-hydroxynonenal to Specific Proteins in Living Cells," *J. Am. Chem. Soc.* 135:14496-99 (2013); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety).

A Platform for Targeted Screening and Discovery of Bona Fide Sensor Genes.

One of the major benefits of T-REX™ delivery is the commercially available HaloTag human and mouse full-length ORF clone libraries (Kazusa Collection, Promega). This gives an added dimension because it makes screening of potential electrophile-sensitive gene products very simple. As proof of concept, an in-house screen of ten HaloTag proteins allowed identification of two proteins that are "first responders" to basal amounts of HNE (FIG. 22 and FIG. 23). The majority of the candidates chosen were previously identified as potentially LDE sensitive by global proteomic profiling (Weerapana et al., "Quantitative Reactivity Profiling Predicts Functional Cysteines in Proteomes," *Nature* 468:790-95 (2010); Codreanu et al., "Alkylation Damage by Lipid Electrophiles Targets Functional Protein Systems," *Mol. Cell. Proteomics* 13:849-59 (2014); Wang et al., "A Chemoproteomic Platform to Quantitatively Map Targets of Lipid-Derived Electrophiles," *Nat. Methods* 11:79-85 (2014); Yang et al., "Quantitative Chemoproteomics for Site-Specific Analysis of Protein Alkylation by 4-hydroxy-2-nonenal in Cells," *Anal. Chem.* 87:2535-41 (2015); Kim et al., "An Azido-Biotin Reagent for Use in the Isolation of Protein Adducts of Lipid-Derived Electrophiles by Streptavidin Catch and Photorelease," *Mol. Cell. Proteomics* 8:2080-89 (2009); Codreanu et al., "Global Analysis of Protein Damage by The Lipid Electrophile 4-hydroxy-2-nonenal," *Mol. Cell. Proteomics* 8:670-80 (2009), which are hereby incorporated by reference in their entirety), such as: (1) human ribonucleotide reductase (RNR) subunits—RRM1 and RRM2 (and its isoform p53R2). Each subunit pair—RRM1/RRM2 or RRM1/p53R2—constitutes an active RNR complex essential for nuclear and mitochondrial DNA replication, respectively (Aye et al., "Ribonucleotide Reductase and Cancer: Biological Mechanisms and Targeted Therapies," *Oncogene* 34:2011-21 (2015), which is hereby incorporated by reference in its entirety); (2) PI3K and PRKCD—two of several kinases that regulate the Nrf2-transcription-factor-driven antioxidant response (AR) pathway in mammals (Hayes et al., "The Nrf2 Regulatory Network Provides an Interface Between Redox and Intermediary Metabolism," *Trends Biochem. Sci.* 39:199-218 (2014), which is hereby incorporated by reference in its entirety); (3) Cul3—a ligase that mediates proteasomal degradation of mammalian Nrf2 (Kobayashi et al., "Oxidative Stress Sensor Keap1 Functions as an Adaptor for Cul3-based E3 Ligase to Regulate Proteasomal Degradation of Nrf2," *Mol. Cell. Biol.* 24:7130-9 (2004), which is hereby incorporated by reference in its entirety); (4) DCAF11—a mammalian analog of a stress-responsive protein in *C. elegans*. Zebrafish HSPB7—a member of small heat shock protein family that is expressed highly and selectively in the heart (Krief et al., "Identification and Characterization of cvHsp: A Novel Human Small Stress Protein Selectively Expressed in Cardiovascular and Insulin-Sensitive Tissues," *J. Biol. Chem.* 274:36592-36600 (1999); Rosenfeld et al., "Small Heat Shock Proteins Hspb7 and Hspb12 Regulate Early Steps of Cardiac Morphogenesis," *Dev. Biol.* 381:389-400 (2013), which are hereby incorporated by reference in their entirety) was also screened. hspb7 is not upregulated by heat shock (Marvin et al., "Developmental Expression Patterns of the Zebrafish Small Heat Shock Proteins," *Dev. Dyn.* 237:454-63 (2008), which is hereby incorporated by reference in its entirety) and thus likely has other regulation mechanisms that are as yet unidentified. Keap1—a redox-sensitive negative regulator of Nrf2-AR pathway—served as a positive control in the screen (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137: 10-13 (2015), which are hereby incorporated by reference in their entirety). Expression of these proteins was assessed by blotting for Halo protein (assumed to be present in a 1:1 ratio with the fused POI). By this metric, most proteins were successfully expressed, although expression varied. However, only two proteins from this screen—RRM1 and HSPB7—were modified by HNE in addition to the positive control Keap1 (FIG. 22A and FIG. 23) under the conditions in which HNE signals are delivered in controlled amounts.

Since P53R2 and RRM1 expression was similar and RRM2 (a protein known to have a short half-life (Aye et al., "Ribonucleotide Reductase and Cancer: Biological Mechanisms and Targeted Therapies," *Oncogene* 34:2011-21 (2015), which is hereby incorporated by reference in its entirety)) was also detectable, these data show that likely RRM1 is the HNE-sensitive subunit of active RNR complexes—RRM1/RRM2 and RRM1/p53R2 heterodimers. Other proteins were not significantly HNEylated. Remarkably, RRM1, p53R2, and PRKCD—previously identified HNE-sensitive hits from global treatment approaches (Weerapana et al., "Quantitative Reactivity Profiling Predicts Functional Cysteines in Proteomes," *Nature* 468:790-95 (2010); —had expression similar to Keap1; yet, T-REX™ delivery-assisted HNE delivery was markedly different. By contrast, whole-cell HNE treatment led to non-specific targeting under otherwise identical conditions (FIG. 22A and FIG. 23A). While the reasons behind these differences are likely multifactorial and system- and/or context-dependent, when an entire cell is swamped with reactive LDE in excess, the time-dependent nature of the underlying covalent chemistry in LDE modification typically controls the extent of off-target labeling and thus unresponsive proteins in the T-REX™ delivery screen may react too slowly with HNE to serve as "first responders". Less reactive subunits or targets could Codreanu et al., "Alkylation Damage by Lipid Electrophiles Targets Functional Protein Systems," *Mol. Cell. Proteomics* 13:849-59 (2014); Wang et al., "A Chemoproteomic Platform to Quantitatively Map Targets of Lipid-Derived Electrophiles," *Nat. Methods* 11:79-85 (2014); Yang et al., "Quantitative Chemoproteomics for Site-Specific Analysis of Protein Alkylation by 4-hydroxy-2-nonenal in Cells," *Anal. Chem.* 87:2535-41 (2015); Codreanu et al., "Global Analysis of Protein Damage by The Lipid Electrophile 4-hydroxy-2-nonenal," *Mol. Cell. Proteomics* 8:670-80 (2009), which are hereby incorporated by reference in their entirety) HNE transfer to other subunits could also happen under these circumstances. On the other hand, T-REX™ delivery releases maximum of one LDE molecule per HaloTag-POI (Fang et al., "Temporally Controlled Targeting of 4-hydroxynonenal to Specific Proteins in Living Cells," *J. Am. Chem. Soc.* 135:14496-99 (2013); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety) and the labeling is low stoichiometry (Fang et al., "Temporally Controlled Targeting of 4-hydroxynonenal to Specific Proteins in Living Cells," *J. Am. Chem. Soc.* 135:14496-99 (2013); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety). Aspects of existing methods and considerations for potential artifacts are discussed below.

Determining Residue Specificity.

Once the positive result of LDE sensitivity has been established by gel-based analysis, the identity of specific amino acid residues modified can be determined by standard affinity enrichment followed by LC-MS/MS characterizations (FIG. 21). For Keap1, the position of the HaloTag (N or C terminus) exerted no influence on cysteine residue labeling by T-REX™ delivery (FIG. 24 and FIG. 30) (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety).

Furthermore, since similar levels of signaling responses are achieved by T-REX™ delivery and whole-cell LDE stimulation (see applications section), the ability of T-REX™ delivery to elicit a response indicates that functionally relevant residues are targeted (Lin et al., "A Generalizable Platform for Interrogating Target- and Signal-Specific Consequences of Electrophilic Modifications in Redox-Dependent Cell Signaling," *J. Am. Chem. Soc.* 137: 6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety).

Selection of specific Cys residues is likely dominated by individual Cys nucleophilicity in its native microenvironment. For example, LC/MS-MS analysis showed C613 modification of Keap1 by cyclohexenone-derived LDE (namely, CHE, FIG. 17, inset), regardless of N or C terminal HaloTag fusion (FIG. 24C and FIG. 30). Mutagenesis studies previously suggested other Cys residues within Keap1 can compensate for the lack of C613, underscoring functional redundancy across multiple Cys residues on Keap1 (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety). Interestingly, global treatment of cells with CHE also resulted in the modification of the same Cys residue on Halo-Keap1 protein (FIG. 31). Previous LC/MS analysis of Keap1 modifications by HNE, an LDE of much higher reactivity than CHE, under T-REX™ delivery versus global conditions resulted in non-overlapping residues as well as a wider scope of residues modified.

Versatility Both in Mammalian Cells and *E. coli.*

It was also shown that the method can afford similar precision targeting of reactive LDEs in bacteria using *E coli* as proof of concept. In this example, recombinantly expressed human Keap1 genetically encoded with HaloTag at the N terminus was selectively reacted with HNE(alkyne) using T-REX™ delivery (FIG. 25). As in the case with mammalian cells, photocaged precursors did not show adverse effects on the growth rate of *E. coli* and can permeate within 2 h during the logarithmic growth phase when Halo-Keap1 expression was induced at 19° C. The procedures used for photo-uncaging and downstream labeling analysis for mammalian cell samples were also transposable to *E. coli.*

Establishing Target-Specific Biological Sufficiency in Specific Redox Events.

A major advantage of T-REX™ delivery is that it has the potential to decode the gain-of-function (or dominant loss of function) consequences of specific redox events in living systems in a time-resolved manner. This benefit is not offered by any existing tool despite the growing interest from both the academic and pharmaceutical communities. One critical pathway regulated by redox signaling is the Nrf2-AR axis. The conserved Nrf2-AR pathway is a gatekeeper for the expression of hundreds of detoxification and antioxidant genes essential for cytoprotective defense in all cell types in metazoa. This pathway also plays an essential role in physiology such as organogenesis, lifespan regulation, and conversely in various disease states such as tumor metastasis and drug resistance (Hayes et al., "The Nrf2 Regulatory Network Provides an Interface Between Redox and Intermediary Metabolism," *Trends Biochem. Sci.* 39:199-218 (2014); Ma, Q., "Role of nrf2 in Oxidative Stress and Toxicity," *Annu. Rev. Pharmacol. Toxicol.* 53:401-26 (2013); Sporn et al., "NRF2 and Cancer: the Good, the Bad and the Importance of Context," *Nat. Rev. Cancer* 12:564-71 (2012), which are hereby incorporated by reference in their entirety). There are many electrophilic pharmacophores (e.g., tecfidera, bardoxolone, sulforaphane, curcumin) (Crunkhorn S., "Deal Watch: Abbott Boosts Investment in NRF2 Activators for Reducing Oxidative Stress," *Nat. Rev. Drug Discov.* 11:96 (2012); Dinkova-Kostova et al., "Glucosinolates and Isothiocyanates in Health and Disease," *Trends Mol. Med.* 18:337-47 (2012); Gupta et al., "Therapeutic Roles of Curcumin: Lessons Learned From Clinical Trials," *AAPS J.* 15:195-218 (2013); Fernandez-Fernandez et al., "Therapeutic Approaches to Diabetic Nephropathy-Beyond the RAS," *Nat. Rev. Nephrol.* 10:325-46 (2014); Bomprezzi R., "Dimethyl Fumarate in the Treatment of Relapsing-Remitting Multiple Sclerosis: An Overview," *Ther. Adv. Neurol. Disord.* 8:20-30 (2015); Garber, K., "Biochemistry: A Radical Treatment," *Nature* 489: S4-S6 (2012), which are hereby incorporated by reference in their entirety), with chemical reactivity similar to that of the endogenous AR stimulator HNE-a reactive signaling compound known to have >800 cysteine targets under bolus dosing conditions (Codreanu et al., "Alkylation Damage by Lipid Electrophiles Targets Functional Protein Systems," *Mol. Cell. Proteomics* 13:849-59 (2014); Yang et al., "Quantitative Chemoproteomics for Site-Specific Analysis of Protein Alkylation by 4-hydroxy-2-nonenal in Cells," *Anal. Chem.* 87:2535-41 (2015); Kim et al., "An Azido-Biotin Reagent for Use in the Isolation of Protein Adducts of Lipid-Derived Electrophiles by Streptavidin Catch and Photorelease," *Mol. Cell. Proteomics* 8:2080-89 (2009); Codreanu et al., "Global Analysis of Protein Damage by The Lipid Electrophile 4-hydroxy-2-nonenal," *Mol. Cell. Proteomics* 8:670-80 (2009), which are hereby incorporated by reference in their entirety). These electrophiles are believed to confer therapeutic benefits by upregulating, amongst others, the Nrf2-AR pathway (Crunkhorn S., "Deal Watch: Abbott Boosts Investment in NRF2 Activators for Reducing Oxidative Stress," *Nat. Rev. Drug Discov.* 11:96 (2012); Dinkova-Kostova et al., "Glucosinolates and Isothiocyanates in Health and Disease," *Trends Mol. Med.* 18:337-47 (2012); Gupta et al., "Therapeutic Roles of Curcumin: Lessons Learned From Clinical Trials," *AAPS J.* 15:195-218 (2013); Fernandez-Fernandez et al., "Therapeutic Approaches to Diabetic Nephropathy-Beyond the RAS," *Nat. Rev. Nephrol.* 10:325-46 (2014); Bomprezzi R., "Dimethyl Fumarate in the Treatment of Relapsing-Remitting Multiple Sclerosis: An Overview," *Ther. Adv. Neurol. Disord.* 8:20-30 (2015); Garber, K., "Biochemistry: A Radical Treatment," *Nature* 489:S4-S6 (2012), which are hereby incorporated by reference in their entirety). Use of T-REX™ delivery in cultured human cells enables targeted Nrf2-AR pathway activation with precise timing and without perturbing other redox-sensor protein networks (Fang et al., "Temporally Controlled Targeting of 4-hydroxynonenal to Specific Proteins in Living Cells," *J. Am. Chem. Soc.* 135; 14496-99 (2013); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015); Parvez et al., "Substoichiometric Hydroxynonenylation of a Single Protein Recapitulates Whole-Cell-Stimulated Antioxidant Response," *J. Am. Chem. Soc.* 137:10-13 (2015), which are hereby incorporated by reference in their entirety). T-REX™ delivery has shown that targeted HNEylation of one of the many redox-sensitive AR regulators, Keap1, with low-stoichiometry is sufficient to stimulate maximal AR within the complex multisensor protein networks regulating Nrf2. ("HNEylation" is defined as posttranslational modification of a protein by HNE through covalent chemical conjugation to any residue. The target residue is most often cysteine, but HNE can also react with lysine and histidine residues (Yang et al., "Quantitative Chemoproteomics for Site-Specific Analysis of Protein Alkylation by 4-hydroxy-2-nonenal in Cells," *Anal. Chem.* 87:2535-41 (2015); Uchida et al., "Modification of Histidine Residues in Proteins by Reaction with 4-hydroxynonenal," *Proc. Nat'l. Acad. Sci. U.S.A.* 89:4544-8 (1992); Uchida et al., "Covalent Attachment of 4-Hydroxynonenal to Glyceraldehyde-3-Phosphate Dehydrogenase. A Possible Involvement of Intra- and Intermolecular Cross-Linking Reaction," *J. Biol. Chem.* 268:6388-93 (1993); Nadkarni et al., "Structural Definition of Early Lysine and Histidine Adduction Chemistry of 4-Hydroxynonenal," *Chem. Res. Toxicol.* 8:284-91 (1995), which are hereby incorporated by reference in their entirety). The gel-based analysis of T-REX™ delivery targeting assessment gives no prejudice on residue specificity nor the specific chemical identity of adducts formed). In this way, the proposed HNE-sensing ability of Nrf2 itself was also able to be ruled out, since co-overexpression of Nrf2 (that directly binds Halo-Keap1) does not result in HNEylation of Nrf2 in cells (Parvez et al., "Substoichiometric Hydroxynonenylation of a Single Protein Recapitulates Whole-Cell-Stimulated Antioxidant Response," *J. Am. Chem. Soc.* 137: 10-13 (2015), which is hereby incorporated by reference in its entirety). In addition, because reactive LDEs such as HNE will react with any isolated protein bearing Cys (and also His and Lys residues, depending on incubation time and concentration (Schopfer et al., "Formation and Signaling Actions of Electrophilic Lipids," *Chem. Rev.* 111:5997-6021 (2011), which is hereby incorporated by reference in its entirety)), T-REX™ delivery is an ideal method to determine functionally relevant modification events that are sufficient to trigger signaling.

Gel-based fluorescence quantitation shows the amount of LDE, exemplified by cyclohexenone analog CHE (FIG. 17 inset), reacted with Keap1 under whole-cell LDE treatment conditions [25 µM, 20 min, $EC_{50}$ (viability) ~90 M] is ~6-fold higher than that achieved under T-REX™ delivery (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). However, global treatment provides no additional bonus in terms of the magnitude of AR upregulation. The percentage of Keap1 molecules modified under T-REX™ delivery conditions can be determined easily based on two independent methods of quantitation: in-gel fluorescence (vide supra) and ion peak integration (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). For a representative targeted modification of Keap1 with cyclohexenone-derived LDE (FIG. 17, inset), the two methods gave 19% and 15%, respectively (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). Controls showed that the Nrf2-AR upregulation phenotype is not due to T-REX™ delivery affecting the proteasomal pathway that regulates steady-state Nrf2 protein levels (Parvez et al., "Substoichiometric Hydroxynonenylation of a Single Protein Recapitulates Whole-Cell-Stimulated Antioxidant Response," *J. Am. Chem. Soc.* 137:10-13 (2015), which is hereby incorporated by reference in its entirety). Nrf2-AR was also not due to untargeted delivery, because AR activation did not occur when HaloTag and target POI, Keap1, were overexpressed as two separate proteins (Parvez et al., "Substoichiometric Hydroxynonenylation of a Single Protein Recapitulates Whole-Cell-Stimulated Antioxidant Response," *J. Am. Chem. Soc.* 137:10-13 (2015); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety). Keap1 is unusually cysteine-rich and reacts rapidly with electrophiles so this experiment gives a high degree of confidence that T-REX™ delivery does not perturb other sensor proteins that regulate Nrf2-AR in the cell. In fact, the result allowed us to postulate that T-REX™ delivery proceeds via a target-signal encounter complex formed specifically because the electrophile is juxtaposed to the target upon photo-uncaging (Lin et al., "A Generalizable Platform for Interrogating Target- and Signal- Specific Consequences of Electrophilic Modifications in Redox-Dependent Cell Signaling," *J. Am. Chem. Soc.* 137: 6232-44 (2015), which is hereby incorporated by reference in its entirety).

Interrogating Signal-Specific and On-Target Signaling Strength.

An integrated electrophile toolbox has also been developed that enables targeted delivery of various linear enal, enone and cyclic enone-based LDEs to specific sensor proteins in cells (FIG. 17, inset) (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). Targeting efficiency is not largely influenced by intrinsic electrophilicity of the reactive signals. This observation is consistent with in vitro kinetic data, which show largely similar initial on-rates of LDE adduction of Keap1 (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). Thus T-REX™ delivery likely creates a microenvironment that behaves as if the target POI has been transiently treated with saturating LDE. The ability of T-REX™ delivery LDE toolbox to provide a range of signaling LDEs opens a new avenue to quantitatively dissect how a specific sensor protein or pathway deals with specific reactive LDEs. Using Keap1 as a model sensor protein in cells, T-REX™ delivery provides a means to elucidate how reactive LDE modifications directly translate to the strength of Nrf2-AR activation. In addition, the case with a cyclopentenone-based LDE (namely, CPE, FIG. 17 inset) (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety) helps exemplify potential utility of T-REX™ delivery in the identification of novel small-molecules that elicit pathway activation only through targeted delivery, but fail to activate AR from whole-cell flooding prior to toxicity (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety).

Quantitating Signaling Response in Subpopulations.

Various methods have been described that report on average increases in AR signal across the whole population. To identify new signaling effects of POI-targeted redox modifications on any other transcriptional pathways of interest, users can simply replace Nrf2-AR activation reporter plasmids used herein with any of the tens of signal transduction reporter plasmids commercially available in both luciferase- and GFP-reporter formats. So far, it has been shown pathway modulation using the dual-luciferase assay reporting transcriptional activation of Nrf2-driven AR (Parvez et al., "Substoichiometric Hydroxynonenylation of a Single Protein Recapitulates Whole-Cell-Stimulated Antioxidant Response," *J. Am. Chem. Soc.* 137:10-13 (2015); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety), and qRT-PCR technique (Parvez et al., "Substoichiometric Hydroxynonenylation of a Single Protein Recapitulates Whole-Cell-Stimulated Antioxidant Response," *J. Am. Chem. Soc.* 137:10-13 (2015), which is hereby incorporated by reference in its entirety) and western blot analysis both evaluating AR-driven downstream genes at the mRNA and protein levels, respectively (Parvez et al., "Substoichiometric Hydroxynonenylation of a Single Protein Recapitulates Whole-Cell-Stimulated Antioxidant Response," *J. Am. Chem. Soc.* 137:10-13 (2015); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety). These data that look at AR upregulation in ensembles of cells on the whole show little or no difference in the way through which T-REX™ delivery and whole-cell HNE bathing stimulate AR. Herein, an orthogonal flow cytometry assay reporting the extent of AR-driven GFP expression ("the GFP reporter assay" hereafter) is reported (FIG. 26). This assay allows one to compare the effects of whole-cell HNE flooding and T-REX™ delivery approach on AR on a cell-to-cell basis.

In this flow cytometry assay, live cells are first gated by forward (size) and side scatter to give a general population of healthy cells (FIG. 26A). This specific gating is applied to each data set (e.g., photocaged precursor Ht-PreHNE alone, light alone, etc.). This population should be a single group and be the largest single population for each data set. The scatter group was gated in several ways, and similar downstream results were obtained, but it is important that every data set (including all appropriate controls) is gated the same way. Analyzing this scatter group for green fluorescence (AR reporter) told a slightly different story to that painted by previous ensemble experiments (Parvez et al., "Substoichiometric Hydroxynonenylation of a Single Protein Recapitulates Whole-Cell-Stimulated Antioxidant Response," *J. Am. Chem. Soc.* 137:10-13 (2015); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety). Intriguingly, whole-cell HNE treatment strongly increases AR in a subset of cells, principally those showing a medium level of AR in the ground state. Notably, there is little change in cells with low basal AR (FIG. 26B).

On the other hand, with T-REX™ delivery, the increase in GFP signal stemmed from an increase in AR in all but cells with the highest basal AR (FIGS. 26B-26D). The lack of effect on cells with high basal AR was attributed to the fact that these cells express a lower level of Keap1 protein with respect to Nrf2, rendering them less susceptible to specific AR upregulation by T-REX™ delivery. Nonetheless, T-REX™ delivery enables initiation of AR in a larger fraction of the cell pool than global HNEylation, and does not hyperstimulate AR. Given that T-REX™ delivery shows most cells can respond to low-occupancy HNE stimulation through Keap1 modification, it is likely that the small number of responders seen with HNE is due to compensatory suppression of AR due to alkylation of multiple proteins. Such an observation would be consistent with T-REX™ delivery being able to mimic endogenous LDE signaling, and is thus further consistent with the low off-target spectrum associated with T-REX™ delivery coupled with the fact that T-REX™ delivery faithfully reports on AR signaling selectively through Keap1 (Parvez et al., "Substoichiometric Hydroxynonenylation of a Single Protein Recapitulates Whole-Cell-Stimulated Antioxidant Response," *J. Am. Chem. Soc.* 137:10-13 (2015); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety).

Generality Across Other Redox-Sensor Targets and Pathways.

The application of T-REX™ delivery was further validated beyond the targeted perturbation of Nrf2-AR signaling axis by selective downregulation of a key redox-sensitive tumor suppressor protein PTEN (Papa et al., "Cancer-Associated PTEN Mutants Act in a Dominant-Negative Manner to Suppress PTEN Protein Function," *Cell* 157:595-610 (2014), which is hereby incorporated by reference in its entirety). Oxidation or alkylation of PTEN by LDEs is known to inactivate PTEN phosphatase activity (Covey et al., "Alkylation of the Tumor Suppressor PTEN Activates Akt and Beta-Catenin Signaling: A Mechanism Linking Inflammation and Oxidative Stress with Cancer," *PLoS One* 5:e13545 (2010); Shearn et al., "Increased Carbonylation of the Lipid Phosphatase PTEN Contributes to Akt2 Activation in a Murine Model of Early Alcohol-Induced Steatosis," *Free Radic. Biol. Med.* 65:680-92 (2013); Shearn et al., "Phosphatase and Tensin Homolog Deleted on Chromosome 10 (PTEN) Inhibition by 4-Hydroxynonenal Leads to Increased Akt Activation in Hepatocytes," *Mol. Pharmacol.* 79:941-52 (2011), which are hereby incorporated by reference in their entirety). PTEN modifications elicit dominant loss of function of PTEN (Leslie et al., "Non-Genomic Loss of PTEN Function in Cancer: Not in My Genes," *Trends Pharmacol. Sci.* 32:131-40 (2011); Trotman et al., "Pten Dose Dictates Cancer Progression in the Prostate," *PLoS Biol.* 1:E59 (2003); Covey et al., "Akt Activation by Arachidonic Acid Metabolism Occurs via Oxidation and Inactivation of PTEN Tumor Suppressor," *Oncogene* 26:5784-92 (2007), which are hereby incorporated by reference in their entirety), and thus minor modifications can result in measurable accumulation of its cellular substrate, phosphatidylinositol 3,4,5-triphosphate (PIP3). Building on previous work that establishes T-REX™ delivery-assisted HNEylation of PTEN (Fang et al., "Temporally Controlled Targeting of 4-hydroxynonenal to Specific Proteins in Living Cells," *J. Am. Chem. Soc.* 135:14496-99 (2013), which is hereby incorporated by reference in its entirety), T-REX™ delivery also offers a means to temporally modulate the PTEN signaling. Two different orthogonal and established readouts-immunofluorescence (IF) analysis of endogenous PIP3 levels in fixed cells (FIG. 27) and fluorescence resonance energy transfer (FRET)-based "lnPAkt" reporter assay (Ananthanarayanan et al., "Signal Propagation From Membrane Messengers to Nuclear Effectors Revealed by Reporters of Phosphoinositide Dynamics and Akt Activity," *Proc. Nat'l. Acad. Sci. U.S.A.* 102:15081-6 (2005); Antal et al., "Spatiotemporal Dynamics of Phosphorylation in Lipid Second Messenger Signaling," *Mol. Cell Proteomics* 12:3498-508 (2013), which are hereby incorporated by reference in their entirety) in live cells (FIG. 28)—were employed. The representative images of fixed cells in FIG. 27 and live cells in FIG. 28 both underscored that T-REX™ delivery coupled with either IF or FRET assays is non-intrusive to cellular integrity—an aspect that users should be aware of before proceeding to data quantitation. Although the fold-changes in the measured FRET signals (FIG. 28) are small, they are within the range previously established for growth factor-induced or pharmacological perturbation of the same pathway using the identical lnPAkt FRET reporter plasmid (Ananthanarayanan et al., "Signal Propagation From Membrane Messengers to Nuclear Effectors Revealed by Reporters of Phosphoinositide Dynamics and Akt Activity," *Proc. Nat'l. Acad. Sci. U.S.A.* 102:15081-6 (2005); Antal et al., "Spatiotemporal Dynamics of Phosphorylation in Lipid Second Messenger Signaling," *Mol. Cell Proteomics* 12:3498-508 (2013), which are hereby incorporated by reference in their entirety) (FIGS. 27 and 28). These outcomes also suggested that as in Nrf2-AR signaling (Parvez et al., "Substoichiometric Hydroxynonenylation of a Single Protein Recapitulates Whole-Cell-Stimulated Antioxidant Response," *J. Am. Chem. Soc.* 137:10-13 (2015); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety), single target redox modulation events can be important physiological events that can fully recapitulate a variety of cellular redox processes.

Discovering Novel Redox Regulators Sufficient for a Specific Response.

This can be accomplished using the procedure for the representative HaloTag ORFclone library screen (FIG. 22 and FIG. 23) and subsequent probing of transcriptional response (FIG. 17). The initial screen, target validation, and downstream response studies are all built on T-REX™ delivery.

Precise Assessment of Redox Sensitivity in Combination with Proteomics and Transcriptomics-Based Target ID Approaches.

T-REX™ delivery in unison with these existing technologies provides unparalleled opportunities for accurate characterizations of their precision response to specific LDE signals delivered to a specific sensor protein at a specific time (FIG. 22A and FIG. 23A).

Comparison with Genetic and Chemoproteomics Approaches.

Redox signaling is a chemical signaling paradigm radically different from enzyme-assisted post-translational modifications such as phosphorylation. Accordingly, classical genetic approaches are not optimal for studying the temporal and spatial dynamics underpinning redox signaling. Targeted knockdown and/or knock-in approaches (Doudna et al., "Genome Editing. The New Frontier of Genome Engineering with CRISPR-Cas9," *Science* 346: 1258096 (2014); Fellmann et al., "Stable RNA Interference Rules for Silencing," *Nat. Cell Biol.* 16:10-18 (2014), which are hereby incorporated by reference in their entirety) assume that one protein will be necessary for the desired response to occur. While this may be possible under signaling conditions, this is less likely under the typical bolus dosing settings due to functional redundancy among sensor proteins and the pathways that the regulate. Knockdown also often disrupt protein-protein interactions essential for functional intercommunication within multicomponent signaling networks. Specifically, protein expression levels fluctuate so drastically during dynamic physiological processes such as development (Assou et al., "Dynamic Changes in Gene Expression During Human Early Embryo Development: From Fundamental Aspects to Clinical Applications," *Hum. Reprod. Update* 17:272-90 (2011). which is hereby incorporated by reference in its entirety) that redox perturbation under steady-state conditions often elicits pleiotropic effects that are challenging to interpret. The modifications are also largely non-sequence- and non-site-specific (Jacob, eds., REDOX SIGNALING AND REGULATION IN BIOLOGY AND MEDICINE, Weinheim, Germany: Wiley-VCH Verlag GmbH & Co.

KGaA (2009), which is hereby incorporated by reference in its entirety), and many redox sensor proteins have multiple functionally redundant Cys residues (Jacob, eds., REDOX SIGNALING AND REGULATION IN BIOLOGY AND MEDICINE, Weinheim, Germany: Wiley-VCH Verlag GmbH & Co. KGaA (2009); Foyer, eds., REDOX METABOLISM AND LONGEVITY RELATIONSHIPS IN ANIMALS AND PLANTS, New York, N.Y.: Taylor & Francis (2009), which are hereby incorporated by reference in their entirety). Mutagenesis strategies are thus not always effective. Innovative quantitative proteomics platforms on the other hand have opened exciting doors to profiling relative Cys reactivity within the human proteome (Weerapana et al., "Quantitative Reactivity Profiling Predicts Functional Cysteines in Proteomes," Nature 468:790-95 (2010); Wang et al., "A Chemoproteomic Platform to Quantitatively Map Targets of Lipid-Derived Electrophiles," Nat. Methods 11:79-85 (2014); Niphakis et al., "A Global Map of Lipid-Binding Proteins and Their Ligandability in Cells," Cell 161:1668-80 (2015); Yang et al., "Quantitative Chemoproteomics for Site-Specific Analysis of Protein Alkylation by 4-hydroxy-2-nonenal in Cells," Anal. Chem. 87:2535-41 (2015); Furdui et al., "Chemical Approaches to Detect and Analyze Protein Sulfenic Acids," Mass. Spectrom. Rev. 33:126-46 (2014); Yang et al., "The Expanding Landscape of the Thiol Redox Proteome," Mol. Cell. Proteomics 15:1-11 (2016); Yang et al., "Global, In situ, Site-Specific Analysis of Protein S-Sulfenylation," Nat. Protoc. 10:1022-37 (2015), which are hereby incorporated by reference in their entirety). Chemical biology methods for site-specific analysis and global mapping of cysteine modifications onto the redoxome are also established (Weerapana et al., "Quantitative Reactivity Profiling Predicts Functional Cysteines in Proteomes," Nature 468:790-95 (2010); Wang et al., "A Chemoproteomic Platform to Quantitatively Map Targets of Lipid-Derived Electrophiles," Nat. Methods 11:79-85 (2014); Yang et al., "Quantitative Chemoproteomics for Site-Specific Analysis of Protein Alkylation by 4-hydroxy-2-nonenal in Cells," Anal. Chem. 87:2535-41 (2015); Furdui et al., "Chemical Approaches to Detect and Analyze Protein Sulfenic Acids," Mass. Spectrom. Rev. 33:126-46 (2014); Yang et al., "The Expanding Landscape of the Thiol Redox Proteome," Mol. Cell. Proteomics 15:1-11 (2016); Yang et al., "Global, In situ, Site-Specific Analysis of Protein S-Sulfenylation," Nat. Protoc. 10:1022-37 (2015), which are hereby incorporated by reference in their entirety). Despite the powerful capability to rank reactivities and define the sites of modifications, the chemoproteomics strategies with global LDE exposure provide no ability to perturb specific targets on demand. Downstream validation is difficult, because it typically involves replicating the swamping experiments in knockdown cells, and measuring changes to the pleiotropic response, conditions in which temporal and target resolution are both low. T-REX™ delivery is an exciting starting point in addressing these outstanding biological questions, and strongly complements, but answers a different subset of important questions from, existing whole-cell probing and profiling methods.

HaloTagging Vs. Endogenous Protein Targeting.

While the monomeric nature of HaloTag prevents unintended self-association (Janssen D. B., "Evolving Haloalkane Dehalogenases," Curr. Opin. Chem. Biol. 8:150-59 (2004); Los et al., "The Halo Tag: A Novel Technology for Cell Imaging and Protein Analysis," Methods Mol. Biol. 356:195-208 (2007); Los et al., "HaloTag: A Novel Protein Labeling Technology for Cell Imaging and Protein Analysis," ACS Chem. Biol. 3:373-82 (2008); Ohana et al., "HaloTag7: A Genetically Engineered Tag That Enhances Bacterial Expression of Soluble Proteins and Improves Protein Purification," Protein Expr. Purif. 68:110-120 (2009), which are hereby incorporated by reference in their entirety), this 33 kDa protein adds steric bulk to the target POI. Despite the functionally validated HaloTag clones available from Promega, HaloTagging of a protein may affect complex protein function in an unpredictable way. This factor should be evaluated for individual target POIs under study. For example, it has been confirmed that HaloTag does not perturb functional integrity of proteins thus far. For instance, Halo-Keap1 is as expected a dimer (Parvez et al., "Substoichiometric Hydroxynonenylation of a Single Protein Recapitulates Whole-Cell-Stimulated Antioxidant Response," J. Am. Chem. Soc. 137:10-13 (2015), which is hereby incorporated by reference in its entirety), and with both N-(Parvez et al., "Substoichiometric Hydroxynonenylation of a Single Protein Recapitulates Whole-Cell-Stimulated Antioxidant Response," J. Am. Chem. Soc. 137:10-13 (2015), which is hereby incorporated by reference in its entirety) and C-terminal (FIG. 24A) fusion of the tag, the engineered protein binds Nrf2 and maintains cytosolic localization similar to native Keap1 (Box 2). Likewise, Halo-RRM1 has largely similar reductase activity to the non-HaloTagged counterpart.

To date T-REX™ delivery targeting has only been demonstrated with HaloTagging (Fang et al., "Temporally Controlled Targeting of 4-hydroxynonenal to Specific Proteins in Living Cells," J. Am. Chem. Soc. 135:14496-99 (2013); Lin et al., "A Generalizable Platform for Interrogating Target- and Signal-Specific Consequences of Electrophilic Modifications in Redox-Dependent Cell Signaling," J. Am. Chem. Soc. 137:6232-44 (2015); Parvez et al., "Substoichiometric Hydroxynonenylation of a Single Protein Recapitulates Whole-Cell-Stimulated Antioxidant Response," J. Am. Chem. Soc. 137:10-13 (2015), which are hereby incorporated by reference in their entirety). However, one would expect T-REX™ delivery to function equally well on other similar fusion proteins (e.g., SNAP or CLIP tags (Gautier et al., "An Engineered Protein Tag for Multiprotein Labeling in Living Cells," Chem. Biol. 15:128-36 (2008), which is hereby incorporated by reference in its entirety)) providing the appropriate ligands were available. By extension, in cases in which proteins of interest have high-specificity and/or high-affinity ligands that tolerate chemical modification, a specific T-REX™ delivery photocaged precursor targeting an endogenous POI could be tailor made. In other words, the chloroalkane recognition unit within the photocaged precursor could be replaced with a known ligand of the endogenous target POI under study. It should be first evaluated, however, that the modification of the known ligands with photocaged motif is non-intrusive to ligand-endogenous POI interactions as well as photo-uncaging efficiency.

Overexpression and Non-Specific Response.

Although the technique currently uses overexpressed proteins, overexpression does not appear to bias the outcomes in favor of delivery (Fang et al., "Temporally Controlled Targeting of 4-hydroxynonenal to Specific Proteins in Living Cells," J. Am. Chem. Soc. 135:14496-99 (2013); Lin et al., "A Generalizable Platform for Interrogating Target- and Signal-Specific Consequences of Electrophilic Modifications in Redox-Dependent Cell Signaling," J. Am. Chem. Soc. 137:6232-44 (2015); Parvez et al., "Substoichiometric Hydroxynonenylation of a Single Protein Recapitulates Whole-Cell-Stimulated Antioxidant Response," J. Am. Chem. Soc. 137:10-13 (2015), which are hereby incorporated by reference in their entirety)—an outcome that was part of the initial design concept and must hold for a pseudo-intramolecular delivery mechanism. Nonetheless, independent case-by-case assessments are recommended using controls similar to the following. In the study of Nrf2-AR pathway, untargeted delivery contributing to T-REX™ delivery-mediated pseudo-intramolecular delivery was ruled out, using three independent lines of evidence (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). The best and most general control is to simultaneously overexpress HaloTag and target POI as two separate proteins (termed the non-fused system), and replicate the experiments and look for loss of downstream response (Parvez et al., "Substoichiometric Hydroxynonenylation of a Single Protein Recapitulates Whole-Cell-Stimulated Antioxidant Response," *J. Am. Chem. Soc.* 137: 10-13 (2015); Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which are hereby incorporated by reference in their entirety) (Box 3). To validate that the photocaged precursor molecule interaction with HaloTag is required for delivery, the D106A HaloTag point mutant (Los et al., "HaloTag: A Novel Protein Labeling Technology for Cell Imaging and Protein Analysis," *ACS Chem. Biol.* 3:373-82 (2008), which is hereby incorporated by reference in its entirety), which is unable to form a covalent bond with the chloroalkane unit, is recommended. It has also been found empirically that overexpression levels of many proteins can be dialed down by selecting for cell lines that have integrated the plasmid post transfection. This approach also limits potential variability due to transient transfection of the POI (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). One can also use less powerful or inducible promoters in mammalian cells or *E. coli* which lack a specific importer (lacZY), allowing IPTG concentrations to be more accurately titrated (Tuner™, Novagen). Alternatively, overexpression of Halo proteins may be executed in null background using cells in which the endogenous variant is knocked out (Doudna et al., "Genome Editing. The New Frontier of Genome Engineering with CRISPR-Cas9," *Science* 346:1258096 (2014), which is hereby incorporated by reference in its entirety).

Comparison to Existing Methods.

Most small-molecule based methods to identify HNE sensitive proteins rely to some extent on bolus dosing (Codreanu et al., "Alkylation Damage by Lipid Electrophiles Targets Functional Protein Systems," *Mol. Cell. Proteomics* 13:849-59 (2014); Yang et al., "Quantitative Chemoproteomics for Site-Specific Analysis of Protein Alkylation by 4-hydroxy-2-nonenal in Cells," *Anal. Chem.* 87:2535-41 (2015); Kim et al., "An Azido-Biotin Reagent for Use in the Isolation of Protein Adducts of Lipid-Derived Electrophiles by Streptavidin Catch and Photorelease," *Mol. Cell. Proteomics* 8:2080-89 (2009), which are hereby incorporated by reference in their entirety). The principal alternative to T-REX™ delivery is activity profiling. This has been carried out mostly in lysates (Weerapana et al., "Quantitative Reactivity Profiling Predicts Functional Cysteines in Proteomes," *Nature* 468:790-95 (2010); Wang et al., "A Chemoproteomic Platform to Quantitatively Map Targets of Lipid-Derived Electrophiles," *Nat. Methods* 11:79-85 (2014), which are hereby incorporated by reference in their entirety), but also more recently in cells (Yang et al., "Quantitative Chemoproteomics for Site-Specific Analysis of Protein Alkylation by 4-hydroxy-2-nonenal in Cells," *Anal. Chem.* 87:2535-41 (2015); Niphakis et al., "A Global Map of Lipid-Binding Proteins and Their Ligandability in Cells," *Cell* 161:1668-80 (2015), which are hereby incorporated by reference in their entirety). Importantly, several differences between lysate and cell-based data have been delineated (Yang et al., "Quantitative Chemoproteomics for Site-Specific Analysis of Protein Alkylation by 4-hydroxy-2-nonenal in Cells," *Anal. Chem.* 87:2535-41 (2015), which is hereby incorporated by reference in its entirety), which underscores the need for better methods to probe reactivity in biologically relevant contexts. Powerful approaches to profile both serine and cysteine residues—the latter the most likely HNE-modified residue (Weerapana et al., "Quantitative Reactivity Profiling Predicts Functional Cysteines in Proteomes," *Nature* 468:790-95 (2010); Wang et al., "A Chemoproteomic Platform to Quantitatively Map Targets of Lipid-Derived Electrophiles," *Nat. Methods* 11:79-85 (2014); Yang et al., "Quantitative Chemoproteomics for Site-Specific Analysis of Protein Alkylation by 4-hydroxy-2-nonenal in Cells," *Anal. Chem.* 87:2535-41 (2015), which are hereby incorporated by reference in their entirety)—exist in the literature. Histidine and lysine—residues that may react with HNE (Uchida et al., "Modification of Histidine Residues in Proteins by Reaction with 4-hydroxynonenal," *Proc. Nat'l. Acad. Sci. U.S.A.* 89:4544-8 (1992); Nadkarni et al., "Structural Definition of Early Lysine and Histidine Adduction Chemistry of 4-Hydroxynonenal," *Chem. Res. Toxicol.* 8:284-91 (1995), which are hereby incorporated by reference in their entirety)—are currently not able to be profiled. Thus, activity profiling can identify many potential LDE-reactive cysteines (around 1,000) in a high-throughput manner (Weerapana et al., "Quantitative Reactivity Profiling Predicts Functional Cysteines in Proteomes," *Nature* 468: 790-95 (2010); Wang et al., "A Chemoproteomic Platform to Quantitatively Map Targets of Lipid-Derived Electrophiles," *Nat. Methods* 11:79-85 (2014); Yang et al., "Quantitative Chemoproteomics for Site-Specific Analysis of Protein Alkylation by 4-hydroxy-2-nonenal in Cells," *Anal. Chem.* 87:2535-41 (2015), which are hereby incorporated by reference in their entirety): addition of an excess of LDE that competitively binds to the profiled cysteines can be detected because those cysteines that bind the LDE are lost from the profiling pool. Profiling thus has benefits over T-REX™ delivery in that it can identify many specific cysteine targets on specific proteins rapidly (T-REX™ delivery can be used to identify specific cysteines but it is more time consuming). Furthermore, because the proteomics profiling method profiles activity, it can potentially report on cysteines or enzymes that are not HNEylated, but are functionally coupled to an off-target HNEylation event, e.g., through changes in complexation or cysteines that are on enzymes whose stability is compromised under reaction conditions. Depending on the goal of the experiment, such an outcome may or may not be desired. But ultimately, a hit on profiling does not necessarily mean a bona fide HNEylation event has occurred and thus multiple downstream validations are required after the initial hits have been identified. Furthermore, profiling is limited by the number of cysteines that can be identified by the activity probe used, which although high, is not exhaustive. Many well-known reactive enzymes are rarely observed in reactivity profiling, such as Keap1.

By contrast, the whole ORFeome of mouse and human is available as Halo-tagged clones (Kazusa collection, Promega) making high-throughput screening with T-REX™ delivery possible. Although initial screening is more laborious than profiling, T-REX™ delivery is streamlined to allow downstream pathway interrogation using reporter assays such as dual luciferase- and GFP-based transcriptional reporters (shown in Steps 40C and 40D of the Procedure). It is believed that a combination of profiling (to generate potential hits) and T-REX™ delivery (for validation and downstream signal interrogation) is the most powerful approach.

Alternatives to profiling include direct identification of HNEylated proteins by MS (Rossi et al., "Anti-Inflammatory Cyclopentenone Prostaglandins are Direct Inhibitors of IkappaB Kinase," Nature 403:103-8 (2000); Ji et al., "IkappaB Kinase, a Molecular Target for Inhibition by 4-hydroxy-2-nonenal," J. Biol. Chem. 276:18223-28 (2001); Fritz et al., "4-Hydroxynonenal Inhibits SIRT3 Via Thiol-Specific Modification," Chem. Res. Toxicol. 24:651-62 (2011); Galligan et al., "Stable Histone Adduction by 4-oxo-2-nonenal: A Potential Link Between Oxidative Stress and Epigenetics," J. Am. Chem. Soc. 136:11864-66 (2014), which are hereby incorporated by reference in their entirety) pull down assays using radiolabeled HNE (Grune et al., "Metabolism of 4-Hydroxynonenal, a Cytotoxic Lipid Peroxidation Product, in Ehrlich Mouse Ascites Cells at Different Proliferation Stages," Cancer Res. 54:5231-5 (1994); Srivastava et al., "Metabolism of the Lipid Peroxidation Product, 4-Hydroxy-Trans-2-Nonenal, in Isolated Perfused Rat Heart," J. Biol. Chem. 273:10893-900 (1998), which are hereby incorporated by reference in their entirety), and in vitro HNEylation (Fritz et al., "4-Hydroxynonenal Inhibits SIRT3 Via Thiol-Specific Modification," Chem. Res. Toxicol. 24:651-62 (2011); Uchida et al., "Covalent Attachment of 4-Hydroxynonenal to Glyceraldehyde-3-Phosphate Dehydrogenase. A Possible Involvement of Intra- and Intermolecular Cross-Linking Reaction," J. Biol. Chem. 268:6388-93 (1993), which are hereby incorporated by reference in their entirety). These methods are all relatively low throughput and do not lend themselves to downstream signaling pathway interrogation. However, like T-REX™ delivery, they do identify a specific modification of a specific protein but under uncontrolled swamping conditions.

Further Modifications of LDE Signal.

LDE signals themselves can be modified by reduction (Schopfer et al., "Formation and Signaling Actions of Electrophilic Lipids," Chem. Rev. 111:5997-6021 (2011); Grune et al., "Metabolism of 4-Hydroxynonenal, a Cytotoxic Lipid Peroxidation Product, in Ehrlich Mouse Ascites Cells at Different Proliferation Stages," Cancer Res. 54:5231-5 (1994), which are hereby incorporated by reference in their entirety), oxidation (Schopfer et al., "Formation and Signaling Actions of Electrophilic Lipids," Chem. Rev. 111:5997-6021 (2011), which is hereby incorporated by reference in its entirety), alkylation (Grune et al., "Metabolism of 4-Hydroxynonenal, a Cytotoxic Lipid Peroxidation Product, in Ehrlich Mouse Ascites Cells at Different Proliferation Stages," Cancer Res. 54:5231-5 (1994); Codreanu et al., "Alkylation Damage by Lipid Electrophiles Targets Functional Protein Systems," Mol. Cell. Proteomics 13:849-59 (2014), which are hereby incorporated by reference in their entirety), and other secondary processes. This is an intrinsic property of LDEs, and for this reason in all methods using LDEs one cannot assume that the active species is the specific LDE added. Although little work has been carried out to compare how faithfully each method reports on modification by the intended electrophile as opposed to a metabolite thereof, because of the low dose of LDE generated and the "faster than diffusion" kinetics required for T-REX™ delivery to occur, it seems likely that T-REX™ delivery will be relatively less susceptible to chemical modification of the LDE than approaches based on bolus dosing (where electrophile is in excess).

Relevance to "Real Life" Situations.

T-REX™ delivery is a tool to identify and interrogate a single (or potentially a small number of) specific protein modification(s) at a time by a native reactive chemical signal. It is best used to model redox signaling, where modest perturbations to pre-existing cellular reactive lipid electrophile pool elicit a beneficial (Schopfer et al., "Formation and Signaling Actions of Electrophilic Lipids," Chem. Rev. 111:5997-6021 (2011); Rudolph et al., "Transduction of Redox Signaling by Electrophile-Protein Reactions," Sci. Signal. 2:re7 (2009); Paulsen et al., "Cysteine-Mediated Redox Signaling: Chemistry, Biology, and Tools for Discovery," Chem. Rev. 113:4633-79 (2013), which are hereby incorporated by reference in their entirety), typically cytoprotective response, such as AR (Schopfer et al., "Formation and Signaling Actions of Electrophilic Lipids," Chem. Rev. 111:5997-6021 (2011); Rudolph et al., "Transduction of Redox Signaling by Electrophile-Protein Reactions," Sci. Signal. 2:re7 (2009); Paulsen et al., "Cysteine-Mediated Redox Signaling: Chemistry, Biology, and Tools for Discovery," Chem. Rev. 113:4633-79 (2013); Hayes et al., "The Nrf2 Regulatory Network Provides an Interface Between Redox and Intermediary Metabolism," Trends Biochem. Sci. 39:199-218 (2014); Sporn et al., "NRF2 and Cancer: the Good, the Bad and the Importance of Context," Nat. Rev. Cancer 12:564-71 (2012), which are hereby incorporated by reference in their entirety) "signaling" can occur because changes in LDE can be compartmentalized, or "directed" to a specific target and because second-order rates of association with LDE vary widely for different enzymes (Weerapana et al., "Quantitative Reactivity Profiling Predicts Functional Cysteines in Proteomes," Nature 468:790-95 (2010); Codreanu et al., "Alkylation Damage by Lipid Electrophiles Targets Functional Protein Systems," Mol. Cell. Proteomics 13:849-59 (2014); Codreanu et al., "Global Analysis of Protein Damage by The Lipid Electrophile 4-hydroxy-2-nonenal," Mol. Cell. Proteomics 8:670-80 (2009), which are hereby incorporated by reference in their entirety). Furthermore, because LDE levels (and hence targeted labeling by T-REX™ delivery) are low, signaling events likely occur through gain of function or dominant loss of function. [If LDE modification causes inhibition of enzymatic activity, unless this is a dominant phenotype (as is the case for PTEN (Papa et al., "Cancer-Associated PTEN Mutants Act in a Dominant-Negative Manner to Suppress PTEN Protein Function," Cell 157:595-610 (2014); Leslie et al., "Non-Genomic Loss of PTEN Function in Cancer: Not in My Genes," Trends Pharmacol. Sci. 32:131-40 (2011); Trotman et al., "Pten Dose Dictates Cancer Progression in the Prostate," PLoS Biol. 1:E59 (2003); Covey et al., "Akt Activation by Arachidonic Acid Metabolism Occurs via Oxidation and Inactivation of PTEN Tumor Suppressor," Oncogene 26:5784-92 (2007), which are hereby incorporated by reference in their entirety)), the modification may not be phenotypic during redox signaling because of the low concentrations of HNE leading to low target protein occupancy]. Because T-REX™ delivery can only label a small percentage of the total target protein present, the requirements for observing a response are similar to those for lipid signaling. Furthermore, T-REX™ delivery "directs" HNE to a target enzyme in a similar manner to endogenous signaling, thereby mimicking "redox signaling" reasonably well. Individual pathological effects of overproduction of LDEs can also be in principle interrogated using T-REX™ delivery, such as to interrogate the extent to which HNEylation of a specific protein may elicit apoptosis. However, since pathological effects stem from hyper-production of LDE in which complete loss of function could occur, ancillary factors or high percentage of modifications of the target may be required to recapitulate these scenarios, which would render T-REX™ delivery less useful.

LDE Chain Length.

HaloTag is unreactive to the reactive electrophiles and thus generally serves as a good point source of reactive signals (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). However, it has been have found that hydrophobic surface of Halo can interfere with efficient release of long-chain (>~15 carbon) fatty acid-derived LDEs—for instance, 2-HD (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety) (FIG. 17, inset). This was presumed to occur because 2-HD binds non-specifically to Halo, allowing non-covalent association to occur post photo-uncaging. Consistent with this assertion, in vitro 2-HD release assays in the presence of 1% SDS led to efficient liberation, whereas no liberation was observed without SDS (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). In principle, the problem may be solved by the use of alternative tags such as CLIP and SNAP tags in place of HaloTag, along with modification of chloroalkane unit of the photocaged precursors to the benzylcytosine or -guanine motif—the covalent recognition unit for CLIP- and SNAP tags, respectively (Gautier et al., "An Engineered Protein Tag for Multiprotein Labeling in Living Cells," *Chem. Biol.* 15:128-36 (2008), which is hereby incorporated by reference in its entirety).

Number of Reactive Motifs on LDEs.

If the LDE signal houses more than one reactive group as in the case with 4-oxononenal (ONE, FIG. 17 inset), the specificity will be lost because a reactive enone moiety is exposed within the photocaged precursor itself prior to photo-uncaging (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety). Dual-photocaging of the ketone as well as the aldehyde of ONE is a viable solution. Both anthraquinone-based, and for instance, the bioorthogonal nitrobenzyl-based photocaged groups, respectively, for the aldehyde and ketone functions within ONE, could then be simultaneously uncaged to deliver ONE on demand. Alternatively, one could use a semi-stable protecting group for the ketone motif—such as an acetal—with a half-life longer than the 2-h incubation time. In this way, post 2-h incubation of cells with the photocaged precursor, light exposure would liberate the aldehyde while unmasking of the ketone motif would happen on a similar time scale, and only after photo-uncaging of the aldehyde.

Cell Type and Viability.

Although the light-source is of low energy (FIG. 17 and FIG. 18) and does not affect cellular viability within the time scale and types of cells thus far employed (assessed by AlamarBlue® and Trypan blue assays (Lin et al., "A Generalizable Platform for Interrogating Target- and Signal-Specific Consequences of Electrophilic Modifications in Redox-Dependent Cell Signaling," *J. Am. Chem. Soc.* 137:6232-44 (2015), which is hereby incorporated by reference in its entirety); in HEK-293, COS-1, and *E. coli*), it is important to independently validate potential effects on cell viability.

CONCLUSION

In sum, a regimen to identify functional electrophile-sensor proteins and surgically interrogate their specific responses in the backdrop of an otherwise largely unperturbed cell or animal has been devised. Previous studies to model electrophilic signalling subsystems have made use of global HNE flooding. Here, a different track is taken: a 'low-occupancy modification' setting is configured, in which a brief 'pulse' of HNE is delivered in situ, such that only first responders (regardless of expression level) are tagged. This approach offers a much-needed user-controlled protocol to tag, and (when coupled to T-REX™ delivery) road-test functional cysteines. Importantly, G-REX™ profiling uses direct affinity capture of modified cysteines, as opposed to current strategies that detect loss of labeling. Thus, G-REX™ profiling minimizes false positives associated with off-target reactivity. G-REX™ profiling regimen could readily be applied to target-ID of a specific electrophile; to identify new RES-sensors for drug discovery; or extended to identification of off-target proteins hit by electrophilic drugs and linking these specific events to phenotypes, such as drug-induced hepatotoxicity.

G-REX™ profiling was validated by investigating the signaling ramifications of HNEylation of a specific, conserved redox-sensor cysteine found in two homologous, yet independently-regulated/functionally-distinct regulatory proteins. Each protein acts as an allosteric adapter for the E2 ubiquitin ligase, Ube2N. Remarkably, mono-HNEylation of either privileged sensor was sufficient to elicit hyper-stimulation of Ube2V1- or Ube2V2-specific downstream signaling. The outcomes from the Ube2V2-point-mutant that is competent for all other functions, except HNE-sensitivity, strikingly support this functional sensing and signal propagation. These data support an HNE-shunt mechanism, whereby flux through the ubiquitin signaling node, Ube2N, is elevated by HNEylation of its allosteric binding-partner, Ube2V2.

It is proposed that this new signaling currency exchange to be a functional pathway that operates as a surveillance and maintenance mechanism for DDR (Yi et al., "DNA Repair by Reversal of DNA Damage," *Cold Spring Harb. Perspect. Biol.* 5:a012575 (2013), which is hereby incorporated by reference in its entirety) in response to a transient rise in cellular electrophile flux. These data indicate that redox signaling—HNEylation of one regulatory protein (at a site with no "expected" reactivity)—an affect ubiquitin signaling via a third-party enzyme containing a catalytic cysteine (Ube2N). Given that defects in DDR (O'Driscoll, M., "Diseases Associated with Defective Responses to DNA Damage," *Cold Spring Harb. Perspect. Biol.* 4(12):a012773 (2012), which is hereby incorporated by reference in its entirety) are a common source of heritable disease, it is likely that exquisite regulation by small-molecule electrophiles on specific pathways could be mined for drug discovery and biomedical benefits.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for identifying endogenous first responder protein-cysteines, said method comprising:
   culturing, in a culture medium, living cells either transfected or stably integrated with a nucleic acid encoding only a protein tag under conditions effective to express the protein tag alone with no transgene fused to it;
   treating the culture medium with a bioinert photocaged precursor to a reactive electrophilic species (RES), which binds to the protein tag under conditions effective to form a bioinert photocaged precursor to an RES-protein tag complex;
   subjecting the culture medium to actinic radiation so that the RES is released from the bioinert photocaged precursor to an RES-protein tag complex;
   binding the RES, which has been released from the bioinert photocaged precursor to an RES-protein tag complex, to endogenous first responder protein-cysteines within the living cells, or subcellular locales where the protein tag is selectively expressed, to form a covalent RES-labeled endogenous first responder protein-cysteine complex; and
   isolating the RES-labeled endogenous first responder protein-cysteine complex.

2. The method of claim 1, wherein the living cells are mammalian cells or bacterial cells.

3. The method of claim 1, wherein the RES is a native lipid-derived electrophile.

4. The method of claim 1, wherein the RES is a Michael-acceptor electrophile.

5. The method of claim 1, wherein the released RES is alkyne functionalized.

6. The method of claim 4, wherein the alkyne functionalized RES is 4-hydroxynonenal alkyne.

7. The method of claim 1, wherein the protein tag is selected from the group consisting of a haloalkane dehalogenase, an O2-benzylcytosine derivative, an O6-alkylguanine-DNA-allkytransferase, and *E. coli* dihydrofolate reductase.

8. The method of claim 7, wherein the protein tag is a haloalkane dehalogenase.

9. The method of claim 1, wherein the bioinert photocaged RES precursor is

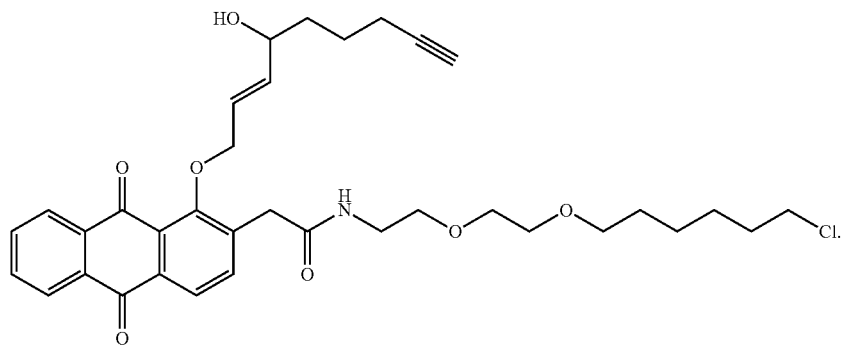 [SMILES: C#CCCCC(O)/C=C/COc1c(CC(=O)NCCOCCOCCCCCCCl)ccc2c1C(=O)c1ccccc1C2=O]

10. The method of claim 1, wherein said isolating comprises:
    biotinylating the RES-labeled endogenous first responder protein-cysteine complex and
    capturing the biotinylated RES-labeled endogenous first responder protein-cysteine complex with streptavidin.

11. The method of claim 1, wherein said subjecting is carried out with ultraviolet light at an energy level of 0.5-5.0 mW/cm$^2$.

12. The method of claim 1 further comprising:
    subjecting the RES-labeled endogenous first responder protein-cysteine complex to chemical analysis effective to identify the first responder protein.

13. The method of claim 12, wherein the chemical analysis is selected from the group consisting of mass spectrometry and protein microarray.

14. The method of claim 1 further comprising:
    preparing a nucleic acid construct encoding a fusion protein comprising the first responder protein obtained from the isolated RES-labeled endogenous first responder protein-cysteine complex, said first responder protein coupled to the protein tag;
    culturing, in a culture medium, living cells transfected with the nucleic acid construct;
    treating the culture medium with a bioinert photocaged precursor to an RES which binds to the protein tag of the fusion protein under conditions effective to form a bioinert photocaged precursor to an RES- protein tag complex; and
    subjecting the culture medium to actinic radiation such that the RES is released from the bioinert photocaged precursor to an RES- protein tag complex and binds to cysteines on the first responder protein component of the fusion protein.

15. The method of claim 14 further comprising:
    assessing cellular responses to said RES binding to cysteines on the first responder protein component of the fusion protein.

16. The method of claim 14, wherein the living cells are mammalian cells or bacterial cells.

17. The method of claim 14, wherein the RES is a native lipid-derived electrophile.

18. The method of claim 14, wherein the released RES is alkyne functionalized.

19. The method of claim 18, wherein the alkyne functionalized RES is 4-hydroxynonenal alkyne.

20. The method of claim 14, wherein the protein tag is selected from the group consisting of a haloalkane dehalogenase, an O2-benzylcytosine derivative, an O6-alkylguanine-DNA-alkytransferase, and *E. coli* dihydrofolate reductase.

21. The method of claim 20, wherein the protein tag is a haloalkane dehalogenase.

22. The method of claim 14, wherein the bioinert photocaged RES precursor is

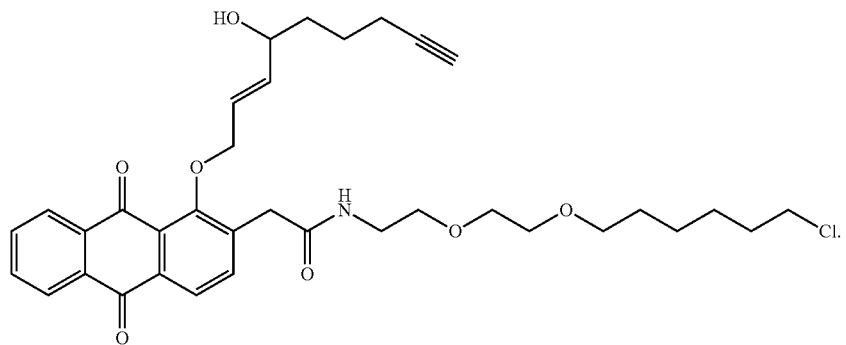 [SMILES: C#CCCCC(O)/C=C/COc1c(CC(=O)NCCOCCOCCCCCCCl)ccc2c1C(=O)c1ccccc1C2=O]

23. The method of claim 14, wherein said subjecting is carried out with ultraviolet light at an energy level of 0.5-5.0 mW/cm².

24. The method of claim 1, wherein the bioinert photocaged RES precursor species is

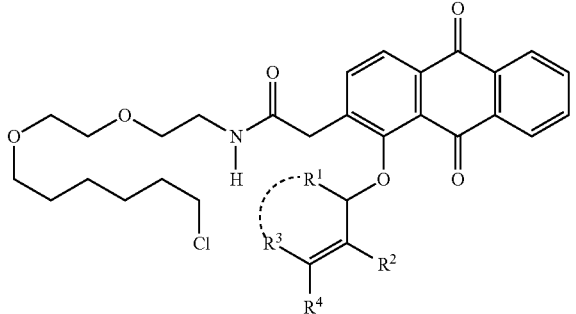

wherein R¹=H, Me; R²=H; R³=H; R⁴=(C3 to C8)-alkynyl, 1-hydroxy(C3 to C8)-alkynyl, 1-oxo(C3 to C8)-alkynyl; R¹/R³=—CH(CH₂C₂H)CH₂CH₂—, —CH₂CH(CH₂C₂H)—.

25. The method of claim 14, wherein the bioinert photocaged RES precursor species is

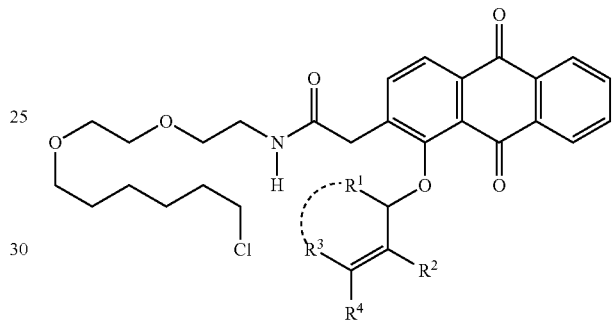

wherein R¹=H, Me; R²=H; R³=H; R⁴=(C3 to C8)-alkynyl, 1-hydroxy(C3 to C8)-alkynyl, 1-oxo(C3 to C8)-alkynyl; R¹/R³=—CH(CH₂C₂H)CH₂CH₂—, —CH₂CH(CH₂C₂H)—.

* * * * *

UNITED STATES PATENT AND TRADEMARK OFFICE
CERTIFICATE OF CORRECTION

PATENT NO. : 11,506,670 B2
APPLICATION NO. : 15/903506
DATED : November 22, 2022
INVENTOR(S) : Aye et al.

It is certified that error appears in the above-identified patent and that said Letters Patent is hereby corrected as shown below:

In the Claims

At Claim 7, Column 209, Line 37, delete "02-benzylcytosine derivative" and insert --O2-benzylcytosine derivative-- in its place.

At Claim 7, Column 209, Lines 37-38, delete "06-alkylguanine-DNA-allkytransferase" and insert --O6-alkylguanine-DNA-allkytransferase-- in its place.

At Claim 24, Column 211, Lines 39-40, delete "—$CH_2CH(CH_2C_2H)$—" and insert -- -$CH_2CH(CH_2C_2H)$- -- in its place.

At Claim 25, Column 212, Lines 37-38, delete "—$CH_2CH(CH_2C_2H)$—" and insert -- -$CH_2CH(CH_2C_2H)$- -- in its place.

Signed and Sealed this
Seventh Day of February, 2023

Katherine Kelly Vidal
*Director of the United States Patent and Trademark Office*

SEQUENCE LISTING

```
<160> NUMBER OF SEQ ID NOS: 66

<210> SEQ ID NO 1
<211> LENGTH: 20
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (5)..(5)
<223> OTHER INFORMATION: X at position 5 is K or R
<220> FEATURE:
<221> NAME/KEY: MISC_FEATURE
<222> LOCATION: (6)..(6)
<223> OTHER INFORMATION: X at position 6 is L or V
<220> FEATURE:
<221> NAME/KEY: MISC_FEATURE
<222> LOCATION: (10)..(10)
<223> OTHER INFORMATION: X at position 10 is S or P
<220> FEATURE:
<221> NAME/KEY: MISC_FEATURE
<222> LOCATION: (15)..(15)
<223> OTHER INFORMATION: X at position 15 is A or V
<220> FEATURE:
<221> NAME/KEY: MISC_FEATURE
<222> LOCATION: (18)..(18)
<223> OTHER INFORMATION: X at position 18 is S or T

<400> SEQUENCE: 1

Ile Tyr Ser Leu Xaa Xaa Glu Cys Gly Xaa Lys Tyr Pro Glu Xaa Pro
1               5                   10                  15

Pro Xaa Val Arg
            20

<210> SEQ ID NO 2
<211> LENGTH: 20
<212> TYPE: PRT
<213> ORGANISM: Artificial
<220> FEATURE:
<223> OTHER INFORMATION: Peptide

<400> SEQUENCE: 2

Ile Tyr Ser Leu Lys Val Glu Cys Gly Pro Lys Tyr Pro Glu Ala Pro
1               5                   10                  15

Pro Ser Val Arg
            20

<210> SEQ ID NO 3
<211> LENGTH: 20
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: X at position 1 is M or I
<220> FEATURE:
<221> NAME/KEY: MISC_FEATURE
<222> LOCATION: (5)..(5)
```

```
<223> OTHER INFORMATION: X at position 5 is K or R
<220> FEATURE:
<221> NAME/KEY: MISC_FEATURE
<222> LOCATION: (6)..(6)
<223> OTHER INFORMATION: X at position 6 is V or I
<220> FEATURE:
<221> NAME/KEY: MISC_FEATURE
<222> LOCATION: (11)..(11)
<223> OTHER INFORMATION: X at position 11 is K or R
<220> FEATURE:
<221> NAME/KEY: MISC_FEATURE
<222> LOCATION: (15)..(15)
<223> OTHER INFORMATION: X at position 15 is S, A, or T
<220> FEATURE:
<221> NAME/KEY: MISC_FEATURE
<222> LOCATION: (18)..(18)
<223> OTHER INFORMATION: X at position 18 is F, S, or Y

<400> SEQUENCE: 3

Xaa Tyr Ser Leu Xaa Xaa Glu Cys Gly Pro Xaa Tyr Pro Glu Xaa Pro
1               5                   10                  15

Pro Xaa Val Arg
            20

<210> SEQ ID NO 4
<211> LENGTH: 20
<212> TYPE: PRT
<213> ORGANISM: Artificial
<220> FEATURE:
<223> OTHER INFORMATION: Peptide

<400> SEQUENCE: 4

Ile Tyr Ser Leu Lys Ile Glu Cys Gly Pro Lys Tyr Pro Glu Ala Pro
1               5                   10                  15

Pro Phe Val Arg
            20

<210> SEQ ID NO 5
<211> LENGTH: 170
<212> TYPE: PRT
<213> ORGANISM: homo sapiens

<400> SEQUENCE: 5

Met Pro Gly Glu Val Gln Ala Ser Tyr Leu Lys Ser Gln Ser Lys Leu
1               5                   10                  15

Ser Asp Glu Gly Arg Leu Glu Pro Arg Lys Phe His Cys Lys Gly Ser
            20                  25                  30

Lys Ser Pro Ser Gln Phe Arg Leu Leu Glu Glu Leu Glu Glu Gly Gln
        35                  40                  45

Lys Gly Val Gly Asp Gly Thr Val Ser Trp Gly Leu Glu Asp Asp Glu
    50                  55                  60

Asp Met Thr Leu Thr Arg Trp Thr Gly Met Ile Ile Gly Pro Pro Arg
65                  70                  75                  80

Thr Ile Tyr Glu Asn Arg Ile Tyr Ser Leu Lys Ile Glu Cys Gly Pro
                85                  90                  95

Lys Tyr Pro Glu Ala Pro Pro Phe Val Arg Phe Val Thr Lys Ile Asn
            100                 105                 110

Met Asn Gly Val Asn Ser Ser Asn Gly Val Val Asp Pro Arg Ala Ile
        115                 120                 125

Ser Val Leu Ala Lys Trp Gln Asn Ser Tyr Ser Ile Lys Val Val Leu
    130                 135                 140

Gln Glu Leu Arg Arg Leu Met Met Ser Lys Glu Asn Met Lys Leu Pro
145                 150                 155                 160
```

Gln Pro Pro Glu Gly Gln Cys Tyr Ser Asn
            165                 170

<210> SEQ ID NO 6
<211> LENGTH: 145
<212> TYPE: PRT
<213> ORGANISM: homo sapiens

<400> SEQUENCE: 6

Met Ala Val Ser Thr Gly Val Lys Val Pro Arg Asn Phe Arg Leu Leu
1               5                   10                  15

Glu Glu Leu Glu Glu Gly Gln Lys Gly Val Gly Asp Gly Thr Val Ser
            20                  25                  30

Trp Gly Leu Glu Asp Asp Glu Asp Met Thr Leu Thr Arg Trp Thr Gly
        35                  40                  45

Met Ile Ile Gly Pro Pro Arg Thr Asn Tyr Glu Asn Arg Ile Tyr Ser
    50                  55                  60

Leu Lys Val Glu Cys Gly Pro Lys Tyr Pro Ala Pro Pro Ser Val
65                  70                  75                  80

Arg Phe Val Thr Lys Ile Asn Met Asn Gly Ile Asn Asn Ser Ser Gly
                85                  90                  95

Met Val Asp Ala Arg Ser Ile Pro Val Leu Ala Lys Trp Gln Asn Ser
            100                 105                 110

Tyr Ser Ile Lys Val Val Leu Gln Glu Leu Arg Arg Leu Met Met Ser
        115                 120                 125

Lys Glu Asn Met Lys Leu Pro Gln Pro Pro Glu Gly Gln Thr Tyr Asn
    130                 135                 140

Asn
145

<210> SEQ ID NO 7
<211> LENGTH: 163
<212> TYPE: PRT
<213> ORGANISM: Danio rerio

<400> SEQUENCE: 7

Met Arg Arg Leu Phe Thr Val Gly Ala Ser Pro Leu Leu Ser Asn Lys
1               5                   10                  15

Met Ala Ala Ala Gly Ser Gly Val Lys Val Pro Arg Asn Phe Arg
            20                  25                  30

Leu Leu Glu Glu Leu Glu Glu Gly Gln Lys Gly Val Gly Asp Gly Thr
        35                  40                  45

Val Ser Trp Gly Leu Glu Asp Asp Glu Asp Met Thr Leu Thr Arg Trp
    50                  55                  60

Arg Gly Met Ile Ile Gly Pro Pro Arg Thr Ile Tyr Glu Asn Arg Met
65                  70                  75                  80

Tyr Ser Leu Arg Val Glu Cys Gly Pro Arg Tyr Pro Glu Thr Pro Pro
                85                  90                  95

Phe Val Arg Phe Val Thr Lys Ile Asn Leu Asn Gly Val His Asn Ser
            100                 105                 110

Asn Gly Val Val Asp Met Arg Ala Val Ser Ser Leu Ala Lys Trp Gln
        115                 120                 125

Asn Ser Tyr Ser Ile Arg Val Val Leu Gln Glu Leu Arg Arg Leu Met
    130                 135                 140

Met Cys Lys Glu Asn Met Lys Leu Pro Gln Pro Pro Glu Gly Gln Ile
145                 150                 155                 160

Tyr Ser Asn

<210> SEQ ID NO 8
<211> LENGTH: 170
<212> TYPE: PRT
<213> ORGANISM: Pan troglodytes

<400> SEQUENCE: 8

Met Pro Gly Glu Val Gln Ala Ser Tyr Leu Lys Ser Gln Ser Lys Leu
1               5                   10                  15

Ser Asp Glu Gly Arg Leu Glu Pro Arg Lys Phe His Cys Lys Gly Val
            20                  25                  30

Lys Val Pro Arg Asn Phe Arg Leu Leu Glu Glu Leu Glu Glu Gly Gln
        35                  40                  45

Lys Gly Val Gly Asp Gly Thr Val Ser Trp Gly Leu Glu Asp Asp Glu
    50                  55                  60

Asp Met Thr Leu Thr Arg Trp Thr Gly Met Ile Ile Gly Pro Pro Arg
65                  70                  75                  80

Thr Ile Tyr Glu Asn Arg Ile Tyr Ser Leu Lys Ile Glu Cys Gly Pro
                85                  90                  95

Lys Tyr Pro Glu Ala Pro Pro Phe Val Arg Phe Val Thr Lys Ile Asn
            100                 105                 110

Met Asn Gly Val Asn Ser Ser Asn Gly Val Val Asp Pro Arg Ala Ile
        115                 120                 125

Ser Val Leu Ala Lys Trp Gln Asn Ser Tyr Ser Ile Lys Val Val Leu
    130                 135                 140

Gln Glu Leu Arg Arg Leu Met Met Ser Lys Glu Asn Met Lys Leu Pro
145                 150                 155                 160

Gln Pro Pro Glu Gly Gln Cys Tyr Ser Asn
                165                 170

<210> SEQ ID NO 9
<211> LENGTH: 147
<212> TYPE: PRT
<213> ORGANISM: mus musculus

<400> SEQUENCE: 9

Met Ala Ala Thr Thr Gly Ser Gly Val Lys Val Pro Arg Asn Phe Arg
1               5                   10                  15

Leu Leu Glu Glu Leu Glu Glu Gly Gln Lys Gly Val Gly Asp Gly Thr
            20                  25                  30

Val Ser Trp Gly Leu Glu Asp Asp Glu Asp Met Thr Leu Thr Arg Trp
        35                  40                  45

Thr Gly Met Ile Ile Gly Pro Pro Arg Thr Ile Tyr Glu Asn Arg Ile
    50                  55                  60

Tyr Ser Leu Lys Ile Glu Cys Gly Pro Lys Tyr Pro Glu Ala Pro Pro
65                  70                  75                  80

Ser Val Arg Phe Val Thr Arg Val Asn Met Ser Gly Val Ser Ser Ser
                85                  90                  95

Asn Gly Val Val Asp Pro Arg Ala Thr Ala Val Leu Ala Lys Trp Gln
            100                 105                 110

Asn Ser His Ser Ile Lys Val Ile Leu Gln Glu Leu Arg Arg Leu Met
        115                 120                 125

Met Ser Lys Glu Asn Met Lys Leu Pro Gln Pro Pro Glu Gly Gln Cys
    130                 135                 140

Tyr Ser Asn
145

<210> SEQ ID NO 10
<211> LENGTH: 150
<212> TYPE: PRT
<213> ORGANISM: Xenopus laevis

<400> SEQUENCE: 10

Gly Arg Val Gly Ala Ala Thr Thr Val Ser Gly Val Lys Val Pro Arg
1               5                   10                  15

Asn Phe Arg Leu Leu Glu Glu Leu Glu Glu Gly Gln Lys Gly Val Gly
                20                  25                  30

Asp Gly Thr Val Ser Trp Gly Leu Glu Asp Asp Glu Asp Met Thr Leu
            35                  40                  45

Thr Arg Trp Thr Gly Met Ile Ile Gly Pro Pro Arg Thr Gly Tyr Glu
        50                  55                  60

Asn Arg Ile Tyr Ser Leu Lys Val Glu Cys Gly Pro Lys Tyr Pro Glu
65                  70                  75                  80

Ser Pro Pro Tyr Val Arg Phe Val Thr Lys Val Asn Met Ser Gly Val
                85                  90                  95

Asn Asn Ser Asn Gly Val Val Asp Pro Arg Ala Val Ser Val Leu Val
                100                 105                 110

Lys Trp Gln Asn Ser Tyr Ser Ile Lys Val Val Leu Gln Glu Met Arg
            115                 120                 125

Arg Leu Met Met Ser Lys Glu Asn Met Lys Leu Pro Gln Pro Pro Glu
        130                 135                 140

Gly Gln Cys Tyr Ser Asn
145                 150

<210> SEQ ID NO 11
<211> LENGTH: 145
<212> TYPE: PRT
<213> ORGANISM: Xenopus laevis

<400> SEQUENCE: 11

Met Ala Val Cys Ala Gly Ile Lys Val Pro Arg Asn Phe Arg Leu Leu
1               5                   10                  15

Glu Glu Leu Glu Glu Gly Gln Lys Gly Val Gly Asp Gly Thr Val Ser
                20                  25                  30

Trp Gly Leu Glu Asp Asp Glu Asp Met Thr Leu Thr Arg Trp Thr Gly
            35                  40                  45

Met Ile Ile Gly Pro Pro Arg Thr Asn Tyr Glu Asn Arg Ile Tyr Ser
        50                  55                  60

Leu Arg Leu Glu Cys Gly Pro Lys Tyr Pro Glu Ala Pro Pro Thr Val
65                  70                  75                  80

Arg Phe Val Thr Lys Met Asn Met Asn Gly Ile Asn Asn Ser Asn Gly
                85                  90                  95

Thr Val Asp Tyr Arg Ser Ile Pro Val Leu Ala Lys Trp Gln Asn Ser
                100                 105                 110

Phe Ser Ile Lys Val Leu Leu Gln Glu Leu Arg Arg Leu Met Met Ser
            115                 120                 125

Lys Glu Asn Met Lys Leu Pro Gln Pro Pro Glu Gly Gln Thr Tyr Asn
        130                 135                 140

Asn
145

-continued

<210> SEQ ID NO 12
<211> LENGTH: 145
<212> TYPE: PRT
<213> ORGANISM: Danio rerio

<400> SEQUENCE: 12

Met Ala Ala Ser Ser Gly Val Lys Val Pro Arg Asn Phe Arg Leu Leu
1               5                   10                  15

Glu Glu Leu Glu Glu Gly Gln Lys Gly Val Gly Asp Gly Thr Val Ser
            20                  25                  30

Trp Gly Leu Glu Asp Asp Glu Asp Met Thr Leu Thr Arg Trp Thr Gly
        35                  40                  45

Met Ile Ile Gly Pro Ala Arg Thr Asn Tyr Glu Asn Arg Ile Tyr Ser
 50                  55                  60

Leu Lys Val Glu Cys Gly Pro Lys Tyr Pro Glu Val Pro Pro Thr Val
65                  70                  75                  80

Arg Phe Val Thr Lys Ile Ser Met Asn Gly Ile Asn Asn Ser Asn Gly
                85                  90                  95

Met Val Asp Ala Arg Ser Ile Pro Ile Leu Ala Lys Trp Gln Asn Ser
            100                 105                 110

Tyr Ser Ile Lys Val Val Leu Gln Glu Leu Arg Arg Leu Met Met Ser
        115                 120                 125

Lys Glu Asn Met Lys Leu Pro Gln Pro Pro Glu Gly Gln Thr Tyr Ser
    130                 135                 140

Asn
145

<210> SEQ ID NO 13
<211> LENGTH: 145
<212> TYPE: PRT
<213> ORGANISM: Pan troglodytes

<400> SEQUENCE: 13

Met Ala Val Ser Thr Gly Val Lys Val Pro Arg Asn Phe Arg Leu Leu
1               5                   10                  15

Glu Glu Leu Glu Glu Gly Gln Lys Gly Val Gly Asp Gly Thr Val Ser
            20                  25                  30

Trp Gly Leu Glu Asp Asp Glu Asp Met Thr Leu Thr Arg Trp Thr Gly
        35                  40                  45

Met Ile Ile Gly Pro Pro Arg Thr Asn Tyr Glu Asn Arg Ile Tyr Ser
 50                  55                  60

Leu Lys Val Glu Cys Gly Pro Lys Tyr Pro Glu Ala Pro Pro Ser Val
65                  70                  75                  80

Arg Phe Val Thr Lys Ile Asn Met Asn Gly Ile Asn Asn Ser Ser Gly
                85                  90                  95

Met Val Asp Ala Arg Ser Ile Pro Val Leu Ala Lys Trp Gln Asn Ser
            100                 105                 110

Tyr Ser Ile Lys Val Val Leu Gln Glu Leu Arg Arg Leu Met Met Ser
        115                 120                 125

Lys Glu Asn Met Lys Leu Pro Gln Pro Pro Glu Gly Gln Thr Tyr Asn
    130                 135                 140

Asn
145

<210> SEQ ID NO 14
<211> LENGTH: 145

```
<212> TYPE: PRT
<213> ORGANISM: mus musculus

<400> SEQUENCE: 14

Met Ala Val Ser Thr Gly Val Lys Val Pro Arg Asn Phe Arg Leu Leu
1               5                   10                  15

Glu Glu Leu Glu Glu Gly Gln Lys Gly Val Gly Asp Gly Thr Val Ser
            20                  25                  30

Trp Gly Leu Glu Asp Asp Glu Asp Met Thr Leu Thr Arg Trp Thr Gly
        35                  40                  45

Met Ile Ile Gly Pro Pro Arg Thr Asn Tyr Glu Asn Arg Ile Tyr Ser
    50                  55                  60

Leu Lys Val Glu Cys Gly Ser Lys Tyr Pro Glu Ala Pro Pro Ser Val
65                  70                  75                  80

Arg Phe Val Thr Lys Ile Asn Met Asn Gly Ile Asn Asn Ser Ser Gly
                85                  90                  95

Met Val Asp Ala Arg Ser Ile Pro Val Leu Ala Lys Trp Gln Asn Ser
            100                 105                 110

Tyr Ser Ile Lys Val Ile Leu Gln Glu Leu Arg Arg Leu Met Met Ser
        115                 120                 125

Lys Glu Asn Met Lys Leu Pro Gln Pro Pro Glu Gly Gln Thr Tyr Asn
    130                 135                 140

Asn
145

<210> SEQ ID NO 15
<211> LENGTH: 624
<212> TYPE: PRT
<213> ORGANISM: homo sapiens

<400> SEQUENCE: 15

Met Gln Pro Asp Pro Arg Pro Ser Gly Ala Gly Ala Cys Cys Arg Phe
1               5                   10                  15

Leu Pro Leu Gln Ser Gln Cys Pro Glu Gly Ala Gly Asp Ala Val Met
            20                  25                  30

Tyr Ala Ser Thr Glu Cys Lys Ala Glu Val Thr Pro Ser Gln His Gly
        35                  40                  45

Asn Arg Thr Phe Ser Tyr Thr Leu Glu Asp His Thr Lys Gln Ala Phe
    50                  55                  60

Gly Ile Met Asn Glu Leu Arg Leu Ser Gln Gln Leu Cys Asp Val Thr
65                  70                  75                  80

Leu Gln Val Lys Tyr Gln Asp Ala Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
        115                 120                 125

His Pro Lys Val Met Glu Arg Leu Ile Glu Phe Ala Tyr Thr Ala Ser
    130                 135                 140

Ile Ser Met Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190
```

```
Gln Ile Gly Cys Val Glu Leu His Gln Arg Ala Arg Glu Tyr Ile Tyr
            195                 200                 205

Met His Phe Gly Glu Val Ala Lys Gln Glu Phe Phe Asn Leu Ser
    210                 215                 220

His Cys Gln Leu Val Thr Leu Ile Ser Arg Asp Asp Leu Asn Val Arg
225                 230                 235                 240

Cys Glu Ser Glu Val Phe His Ala Cys Ile Asn Trp Val Lys Tyr Asp
                245                 250                 255

Cys Glu Gln Arg Arg Phe Tyr Val Gln Ala Leu Leu Arg Ala Val Arg
            260                 265                 270

Cys His Ser Leu Thr Pro Asn Phe Leu Gln Met Gln Leu Gln Lys Cys
        275                 280                 285

Glu Ile Leu Gln Ser Asp Ser Arg Cys Lys Asp Tyr Leu Val Lys Ile
    290                 295                 300

Phe Glu Glu Leu Thr Leu His Lys Pro Thr Gln Val Met Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asp Gly Thr Trp
            340                 345                 350

Leu Arg Leu Ala Asp Leu Gln Val Pro Arg Ser Gly Leu Ala Gly Cys
        355                 360                 365

Val Val Gly Gly Leu Leu Tyr Ala Val Gly Gly Arg Asn Asn Ser Pro
    370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Pro Met Ser Val Pro Arg Asn Arg Ile
                405                 410                 415

Gly Val Gly Val Ile Asp Gly His Ile Tyr Ala Val Gly Gly Ser His
            420                 425                 430

Gly Cys Ile His His Asn Ser Val Glu Arg Tyr Glu Pro Glu Arg Asp
        435                 440                 445

Glu Trp His Leu Val Ala Pro Met Leu Thr Arg Arg Ile Gly Val Gly
    450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Ala Met Asn Thr Ile Arg Ser Gly Ala Gly Val
            500                 505                 510

Cys Val Leu His Asn Cys Ile Tyr Ala Ala Gly Gly Tyr Asp Gly Gln
        515                 520                 525

Asp Gln Leu Asn Ser Val Glu Arg Tyr Asp Val Glu Thr Glu Thr Trp
    530                 535                 540

Thr Phe Val Ala Pro Met Lys His Arg Arg Ser Ala Leu Gly Ile Thr
545                 550                 555                 560

Val His Gln Gly Arg Ile Tyr Val Leu Gly Gly Tyr Asp Gly His Thr
                565                 570                 575

Phe Leu Asp Ser Val Glu Cys Tyr Asp Pro Asp Thr Asp Thr Trp Ser
            580                 585                 590

Glu Val Thr Arg Met Thr Ser Gly Arg Ser Gly Val Gly Val Ala Val
        595                 600                 605

Thr Met Glu Pro Cys Arg Lys Gln Ile Asp Gln Gln Asn Cys Thr Cys
```

<210> SEQ ID NO 16
<211> LENGTH: 13
<212> TYPE: PRT
<213> ORGANISM: Artificial
<220> FEATURE:
<223> OTHER INFORMATION: Peptide

<400> SEQUENCE: 16

Ser Gly Val Gly Val Ala Val Thr Met Glu Pro Cys Arg
1               5                   10

<210> SEQ ID NO 17
<211> LENGTH: 60
<212> TYPE: DNA
<213> ORGANISM: Artificial
<220> FEATURE:
<223> OTHER INFORMATION: Primer

<400> SEQUENCE: 17
agcgataacg cgatcgccga ctacaaggat gacgacgata agatggcggt ctccacagga      60

<210> SEQ ID NO 18
<211> LENGTH: 58
<212> TYPE: DNA
<213> ORGANISM: Artificial
<220> FEATURE:
<223> OTHER INFORMATION: Primer

<400> SEQUENCE: 18
gatttccggc gagccaacca ctgaggatct gtactttcag agcgataacg cgatcgcc        58

<210> SEQ ID NO 19
<211> LENGTH: 60
<212> TYPE: DNA
<213> ORGANISM: Artificial
<220> FEATURE:
<223> OTHER INFORMATION: Primer

<400> SEQUENCE: 19
tagaggatcc ccgggtaccg agcccgaatt cgtttaattg ttgtatgttt gtccttctgg      60

<210> SEQ ID NO 20
<211> LENGTH: 60
<212> TYPE: DNA
<213> ORGANISM: Artificial
<220> FEATURE:
<223> OTHER INFORMATION: Primer

<400> SEQUENCE: 20
tgttagcagc cggatcagct tgcatgcctg caggtcgact ctagaggatc cccgggtacc      60

<210> SEQ ID NO 21
<211> LENGTH: 59
<212> TYPE: DNA
<213> ORGANISM: Artificial
<220> FEATURE:
<223> OTHER INFORMATION: Primer

<400> SEQUENCE: 21
gaaaacagaa tatatagcct gaaagtagaa agtggaccta aatacccaga agctcctcc       59

<210> SEQ ID NO 22
<211> LENGTH: 59
<212> TYPE: DNA

```
<213> ORGANISM: Artificial
<220> FEATURE:
<223> OTHER INFORMATION: Primer

<400> SEQUENCE: 22
ggaggagctt ctgggtattt aggtccactt tctactttca ggctatatat tctgttttc    59

<210> SEQ ID NO 23
<211> LENGTH: 55
<212> TYPE: DNA
<213> ORGANISM: Artificial
<220> FEATURE:
<223> OTHER INFORMATION: Primer

<400> SEQUENCE: 23
tgacgacgat aaggactaca aggatgacga cgataagatg gcggtctcca cagga        55

<210> SEQ ID NO 24
<211> LENGTH: 59
<212> TYPE: DNA
<213> ORGANISM: Artificial
<220> FEATURE:
<223> OTHER INFORMATION: Primer

<400> SEQUENCE: 24
atagggctag caaagccacc atggattaca aggatgacga cgataaggac tacaaggat    59

<210> SEQ ID NO 25
<211> LENGTH: 60
<212> TYPE: DNA
<213> ORGANISM: Artificial
<220> FEATURE:
<223> OTHER INFORMATION: Primer

<400> SEQUENCE: 25
tagaggatcc ccgggtaccg agcccgaatt cgtttaattg ttgtatgttt gtccttctgg    60

<210> SEQ ID NO 26
<211> LENGTH: 60
<212> TYPE: DNA
<213> ORGANISM: Artificial
<220> FEATURE:
<223> OTHER INFORMATION: Primer

<400> SEQUENCE: 26
tgttagcagc cggatcagct tgcatgcctg caggtcgact ctagaggatc cccgggtacc    60

<210> SEQ ID NO 27
<211> LENGTH: 59
<212> TYPE: DNA
<213> ORGANISM: Artificial
<220> FEATURE:
<223> OTHER INFORMATION: Primer

<400> SEQUENCE: 27
gaaaacagaa tatatagcct gaaagtagaa agtggaccta atacccaga agctcctcc     59

<210> SEQ ID NO 28
<211> LENGTH: 59
<212> TYPE: DNA
<213> ORGANISM: Artificial
<220> FEATURE:
<223> OTHER INFORMATION: Primer

<400> SEQUENCE: 28
ggaggagctt ctgggtattt aggtccactt tctactttca ggctatatat tctgttttc    59
```

```
<210> SEQ ID NO 29
<211> LENGTH: 60
<212> TYPE: DNA
<213> ORGANISM: Artificial
<220> FEATURE:
<223> OTHER INFORMATION: Primer

<400> SEQUENCE: 29
agcgataacg cgatcgccga ctacaaggat gacgacgata agatgccagg agaggttcaa      60

<210> SEQ ID NO 30
<211> LENGTH: 58
<212> TYPE: DNA
<213> ORGANISM: Artificial
<220> FEATURE:
<223> OTHER INFORMATION: Primer

<400> SEQUENCE: 30
gatttccggc gagccaacca ctgaggatct gtactttcag agcgataacg cgatcgcc        58

<210> SEQ ID NO 31
<211> LENGTH: 58
<212> TYPE: DNA
<213> ORGANISM: Artificial
<220> FEATURE:
<223> OTHER INFORMATION: Primer

<400> SEQUENCE: 31
tagaggatcc ccgggtaccg agcccgaatt cgtttaattg ctgtaacact gtccttcg        58

<210> SEQ ID NO 32
<211> LENGTH: 60
<212> TYPE: DNA
<213> ORGANISM: Artificial
<220> FEATURE:
<223> OTHER INFORMATION: Primer

<400> SEQUENCE: 32
tgttagcagc cggatcagct tgcatgcctg caggtcgact ctagaggatc cccgggtacc      60

<210> SEQ ID NO 33
<211> LENGTH: 60
<212> TYPE: DNA
<213> ORGANISM: Artificial
<220> FEATURE:
<223> OTHER INFORMATION: Primer

<400> SEQUENCE: 33
gcaaagccac catggccagc atgaccggcg ccagcagat gggcatggcc gggctgcccc       60

<210> SEQ ID NO 34
<211> LENGTH: 60
<212> TYPE: DNA
<213> ORGANISM: Artificial
<220> FEATURE:
<223> OTHER INFORMATION: Primer

<400> SEQUENCE: 34
agctcttaag gctagagtat taatacgact cactataggg ctagcaaagc caccatggcc      60

<210> SEQ ID NO 35
<211> LENGTH: 60
<212> TYPE: DNA
<213> ORGANISM: Artificial
<220> FEATURE:
```

<223> OTHER INFORMATION: Primer

<400> SEQUENCE: 35
tagaggatcc ccgggtaccg agcccgaatt cgtttaattg ttgtatgttt gtccttctgg     60

<210> SEQ ID NO 36
<211> LENGTH: 60
<212> TYPE: DNA
<213> ORGANISM: Artificial
<220> FEATURE:
<223> OTHER INFORMATION: Primer

<400> SEQUENCE: 36
tgttagcagc cggatcagct tgcatgcctg caggtcgact ctagaggatc cccgggtacc     60

<210> SEQ ID NO 37
<211> LENGTH: 45
<212> TYPE: DNA
<213> ORGANISM: Artificial
<220> FEATURE:
<223> OTHER INFORMATION: Primer

<400> SEQUENCE: 37
gagctcgcta gcgggaattt ccggggactt ccgggaatt tccgg     45

<210> SEQ ID NO 38
<211> LENGTH: 29
<212> TYPE: DNA
<213> ORGANISM: Artificial
<220> FEATURE:
<223> OTHER INFORMATION: Primer

<400> SEQUENCE: 38
tggccggtac ctgagctcgc tagcgggaa     29

<210> SEQ ID NO 39
<211> LENGTH: 42
<212> TYPE: DNA
<213> ORGANISM: Artificial
<220> FEATURE:
<223> OTHER INFORMATION: Primer

<400> SEQUENCE: 39
aagtccccgg aaattcccgc tagcgagctc aggtaccggc ca     42

<210> SEQ ID NO 40
<211> LENGTH: 50
<212> TYPE: DNA
<213> ORGANISM: Artificial
<220> FEATURE:
<223> OTHER INFORMATION: Primer

<400> SEQUENCE: 40
cgaggccaga tctggaaatt cccggaaagt ccccggaaat tcccggaaag     50

<210> SEQ ID NO 41
<211> LENGTH: 27
<212> TYPE: DNA
<213> ORGANISM: Artificial
<220> FEATURE:
<223> OTHER INFORMATION: Primer

<400> SEQUENCE: 41
tggccgccga ggccagatct ggaaatt     27

```
<210> SEQ ID NO 42
<211> LENGTH: 41
<212> TYPE: DNA
<213> ORGANISM: Artificial
<220> FEATURE:
<223> OTHER INFORMATION: Primer

<400> SEQUENCE: 42
agatctggcc tcggcggcca agcttagaca ctagagggta t                    41

<210> SEQ ID NO 43
<211> LENGTH: 50
<212> TYPE: DNA
<213> ORGANISM: Artificial
<220> FEATURE:
<223> OTHER INFORMATION: Primer

<400> SEQUENCE: 43
ctacccatac gacgtcccag actacgctgt acctaggatc cagtcgggac            50

<210> SEQ ID NO 44
<211> LENGTH: 60
<212> TYPE: DNA
<213> ORGANISM: Artificial
<220> FEATURE:
<223> OTHER INFORMATION: Primer

<400> SEQUENCE: 44
ctagagtatt aatacgactc actatagggc tagcaaagcc acctacccat acgacgtccc 60

<210> SEQ ID NO 45
<211> LENGTH: 60
<212> TYPE: DNA
<213> ORGANISM: Artificial
<220> FEATURE:
<223> OTHER INFORMATION: Primer

<400> SEQUENCE: 45
tcgactctag aggatccccg ggtaccgagc ccgaattcgt ctacttgccc ttggccttgt 60

<210> SEQ ID NO 46
<211> LENGTH: 60
<212> TYPE: DNA
<213> ORGANISM: Artificial
<220> FEATURE:
<223> OTHER INFORMATION: Primer

<400> SEQUENCE: 46
gggctttgtt agcagccgga tcagcttgca tgcctgcagg tcgactctag aggatccccg 60

<210> SEQ ID NO 47
<211> LENGTH: 50
<212> TYPE: DNA
<213> ORGANISM: Artificial
<220> FEATURE:
<223> OTHER INFORMATION: Primer

<400> SEQUENCE: 47
acaaaaactc atctcagaag aggatctggt acctaggatc cagtcgggac            50

<210> SEQ ID NO 48
<211> LENGTH: 60
<212> TYPE: DNA
<213> ORGANISM: Artificial
<220> FEATURE:
<223> OTHER INFORMATION: Primer
```

<400> SEQUENCE: 48
taatacgact cactataggg ctagcaaagc caccgaacaa aaactcatct cagaagagga    60

<210> SEQ ID NO 49
<211> LENGTH: 60
<212> TYPE: DNA
<213> ORGANISM: Artificial
<220> FEATURE:
<223> OTHER INFORMATION: Primer

<400> SEQUENCE: 49
tcgactctag aggatccccg ggtaccgagc ccgaattcgt ctacttgccc ttggccttgt    60

<210> SEQ ID NO 50
<211> LENGTH: 60
<212> TYPE: DNA
<213> ORGANISM: Artificial
<220> FEATURE:
<223> OTHER INFORMATION: Primer

<400> SEQUENCE: 50
gggctttgtt agcagccgga tcagcttgca tgcctgcagg tcgactctag aggatccccg    60

<210> SEQ ID NO 51
<211> LENGTH: 51
<212> TYPE: DNA
<213> ORGANISM: Artificial
<220> FEATURE:
<223> OTHER INFORMATION: Primer

<400> SEQUENCE: 51
ccagcatgac cggcggccag cagatgggcg tacctaggat ccagtcggga c             51

<210> SEQ ID NO 52
<211> LENGTH: 60
<212> TYPE: DNA
<213> ORGANISM: Artificial
<220> FEATURE:
<223> OTHER INFORMATION: Primer

<400> SEQUENCE: 52
agagtattaa tacgactcac tatagggcta gcaaagccac catggccagc atgaccggcg    60

<210> SEQ ID NO 53
<211> LENGTH: 60
<212> TYPE: DNA
<213> ORGANISM: Artificial
<220> FEATURE:
<223> OTHER INFORMATION: Primer

<400> SEQUENCE: 53
tcgactctag aggatccccg ggtaccgagc ccgaattcgt ctacttgccc ttggccttgt    60

<210> SEQ ID NO 54
<211> LENGTH: 60
<212> TYPE: DNA
<213> ORGANISM: Artificial
<220> FEATURE:
<223> OTHER INFORMATION: Primer

<400> SEQUENCE: 54
gggctttgtt agcagccgga tcagcttgca tgcctgcagg tcgactctag aggatccccg    60

<210> SEQ ID NO 55
<211> LENGTH: 50

```
<212> TYPE: DNA
<213> ORGANISM: Artificial
<220> FEATURE:
<223> OTHER INFORMATION: Primer

<400> SEQUENCE: 55
taattaaagg ccggccagcg atcgccggac atggcagaaa tcggtactgg          50

<210> SEQ ID NO 56
<211> LENGTH: 60
<212> TYPE: DNA
<213> ORGANISM: Artificial
<220> FEATURE:
<223> OTHER INFORMATION: Primer

<400> SEQUENCE: 56
gctacttgtt cttttttgcag gatccactag tggcgcgcca ttaattaaag gccggccagc    60

<210> SEQ ID NO 57
<211> LENGTH: 39
<212> TYPE: DNA
<213> ORGANISM: Artificial
<220> FEATURE:
<223> OTHER INFORMATION: Primer

<400> SEQUENCE: 57
ttctagaggc tcgagaggcc ttcatgtctg ctcgaagcg                       39

<210> SEQ ID NO 58
<211> LENGTH: 60
<212> TYPE: DNA
<213> ORGANISM: Artificial
<220> FEATURE:
<223> OTHER INFORMATION: Primer

<400> SEQUENCE: 58
cttatcatgt ctggatctac gtaatacgac tcactatagt tctagaggct cgagaggcct    60

<210> SEQ ID NO 59
<211> LENGTH: 49
<212> TYPE: DNA
<213> ORGANISM: Artificial
<220> FEATURE:
<223> OTHER INFORMATION: Primer

<400> SEQUENCE: 59
taattaaagg ccggccagcg atcgccggac tacccatacg acgtcccag            49

<210> SEQ ID NO 60
<211> LENGTH: 60
<212> TYPE: DNA
<213> ORGANISM: Artificial
<220> FEATURE:
<223> OTHER INFORMATION: Primer

<400> SEQUENCE: 60
gctacttgtt cttttttgcag gatccactag tggcgcgcca ttaattaaag gccggccagc    60

<210> SEQ ID NO 61
<211> LENGTH: 41
<212> TYPE: DNA
<213> ORGANISM: Artificial
<220> FEATURE:
<223> OTHER INFORMATION: Primer

<400> SEQUENCE: 61
```

```
ttctagaggc tcgagaggcc tcctctagat gcatgctcga g                 41
```

<210> SEQ ID NO 62
<211> LENGTH: 60
<212> TYPE: DNA
<213> ORGANISM: Artificial
<220> FEATURE:
<223> OTHER INFORMATION: Primer

<400> SEQUENCE: 62

```
cttatcatgt ctggatctac gtaatacgac tcactatagt tctagaggct cgagaggcct    60
```

<210> SEQ ID NO 63
<211> LENGTH: 58
<212> TYPE: DNA
<213> ORGANISM: Artificial
<220> FEATURE:
<223> OTHER INFORMATION: Primer

<400> SEQUENCE: 63

```
ccggccatag aaacagctag agcatctcga gatgctctag ctgtttctat ggttttg       58
```

<210> SEQ ID NO 64
<211> LENGTH: 58
<212> TYPE: DNA
<213> ORGANISM: Artificial
<220> FEATURE:
<223> OTHER INFORMATION: Primer

<400> SEQUENCE: 64

```
ccggagacaa gttgggaaga atatgctcga gcatattctt cccaacttgt cttttttg      58
```

<210> SEQ ID NO 65
<211> LENGTH: 57
<212> TYPE: DNA
<213> ORGANISM: Artificial
<220> FEATURE:
<223> OTHER INFORMATION: Primer

<400> SEQUENCE: 65

```
ccgggctgag gcatttgtga gtcttctcga gaagactcac aaatgcctca gcttttt       57
```

<210> SEQ ID NO 66
<211> LENGTH: 21
<212> TYPE: DNA
<213> ORGANISM: Artificial
<220> FEATURE:
<223> OTHER INFORMATION: Primer

<400> SEQUENCE: 66

```
cgcgatcgta atcacccgag t                                       21
```